(12) United States Patent
Horne et al.

(10) Patent No.: US 11,230,560 B2
(45) Date of Patent: Jan. 25, 2022

(54) SYNTHESIS OF ETP DERIVATIVES

(71) Applicant: CITY OF HOPE, Duarte, CA (US)

(72) Inventors: David Horne, Altadena, CA (US); Jun Xie, Duarte, CA (US)

(73) Assignee: CITY OF HOPE, Duarte, CA (US)

( * ) Notice: Subject to any disclaimer, the term of this patent is extended or adjusted under 35 U.S.C. 154(b) by 0 days.

(21) Appl. No.: 16/615,300

(22) PCT Filed: May 22, 2018

(86) PCT No.: PCT/US2018/033967
§ 371 (c)(1),
(2) Date: Nov. 20, 2019

(87) PCT Pub. No.: WO2018/217811
PCT Pub. Date: Nov. 29, 2018

(65) Prior Publication Data
US 2020/0277307 A1    Sep. 3, 2020

Related U.S. Application Data

(60) Provisional application No. 62/509,561, filed on May 22, 2017.

(51) Int. Cl.
*C07D 513/18*    (2006.01)
(52) U.S. Cl.
CPC .................. *C07D 513/18* (2013.01)
(58) Field of Classification Search
CPC .................................................. C07D 513/18
See application file for complete search history.

(56) References Cited

U.S. PATENT DOCUMENTS

| | | |
|---|---|---|
| 4,396,589 A | 8/1983 | Bogdanovic |
| 5,380,923 A | 1/1995 | Wright et al. |
| 2009/0131311 A1 | 5/2009 | Becker et al. |

OTHER PUBLICATIONS

International Search Report dated Aug. 2, 2018, for PCT Application No. PCT/US2018/033967, filed May 22, 2018, 3 pages.
Written Opinion dated Aug. 2, 2018, for PCT Application No. PCT/US2018/033967, filed May 22, 2018, 4 pages.

*Primary Examiner* — Susanna Moore
(74) *Attorney, Agent, or Firm* — Irina E. Britva; Mintz, Levin, Cohn, Ferris, Glovsky and Popeo, P.C.

(57) ABSTRACT

Provided herein, inter alia, is the synthesis of ETP derivatives. The synthetic methods described herein include converting a ring bridging trisulfide compound of formula

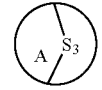

to a ring bridging disulfide compound of formula

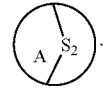

Also provided herein are compositions comprising thereof.

23 Claims, No Drawings

SYNTHESIS OF ETP DERIVATIVES

CROSS-REFERENCE TO RELATED APPLICATIONS

This application is a national stage of International Application PCT/US2018/033967, filed May 22, 2018, which claims the benefit of U.S. Provisional Application No. 62/509,561, filed May 22, 2017, which is incorporated herein by reference in its entirety and for all purposes.

BACKGROUND

ETP natural products represent an intriguing class of (typically) fungal secondary metabolites with a large variety of biological activities ranging from antibiotic to antiviral to antimalarial properties. High levels of toxicity, however, have so far prevented any clinical studies of known ETP structures. No detailed SAR studies of ETPs and their analogues have been reported to date. Furthermore, introduction and elaboration of functional groups for ETP structures has not been previously reported, thereby preventing modification of crucial properties such as water solubility, membrane permeability or metabolic stability in biological systems. Accordingly, a synthetic route to synthesize ETP analogues for medicinal purposes is crucial and has significant value. Provided herein are solutions to these and other problems in the art.

BRIEF SUMMARY

Provided herein, inter alia, are methods for converting a ring bridging trisulfide compound to a ring bridging disulfide compound. The method includes combining the ring bridging trisulfide compound with a non-nucleophilic base, thereby affording the corresponding ring bridging disulfide compound.

DETAILED DESCRIPTION

Definitions

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., —CH$_2$O— is equivalent to —OCH$_2$—.

The term "alkyl," by itself or as part of another substituent, means, unless otherwise stated, a straight (i.e., unbranched) or branched carbon chain (or carbon), or combination thereof, which may be fully saturated, mono- or polyunsaturated and can include mono-, di- and multivalent radicals, having the number of carbon atoms designated (i.e., C$_1$-C$_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, (cyclohexyl)methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—).

The term "alkylene," by itself or as part of another substituent, means, unless otherwise stated, a divalent radical derived from an alkyl, as exemplified, but not limited by, —CH$_2$CH$_2$CH$_2$CH$_2$—. Typically, an alkyl (or alkylene) group will have from 1 to 24 carbon atoms, with those groups having 10 or fewer carbon atoms being preferred in the present disclosure. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene.

The term "heteroalkyl," by itself or in combination with another term, means, unless otherwise stated, a stable straight or branched chain, or combinations thereof, including at least one carbon atom and at least one heteroatom (e.g., O, N, P, Si, and S), and wherein the nitrogen and sulfur atoms may optionally be oxidized, and the nitrogen heteroatom may optionally be quaternized. The heteroatom(s) (e.g., N, S, Si, or P) may be placed at any interior position of the heteroalkyl group or at the position at which the alkyl group is attached to the remainder of the molecule. Heteroalkyl is an uncyclized chain. Examples include, but are not limited to: —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—S—CH$_2$, —S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, —CH=CH—N(CH$_3$)—CH$_3$, —O—CH$_3$, —O—CH$_2$—CH$_3$, and —CN. Up to two or three heteroatoms may be consecutive, such as, for example, —CH$_2$—NH—OCH$_3$ and —CH$_2$—O—Si(CH$_3$)$_3$. A heteroalkyl moiety may include one heteroatom (e.g., O, N, S, Si, or P). A heteroalkyl moiety may include two optionally different heteroatoms (e.g., O, N, S, Si, or P). A heteroalkyl moiety may include three optionally different heteroatoms (e.g., O, N, S, Si, or P). A heteroalkyl moiety may include four optionally different heteroatoms (e.g., O, N, S, Si, or P). A heteroalkyl moiety may include five optionally different heteroatoms (e.g., O, N, S, Si, or P). A heteroalkyl moiety may include up to eight optionally different heteroatoms (e.g., O, N, S, Si, or P).

Similarly, the term "heteroalkylene," by itself or as part of another substituent, means, unless otherwise stated, a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—. As described above, heteroalkyl groups, as used herein, include those groups that are attached to the remainder of the molecule through a heteroatom, such as —C(O)R', —C(O)NR', —NR'R", —OR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, cyclic versions of "alkyl" and "heteroalkyl," respectively. Cycloalkyl and heterocycloalkyl are not aromatic. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively. "Cycloalkyl" is also meant to refer to bicyclic and polycyclic hydrocarbon rings such as, for example, bicyclo[2.2.1]heptane, bicyclo[2.2.2]octane, etc.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo($C_1$-$C_4$) alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. A heteroaryl group substituent may be a —O— bonded to a ring heteroatom nitrogen.

A "fused ring aryl-heterocycloalkyl" is an aryl fused to a heterocycloalkyl. A "fused ring heteroaryl-heterocycloalkyl" is a heteroaryl fused to a heterocycloalkyl. A "fused ring heterocycloalkyl-cycloalkyl" is a heterocycloalkyl fused to a cycloalkyl. A "fused ring heterocycloalkyl-heterocycloalkyl" is a heterocycloalkyl fused to another heterocycloalkyl. Fused ring aryl-heterocycloalkyl, fused ring heteroaryl-heterocycloalkyl, fused ring heterocycloalkyl-cycloalkyl, or fused ring heterocycloalkyl-heterocycloalkyl may each independently be unsubstituted or substituted with one or more of the substitutents described herein. Fused ring aryl-heterocycloalkyl, fused ring heteroaryl-heterocycloalkyl, fused ring heterocycloalkyl-cycloalkyl, or fused ring heterocycloalkyl-heterocycloalkyl may each independently be named according to the size of each of the fused rings. Thus, for example, 6,5 aryl-heterocycloalkyl fused ring describes a 6 membered aryl moiety fused to a 5 membered heterocycloalkyl.

Spirocyclic rings are two or more rings wherein adjacent rings are attached through a single atom. The individual rings within spirocyclic rings may be identical or different. Individual rings in spirocyclic rings may be substituted or unsubstituted and may have different substituents from other individual rings within a set of spirocyclic rings. Possible substituents for individual rings within spirocyclic rings are the possible substituents for the same ring when not part of spirocyclic rings (e.g. substitutents for cycloalkyl or heterocycloalkyl rings). Spirocylic rings may be substituted or unsubstituted cycloalkyl, substituted or unsubstituted cycloalkylene, substituted or unsubstituted heterocycloalkyl or substituted or unsubstituted heterocycloalkylene and individual rings within a spirocyclic ring group may be any of the immediately previous list, including having all rings of one type (e.g. all rings being substituted heterocycloalkylene wherein each ring may be the same or different substituted heterocycloalkylene). When referring to a spirocyclic ring system, heterocyclic spirocyclic rings means a spirocyclic rings wherein at least one ring is a heterocyclic ring and wherein each ring may be a different ring. When referring to a spirocyclic ring system, substituted spirocyclic rings means that at least one ring is substituted and each substituent may optionally be different.

The term "oxo," as used herein, means an oxygen that is double bonded to a carbon atom.

The term "thio," as used herein, means a sulfur that is single bonded to carbon or to another sulfur.

The term "alkylarylene" as an arylene moiety covalently bonded to an alkylene moiety (also referred to herein as an alkylene linker). In embodiments, the alkylarylene group has the formula:

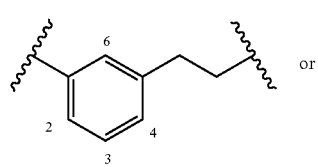 or

-continued

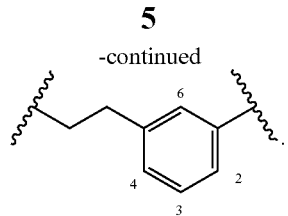

An alkylarylene moiety may be substituted (e.g. with a substituent group) on the alkylene moiety or the arylene linker (e.g. at carbons 2, 3, 4, or 6) with halogen, oxo, —N$_3$, —CF$_3$, —CCl$_3$, —CBr$_3$, —CI$_3$, —CN, —CHO, —OH, —NH$_2$, —COOH, —CONH$_2$, —NO$_2$, —SH, —SO$_2$CH$_3$— SO$_3$H, —OSO$_3$H, —SO$_2$NH$_2$, —NHNH$_2$, —ONH$_2$, —NHC(O)NHNH$_2$, substituted or unsubstituted C$_1$-C$_5$ alkyl or substituted or unsubstituted 2 to 5 membered heteroalkyl). In embodiments, the alkylarylene is unsubstituted.

Each of the above terms (e.g., "alkyl," "heteroalkyl," "cycloalkyl," "heterocycloalkyl," "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R'', —SR', -halogen, —SiR'R''R''', —OC(O)R', —C(O)R', —CO$_2$R', —CONR'R'', —OC(O)NR'R'', —NR''C(O)R', —NR'—C(O)NR''R''', —NR''C(O)$_2$R', —NR—C(NR'R''R''')=NR'''', —NR—C(NR'R'')=NR''', —S(O)R', —S(O)$_2$R', —S(O)$_2$NR'R'', —NRSO$_2$R', —NR'NR''R''', —ONR'R'', —NR'C(O)NR''NR'''R'''', —CN, —NO$_2$, —NR'SO$_2$R'', —NR'C(O)R'', —NR'C(O)—OR'', —NR'OR'', in a number ranging from zero to (2m'+1), where m' is the total number of carbon atoms in such radical. R, R', R'', R''', and R'''' each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound described herein includes more than one R group, for example, each of the R groups is independently selected as are each R', R'', R''', and R'''' group when more than one of these groups is present. When R' and R'' are attached to the same nitrogen atom, they can be combined with the nitrogen atom to form a 4-, 5-, 6-, or 7-membered ring. For example, —NR'R'' includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are varied and are selected from, for example: —OR', —NR'R'', —SR', -halogen, —SiR'R''R''', —OC(O)R', —C(O)R', —CO$_2$R', —CONR'R'', —OC(O)NR'R'', —NR''C(O)R', —NR'—C(O)NR''R''', —NR''C(O)$_2$R', —NR—C(NR'R''R''')=NR'''', —NR—C(NR'R'')=NR''', —S(O)R', —S(O)$_2$R', —S(O)$_2$NR'R'', —NRSO$_2$R', —NR'NR''R''', —ONR'R'', —NR'C(O)NR''NR'''R'''', —CN, —NO$_2$, —R', —N$_3$, —CH (Ph)$_2$, fluoro(C$_1$-C$_4$)alkoxy, and fluoro(C$_1$-C$_4$)alkyl, —NR'SO$_2$R'', —NR'C(O)R'', —NR'C(O)—OR'', —NR'OR'', in a number ranging from zero to the total number of open valences on the aromatic ring system; and where R', R'', R''', and R'''' are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound described herein includes more than one R group, for example, each of the R groups is independently selected as are each R', R'', R''', and R'''' groups when more than one of these groups is present.

Substituents for rings (e.g. cycloalkyl, heterocycloalkyl, aryl, heteroaryl, cycloalkylene, heterocycloalkylene, arylene, or heteroarylene) may be depicted as substituents on the ring rather than on a specific atom of a ring (commonly referred to as a floating substituent). In such a case, the substituent may be attached to any of the ring atoms (obeying the rules of chemical valency) and in the case of fused rings or spirocyclic rings, a substituent depicted as associated with one member of the fused rings or spirocyclic rings (a floating substituent on a single ring), may be a substituent on any of the fused rings or spirocyclic rings (a floating substituent on multiple rings). When a substituent is attached to a ring, but not a specific atom (a floating substituent), and a subscript for the substituent is an integer greater than one, the multiple substituents may be on the same atom, same ring, different atoms, different fused rings, different spirocyclic rings, and each substituent may optionally be different. Where a point of attachment of a ring to the remainder of a molecule is not limited to a single atom (a floating substituent), the attachment point may be any atom of the ring and in the case of a fused ring or spirocyclic ring, any atom of any of the fused rings or spirocyclic rings while obeying the rules of chemical valency. Where a ring, fused rings, or spirocyclic rings contain one or more ring heteroatoms and the ring, fused rings, or spirocyclic rings are shown with one more floating substituents (including, but not limited to, points of attachment to the remainder of the molecule), the floating substituents may be bonded to the heteroatoms. Where the ring heteroatoms are shown bound to one or more hydrogens (e.g. a ring nitrogen with two bonds to ring atoms and a third bond to a hydrogen) in the structure or formula with the floating substituent, when the heteroatom is bonded to the floating substituent, the substituent will be understood to replace the hydrogen, while obeying the rules of chemical valency.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -T-C(O)—(CRR')$_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-$(CH_2)_r$—B—, wherein A and B are independently —CRR'—, —O—, —NR—, —S—, —S(O)—, —S(O)$_2$—, —S(O)$_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'—(C"R"R''')$_d$—, where s and d are independently integers of from 0 to 3, and X' is —O—, —NR'—, —S—, —S(O)—, —S(O)$_2$—, or —S(O)$_2$NR'—. The substituents R, R', R", and R''' are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include, oxygen (O), nitrogen (N), sulfur (S), phosphorus (P), Boron (B), Arsenic (As), and silicon (Si).

A "substituent group," as used herein, means a group selected from the following moieties:

(A) oxo, halogen, —CCl$_3$, —CBr$_3$, —CF$_3$, —CI$_3$, CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl), and (B) alkyl, heteroalkyl, cycloalkyl, heterocycloalkyl, aryl, heteroaryl, substituted with at least one substituent selected from:

(i) oxo, halogen, —CCl$_3$, —CBr$_3$, —CF$_3$, —CI$_3$, CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl), and (ii) alkyl, heteroalkyl, cycloalkyl, heterocycloalkyl, aryl, heteroaryl, substituted with at least one substituent selected from:

(a) oxo, halogen, —CCl$_3$, —CBr$_3$, —CF$_3$, —CI$_3$, CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl), and (b) alkyl, heteroalkyl, cycloalkyl, heterocycloalkyl, aryl, heteroaryl, substituted with at least one substituent selected from: oxo, halogen, —CCl$_3$, —CBr$_3$, —CF$_3$, —CI$_3$, CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OC H$_2$Cl, —OCH$_2$Br, —OCH$_2$I, —OCH$_2$F, —N$_3$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

A "size-limited substituent" or "size-limited substituent group," as used herein, means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, and each substituted or unsubstituted heterocycloalkyl is a substituted or unsubstituted 3 to 8 membered heterocycloalkyl.

A "lower substituent" or "lower substituent group," as used herein, means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, and each substituted or unsubstituted heterocycloalkyl is a substituted or unsubstituted 3 to 7 membered heterocycloalkyl.

In some embodiments, each substituted group described in the compounds herein is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In other embodiments, each substituted or unsubstituted alkyl may be a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, and/or each substituted or unsubstituted heterocycloalkyl is a substituted or unsubstituted 3 to 8 membered heterocycloalkyl. In some embodiments of the compounds herein, each substituted or unsubstituted alkylene is a substituted or unsubstituted $C_1$-$C_{20}$ alkylene, each substituted or unsubstituted heteroalkylene is a substituted or unsubstituted 2 to 20 membered heteroalkylene, each substituted or unsubstituted cycloalkylene is a substituted or unsubstituted $C_3$-$C_8$ cycloalkylene, and/or each substituted or unsubstituted heterocycloalkylene is a substituted or unsubstituted 3 to 8 membered heterocycloalkylene.

In some embodiments, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, and/or each substituted or unsubstituted heterocycloalkyl is a substituted or unsubstituted 3 to 7 membered heterocycloalkyl. In some embodiments, each substituted or unsubstituted alkylene is a substituted or unsubstituted $C_1$-$C_8$ alkylene, each substituted or unsubstituted heteroalkylene is a substituted or unsubstituted 2 to 8 membered heteroalkylene, each substituted or unsubstituted cycloalkylene is a substituted or unsubstituted $C_3$-$C_7$ cycloalkylene, and/or each substituted or unsubstituted heterocycloalkylene is a substituted or unsubstituted 3 to 7 membered heterocycloalkylene.

Certain compounds of the present disclosure possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present disclosure. The compounds of the present disclosure do not include those which are known in art to be too unstable to synthesize and/or isolate. The present disclosure is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

It will be apparent to one skilled in the art that certain compounds of this disclosure may exist in tautomeric forms, all such tautomeric forms of the compounds being within the scope of the disclosure.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds, generally recognized as stable by those skilled in the art, are within the scope of the disclosure.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of this disclosure.

The compounds of the present disclosure may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I), or carbon-14 ($^{14}$C). All isotopic variations of the compounds of the present disclosure, whether radioactive or not, are encompassed within the scope of the present disclosure.

The symbol "〜" denotes the point of attachment of a chemical moiety to the remainder of a molecule or chemical formula.

"$S_p$", "$S_t$", or "$S_n$" refers to a sulfide bridge having p, t, or n sulfurs (e.g. $S_2$ is —S—S—, $S_3$ is —S—S—S—, $S_4$ is —S—S—S—S—).

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls.

Moreover, where a moiety is substituted with an R substituent, the group may be referred to as "R-substituted." Where a moiety is R-substituted, the moiety is substituted with at least one R substituent and each R substituent is optionally different. Where a particular R group is present in the description of a chemical genus (such as Formula (I)), a Roman alphabetic symbol may be used to distinguish each appearance of that particular R group. For example, where multiple $R^{13}$ substituents are present, each $R^{13}$ substituent may be distinguished as $R^{13A}$, $R^{13B}$, $R^{13C}$, $R^{13D}$, etc., wherein each of $R^{13A}$, $R^{13B}$, $R^{13C}$, $R^{13D}$, etc. is defined within the scope of the definition of $R^{13}$ and optionally differently.

Description of compounds of the present disclosure is limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

The term "pharmaceutically acceptable salts" is meant to include salts of the active compounds that are prepared with relatively nontoxic acids or bases, depending on the particular substituents found on the compounds described herein. When compounds of the present disclosure contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present disclosure contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, oxalic, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science*, 1977, 66, 1-19). Certain specific compounds of the present disclosure contain both basic and acidic functionalities that allow the compounds to be converted into either base or acid addition salts.

Thus, the compounds of the present disclosure may exist as salts, such as with pharmaceutically acceptable acids. The present disclosure includes such salts. Examples of such salts include hydrochlorides, hydrobromides, sulfates, methanesulfonates, nitrates, maleates, acetates, citrates, fumarates, tartrates (e.g., (+)-tartrates, (−)-tartrates, or mixtures thereof including racemic mixtures), succinates, benzoates, and salts with amino acids such as glutamic acid. These salts may be prepared by methods known to those skilled in the art.

The neutral forms of the compounds are preferably regenerated by contacting the salt with a base or acid and isolating the parent compound in the conventional manner. The parent form of the compound differs from the various salt forms in certain physical properties, such as solubility in polar solvents.

In addition to salt forms, the present disclosure provides compounds, which are in a prodrug form. Prodrugs of the compounds described herein include those compounds that readily undergo chemical changes under physiological conditions to provide the compounds of the present disclosure. Additionally, prodrugs can be converted to the compounds of the present disclosure by chemical or biochemical methods in an ex vivo environment. For example, prodrugs can be slowly converted to the compounds of the present disclosure when placed in a transdermal patch reservoir with a suitable enzyme or chemical reagent.

Certain compounds of the present disclosure can exist in unsolvated forms as well as solvated forms, including hydrated forms. In general, the solvated forms are equivalent to unsolvated forms and are encompassed within the scope of the present disclosure. Certain compounds of the present disclosure may exist in multiple crystalline or amorphous forms. In general, all physical forms are equivalent for the uses contemplated by the present disclosure and are intended to be within the scope of the present disclosure.

As used herein, the term "salt" refers to acid or base salts of the compounds used in the methods of the present disclosure. Illustrative examples of acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts.

As used herein, the term "non-nucleophilic base" refers to a sterically hindered base that is a poor nucleophile. Non-nucleophilic bases are mostly organic and can contain nitrogen. The non-limiting examples of non-nucleophilic organic bases are 1,5,7-triazabicyclo(4.4.0)dec-5-ene (TBD), 7-methyl-1,5,7-triazabicyclo(4.4.0)dec-5-ene (MTBD), 1,8-diazabicyclo[5.4.0]undec-7-ene (DBU), 1,5-diazabicyclo[4.3.0]non-5-ene (DBN), 1,1,3,3-tetramethylguanidine (TMG), quinuclidine, 2,2,6,6-tetramethylpiperidine (TMP), pempidine (PMP), tributylamine, triethylamine, N,N-diisopropylamine, 1,4-diazabicyclo[2.2.2]octan (TED), collidine, 2,6-dimethylpyridine, sodium tert-butoxide, potassium tert-butoxide, lithium diisopropylamide (LDA), potassium bis(trimethylsilyl)amide (KHMDS) or sodium trimethylsilyl)amide (NaHMDS). Examples of inorganic non-nucleophilic bases include, but are not limited to, sodium hydride, potassium hydride or potassium bicarbonate.

As used herein, the term "sterically hindered non-nucleophilic base" refers to a base having proton-removing ability. In general, a group is said to be sterically hindered when the 3-D molecular shape prevents ready access to that group. This means that a chemical reaction which might occur with a chemically similar but smaller molecule may not occur with a sterically hindered one because the reactants can't get to the group.

A "therapeutically effective amount" or "effective amount" is an amount sufficient for a compound to accomplish a stated purpose relative to the absence of the compound (e.g. achieve the effect for which it is administered, treat a disease, reduce enzyme activity, increase enzyme activity, reduce a signaling pathway, or reduce one or more symptoms of a disease or condition). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins).

The compositions disclosed herein can be delivered by transdermally, by a topical route, formulated as applicator sticks, solutions, suspensions, emulsions, gels, creams, ointments, pastes, jellies, paints, powders, and aerosols. Oral preparations include tablets, pills, powder, dragees, capsules, liquids, lozenges, cachets, gels, syrups, slurries, suspensions, etc., suitable for ingestion by the patient. Solid form preparations include powders, tablets, pills, capsules, cachets, suppositories, and dispersible granules. Liquid form preparations include solutions, suspensions, and emulsions, for example, water or water/propylene glycol solutions. The compositions of the present disclosure may additionally include components to provide sustained release and/or comfort. Such components include high molecular weight, anionic mucomimetic polymers, gelling polysaccharides and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes. The compositions disclosed herein can also be delivered as microspheres for slow release in the body. For example, microspheres can be administered via intradermal injection of drug-containing microspheres, which slowly release subcutaneously (see Rao, *J. Biomater Sci. Polym.* Ed. 7:623-645, 1995; as biodegradable and injectable gel formulations (see, e.g., Gao *Pharm. Res.* 12:857-863, 1995); or, as microspheres for oral administration (see, e.g., Eyles, *J. Pharm. Pharmacol.* 49:669-674, 1997). In another embodiment, the formulations of the compositions of the present disclosure can be delivered by the use of liposomes which fuse with the cellular membrane or are endocytosed, i.e., by employing receptor ligands attached to the liposome, that bind to surface membrane protein receptors of the cell resulting in endocytosis. By using liposomes, particularly where the liposome surface carries receptor ligands specific for target cells, or are otherwise preferentially directed to a specific organ, one can focus the delivery of the compositions of the present invention into the target cells in vivo. (See, e.g., Al-Muhammed, *J. Microencapsul.* 13:293-306, 1996; Chonn, *Curr. Opin. Biotechnol.* 6:698-708, 1995; Ostro, *Am. J. Hosp. Pharm.* 46:1576-1587, 1989). The compositions can also be delivered as nanoparticles.

Pharmaceutical compositions may include compositions wherein the active ingredient (e.g. compounds described herein, including embodiments or examples) is contained in a therapeutically effective amount, i.e., in an amount effective to achieve its intended purpose. The actual amount effective for a particular application will depend, inter alia, on the condition being treated. When administered in methods to treat a disease, such compositions will contain an amount of active ingredient effective to achieve the desired result, e.g., modulating the activity of a target molecule, and/or reducing, eliminating, or slowing the progression of disease symptoms.

A bridged compound is a chemical compound that has two or more rings (a ring system) that contains a bridge—a single atom or an unbranched chain of atoms (or even a valence bond) that connects two or more "bridgehead" atoms. Bridged sulfide compounds include, but are not limited to, the following rings:

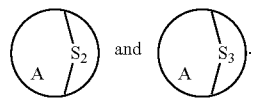

Methods of Synthesis

In a first aspect, there is provided a method for converting a ring bridging trisulfide compound to a ring bridging disulfide compound. The method includes combining the ring bridging trisulfide compound with a non-nucleophilic base, thereby affording the corresponding ring bridging disulfide compound.

In embodiments, prior to the combining, the ring bridging trisulfide compound is present as a mixture with a ring bridging disulfide compound.

In embodiments, the ring bridging trisulfide compound is:

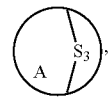

and the ring bridging disulfide compound is:

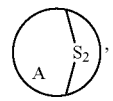

wherein A is substituted or unsubstituted cycloalkyl, substituted or unsubstituted heterocycloalkyl, substituted or unsubstituted aryl or substituted or unsubstituted heteroaryl. In embodiments, where A is substituted, it is substituted with one or more substituent groups as defined herein. In embodiments, where A is substituted, it is substituted with one or more size-limited substituent groups as defined herein. In embodiments, where A is substituted, it is substituted with one or more lower substituent groups as defined herein.

In embodiments, the non-nucleophilic base is an organic non-nucleophilic base. In embodiments, the organic non-nucleophilic base comprises an amino group. In embodiments, the organic non-nucleophilic base is a sterically hindered organic non-nucleophilic base.

In embodiments, the non-nucleophilic base is 1,5,7-triazabicyclo(4.4.0)dec-5-ene (TBD), 7-methyl-1,5,7-triazabicyclo(4.4.0)dec-5-ene (MTBD), 1,8-diazabicyclo[5.4.0]undec-7-ene (DBU), 1,5-diazabicyclo[4.3.0]non-5-ene (DBN), 1,1,3,3-tetramethylguanidine (TMG), quinuclidine, 2,2,6,6-tetramethylpiperidine (TMP), pempidine (PMP), tributylamine, triethylamine, N,N-diisopropylamine, 1,4-diazabicyclo[2.2.2]octan (TED), collidine, 2,6-dimethylpyridine, sodium tert-butoxide, potassium tert-butoxide, lithium diisopropylamide (LDA), potassium bis(trimethylsilyl)amide (KHMDS) or sodium trimethylsilyl)amide (NaHMDS).

In embodiments, the non-nucleophilic base is an inorganic non-nucleophilic base. In embodiments, the non-nucleophilic inorganic base is potassium bicarbonate, sodium hydride, or potassium hydride.

Further to any embodiments disclosed above, in embodiments the ring bridging trisulfide compound is:

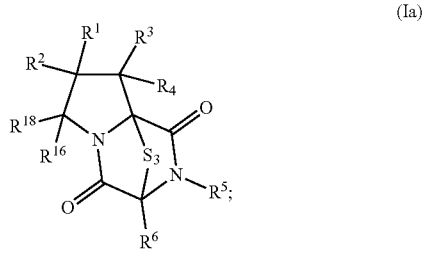

(Ia)

and the ring bridging disulfide compound is:

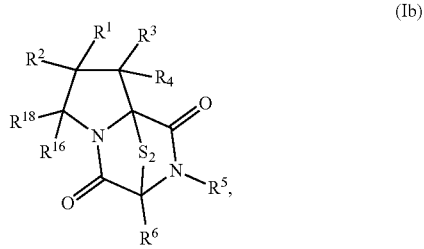

(Ib)

wherein: $R^1$ is hydrogen, halogen, $-N_3$, $-CF_3$, $-CCl_3$, $-CBr_3$, $-CI_3$, $-CN$, $-CHO$, $-OR^{33A}$, $-NR^{34A}R^{35A}$, $-COOR^{33A}$, $-CONR^{34A}R^{35A}$, $-NO_2$, $-SR^{36A}$, $-SO_{n1}R^{34A}$, $-SO_{n1}OR^{34A}$, $-SO_{n1}NR^{34A}R^{35A}$, $-NHNR^{34A}R^{35A}$, $-ONR^{34A}R^{35A}$, $-NHC(O)NHNR^{34A}R^{35A}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^2$ is hydrogen, halogen, $-N_3$, $-CF_3$, $-CCl_3$, $-CBr_3$, $-CI_3$, $-CN$, $-CHO$, $-OR^{33B}$, $-NR^{34B}R^{35B}$, $-COOR^{33B}$, $-CONR^{34B}R^{35B}$, $-NO_2$, $-SR^{36B}$, $-SO_{n2}R^{34B}$, $-SO_{n2}OR^{34B}$, $-SO_{n2}NR^{34B}R^{35B}$, $-NHNR^{34B}R^{35B}$, $-ONR^{34B}R^{35B}$, $-NHC(O)NHNR^{34B}R^{35B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^3$ is hydrogen, halogen, $-N_3$, $-CF_3$, $-CCl_3$, $-CBr_3$, $-CI_3$, $-CN$, $-CHO$, $-OR^{33C}$, $-NR^{34C}R^{35C}$, $-COOR^{33C}$, $-CONR^{34C}R^{35C}$, $-NO_2$, $-SR^{36C}$, $-SO_{n3}R^{34C}$, $-SO_{n3}OR^{34C}$, $-SO_{n3}NR^{34C}R^{35C}$, $-NHNR^{34C}R^{35C}$, $-ONR^{34C}R^{35C}$, $-NHC(O)NHNR^{34C}R^{35C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^4$ is hydrogen, halogen, $-N_3$, $-CF_3$, $-CCl_3$, $-CBr_3$, $-CI_3$, $-CN$, $-CHO$, $-OR^{33D}$, $-NR^{34D}R^{35D}$, $-COOR^{33D}$, $-CONR^{34D}R^{35D}$, $-NO_2$, $-SR^{36D}$, $-SO_{n4}R^{34D}$, $-SO_{n4}OR^{34D}$, $-SO_{n4}NR^{34D}R^{35D}$, $-NHNR^{34D}R^{35D}$, $-ONR^{34D}R^{35D}$, $-NHC(O)NHNR^{34D}R^{35D}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^5$ is hydrogen, halogen, $-N_3$, $-CF_3$, $-CCl_3$, $-CBr_3$, $-CI_3$, $-CN$, $-CHO$, $-OR^{33E}$, $-NR^{34E}R^{35E}$, $-COOR^{33E}$, $-CONR^{34E}R^{35E}$, $-NO_2$, $-SR^{36E}$, $-SO_{n5}R^{34E}$, $-SO_{n5}OR^{34E}$, $-SO_{n5}NR^{34E}R^{35E}$, $-NHNR^{34E}R^{35E}$, $-ONR^{34E}R^{35E}$, $-NHC(O)NHNR^{34E}R^{35E}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^6$ is hydrogen, halogen, $-N_3$, $-CF_3$, $-CCl_3$, $-CBr_3$, $-CI_3$, $-CN$, $-CHO$, $-OR^{33F}$, $-NR^{34F}R^{35F}$, $-COOR^{33F}$, $-CONR^{34F}R^{35F}$, $-NO_2$, $-SR^{36F}$, $-SO_{n6}R^{34F}$, $-SO_{n6}OR^{34F}$, $-SO_{n6}NR^{34F}R^{35F}$, $-NHNR^{34F}R^{35F}$, $-ONR^{34F}R^{35F}$, $-NHC(O)NHNR^{34F}R^{35F}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{16}$ is hydrogen, halogen, $-N_3$, $-CF_3$, $-CCl_3$, $-CBr_3$, $-CI_3$, $-CN$, $-CHO$, $-OR^{33G}$, $-NR^{34G}R^{35G}$, $-COOR^{33G}$, $-CONR^{34G}R^{35G}$, $-NO_2$, $-SR^{36G}$, $-SO_{n7}R^{34G}$, $-SO_{n7}OR^{34G}$, $-SO_{n7}NR^{34G}R^{35G}$, $-NHNR^{34G}R^{35G}$, $-ONR^{34G}R^{35G}$, $-NHC(O)NHNR^{34G}R^{35G}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{18}$ is hydrogen, halogen, $-N_3$, $-CF_3$, $-CCl_3$, $-CBr_3$, $-CI_3$, $-CN$, $-CHO$, $-OR^{33H}$, $-NR^{34H}R^{35H}$, $-COOR^{33H}$, $-CONR^{34H}R^{35H}$, $-NO_2$, $-SR^{36H}$, $-SO_{n8}R^{34H}$, $-SO_{n8}OR^{34H}$, $-SO_{n8}NR^{34H}R^{35H}$, $-NHNR^{34H}R^{35H}$, $-ONR^{34H}R^{35H}$, $-NHC(O)NHNR^{34H}R^{35H}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{33A}$, $R^{34A}$, $R^{35A}$, $R^{36A}$, $R^{33B}$, $R^{34B}$, $R^{35B}$, $R^{36B}$, $R^{33C}$, $R^{34C}$, $R^{35C}$, $R^{36C}$, $R^{33D}$, $R^{34D}$, $R^{35D}$, $R^{36D}$, $R^{33E}$, $R^{34E}$, $R^{35E}$, $R^{36E}$, $R^{33F}$, $R^{34F}$, $R^{35F}$, $R^{36F}$, $R^{33G}$, $R^{34G}$, $R^{35G}$, $R^{36G}$, $R^{33H}$, $R^{34H}$, $R^{35H}$, and $R^{36H}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and n1, n2, n3, n4, n5, n6, n7, and n8 are independently 1 or 2.

In embodiments, $R^{18}$ is substituted or unsubstituted heterocycloalkyl, substituted or unsubstituted aryl, or substituted or unsubstituted heteroaryl. In embodiments, $R^{18}$ is $R^{18a}$-substituted or unsubstituted 5 membered heterocycloalkyl, $R^{18a}$-substituted or unsubstituted 6 membered aryl, $R^{18a}$-substituted or unsubstituted 6 membered heteroaryl, $R^{18a}$-substituted or unsubstituted 6,6 fused ring aryl-heterocycloalkyl, $R^{18a}$-substituted or unsubstituted 6,5 fused ring aryl-heterocycloalkyl, $R^{18a}$-substituted or unsubstituted 5,6 fused ring aryl-heterocycloalkyl; $R^{18a}$ is halogen, $-N_3$, $-CF_3$, $-CCl_3$, $-CBr_3$, $-CI_3$, $-CN$, $-CHO$, $-OH$, $-NH_2$, $-COOH$, $-CONH_2$, $-NO_2$, $-SH$, $-SO_2Cl$, $-SO_3H$, $-SO_4H$, $-SO_2Ph$, $-SO_2NH_2$, $-NHNH_2$, $-ONH_2$, $-NHC(O)NHNH_2$, $R^{18b}$-substituted or unsubstituted $C_1$-$C_5$ alkyl, $R^{18b}$-substituted or unsubstituted 2 to 8 membered heteroalkyl, $R^{18b}$-substituted or unsubstituted 3 to 8 membered cycloalkyl, $R^{18b}$-substituted or unsubstituted 3 to 6 membered heterocycloalkyl, $R^{18b}$-substituted or unsubstituted 5 to 6 membered aryl, or $R^{18b}$-substituted or unsubstituted 5 to 6 membered heteroaryl; and $R^{18b}$ is halogen, $-N_3$, $-CF_3$, $-CCl_3$, $-CBr_3$, $-CI_3$, $-CN$, —CHO, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC(O)NHNH$_2$, unsubstituted C$_1$-C$_8$ alkyl, unsubstituted 2 to 8 membered heteroalkyl, unsubstituted 3 to 8 membered cycloalkyl, unsubstituted 3 to 6 membered heterocycloalkyl, unsubstituted 5 to 6 membered aryl, or unsubstituted 5 to 6 membered heteroaryl.

In embodiments, R$^{18a}$ is halogen, —SO$_2$Ph, R$^{18b}$-substituted or unsubstituted C$_1$-C$_5$ alkyl, or R$^{18b}$-substituted or unsubstituted 2 to 5 membered heteroalkyl, unsubstituted 5 to 6 membered heterocycloalkyl, or unsubstituted phenyl; and R$^{18b}$ is halogen, unsubstituted C$_1$-C$_8$ alkyl, or unsubstituted 2 to 8 membered heteroalkyl.

In embodiments, the R$^{18a}$— substituted 5 membered heterocycloalkyl is an R$^{18a}$-substituted thiophenyl, R$^{18a}$-substituted thiazolyl, R$^{18a}$-substituted oxazolyl, or R$^{18a}$-substituted imidazolyl, wherein R$^{18a}$ is halogen, unsubstituted C$_1$-C$_5$ alkyl, or unsubstituted 2 to 5 membered heteroalkyl.

In embodiments, R$^{18}$ is unsubstituted heterocycloalkyl, unsubstituted aryl, or unsubstituted heteroaryl.

In embodiments, R$^{16}$ is hydrogen. In embodiments, R$^3$ and R$^4$ are hydrogen. In embodiments, R$^1$ is —CN or unsubstituted 2 to 5 membered heteroalkyl.

In embodiments, R$^1$ is —CN.

In embodiments, R$^1$ is —COOR$^{33A}$, wherein R$^{33A}$ is C$_1$-C$_3$ unsubstituted alkyl.

In embodiments, R$^2$ is —N$_3$, —CF$_3$, —CCl$_3$, —CBr$_3$, —CI$_3$, —CN, —CHO, —OH, —NH$_2$, —COOH, —CONH$_2$, —NO$_2$, —SH, —SO$_2$Cl, —SO$_3$H, —SO$_4$H, —SO$_2$Ph, —SO$_2$NH$_2$, —NHNH$_2$, —ONH$_2$, R$^{2a}$-substituted or unsubstituted C$_1$-C$_3$ alkyl, or 2 to 3 membered R$^{2a}$-substituted or unsubstituted heteroalkyl; R$^{2a}$ is —N$_3$, —CF$_3$, —CCl$_3$, —CBr$_3$, —CI$_3$, —CN, —CHO, —OH, —NH$_2$, —COOH, —CONH$_2$, —NO$_2$, —SH, —SO$_2$Cl, —SO$_3$H, —SO$_4$H, —SO$_2$Ph, —SO$_2$NH$_2$, —NHNH$_2$, —ONH$_2$, R$^{2b}$-substituted or unsubstituted C$_1$-C$_5$ alkyl, R$^{2b}$-substituted or unsubstituted 2 to 5 membered heteroalkyl, R$^{2b}$-substituted or unsubstituted 3 to 6 membered heterocycloalkyl, R$^{2b}$-substituted or unsubstituted 5 or 6 membered aryl, or R$^{2b}$-substituted or unsubstituted 5 or 6 membered heteroaryl; and R$^{2b}$ is halogen, —N$_3$, —CF$_3$, —CCl$_3$, —CBr$_3$, —CI$_3$, —CN, —CHO, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC(O)NHNH$_2$, unsubstituted C$_1$-C$_8$ alkyl, unsubstituted 2 to 8 membered heteroalkyl, unsubstituted 3 to 8 membered cycloalkyl, unsubstituted 3 to 6 membered heterocycloalkyl, unsubstituted 5 to 6 membered aryl, or unsubstituted 5 to 6 membered heteroaryl.

In embodiments, R$^2$ is methyl or methoxy. In embodiments, R$^2$ is R$^{2a}$-substituted or unsubstituted C$_1$-C$_5$ alkyl, or R$^{2a}$-substituted or unsubstituted 2 to 5 membered heteroalkyl; and R$^{2a}$ is unsubstituted 3 to 6 membered heterocycloalkyl, unsubstituted 5 or 6 membered aryl, or unsubstituted 5 or 6 membered heteroaryl. In embodiments, R$^{2a}$ is unsubstituted pyridinyl. In embodiments, R$^2$ is substituted or unsubstituted C$_1$-C$_5$ heteroalkyl. In embodiments, R$^2$ is a polar substituent.

In embodiments, R$^5$ and R$^6$ are independently hydrogen, halogen, —N$_3$, —CF$_3$, —CCl$_3$, —CBr$_3$, —CI$_3$, —CN, —CHO, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, unsubstituted alkyl, or unsubstituted cycloalkyl.

In embodiments, R$^5$ and R$^6$ are independently hydrogen, unsubstituted C$_1$-C$_3$ alkyl or unsubstituted 3 to 5 membered cycloalkyl. In embodiments, R$^5$ and R$^6$ are independently hydrogen, methyl, ethyl, allyl or cyclopropyl.

In embodiments, the ring bridging trisulfide compound is:

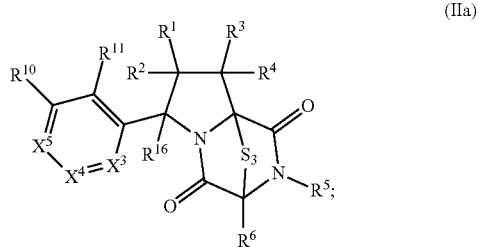

(IIa)

and the ring bridging disulfide compound is:

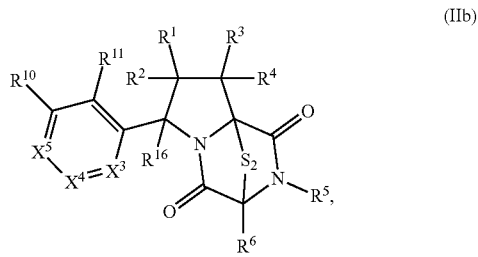

(IIb)

wherein R$^1$—R$^6$ and R$^{16}$ are as described herein. X$^3$ is N or CR$^7$; X$^4$ is N or CR$^8$; X$^5$ is N or CR$^9$; R$^7$ is hydrogen, halogen, —N$_3$, —CF$_3$, —CCl$_3$, —CBr$_3$, —CI$_3$, —CN, —CHO, —OR$^{33I}$, —NR$^{34I}$R$^{35I}$, —COOR$^{33I}$, —CONR$^{34I}$R$^{35I}$, —NO$_2$, —SR$^{36I}$, —SO$_{n9}$R$^{34I}$, —SO$_{n9}$OR$^{34I}$, —SO$_{n9}$NR$^{34I}$R$^{35I}$, —NHNR$^{34I}$R$^{35I}$, —ONR$^{34I}$R$^{35I}$, —NHC(O)NHNR$^{34I}$R$^{35I}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^8$ is hydrogen, halogen, —N$_3$, —CF$_3$, —CCl$_3$, —CBr$_3$, —CI$_3$, —CN, —CHO, —OR$^{33J}$, —NR$^{34J}$R$^{35J}$, —COOR$^{33J}$, —CONR$^{34J}$R$^{35J}$, —NO$_2$, —SR$^{36J}$, —SO$_{n10}$R$^{34J}$, —SO$_{n10}$OR$^{34J}$, —SO$_{n10}$NR$^{34J}$R$^{35J}$, —NHNR$^{34J}$R$^{35J}$, —ONR$^{34J}$R$^{35J}$, —NHC(O)NHNR$^{34J}$R$^{35J}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^9$ is hydrogen, halogen, —N$_3$, —CF$_3$, —CCl$_3$, —CBr$_3$, —CI$_3$, —CN, —CHO, —OR$^{33K}$, —NR$^{34K}$R$^{35K}$, —COOR$^{33K}$, —CONR$^{34K}$R$^{35K}$, —NO$_2$, —SR$^{36K}$, —SO$_{n11}$R$^{34K}$, —SO$_{n11}$OR$^{34K}$, —SO$_{n11}$NR$^{34K}$R$^{35K}$, —NHNR$^{34K}$R$^{35K}$, —ONR$^{34K}$R$^{35K}$, —NHC(O)NHNR$^{34K}$R$^{35K}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^{10}$ and R$^{11}$ are independently hydrogen, halogen, —N$_3$, —CF$_3$, —CCl$_3$, —CBr$_3$, —CI$_3$, —CN, —CHO, —OR$^{33L}$, —NR$^{34L}$R$^{35L}$, —COOR$^{33L}$, —CONR$^{34L}$R$^{35L}$, —NO$_2$, —SR$^{36L}$, —SO$_{n112}$R$^{34L}$, —SO$_{n12}$OR$^{34L}$, —SO$_{n12}$NR$^{34L}$R$^{35L}$, —NHNR$^{34L}$R$^{35L}$, —ONR$^{34L}$R$^{35L}$, —NHC(O)NHNR$^{34L}$R$^{35L}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, or are optionally joined together to form a substituted or unsubstituted cycloalkyl, a substituted or unsubstituted heterocycloalkyl, a substituted or unsubstituted aryl, or a substituted or unsubstituted heteroaryl; $R^{33I}$, $R^{34I}$, $R^{35I}$, $R^{36I}$, $R^{33J}$, $R^{34J}$, $R^{35J}$, $R^{36J}$, $R^{33K}$, $R^{34K}$, $R^{35K}$, $R^{36K}$, $R^{33L}$, $R^{34L}$, $R^{35L}$, and $R^{36L}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and n9, n10, n11, and n12 are independently 1 or 2.

In embodiments, the ring bridging disulfide compound is:

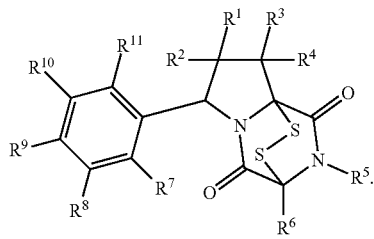

(III)

In embodiments, the ring bridging trisulfide compound is:

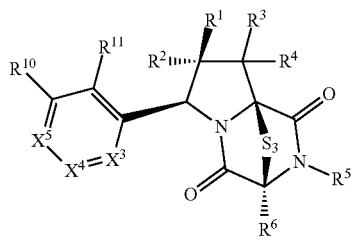

(IIa(S))

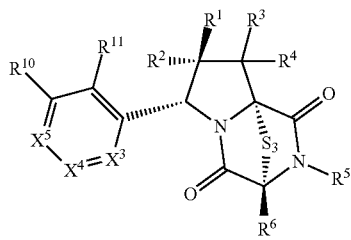

(IIa(R))

and the ring bridging disulfide compound is:

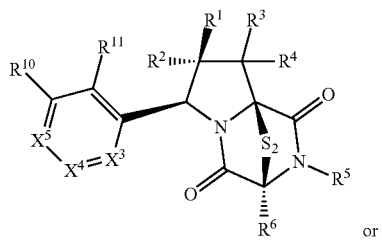

(IIb(S))

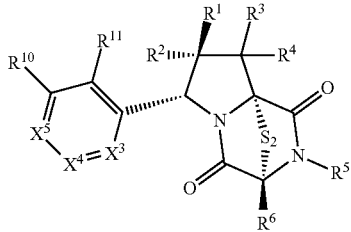

(IIb(R))

In embodiments, $R^1$ is —CN or unsubstituted 2 to 5 membered heteroalkyl. In embodiments, $R^3$ and $R^4$ are hydrogen.

In embodiments, the ring bridging disulfide compound is:

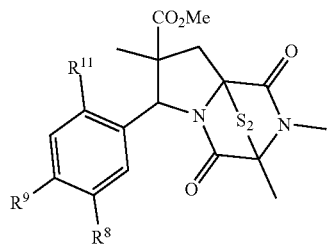

or

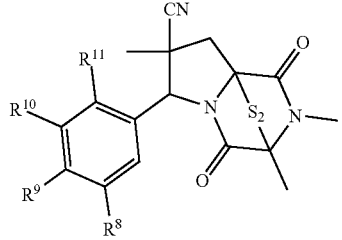

wherein: $R^8$ is hydrogen or —$OR^{33J}$; $R^9$, $R^{10}$, and $R^{11}$ are independently hydrogen or halogen; and $R^{33J}$ is hydrogen, or unsubstituted alkyl.

In embodiments the ring bridging trisulfide compound is:

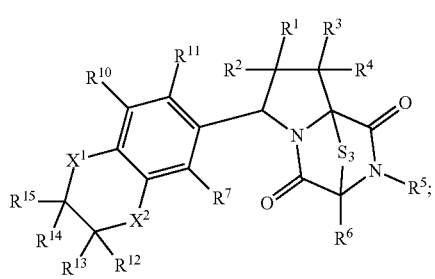

(IVa)

and the ring bridging disulfide compound is:

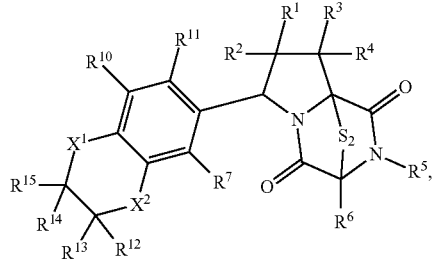

(IVb)

wherein $R^1$—$R^7$, $R^{10}$, and $R^{11}$ are as described herein. $X^1$ is $CR^{21}R^{21A}$, O, $NR^{21A}$, or S; $X^2$ is $CR^{22}R^{22A}$, O, $NR^{22A}$, or S; and $R^{12}$, $R^{13}$, $R^{14}$, $R^{15}$ $R^{21}$, $R^{21A}$, $R^{22}$, and $R^{22A}$ are independently hydrogen, halogen, —$N_3$, —$CF_3$, —$CCl_3$, —$CBr_3$, —$CI_3$, —CN, —CHO, —$OR^{33M}$, —$NR^{34M}R^{35M}$, —$COOR^{33M}$, —$CONR^{34M}R^{35M}$, —$NO_2$, —$SR^{36M}$, —$SO_{n13}R^{34M}$, —$SO_{n13}OR^{34M}$, —$SO_{n13}NR^{34M}R^{35M}$, —$NHNR^{34M}R^{35M}$, —$ONR^{34M}R^{35M}$, —NHC(O)$NHNR^{34M}R^{35M}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{33M}$, $R^{34M}$, $R^{35M}$, and $R^{36M}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and n13 is 1 or 2.

In embodiments the ring bridging trisulfide compound is:

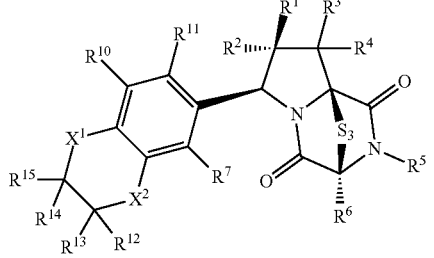

(IVa(S))

or

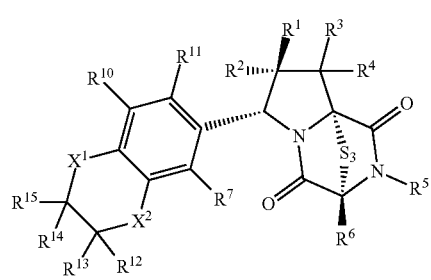

(IVa(R))

and the ring bridging disulfide compound is:

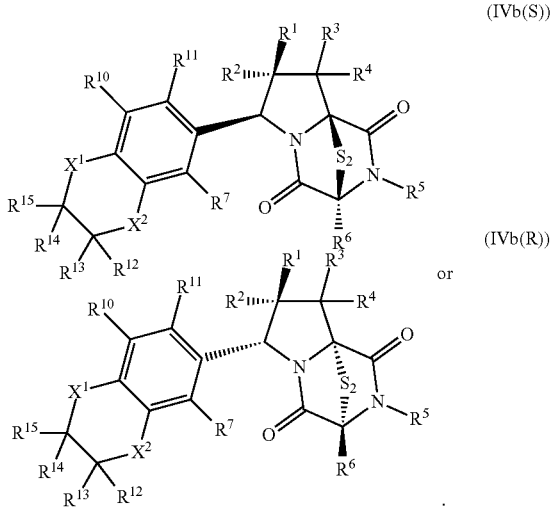

(IVb(S))

or (IVb(R))

In embodiments, $R^1$ is —CN or unsubstituted 2 to 5 membered heterocycloalkyl. In embodiments, $R^3$ and $R^4$ are hydrogen. In embodiments, $R^{10}$ and $R^{11}$ are hydrogen. In embodiments, $R^{12}$, $R^{13}$, $R^{14}$, and $R^{15}$ are hydrogen.

In embodiments, the ring bridging disulfide compound is:

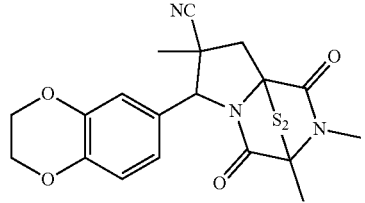

In embodiments, the ring bridging trisulfide compound is:

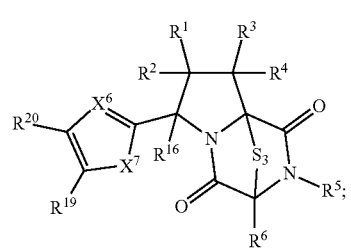

(IIIa)

and ring bridging disulfide compound is:

(IIIb)

wherein $R^1$—$R^6$ and $R^{16}$ are as described herein. $X^6$ is $CR^{23}$ or N; $X^7$ is $CR^{24}R^{24A}$, S, O, or $NR^{24A}$; $R^{19}$, $R^{20}$, $R^{23}$, $R^{24}$ and $R^{24A}$, are independently hydrogen, halogen, —$N_3$, —$CF_3$, —$CCl_3$, —$CBr_3$, —$CI_3$, —CN, —CHO, —$OR^{33M}$, —NR$^{34M}$R$^{35M}$, —COOR$^{33M}$, —CONR$^{34M}$R$^{35M}$, —NO$_2$, —SR$^{36M}$, —SO$_{n13}$R$^{34M}$, —SO$_{n13}$OR$^{34M}$, —SO$_{n13}$NR$^{34M}$R$^{35M}$, —NHNR$^{34M}$R$^{35M}$, —ONR$^{34M}$R$^{35M}$, NHC(O)NHNR$^{34M}$R$^{35M}$ substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^{33M}$, R$^{34M}$, R$^{35M}$, and R$^{36M}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and n13 is 1 or 2.

In embodiments, the ring bridging trisulfide compound is:

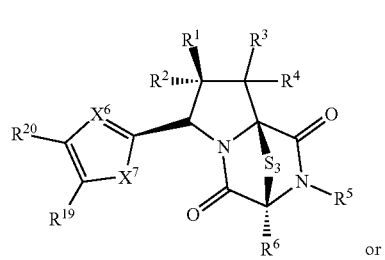

(IIIa(S))

or

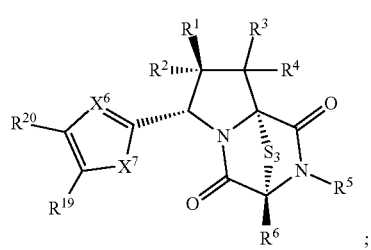

(IIIa(R))

and the ring bridging disulfide compound is:

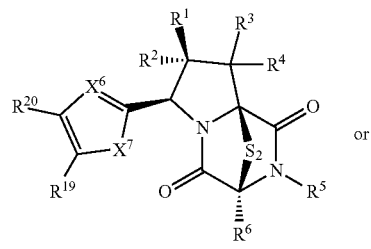

(IIIb(S))

or

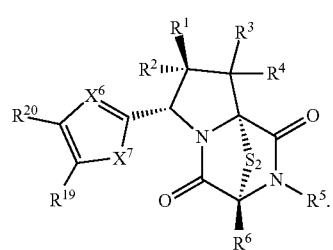

(IIIb(R))

In embodiments, R$^1$ is —CN or unsubstituted 2 to 5 membered heteroalkyl. In embodiments, R$^3$ and R$^4$ are hydrogen. In embodiments, R$^{19}$ and R$^{20}$ are hydrogen.

In embodiments, the ring bridging trisulfide compound is:

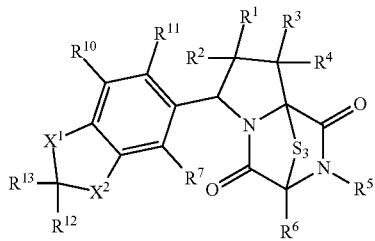

(Va)

and the ring bridging disulfide compound is:

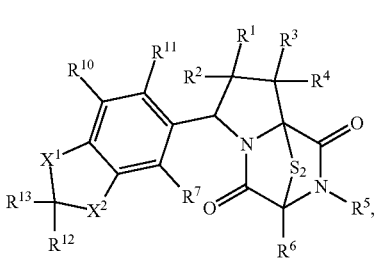

(Vb)

wherein R$^1$—R$^7$, R$^{10}$—R$^{13}$, X$^1$ and X$^2$ are as described herein, including embodiments thereof.

In embodiments, the ring bridging trisulfide compound is:

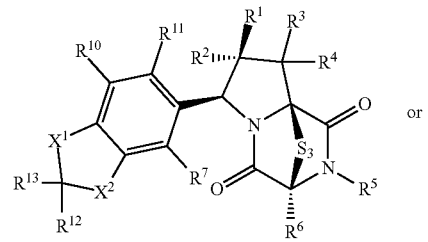

(Va(S))

or

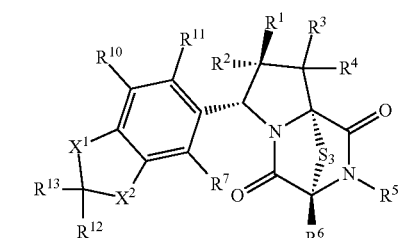

(Va(R))

and the ring bridging disulfide compound is:

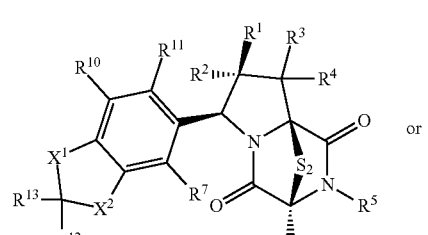

(Vb(S))

or

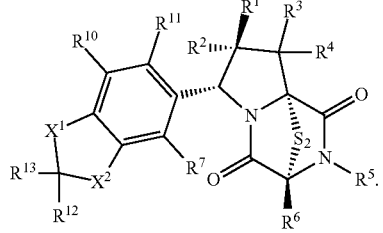

(Vb(R))

In embodiments, the ring bridging disulfide compound is:

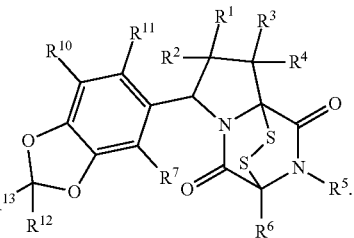

(V2)

In embodiments, the ring bridging disulfide compound is:

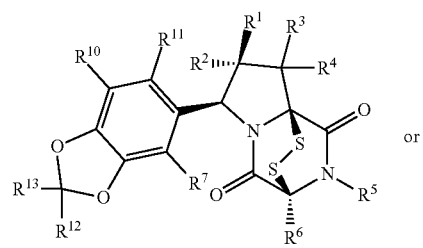

(V2(S))

or

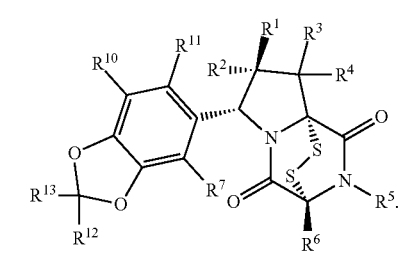

(V2(R))

In embodiments, $R^1$ is —CN or unsubstituted 2 to 5 membered heteroalkyl.

In embodiments, $R^3$ and $R^4$ are hydrogen. In embodiments, $R^{12}$ and $R^{13}$ are hydrogen. In embodiments, $R^{10}$ and $R^{11}$ are hydrogen.

In embodiments, the ring bridging disulfide compound is:

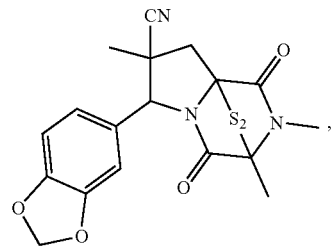

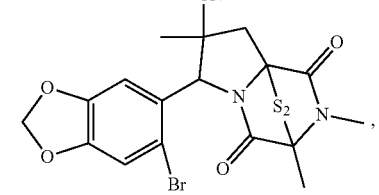

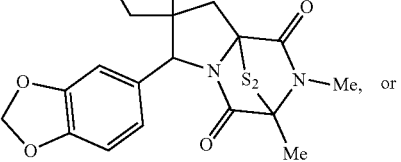

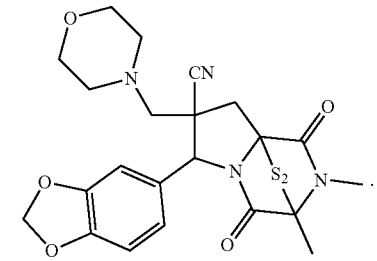

In embodiments, the ring bridging trisulfide compound is:

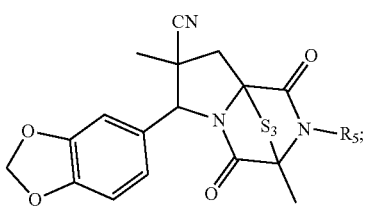

(V3a)

and the ring bridging disulfide compound is:

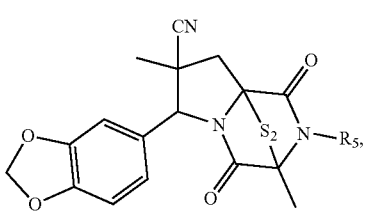

(V3b)

wherein: $R^5$ is unsubstituted 3 to 5 membered cycloalkyl, or $R^{5a}$-substituted or unsubstituted $C_1$-$C_5$ alkyl; and $R^{5a}$ is unsubstituted 2 to 5 membered heteroalkyl or 5 to 6 membered heterocycloalkyl.

In embodiments, the ring bridging disulfide compound is:
(ETP69)
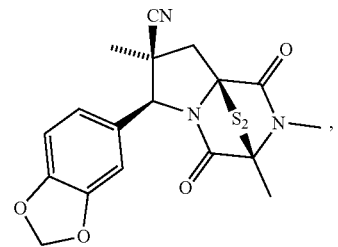
(ETP128)
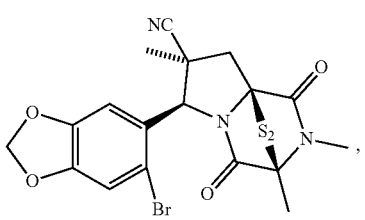
(ETP344)
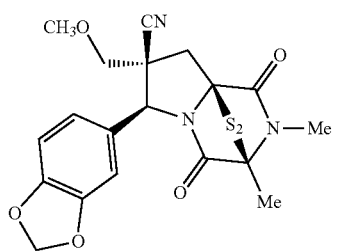
(ETP382)
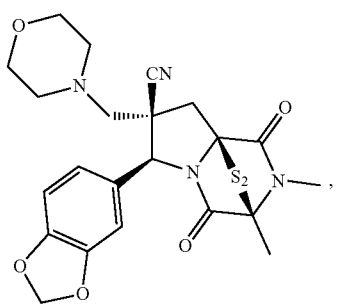
(ETP406)
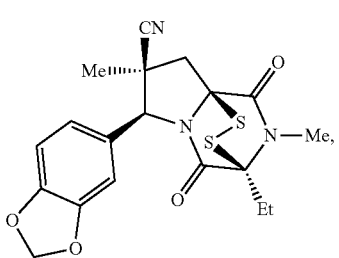
(ETP417)
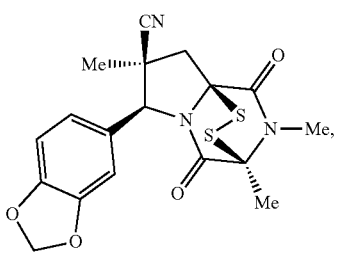
-continued
(ETP422)
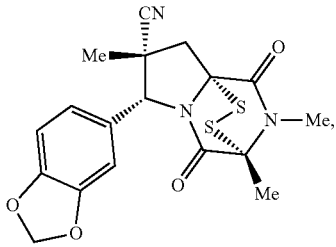
(ETP425)
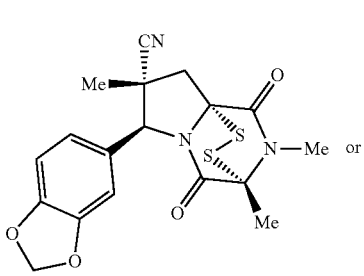 or
(ETP452)
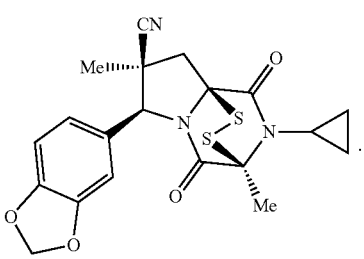
In embodiments, the ring bridging trisulfide compound is:
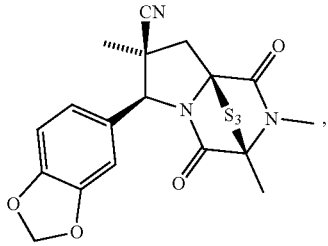
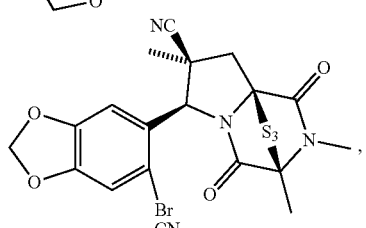
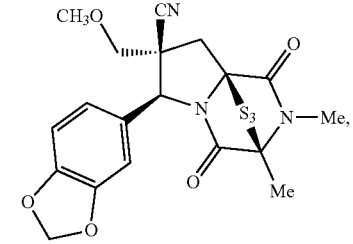

-continued

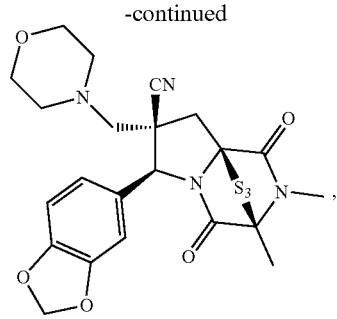

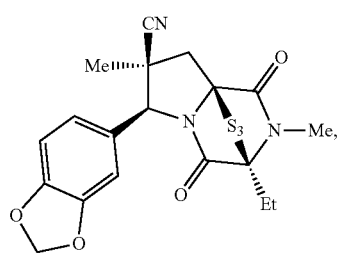

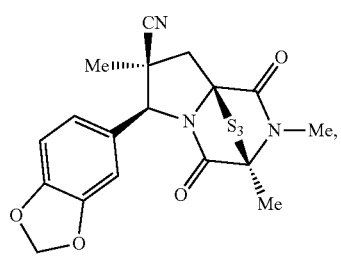

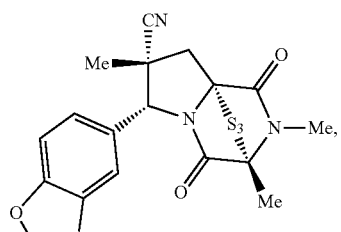

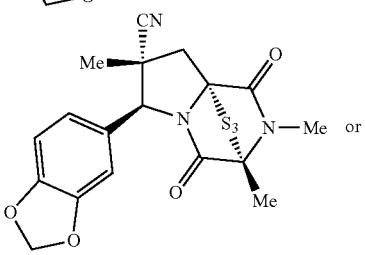

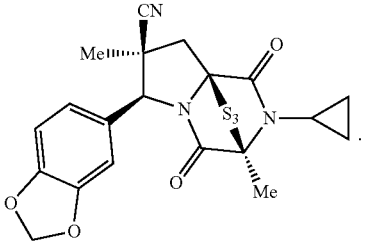

In embodiments the ring bridging trisulfide compound is:

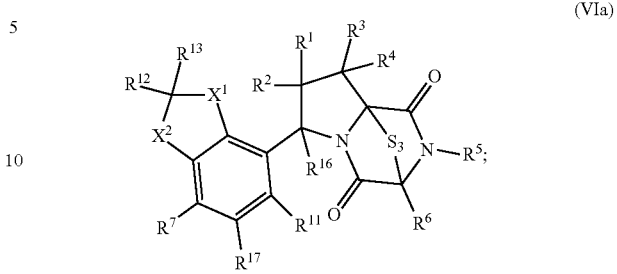

(VIa)

and the ring bridging disulfide compound is:

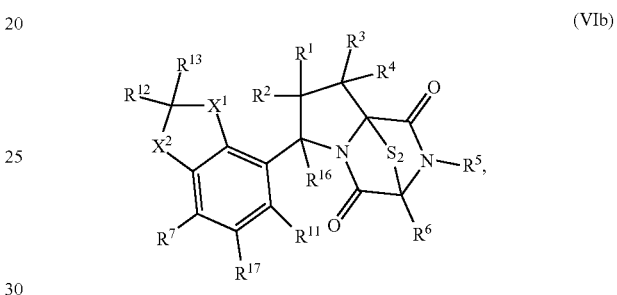

(VIb)

wherein $R^1$—$R^7$, $R^{11}$—$R^{13}$, $R^{16}$, $X^1$, and $X^2$ are as described herein, including embodiments thereof. $R^{17}$ is hydrogen, halogen, —$N_3$, —$CF_3$, —$CCl_3$, —$CBr_3$, —$CI_3$, —CN, —CHO, —$OR^{33P}$, —$NR^{34P}R^{35P}$, —$COOR^{33P}$, —$CONR^{34P}R^{35P}$, —$NO_2$, —$SR^{36P}$, —$SO_{n14}R^{34P}$, —$SO_{n14}OR^{34P}$, —$SO_{n14}NR^{34P}R^{35P}$, —$NHNR^{34P}R^{35P}$, —$ONR^{34P}R^{35P}$, —NHC(O)NHNR$^{34P}$R$^{35P}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, or are optionally bonded together to form a substituted or unsubstituted cycloalkyl, a substituted or unsubstituted heterocycloalkyl, a substituted or unsubstituted aryl, or a substituted or unsubstituted heteroaryl; $R^{33P}$, $R^{34P}$, $R^{35P}$, and $R^{36P}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and n14 is 1 or 2.

In embodiments, the ring bridging trisulfide compound is:

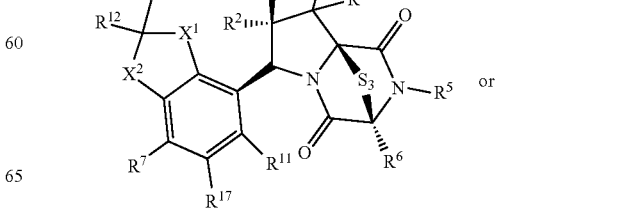

(VIa(S))

or

-continued

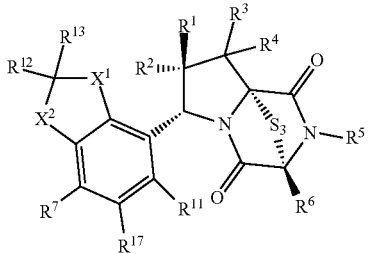
(VIa(R))

and the ring bridging disulfide compound is:

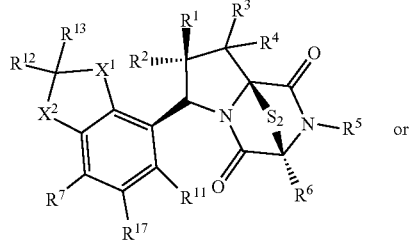
(VIb(S))

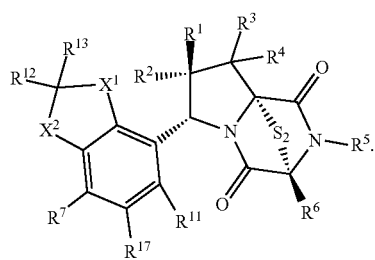
(VIb(R))

In embodiments, $R^1$ is —CN or unsubstituted 2 to 5 membered heteroalkyl. In embodiments, wherein $R^3$ and $R^4$ are hydrogen. In embodiments, $R^{12}$ and $R^{13}$ are hydrogen. In embodiments, $R^7$, $R^{10}$, and $R^{17}$ are hydrogen.

In embodiments, the ring bridging disulfide compound is:

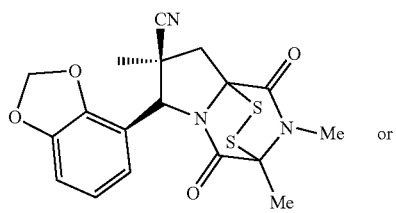

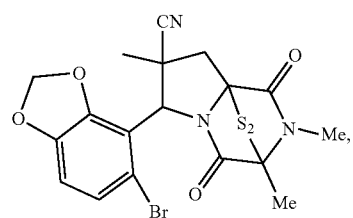

and the ring bridging trisulfide compound is:

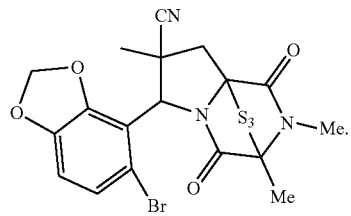

In embodiments, the ring bridging disulfide compound is:

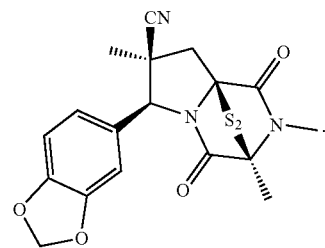

In embodiments $R^2$ is a polar substituent. In embodiments, $R^2$ is —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2Cl$, —$SO_3H$, —$SO_4H$, —$SO_2Ph$, —$SO_2NH_2$, —$NHNH_2$, —$ONH_2$, $R^{2a}$-substituted or unsubstituted $C_1$-$C_3$ alkyl, or $R^{2a}$-substituted or unsubstituted 2 to 3 membered heteroalkyl; $R^{2a}$ is —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2Cl$, —$SO_3H$, —$SO_4H$, —$SO_2Ph$, —$SO_2NH_2$, —$NHNH_2$, —$ONH_2$, $R^{2b}$-substituted or unsubstituted $C_1$-$C_5$ alkyl, $R^{2b}$-substituted or unsubstituted 2 to 5 membered heteroalkyl, $R^{2b}$-substituted or unsubstituted 3 to 6 membered heterocycloalkyl, $R^{2b}$-substituted or unsubstituted 5 or 6 membered aryl, or $R^{2b}$-substituted or unsubstituted 5 or 6 membered heteroaryl; and $R^{2b}$ is halogen, —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC(O)$NHNH_2$, unsubstituted $C_1$-$C_8$ alkyl, unsubstituted 2 to 8 membered heteroalkyl, unsubstituted 3 to 8 membered cycloalkyl, unsubstituted 3 to 6 membered heterocycloalkyl, unsubstituted 5 to 6 membered aryl, or unsubstituted 5 to 6 membered heteroaryl.

In embodiments, $R^2$ is $R^{2a}$-substituted or unsubstituted $C_1$-$C_3$ alkyl, or $R^{2a}$-substituted or unsubstituted 2 to 3 membered heteroalkyl; and $R^{2a}$ is unsubstituted 3 to 6 membered heterocycloalkyl, unsubstituted 5 or 6 membered aryl, or unsubstituted 5 or 6 membered heteroaryl. In embodiments, $R^2$ is methyl or methoxy. In embodiments, $R^{2a}$ is pyridinyl.

In embodiments $R^5$ and $R^6$ are independently hydrogen, halogen, —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, unsubstituted alkyl, or unsubstituted cycloalkyl. In embodiments, $R^5$ and $R^6$ are independently hydrogen, $C_1$-$C_3$ unsubstituted alkyl or 3 to 5 membered cycloalkyl. In embodiments, $R^5$ and $R^6$ are independently hydrogen, methyl, ethyl, allyl, or cyclopropyl.

In embodiments the ratio of the ring bridging trisulfide to the ring bridging disulfide in the mixture is between about 100:0.01 and 0.01:100.

In embodiments the ratio of the ring bridging trisulfide to the ring bridging disulfide in the mixture is between about 10:0.1 and 0.1:10.

In embodiments the ratio of the ring bridging trisulfide to the ring bridging disulfide in the mixture is between about 5:1 and 1:5.

In embodiments the ratio of the ring bridging trisulfide to the ring bridging disulfide in the mixture is about 2:3.

In embodiments the ratio of the ring bridging trisulfide to the ring bridging disulfide in the mixture is about 1:70.

In embodiments the ring bridging trisulfide decreases in amount in the mixture by about 10% (w/w).

In embodiments the ring bridging trisulfide decreases in amount in the mixture by about 30% (w/w).

In embodiments the ring bridging trisulfide decreases in amount in the mixture by about 50% (w/w).

In embodiments the non-nucleophilic base is DBU.

In embodiments, the ring bridging trisulfide compound is present as a mixture with a ring bridging disulfide compound. In embodiments, the ratio of the ring bridging trisulfide to the ring bridging disulfide in the mixture is between about 100:0.01 and 0.01:100. In embodiments, the ratio of the ring bridging trisulfide to the ring bridging disulfide in the mixture is about 100:0.01. In embodiments, the ratio of the ring bridging trisulfide to the ring bridging disulfide in the mixture is about 100:0.1. In embodiments, the ratio of the ring bridging trisulfide to the ring bridging disulfide in the mixture is about 100:1. In embodiments, the ratio of the ring bridging trisulfide to the ring bridging disulfide in the mixture is about 100:1. In embodiments, the ratio of the ring bridging trisulfide to the ring bridging disulfide in the mixture is about 80:1. In embodiments, the ratio of the ring bridging trisulfide to the ring bridging disulfide in the mixture is about 70:1. In embodiments, the ratio of the ring bridging trisulfide to the ring bridging disulfide in the mixture is about 60:1. In embodiments, the ratio of the ring bridging trisulfide to the ring bridging disulfide in the mixture is about 50:1. In embodiments, the ratio of the ring bridging trisulfide to the ring bridging disulfide in the mixture is about 40:1. In embodiments, the ratio of the ring bridging trisulfide to the ring bridging disulfide in the mixture is about 30:1. In embodiments, the ratio of the ring bridging trisulfide to the ring bridging disulfide in the mixture is about 10:1. In embodiments, the ratio of the ring bridging trisulfide to the ring bridging disulfide in the mixture is about 9:1. In embodiments, the ratio of the ring bridging trisulfide to the ring bridging disulfide in the mixture is about 8:1. In embodiments, the ratio of the ring bridging trisulfide to the ring bridging disulfide in the mixture is about 7:1. In embodiments, the ratio of the ring bridging trisulfide to the ring bridging disulfide in the mixture is about 6:1. In embodiments, the ratio of the ring bridging trisulfide to the ring bridging disulfide in the mixture is about 5:1. In embodiments, the ratio of the ring bridging trisulfide to the ring bridging disulfide in the mixture is about 4:1. In embodiments, the ratio of the ring bridging trisulfide to the ring bridging disulfide in the mixture is about 3:1. In embodiments, the ratio of the ring bridging trisulfide to the ring bridging disulfide in the mixture is about 2:1. In embodiments, the ratio of the ring bridging trisulfide to the ring bridging disulfide in the mixture is about 1.5:1. In embodiments, the ratio of the ring bridging trisulfide to the ring bridging disulfide in the mixture is about 1:1. In embodiments, the ratio of the ring bridging trisulfide to the ring bridging disulfide in the mixture is about 1:1.5. In embodiments, the ratio of the ring bridging trisulfide to the ring bridging disulfide in the mixture is about 1:2. In embodiments, the ratio of the ring bridging trisulfide to the ring bridging disulfide in the mixture is about 1:3. In embodiments, the ratio of the ring bridging trisulfide to the ring bridging disulfide in the mixture is about 1:4. In embodiments, the ratio of the ring bridging trisulfide to the ring bridging disulfide in the mixture is about 1:5. In embodiments, the ratio of the ring bridging trisulfide to the ring bridging disulfide in the mixture is about 1:6. In embodiments, the ratio of the ring bridging trisulfide to the ring bridging disulfide in the mixture is about 1:7. In embodiments, the ratio of the ring bridging trisulfide to the ring bridging disulfide in the mixture is about 1:8. In embodiments, the ratio of the ring bridging trisulfide to the ring bridging disulfide in the mixture is about 1:9. In embodiments, the ratio of the ring bridging trisulfide to the ring bridging disulfide in the mixture is about 1:10. In embodiments, the ratio of the ring bridging trisulfide to the ring bridging disulfide in the mixture is about 1:20. In embodiments, the ratio of the ring bridging trisulfide to the ring bridging disulfide in the mixture is about 1:30. In embodiments, the ratio of the ring bridging trisulfide to the ring bridging disulfide in the mixture is about 1:40. In embodiments, the ratio of the ring bridging trisulfide to the ring bridging disulfide in the mixture is about 1:50. In embodiments, the ratio of the ring bridging trisulfide to the ring bridging disulfide in the mixture is about 1:60. In embodiments, the ratio of the ring bridging trisulfide to the ring bridging disulfide in the mixture is about 1:70. In embodiments, the ratio of the ring bridging trisulfide to the ring bridging disulfide in the mixture is about 1:80. In embodiments, the ratio of the ring bridging trisulfide to the ring bridging disulfide in the mixture is about 1:90. In embodiments, the ratio of the ring bridging trisulfide to the ring bridging disulfide in the mixture is about 1:100. In embodiments, the ratio of the ring bridging trisulfide to the ring bridging disulfide in the mixture is about 0.1:100. In embodiments, the ratio of the ring bridging trisulfide to the ring bridging disulfide in the mixture is about 0.01:100.

In embodiments, the ratio of the ring bridging trisulfide to the ring bridging disulfide in the mixture is between about 10:0.1 and 0.1:10. In embodiments, the ratio of the ring bridging trisulfide to the ring bridging disulfide in the mixture is about 10:0.1. In embodiments, the ratio of the ring bridging trisulfide to the ring bridging disulfide in the mixture is about 10:0.2. In embodiments, the ratio of the ring bridging trisulfide to the ring bridging disulfide in the mixture is about 10:0.3. In embodiments, the ratio of the ring bridging trisulfide to the ring bridging disulfide in the mixture is about 10:0.4. In embodiments, the ratio of the ring bridging trisulfide to the ring bridging disulfide in the mixture is about 10:0.5. In embodiments, the ratio of the ring bridging trisulfide to the ring bridging disulfide in the mixture is about 10:0.6. In embodiments, the ratio of the ring bridging trisulfide to the ring bridging disulfide in the mixture is about 10:0.7. In embodiments, the ratio of the ring bridging trisulfide to the ring bridging disulfide in the mixture is about 10:0.8. In embodiments, the ratio of the ring bridging trisulfide to the ring bridging disulfide in the mixture is about 10:0.9. In embodiments, the ratio of the ring bridging trisulfide to the ring bridging disulfide in the mixture is about 10:1. In embodiments, the ratio of the ring bridging trisulfide to the ring bridging disulfide in the mixture is about 9:1. In embodiments, the ratio of the ring bridging trisulfide to the ring bridging disulfide in the mixture is about 8:1. In embodiments, the ratio of the ring bridging trisulfide to the ring bridging disulfide in the mixture is about 7:1. In embodiments, the ratio of the ring bridging trisulfide to the ring bridging disulfide in the mixture is about 6:1. In embodiments, the ratio of the ring bridging trisulfide to the ring bridging disulfide in the mixture is about 5:1. In embodiments, the ratio of the ring bridging trisulfide to the ring bridging disulfide in the mixture is about 4:1. In embodiments, the ratio of the ring bridging trisulfide to the ring bridging disulfide in the mixture is about 3:1. In embodiments, the ratio of the ring bridging trisulfide to the ring bridging disulfide in the mixture is about 2:1. In embodiments, the ratio of the ring bridging trisulfide to the ring bridging disulfide in the mixture is about 1.5:1. In embodiments, the ratio of the ring bridging trisulfide to the ring bridging disulfide in the mixture is about 1:1. In embodiments, the ratio of the ring bridging trisulfide to the ring bridging disulfide in the mixture is about 1:1.5. In embodiments, the ratio of the ring bridging trisulfide to the ring bridging disulfide in the mixture is about 1:2. In embodiments, the ratio of the ring bridging trisulfide to the ring bridging disulfide in the mixture is about 1:2. In embodiments, the ratio of the ring bridging trisulfide to the ring bridging disulfide in the mixture is about 1:3. In embodiments, the ratio of the ring bridging trisulfide to the ring bridging disulfide in the mixture is about 1:4. In embodiments, the ratio of the ring bridging trisulfide to the ring bridging disulfide in the mixture is about 1:5. In embodiments, the ratio of the ring bridging trisulfide to the ring bridging disulfide in the mixture is about 1:6. In embodiments, the ratio of the ring bridging trisulfide to the ring bridging disulfide in the mixture is about 1:7. In embodiments, the ratio of the ring bridging trisulfide to the ring bridging disulfide in the mixture is about 1:8. In embodiments, the ratio of the ring bridging trisulfide to the ring bridging disulfide in the mixture is about 1:9. In embodiments, the ratio of the ring bridging trisulfide to the ring bridging disulfide in the mixture is about 1:10. In embodiments, the ratio of the ring bridging trisulfide to the ring bridging disulfide in the mixture is about 0.9:10. In embodiments, the ratio of the ring bridging trisulfide to the ring bridging disulfide in the mixture is about 0.8:10. In embodiments, the ratio of the ring bridging trisulfide to the ring bridging disulfide in the mixture is about 0.7:10. In embodiments, the ratio of the ring bridging trisulfide to the ring bridging disulfide in the mixture is about 0.6:10. In embodiments, the ratio of the ring bridging trisulfide to the ring bridging disulfide in the mixture is about 0.5:10. In embodiments, the ratio of the ring bridging trisulfide to the ring bridging disulfide in the mixture is about 0.4:10. In embodiments, the ratio of the ring bridging trisulfide to the ring bridging disulfide in the mixture is about 0.3:10. In embodiments, the ratio of the ring bridging trisulfide to the ring bridging disulfide in the mixture is about 0.2:10. In embodiments, the ratio of the ring bridging trisulfide to the ring bridging disulfide in the mixture is about 0.1:10. In embodiments, the ratio of the ring bridging trisulfide to the ring bridging disulfide in the mixture is about 0.01:10.

In embodiments, the ratio of the ring bridging trisulfide to the ring bridging disulfide in the mixture is between about 5:1 and 1:5. In embodiments, the ratio of the ring bridging trisulfide to the ring bridging disulfide in the mixture is about 5:1. In embodiments, the ratio of the ring bridging trisulfide to the ring bridging disulfide in the mixture is about 4:1. In embodiments, the ratio of the ring bridging trisulfide to the ring bridging disulfide in the mixture is about 3:1. In embodiments, the ratio of the ring bridging trisulfide to the ring bridging disulfide in the mixture is about 2:1. In embodiments, the ratio of the ring bridging trisulfide to the ring bridging disulfide in the mixture is about 1.5:1. In embodiments, the ratio of the ring bridging trisulfide to the ring bridging disulfide in the mixture is about 1:1. In embodiments, the ratio of the ring bridging trisulfide to the ring bridging disulfide in the mixture is about 1:1.5. In embodiments, the ratio of the ring bridging trisulfide to the ring bridging disulfide in the mixture is about 1:2. In embodiments, the ratio of the ring bridging trisulfide to the ring bridging disulfide in the mixture is about 1:3. In embodiments, the ratio of the ring bridging trisulfide to the ring bridging disulfide in the mixture is about 1:4. In embodiments, the ratio of the ring bridging trisulfide to the ring bridging disulfide in the mixture is about 1:5.

In embodiments, the ring bridging trisulfide decreases in amount in the mixture by about 10% (w/w). In embodiments, the ring bridging trisulfide decreases in amount in the mixture by about 11% (w/w). In embodiments, the ring bridging trisulfide decreases in amount in the mixture by about 12% (w/w). In embodiments, the ring bridging trisulfide decreases in amount in the mixture by about 13% (w/w). In embodiments, the ring bridging trisulfide decreases in amount in the mixture by about 14% (w/w). In embodiments, the ring bridging trisulfide decreases in amount in the mixture by about 15% (w/w). In embodiments, the ring bridging trisulfide decreases in amount in the mixture by about 16% (w/w). In embodiments, the ring bridging trisulfide decreases in amount in the mixture by about 17% (w/w). In embodiments, the ring bridging trisulfide decreases in amount in the mixture by about 18% (w/w). In embodiments, the ring bridging trisulfide decreases in amount in the mixture by about 19% (w/w). In embodiments, the ring bridging trisulfide decreases in amount in the mixture by about 20% (w/w). In embodiments, the ring bridging trisulfide decreases in amount in the mixture by about 21% (w/w). In embodiments, the ring bridging trisulfide decreases in amount in the mixture by about 22% (w/w). In embodiments, the ring bridging trisulfide decreases in amount in the mixture by about 23% (w/w). In embodiments, the ring bridging trisulfide decreases in amount in the mixture by about 24% (w/w). In embodiments, the ring bridging trisulfide decreases in amount in the mixture by about 25% (w/w). In embodiments, the ring bridging trisulfide decreases in amount in the mixture by about 26% (w/w). In embodiments, the ring bridging trisulfide decreases in amount in the mixture by about 27% (w/w). In embodiments, the ring bridging trisulfide decreases in amount in the mixture by about 28% (w/w). In embodiments, the ring bridging trisulfide decreases in amount in the mixture by about 29% (w/w). In embodiments, the ring bridging trisulfide decreases in amount in the mixture by about 30% (w/w). In embodiments, the ring bridging trisulfide decreases in amount in the mixture by about 31% (w/w). In embodiments, the ring bridging trisulfide decreases in amount in the mixture by about 32% (w/w). In embodiments, the ring bridging trisulfide decreases in amount in the mixture by about 33% (w/w). In embodiments, the ring bridging trisulfide decreases in amount in the mixture by about 34% (w/w). In embodiments, the ring bridging trisulfide decreases in amount in the mixture by about 35% (w/w). In embodiments, the ring bridging trisulfide decreases in amount in the mixture by about 36% (w/w). In embodiments, the ring bridging trisulfide decreases in amount in the mixture by about 37% (w/w). In embodiments, the ring bridging trisulfide decreases in amount in the mixture by about 38% (w/w). In embodiments, the ring bridging trisulfide decreases in amount in the mixture by about 39% (w/w). In embodiments, the ring bridging trisulfide decreases in amount in the mixture by about 40% (w/w). In embodiments, the ring bridging trisulfide decreases in amount in the mixture by about 41% (w/w). In embodiments, the ring bridging trisulfide decreases in amount in the mixture by about 42% (w/w). In embodiments, the ring bridging trisulfide decreases in amount in the mixture by about 43% (w/w). In embodiments, the ring bridging trisulfide decreases in amount in the mixture by about 44% (w/w). In embodiments, the ring bridging trisulfide decreases in amount in the mixture by about 45% (w/w). In embodiments, the ring bridging trisulfide decreases in amount in the mixture by about 46% (w/w). In embodiments, the ring bridging trisulfide decreases in amount in the mixture by about 47% (w/w). In embodiments, the ring bridging trisulfide decreases in amount in the mixture by about 48% (w/w). In embodiments, the ring bridging trisulfide decreases in amount in the mixture by about 49% (w/w). In embodiments, the ring bridging trisulfide decreases in amount in the mixture by about 50% (w/w).

Compositions

In an aspect, there is provided a composition, comprising: a ring bridging trisulfide compound; a ring bridging disulfide compound; and a non-nucleophilic base, wherein the molar ratio of the ring bridging trisulfide compound to the ring bridging disulfide compound is greater than 0.1, and further wherein the non-nucleophilic base is present in a quantity effective to convert at least an amount of the ring bridging trisulfide compound to the ring bridging disulfide compound.

In embodiments, there is a reaction vessel, comprising the composition contemplated herein. In embodiments, the mixture comprises at least 0.05 mol of the ring bridging disulfide compound.

In embodiments, the ring bridging trisulfide compound is:

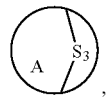

and the ring bridging disulfide compound is:

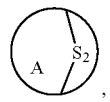

wherein A is substituted or unsubstituted cycloalkyl, substituted or unsubstituted heterocycloalkyl, substituted or unsubstituted aryl or substituted or unsubstituted heteroaryl. In embodiments, where A is substituted, it is substituted with one or more substituent groups as defined herein. In embodiments, where A is substituted, it is substituted with one or more size-limited substituent groups as defined herein. In embodiments, where A is substituted, it is substituted with one or more lower substituent groups as defined herein.

In embodiments, the non-nucleophilic base is an organic non-nucleophilic base.

In embodiments, the non-nucleophilic base comprises an amino group.

In embodiments, the non-nucleophilic base is a sterically hindered organic non-nucleophilic base.

In embodiments, the non-nucleophilic base is 1,5,7-triazabicyclo(4.4.0)dec-5-ene (TBD), 7-methyl-1,5,7-triazabicyclo(4.4.0)dec-5-ene (MTBD), 1,8-diazabicyclo[5.4.0]undec-7-ene (DBU), 1,5-diazabicyclo[4.3.0]non-5-ene (DBN), 1,1,3,3-tetramethylguanidine (TMG), quinuclidine, 2,2,6,6-tetramethylpiperidine (TMP), pempidine (PMP), tributylamine, triethylamine, N,N-triisopropylamine, 1,4-diazabicyclo[2.2.2]octan (TED), collidine, 2,6-dimethylpyridine, sodium tert-butoxide, potassium tert-butoxide, lithium diisopropylamide (LDA), potassium bis(trimethylsilyl)amide (KHMDS) or sodium trimethylsilyl)amide (NaHMDS).

In embodiments, the non-nucleophilic base is an inorganic non-nucleophilic base. In embodiments, the non-nucleophilic inorganic base is potassium bicarbonate, sodium hydride, or potassium hydride.

In embodiments, in the composition comprising: a ring bridging trisulfide compound; a ring bridging disulfide compound; and a non-nucleophilic base, the ring bridging trisulfide compound is:

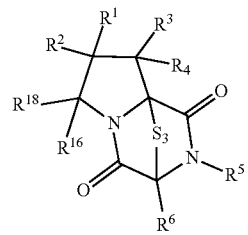

(Ia)

and the ring bridging disulfide compound is:

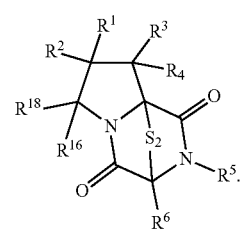

(Ib)

$R^1$ is hydrogen, halogen, $-N_3$, $-CF_3$, $-CCl_3$, $-CBr_3$, $-CI_3$, $-CN$, $-CHO$, $-OR^{33A}$, $-NR^{34A}R^{35A}$, $-COOR^{33A}$, $-CONR^{34A}R^{35A}$, $-NO_2$, $-SR^{36A}$, $-SO_{n1}R^{34A}$, $-SO_{n1}OR^{34A}$, $-SO_{n1}NR^{34A}R^{35A}$, $-NHNR^{34A}R^{35A}$, $-ONR^{34A}R^{35A}$, $-NHC(O)NHNR^{34A}R^{35A}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^2$ is hydrogen, halogen, $-N_3$, $-CF_3$, $-CCl_3$, $-CBr_3$, $-CI_3$, $-CN$, $-CHO$, $-OR^{33B}$, $-NR^{34B}R^{35B}$, $-COOR^{33B}$, $-CONR^{34B}R^{35B}$, $-NO_2$, $-SR^{36B}$, $-SO_{n2}R^{34b}$, $-SO_{n2}OR^{34B}$, $-SO_{n2}NR^{34B}R^{35B}$, $-NHNR^{34B}R^{35B}$, $-ONR^{34B}R^{35B}$, $-NHC(O)NHNR^{34B}R^{35B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^3$ is hydrogen, halogen, $-N_3$, $-CF_3$, $-CCl_3$, $-CBr_3$, $-CI_3$, $-CN$, $-CHO$, $-OR^{33C}$, $-NR^{34C}R^{35C}$, $-COOR^{33C}$, $-CONR^{34C}R^{35C}$, $-NO_2$, $-SR^{36C}$, $-SO_{n30}R^{34C}$, $-SO_{n30}R^{34C}$, $-SO_{n3}NR^{34C}R^{35C}$, $-NHNR^{34C}R^{35C}$, $-ONR^{34C}R^{35C}$, —NHC(O)NHNR$^{34C}$R$^{35C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. R$^4$ is hydrogen, halogen, —N$_3$, —CF$_3$, —CCl$_3$, —CBr$_3$, —CI$_3$, —CN, —CHO, —OR$^{33D}$, —NR$^{34D}$R$^{35D}$, —COOR$^{33D}$, —CONR$^{34D}$R$^{35D}$, —NO$_2$, —SR$^{36D}$, —SO$_{n4}$R$^{34D}$, —SO$_{n4}$OR$^{34D}$, —SO$_{n4}$NR$^{34D}$R$^{35D}$, —NHNR$^{34D}$R$^{35D}$, —ONR$^{34D}$R$^{35D}$, —NHC(O)NHNR$^{34D}$R$^{35D}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. R$^5$ is hydrogen, halogen, —N$_3$, —CF$_3$, —CCl$_3$, —CBr$_3$, —CI$_3$, —CN, —CHO, —OR$^{33E}$, —NR$^{34E}$R$^{35E}$, —COOR$^{33E}$, —CONR$^{34E}$R$^{35E}$, —NO$_2$, —SR$^{36E}$, —SO$_{n5}$R$^{34E}$, —SO$_{n8}$OR$^{34E}$, —SO$_{n5}$NR$^{34E}$R$^{35E}$, —NHNR$^{34E}$R$^{35E}$, —ONR$^{34E}$R$^{35E}$, —NHC(O)NHNR$^{34E}$R$^{35E}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. R$^6$ is hydrogen, halogen, —N$_3$, —CF$_3$, —CCl$_3$, —CBr$_3$, —CI$_3$, —CN, —CHO, —OR$^{33F}$, —NR$^{34F}$R$^{35F}$, —COOR$^{33F}$, —CONR$^{34F}$R$^{35F}$, —NO$_2$, —SR$^{36F}$, —SO$_{n6}$R$^{34F}$, —SO$_{n6}$OR$^{34F}$, —SO$_{n6}$NR$^{34F}$R$^{35F}$, —NHNR$^{34F}$R$^{35F}$, —ONR$^{34F}$R$^{35F}$, —NHC(O)NHNR$^{34F}$R$^{35F}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. R$^{16}$ is hydrogen, halogen, —N$_3$, —CF$_3$, —CCl$_3$, —CBr$_3$, —CI$_3$, —CN, —CHO, —OR$^{33G}$, —NR$^{34G}$R$^{35G}$, —COOR$^{33G}$, —CONR$^{34G}$R$^{35G}$, —NO$_2$, —SR$^{36G}$, —SO$_{n7}$R$^{34G}$, —SO$_{n7}$OR$^{34G}$, —SO$_{n7}$NR$^{34G}$R$^{35G}$, —NHNR$^{34G}$R$^{35G}$, —ONR$^{34G}$R$^{35G}$, —NHC(O)NHNR$^{34G}$R$^{35G}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. R$^{18}$ is hydrogen, halogen, —N$_3$, —CF$_3$, —CCl$_3$, —CBr$_3$, —CI$_3$, —CN, —CHO, —OR$^{33H}$, —NR$^{34H}$R$^{35H}$, —COOR$^{33H}$, —CONR$^{34H}$R$^{35H}$, —NO$_2$, —SR$^{36H}$, —SO$_{n8}$R$^{34H}$, —SO$_{n8}$OR$^{34H}$, —SO$_{n8}$NR$^{34H}$R$^{35H}$, —NHNR$^{34H}$R$^{35H}$, —ONR$^{34H}$R$^{35H}$, —NHC(O)NHNR$^{34H}$R$^{35H}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. R$^{33A}$, R$^{34A}$, R$^{35A}$, R$^{36A}$, R$^{33B}$, R$^{34B}$, R$^{35B}$, R$^{36B}$, R$^{33C}$, R$^{34C}$, R$^{35C}$, R$^{36C}$, R$^{33D}$, R$^{34D}$, R$^{35D}$, R$^{36D}$, R$^{33E}$, R$^{34E}$, R$^{35E}$, R$^{36E}$, R$^{33F}$, R$^{34F}$, R$^{35F}$, R$^{36F}$, R$^{33G}$, R$^{34G}$, R$^{35G}$, R$^{36G}$, R$^{33H}$, R$^{34H}$, R$^{35H}$, and R$^{36H}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. The symbols n1, n2, n3, n4, n5, n6, n7, and n8 are independently 1 or 2.

The symbols n1, n2, n3, n4, n5, n6, n7, and n8 are independently 1 or 2. In embodiments, n1 is 1. In embodiments, n1 is 2. In embodiments, n2 is 1. In embodiments, n2 is 2. In embodiments, n3 is 1. In embodiments, n3 is 2. In embodiments, n4 is 1. In embodiments, n4 is 2. In embodiments, n5 is 1. In embodiments, n5 is 2. In embodiments, n6 is 1. In embodiments, n6 is 2. In embodiments, n7 is 1. In embodiments, n7 is 2. In embodiments, n8 is 1. In embodiments, n8 is 2.

R$^{33A}$, R$^{34A}$, R$^{35A}$, R$^{36A}$, R$^{33B}$, R$^{34B}$, R$^{35B}$, R$^{36B}$, R$^{33C}$, R$^{34C}$, R$^{35C}$, R$^{36C}$, R$^{33D}$, R$^{34D}$, R$^{35D}$, R$^{36D}$, R$^{33E}$, R$^{34E}$, R$^{35E}$, R$^{36E}$, R$^{33F}$, R$^{34F}$, R$^{35F}$, R$^{36F}$, R$^{33G}$, R$^{34G}$, R$^{35G}$, R$^{36G}$, R$^{33H}$, R$^{34H}$, R$^{35H}$, and R$^{36H}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, R$^{33A}$, R$^{34A}$, R$^{35A}$, R$^{36A}$, R$^{33B}$, R$^{34B}$, R$^{35B}$, R$^{36B}$, R$^{33C}$, R$^{34C}$, R$^{35C}$, R$^{36C}$, R$^{33D}$, R$^{34D}$, R$^{35D}$, R$^{36D}$, R$^{33E}$, R$^{34E}$, R$^{35E}$, R$^{36E}$, R$^{33F}$, R$^{34F}$, R$^{35F}$, R$^{36F}$, R$^{33G}$, R$^{34G}$, R$^{35G}$, R$^{36G}$, R$^{33H}$, R$^{34H}$, R$^{35H}$ and R$^{36H}$ are independently hydrogen, R$^{44a}$-substituted or unsubstituted alkyl, R$^{44a}$-substituted or unsubstituted heteroalkyl, R$^{44a}$-substituted or unsubstituted cycloalkyl, R$^{44a}$-substituted or unsubstituted heterocycloalkyl, R$^{44a}$-substituted or unsubstituted aryl, or R$^{44a}$-substituted or unsubstituted heteroaryl. In embodiments, R$^{33A}$, R$^{34A}$, R$^{35A}$, R$^{36A}$, R$^{33B}$, R$^{34B}$, R$^{35B}$, R$^{36B}$, R$^{33C}$, R$^{34C}$, R$^{35C}$, R$^{36C}$, R$^{33D}$, R$^{34D}$, R$^{35D}$, R$^{36D}$, R$^{33E}$, R$^{34E}$, R$^{35E}$, R$^{36E}$, R$^{33F}$, R$^{34F}$, R$^{35F}$, R$^{36F}$, R$^{33G}$, R$^{34G}$, R$^{35G}$, R$^{36G}$, R$^{33H}$, R$^{34H}$, R$^{35H}$, and R$^{36H}$ are independently hydrogen, unsubstituted alkyl, unsubstituted heteroalkyl, unsubstituted cycloalkyl, unsubstituted heterocycloalkyl, unsubstituted aryl, or unsubstituted heteroaryl. In embodiments, R$^{33A}$, R$^{34A}$, R$^{35A}$, R$^{36A}$, R$^{33B}$, R$^{34B}$, R$^{35B}$, R$^{36B}$, R$^{33C}$, R$^{34C}$, R$^{35C}$, R$^{36C}$, R$^{33D}$, R$^{34D}$, R$^{35D}$, R$^{36D}$, R$^{33E}$, R$^{34E}$, R$^{35E}$, R$^{36E}$, R$^{33F}$, R$^{34F}$, R$^{35F}$, R$^{36F}$, R$^{33G}$, R$^{34G}$, R$^{35G}$, R$^{36G}$, R$^{33H}$, R$^{34H}$, R$^{35H}$, and R$^{36H}$ are independently hydrogen, R$^{44a}$-substituted or unsubstituted C$_1$-C$_3$ alkyl, R$^{44a}$-substituted or unsubstituted 2 to 3 membered heteroalkyl, R$^{44a}$-substituted or unsubstituted C$_3$-C$_5$ cycloalkyl, R$^{44a}$-substituted or unsubstituted 5 to 6 membered heterocycloalkyl, R$^{44a}$-substituted or unsubstituted phenyl, or R$^{44a}$-substituted or unsubstituted 5 to 6 membered heteroaryl. In embodiments, R$^{33A}$, R$^{34A}$, R$^{35A}$, R$^{36A}$, R$^{33B}$, R$^{34B}$, R$^{35B}$, R$^{36B}$, R$^{33C}$, R$^{34C}$, R$^{35C}$, R$^{36C}$, R$^{33D}$, R$^{34D}$, R$^{35D}$, R$^{36D}$, R$^{33E}$, R$^{34E}$, R$^{35E}$, R$^{36E}$, R$^{33F}$, R$^{34F}$, R$^{35F}$, R$^{36F}$, R$^{33G}$, R$^{34G}$, R$^{35G}$, R$^{36G}$, R$^{33H}$, R$^{34H}$, R$^{35H}$, and R$^{36H}$ are independently hydrogen, unsubstituted alkyl, unsubstituted 2 to 3 membered heteroalkyl, unsubstituted C$_3$-C$_5$ cycloalkyl, unsubstituted 5 to 6 membered heterocycloalkyl, unsubstituted phenyl, or unsubstituted 5 to 6 membered heteroaryl.

R$^{44a}$ is halogen (e.g. —F, —Cl, —Br, or —I), —N$_3$, —CF$_3$, —CCl$_3$, —CBr$_3$, —CI$_3$, —CN, —CHO, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC(O)NHNH$_2$, substituted or unsubstituted alkyl (e.g., C$_1$-C$_8$, C$_1$-C$_6$, C$_1$-C$_4$, or C$_1$-C$_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., C$_3$-C$_8$, C$_3$-C$_6$, C$_4$-C$_6$, or C$_5$-C$_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., C$_6$-C$_{12}$, C$_6$-C$_{10}$, or phenyl), or substituted or unsubstituted heteroaryl (e.g., 5 to 12 membered, 5 to 10 membered, 5 to 9 membered, or 5 to 6 membered). In embodiments, R$^{44a}$ is halogen (e.g. —F, —Cl, —Br, or —I), —N$_3$, —CF$_3$, —CCl$_3$, —CBr$_3$, —CI$_3$, —CN, —CHO, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC(O)NHNH$_2$, R$^{44b}$-substituted or unsubstituted alkyl (e.g., C$_1$-C$_8$, C$_1$-C$_6$, C$_1$-C$_4$, or C$_1$-C$_2$), R$^{44b}$-substituted or unsubstituted heteroalkyl (e.g., 2 to 8 membered, 2 to 6 membered, 4 to 6 membered, 2 to 3 membered, or 4 to 5 membered), $R^{44b}$-substituted or unsubstituted cycloalkyl (e.g., $C_3$-$C_8$, $C_3$-$C_6$, $C_4$-$C_6$, or $C_5$-$C_6$), $R^{44b}$-substituted or unsubstituted heterocycloalkyl (e.g., 3 to 8 membered, 3 to 6 membered, 4 to 6 membered, 4 to 5 membered, or 5 to 6 membered), $R^{44b}$-substituted or unsubstituted aryl (e.g., $C_6$-$C_{12}$, $C_6$-$C_{10}$, or phenyl), or $R^{44b}$-substituted or unsubstituted heteroaryl (e.g., 5 to 12 membered, 5 to 10 membered, 5 to 9 membered, or 5 to 6 membered). In embodiments, $R^{44a}$ is halogen (e.g. —F, —Cl, —Br, or —I), —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —$NHC(O)NHNH_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered).

$R^{44b}$ is halogen (e.g. —F, —Cl, —Br, or —I), —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —$NHC(O)NHNH_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered).

The compound may have the structure of Formula (I) following:

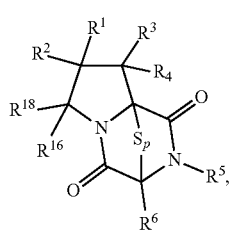

(I)

wherein $R^1$—$R^6$, $R^{16}$, and $R^{18}$ are as described herein, including embodiments thereof. The symbol p may be 2 or 3.

In embodiments, the compound may have the formula:

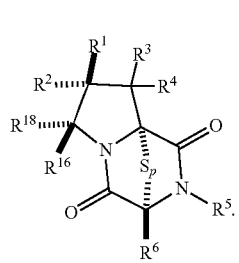

I(R)

In embodiments, the compound may have the formula:

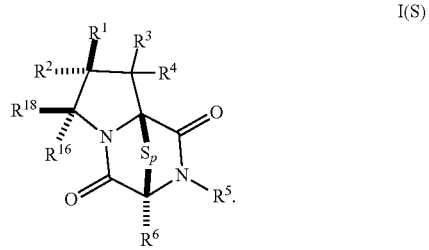

I(S)

The symbol p is 2. The symbol p is 3.

In embodiments, $R^1$ is hydrogen, halogen (e.g. —F, —Cl, —Br, or —I), —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —$NHC(O)NHNH_2$, substituted or unsubstituted alkyl (e.g. $C_1$-$C_8$ alkyl), or substituted or unsubstituted heteroalkyl (e.g. 2 to 8 membered heteroalkyl). In embodiments, $R^1$ is halogen (e.g. —F, —Cl, —Br, or —I), —$CF_3$, —$CCl_3$, —$CBr_3$, —$CI_3$, —CN, substituted or unsubstituted alkyl, or substituted or unsubstituted heteroalkyl. $R^1$ may be —CN, substituted or unsubstituted alkyl, or substituted or unsubstituted heteroalkyl. $R^1$ may be —CN or substituted or unsubstituted alkyl. $R^1$ may be —CN or unsubstituted alkyl. $R^1$ may be —CN, or unsubstituted heteroalkyl.

In embodiments, $R^1$ is substituted or unsubstituted alkyl (e.g., $C_1$-$C_8$, $C_1$-$C_5$, or $C_1$-$C_3$), substituted or unsubstituted heteroalkyl (e.g., 2 to 8 membered, 2 to 5 membered, 2 to 3 membered), substituted or unsubstituted cycloalkyl (e.g., $C_3$-$C_8$, $C_3$-$C_5$, or $C_3$), substituted or unsubstituted heterocycloalkyl (e.g., 3 to 8 membered, 3 to 6 membered, or 4 membered), substituted or unsubstituted aryl (e.g., $C_5$-$C_8$, $C_5$-$C_6$, or phenyl), or substituted or unsubstituted heteroaryl (e.g., 5 to 8 membered, 5 to 6 membered, or 6 membered). In embodiments, $R^1$ is unsubstituted alkyl (e.g., $C_1$-$C_8$, $C_1$-$C_5$, or $C_1$-$C_3$), unsubstituted heteroalkyl (e.g., 2 to 8 membered, 2 to 5 membered, 2 to 3 membered), unsubstituted cycloalkyl (e.g., $C_3$-$C_8$, $C_3$-$C_5$, or $C_3$), unsubstituted heterocycloalkyl (e.g., 3 to 8 membered, 3 to 6 membered, or 4 membered), unsubstituted aryl (e.g., $C_5$-$C_8$, $C_5$-$C_6$, or phenyl), or unsubstituted heteroaryl (e.g., 5 to 8 membered, 5 to 6 membered, or 6 membered).

In embodiments, $R^1$ is substituted or unsubstituted $C_1$-$C_8$ alkyl, substituted or unsubstituted 2 to 8 membered heteroalkyl, substituted or unsubstituted 3 to 8 membered cycloalkyl, substituted or unsubstituted 3 to 8 membered heterocycloalkyl, substituted or unsubstituted 5 to 8 membered aryl, or substituted or unsubstituted 5 or 8 membered heteroaryl. In embodiments, $R^1$ is unsubstituted $C_1$-$C_8$ alkyl, unsubstituted 2 to 8 membered heteroalkyl, unsubstituted 3 to 8 membered cycloalkyl, unsubstituted 3 to 8 membered heterocycloalkyl, unsubstituted 5 to 8 membered aryl, or unsubstituted 5 or 8 membered heteroaryl.

In embodiments, $R^1$ is substituted or unsubstituted $C_1$-$C_5$ alkyl, substituted or unsubstituted 2 to 5 membered heteroalkyl, substituted or unsubstituted 3 to 5 membered cycloalkyl, substituted or unsubstituted 3-6 membered heterocycloalkyl, substituted or unsubstituted 5 to 6 membered aryl, or substituted or unsubstituted 5 to 6 membered heteroaryl. In embodiments, $R^1$ is unsubstituted $C_1$-$C_5$ alkyl, unsubstituted 2 to 5 membered heteroalkyl, unsubstituted 3 to 5 membered cycloalkyl, unsubstituted 3-6 membered heterocycloalkyl, unsubstituted 5 to 6 membered aryl, or unsubstituted 5 to 6 membered heteroaryl.

In embodiments, $R^1$ is substituted or unsubstituted $C_1$-$C_3$ alkyl, substituted or unsubstituted 2 to 3 membered heteroalkyl. In embodiments, $R^1$ is substituted or unsubstituted 3 membered cycloalkyl, substituted or unsubstituted 4 membered cycloalkyl, or substituted or unsubstituted 5 membered cycloalkyl. In embodiments, $R^1$ is substituted or unsubstituted 4 membered heterocycloalkyl, substituted or unsubstituted 5 membered heterocycloalkyl, or substituted or unsubstituted 6 membered heterocycloalkyl. In embodiments, $R^1$ is substituted or unsubstituted 5 membered aryl, substituted or unsubstituted 5 membered aryl, substituted or unsubstituted 6 membered aryl, or substituted or unsubstituted 6 membered heteroaryl. In embodiments, $R^1$ is unsubstituted $C_1$-$C_3$ alkyl or unsubstituted 2 to 3 membered heteroalkyl. In embodiments, $R^1$ is unsubstituted 3 membered cycloalkyl, unsubstituted 4 membered cycloalkyl or unsubstituted 5 membered cycloalkyl. In embodiments, $R^1$ is unsubstituted 4 membered heterocycloalkyl, unsubstituted 5 membered heterocycloalkyl, or unsubstituted 6 membered heterocycloalkyl. In embodiments, $R^1$ is unsubstituted 5 membered aryl, unsubstituted 5 membered aryl, unsubstituted 6 membered aryl, or unsubstituted 6 membered heteroaryl.

In embodiments, $R^1$ is $R^{1a}$-substituted or unsubstituted alkyl, $R^{1a}$-substituted or unsubstituted heteroalkyl, $R^{1a}$-substituted or unsubstituted cycloalkyl, $R^{1a}$-substituted or unsubstituted heterocycloalkyl, $R^{1a}$-substituted or unsubstituted aryl, or $R^{1a}$-substituted or unsubstituted heteroaryl. In embodiments, $R^1$ is unsubstituted alkyl, unsubstituted heteroalkyl, unsubstituted cycloalkyl, unsubstituted heterocycloalkyl, unsubstituted aryl, or unsubstituted heteroaryl.

In embodiments, $R^1$ is $R^{1a}$-substituted or unsubstituted $C_1$-$C_5$ alkyl, $R^{1a}$-substituted or unsubstituted 2 to 8 membered heteroalkyl, $R^{1a}$-substituted or unsubstituted 3 to 8 membered cycloalkyl, $R^{1a}$-substituted or unsubstituted 3 to 8 membered heterocycloalkyl, $R^{1a}$-substituted or unsubstituted 5 to 8 membered aryl, or $R^{1a}$-substituted or unsubstituted 5 to 8 membered heteroaryl. In embodiments, $R^1$ is unsubstituted $C_1$-$C_8$ alkyl, unsubstituted 2 to 8 membered heteroalkyl, unsubstituted 3 to 8 membered cycloalkyl, unsubstituted 3 to 8 membered heterocycloalkyl, unsubstituted 5 to 8 membered aryl, or unsubstituted 5 to 8 membered heteroaryl.

In embodiments, $R^1$ is $R^{1a}$-substituted or unsubstituted $C_1$-$C_5$ alkyl, $R^{1a}$-substituted or unsubstituted 2 to 5 membered heteroalkyl, $R^{1a}$-substituted or unsubstituted 3 to 5 membered cycloalkyl, $R^{1a}$-substituted or unsubstituted 3-6 membered heterocycloalkyl, $R^{1a}$-substituted or unsubstituted 5 to 6 membered aryl, or $R^{1a}$-substituted or unsubstituted 5 to 6 membered heteroaryl. In embodiments, $R^1$ is unsubstituted $C_1$-$C_5$ alkyl, unsubstituted 2 to 5 membered heteroalkyl, unsubstituted 3 to 5 membered cycloalkyl, unsubstituted 3 to 6 membered heterocycloalkyl, or unsubstituted 5 to 6 membered aryl, or unsubstituted 5 to 6 membered heteroaryl.

In embodiments, $R^1$ is $R^{1a}$-substituted or unsubstituted $C_1$-$C_3$ alkyl or $R^{1a}$-substituted or unsubstituted 2 to 3 membered heteroalkyl. In embodiments, $R^1$ is $R^{1a}$-substituted or unsubstituted 3 membered cycloalkyl, $R^{1a}$-substituted or unsubstituted 4 membered cycloalkyl, or $R^{1a}$-substituted or unsubstituted 5 membered cycloalkyl. In embodiments, $R^1$ is $R^{1a}$-substituted or unsubstituted 5 membered heterocycloalkyl, $R^{1a}$-substituted or unsubstituted 6 membered heterocycloalkyl, $R^{1a}$-substituted or unsubstituted 5 membered aryl, $R^{1a}$-substituted or unsubstituted 6 membered aryl, $R^{1a}$-substituted or unsubstituted 5 membered heteroaryl, or $R^{1a}$-substituted or unsubstituted 6 membered heteroaryl. In embodiments, $R^1$ is unsubstituted $C_1$-$C_3$ alkyl or unsubstituted 2 to 3 membered heteroalkyl. In embodiments, $R^1$ is unsubstituted 3 membered cycloalkyl, unsubstituted 4 membered cycloalkyl, or unsubstituted 5 membered cycloalkyl. In embodiments, $R^1$ is unsubstituted 5 membered heterocycloalkyl, unsubstituted 6 membered heterocycloalkyl, unsubstituted 5 membered aryl, unsubstituted 6 membered aryl, unsubstituted 5 membered heteroaryl, or unsubstituted 6 membered heteroaryl.

In embodiments, $R^1$ is $R^{1a}$-substituted or unsubstituted methyl, $R^{1a}$-substituted or unsubstituted ethyl, or $R^{1a}$-substituted or unsubstituted propyl. In embodiments, $R^1$ is methyl, ethyl, or propyl.

In embodiments, $R^1$ is halogen (e.g. —F, —Cl, —Br, or —I), —CF$_3$, —CCl$_3$, —CBr$_3$, —CI$_3$, —CN, —CHO, —OH, —NH$_2$, NO$_2$, or —COOR$^{33A}$. In embodiments, $R^{33A}$ is hydrogen, $C_1$-$C_3$ unsubstituted alkyl, 2 to 5 membered unsubstituted heteroalkyl, or 5 or 6 membered unsubstituted aryl. In embodiments, $R^1$ is —COOR$^{33A}$, wherein $R^{33A}$ is $C_1$-$C_3$ unsubstituted alkyl. In embodiments, $R^{33}$ is unsubstituted methyl, unsubstituted ethyl, or unsubstituted propyl. In embodiments, $R^1$ is —COOCH$_3$. In embodiments, $R^1$ is halogen (e.g. —F, —Cl, —Br, or —I), —CF$_3$, —CCl$_3$, —CBr$_3$, —CI$_3$, —CN, —NH$_2$, or NO$_2$. In embodiments, $R^1$ is —CN. In embodiments, $R^1$ is unsubstituted 2 to 5 membered heteroalkyl.

In embodiments, $R^1$ is hydrogen, halogen (e.g. —F, —Cl, —Br, or —I), —N$_3$, —CF$_3$, —CCl$_3$, —CBr$_3$, —CI$_3$, —CN, —CHO, —OR$^{33A}$, —NR$^{34A}$R$^{35A}$, —COOR$^{33A}$, —CONR$^{34A}$R$^{35A}$, —NO$_2$, —SR$^{36A}$, —SO$_{n1}$R$^{34A}$, —SO$_{n1}$OR$^{34A}$, —SO$_{n1}$NR$^{34A}$R$^{35A}$, —NHNR$^{34A}$R$^{35A}$, —ONR$^{34A}$R$^{35A}$, —NHC(O)NHNR$^{34A}$R$^{35A}$ (e.g., —OH, —OCH$_3$, —NH2, —NHCH$_3$, NCH$_3$NCH$_3$, —COOH, —COOCH$_3$, —CONH$_2$, —CONHCH$_3$, —NO$_2$, —SH, —SCH$_3$, —SOH, —SOCH$_3$, —SO$_2$H, —SO$_2$CH$_3$, —S(O)OH, —S(O)OCH$_3$, —S(O)$_2$H, S(O)$_2$OCH$_3$, —S(O)NH$_2$, —S(O)NHCH$_3$, —S(O)$_2$NH$_2$, S(O)$_2$NHCH$_3$, —NHNH$_2$, —NHNHCH$_3$, —NHNCH$_3$CH$_3$, —ONH$_2$, —ONHCH$_3$, —NHC(O)NHNH$_2$, or —NHC(O)NHNHCH$_3$), substituted or unsubstituted alkyl (e.g., $C_1$-$C_8$, $C_1$-$C_5$, or $C_1$-$C_3$), substituted or unsubstituted heteroalkyl (e.g., 2 to 8 membered, 2 to 5 membered, 2 to 3 membered), substituted or unsubstituted cycloalkyl (e.g., $C_3$-$C_8$, $C_3$-$C_5$, or $C_3$), substituted or unsubstituted heterocycloalkyl (e.g., 3 to 8 membered, 3 to 6 membered, or 4 membered), substituted or unsubstituted aryl (e.g., $C_5$-$C_8$, $C_5$-$C_6$, or phenyl), or substituted or unsubstituted heteroaryl (e.g., 5 to 8 membered, 5 to 6 membered, or 6 membered).

In embodiments, $R^1$ is hydrogen, halogen (e.g. —F, —Cl, —Br, or —I), —N$_3$, —CF$_3$, —CCl$_3$, —CBr$_3$, —CI$_3$, —CN, —CHO, —OR$^{33A}$, —NR$^{34A}$R$^{35A}$, —COOR$^{33A}$, —CONR$^{34A}$R$^{35A}$, —NO$_2$, —SR$^{36A}$, —SO$_{n1}$R$^{34A}$, —SO$_{n1}$OR$^{34A}$, —SO$_{n1}$NR$^{34A}$R$^{35A}$, —NHNR$^{34A}$R$^{35A}$, —ONR$^{34A}$R$^{35A}$, —NHC(O)NHNR$^{34A}$R$^{35A}$ (e.g., —OH, —OCH$_3$, —NH2, —NHCH$_3$, NCH$_3$NCH$_3$, —COOH, —COOCH$_3$, —CONH$_2$, —CONHCH$_3$, —NO$_2$, —SH, —SCH$_3$, —SOH, —SOCH$_3$, —SO$_2$H, —SO$_2$CH$_3$, —S(O)OH, —S(O)OCH$_3$, —S(O)$_2$H, S(O)$_2$OCH$_3$, —S(O)NH$_2$, —S(O)NHCH$_3$, —S(O)$_2$NH$_2$, S(O)$_2$NHCH$_3$, —NHNH$_2$, —NHNHCH$_3$, —NHNCH$_3$CH$_3$, —ONH$_2$, —ONHCH$_3$, —NHC(O)NHNH$_2$, or —NHC(O)NHNHCH$_3$), $R^{1a}$-substituted or unsubstituted alkyl (e.g., $C_1$-$C_8$, $C_1$-$C_5$, or $C_1$-$C_3$), $R^{1a}$-substituted or unsubstituted heteroalkyl (e.g., 2 to 8 membered, 2 to 5 membered, 2 to 3 membered), $R^{1a}$-substituted or unsubstituted cycloalkyl (e.g., $C_3$-$C_8$, $C_3$-$C_3$, or $C_3$), $R^{1a}$-substituted or unsubstituted heterocycloalkyl (e.g., 3 to 8 membered, 3 to 6 membered, or 4 membered), $R^{1a}$-substituted or unsubstituted aryl (e.g., $C_5$-$C_8$, $C_5$-$C_6$, or phenyl), or $R^{1a}$-substituted or unsubstituted heteroaryl (e.g., 5 to 8 membered, 5 to 6 membered, or 6 membered). In embodiments, $R^1$ is hydrogen, halogen (e.g. —F, —Cl, —Br, or —I), —$N_3$, —$CF_3$, —$CCl_3$, —$CBr_3$, —$CI_3$, —CN, —CHO, —$OR^{33A}$, —$NR^{34A}R^{35A}$, —$COOR^{33A}$, —$CONR^{34A}R^{35A}$, —$NO_2$, —$SR^{36A}$, —$SO_{n1}R^{34A}$, —$SO_{n1}OR^{34A}$, —$SO_{n1}NR^{34A}R^{35A}$, —$NHNR^{34A}R^{35A}$, —$ONR^{34A}R^{35A}$, —$NHC(O)NHNR^{34A}R^{35A}$ (e.g., —OH, —$OCH_3$, —NH2, —$NHCH_3$, $NCH_3NCH_3$, —COOH, —$COOCH_3$, —$CONH_2$, —$CONHCH_3$, —$NO_2$, —SH, —$SCH_3$, —SOH, —$SOCH_3$, —$SO_2H$, —$SO_2CH_3$, —S(O)OH, —S(O)$OCH_3$, —S(O)$_2H$, S(O)$_2OCH_3$, —S(O)$NH_2$, —S(O)$NHCH_3$, —S(O)$_2NH_2$, S(O)$_2NHCH_3$, —$NHNH_2$, —$NHNHCH_3$, —$NHNCH_3CH_3$, —$ONH_2$, —$ONHCH_3$, —NHC(O) $NHNH_2$, or —NHC(O)$NHNHCH_3$), unsubstituted alkyl (e.g., $C_1$-$C_8$, $C_1$-$C_5$, or $C_1$-$C_3$), unsubstituted heteroalkyl (e.g., 2 to 8 membered, 2 to 5 membered, 2 to 3 membered), unsubstituted cycloalkyl (e.g., $C_3$-$C_8$, $C_3$-$C_3$, or $C_3$), unsubstituted heterocycloalkyl (e.g., 3 to 8 membered, 3 to 6 membered, or 4 membered), unsubstituted aryl (e.g., $C_5$-$C_8$, $C_5$-$C_6$, or phenyl), or unsubstituted heteroaryl (e.g., 5 to 8 membered, 5 to 6 membered, or 6 membered).

In embodiments, $R^1$ is hydrogen, halogen (e.g. —F, —Cl, —Br, or —I), —OH, —$OCH_3$, —NH2, —$NHCH_3$, $NCH_3NCH_3$, —COOH, —$COOCH_3$, —$CONH_2$, —$CONHCH_3$, —$NO_2$, —SH, —$SCH_3$, —SOH, —$SOCH_3$, —$SO_2H$, —$SO_2CH_3$, —S(O)OH, —S(O)$OCH_3$, —S(O)$_2H$, S(O)$_2OCH_3$, —S(O)$NH_2$, —S(O)$NHCH_3$, —S(O)$_2NH_2$, S(O)$_2NHCH_3$, —$NHNH_2$, —$NHNHCH_3$, —$NHNCH_3CH_3$, —$ONH_2$, —$ONHCH_3$, —NHC(O)$NHNH_2$, or —NHC(O) $NHNHCH_3$), $R^{1a}$-substituted or unsubstituted $C_1$-$C_3$ alkyl, $R^{1a}$-substituted or unsubstituted 2 to 3 membered heteroalkyl, $R^{1a}$-substituted or unsubstituted $C_3$-$C_5$ cycloalkyl, $R^{1a}$-substituted or unsubstituted 5 to 6 membered heterocycloalkyl, $R^{1a}$-substituted or unsubstituted phenyl, or $R^{1a}$-substituted or unsubstituted 5 to 6 membered heteroaryl.

In embodiments, $R^1$ is hydrogen, —F, —Cl, —Br, —I, —OH, —$OCH_3$, —NH2, —$NHCH_3$, $NCH_3NCH_3$, —COOH, —$COOCH_3$, —$CONH_2$, —$CONHCH_3$, —$NO_2$, —SH, —$SCH_3$, —SOH, —$SOCH_3$, —$SO_2H$, —$SO_2CH_3$, —S(O)OH, —S(O)$OCH_3$, —S(O)$_2H$, S(O)$_2OCH_3$, —S(O) $NH_2$, —S(O)$NHCH_3$, —S(O)$_2NH_2$, S(O)$_2NHCH_3$, —$NHNH_2$, —$NHNHCH_3$, —$NHNCH_3CH_3$, —$ONH_2$, —$ONHCH_3$, —NHC(O)$NHNH_2$, or —NHC(O) $NHNHCH_3$), unsubstituted $C_1$-$C_3$ alkyl, unsubstituted 2 to 3 membered heteroalkyl, unsubstituted $C_3$-$C_5$ cycloalkyl, unsubstituted 5 to 6 membered heterocycloalkyl, unsubstituted phenyl, or unsubstituted 5 to 6 membered heteroaryl.

$R^{1a}$ is halogen (e.g. —F, —Cl, —Br, or —I), —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC(O)$NHNH_2$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{12}$, $C_6$-$C_{10}$, or phenyl), or substituted or unsubstituted heteroaryl (e.g., 5 to 12 membered, 5 to 10 membered, 5 to 9 membered, or 5 to 6 membered). In embodiments, $R^{1a}$ is halogen (e.g. —F, —Cl, —Br, or —I), —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC(O)$NHNH_2$, $R^{1b}$-substituted or unsubstituted alkyl (e.g., $C_1$-$C_8$, $C_1$-$C_6$, $C_1$-$C_4$, or $C_1$-$C_2$), $R^{1b}$-substituted or unsubstituted heteroalkyl (e.g., 2 to 8 membered, 2 to 6 membered, 4 to 6 membered, 2 to 3 membered, or 4 to 5 membered), $R^{1b}$-substituted or unsubstituted cycloalkyl (e.g., $C_3$-$C_8$, $C_3$-$C_6$, $C_4$-$C_6$, or $C_5$-$C_6$), $R^{1b}$-substituted or unsubstituted heterocycloalkyl (e.g., 3 to 8 membered, 3 to 6 membered, 4 to 6 membered, 4 to 5 membered, or 5 to 6 membered), $R^{1b}$-substituted or unsubstituted aryl (e.g., $C_6$-$C_{12}$, $C_6$-$C_{10}$, or phenyl), or $R^{1b}$-substituted or unsubstituted heteroaryl (e.g., 5 to 12 membered, 5 to 10 membered, 5 to 9 membered, or 5 to 6 membered). In embodiments, $R^{1a}$ is halogen (e.g. —F, —Cl, —Br, or —I), —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC(O)$NHNH_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered).

$R^{1b}$ is halogen (e.g. —F, —Cl, —Br, or —I), —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC(O)$NHNH_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered).

In embodiments, $R^1$ is an electron withdrawing group (EWG) (e.g. halogen (e.g. —F, —Cl, —Br, or —I), —$N_3$, —$NO_2$, —$CF_3$, —$CCl_3$, —$CBr_3$, —$CI_3$, —CN, —CHO, —$CONH_2$, or substituted or unsubstituted 2 to 8 membered heteroalkyl). An "electron withdrawing group" is used herein according to its common meaning in the art and refers to a chemical moiety that tends to remove electrons (electron density) from a portion of the compound to which it is attached (e.g. a deactivating group). In embodiments, $R^1$ is —CN. In embodiments, $R^1$ is —$NO_2$. In embodiments, $R^1$ is —$CF_3$, —$CCl_3$, —$CBr_3$, or —$CI_3$. In embodiments, $R^1$ is substituted or unsubstituted 2 to 8 membered heteroalkyl. In embodiments, $R^1$ is —$COOCH_3$.

In embodiments, $R^2$ is hydrogen, halogen (e.g. —F, —Cl, —Br, or —I), —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC(O)$NHNH_2$, substituted or unsubstituted alkyl (e.g. $C_1$-$C_5$ alkyl), or substituted or unsubstituted heteroalkyl (e.g. 2 to 8 membered heteroalkyl), or substituted or unsubstituted heterocycloalkyl (e.g. 3 to 6 membered heterocycloalkyl). In embodiments, $R^2$ is halogen (e.g. —F, —Cl, —Br, or —I), —$CF_3$, —$CCl_3$, —$CBr_3$, —$CI_3$, —CN, substituted or unsubstituted alkyl, or substituted or unsubstituted heteroalkyl. In embodiments, $R^2$ is —CN, substituted or unsubstituted alkyl, or substituted or unsubstituted heteroalkyl. In embodiments, $R^2$ is —CN or substituted or unsubstituted alkyl. In embodiments, $R^2$ is —CN or unsubstituted methyl. In embodiments, $R^2$ is —CN, or unsubstituted heteroalkyl. In embodiments, $R^2$ is substituted alkyl or substituted heteroalkyl.

In embodiments, $R^2$ is substituted or unsubstituted alkyl (e.g., $C_1$-$C_8$, $C_1$-$C_5$, or $C_1$-$C_3$), substituted or unsubstituted heteroalkyl (e.g., 2 to 8 membered, 2 to 5 membered, 2 to 3 membered), substituted or unsubstituted cycloalkyl (e.g., $C_3$-$C_8$, $C_3$-$C_5$, or $C_3$), substituted or unsubstituted heterocycloalkyl (e.g., 3 to 8 membered, 3 to 6 membered, or 4 membered), substituted or unsubstituted aryl (e.g., $C_5$-$C_8$, $C_5$-$C_6$, or phenyl), or substituted or unsubstituted heteroaryl (e.g., 5 to 8 membered, 5 to 6 membered, or 6 membered). In embodiments, $R^2$ is unsubstituted alkyl (e.g., $C_1$-$C_8$, $C_1$-$C_5$, or $C_1$-$C_3$), unsubstituted heteroalkyl (e.g., 2 to 8 membered, 2 to 5 membered, 2 to 3 membered), unsubstituted cycloalkyl (e.g., $C_3$-$C_8$, $C_3$-$C_5$, or $C_3$), unsubstituted heterocycloalkyl (e.g., 3 to 8 membered, 3 to 6 membered, or 4 membered), unsubstituted aryl (e.g., $C_5$-$C_8$, $C_5$-$C_6$, or phenyl), or unsubstituted heteroaryl (e.g., 5 to 8 membered, 5 to 6 membered, or 6 membered).

In embodiments, $R^2$ is substituted or unsubstituted $C_1$-$C_8$ alkyl, substituted or unsubstituted 2 to 8 membered heteroalkyl, substituted or unsubstituted 3 to 8 membered cycloalkyl, substituted or unsubstituted 3 to 8 membered heterocycloalkyl, substituted or unsubstituted 5 or 8 membered aryl, or substituted or unsubstituted 5 or 8 membered heteroaryl. In embodiments, $R^2$ is unsubstituted $C_1$-$C_8$ alkyl, unsubstituted 2 to 8 membered heteroalkyl, unsubstituted 3 to 8 membered cycloalkyl, unsubstituted 3 to 8 membered heterocycloalkyl, unsubstituted 5 or 8 membered aryl, or unsubstituted 5 or 8 membered heteroaryl.

In embodiments, $R^2$ is substituted or unsubstituted $C_1$-$C_5$ alkyl, substituted or unsubstituted 2 to 5 membered heteroalkyl, substituted or unsubstituted 3 to 5 membered cycloalkyl, or substituted or unsubstituted 3 to 6 membered heterocycloalkyl, substituted or unsubstituted 5 or 6 membered aryl, or substituted or unsubstituted 5 or 6 membered heteroaryl. In embodiments, $R^2$ is unsubstituted $C_1$-$C_5$ alkyl, unsubstituted 2 to 5 membered heteroalkyl, unsubstituted 3 to 5 membered cycloalkyl, or unsubstituted 3 to 6 membered heterocycloalkyl, unsubstituted 5 or 6 membered aryl, or unsubstituted 5 or 6 membered heteroaryl. In embodiments, $R^2$ is unsubstituted $C_1$-$C_5$ alkyl or unsubstituted 2 to 5 membered heteroalkyl.

In embodiments, $R^2$ is substituted or unsubstituted $C_1$-$C_3$ alkyl or substituted or unsubstituted 2 to 3 membered heteroalkyl. In embodiments, $R^2$ is substituted or unsubstituted 3 membered cycloalkyl, substituted or unsubstituted 4 membered cycloalkyl, or substituted or unsubstituted 5 membered cycloalkyl. In embodiments, $R^2$ is substituted or unsubstituted 4 membered heterocycloalkyl, substituted or unsubstituted 5 membered heterocycloalkyl, substituted or unsubstituted 6 membered heterocycloalkyl, substituted or unsubstituted 5 membered aryl, substituted or unsubstituted 6 membered aryl, substituted or unsubstituted 5 membered heteroaryl, or substituted or unsubstituted 6 membered heteroaryl. In embodiments, $R^2$ is unsubstituted $C_1$-$C_3$ alkyl or unsubstituted 2 to 3 membered heteroalkyl. In embodiments, $R^2$ is unsubstituted 3 membered cycloalkyl, unsubstituted 4 membered cycloalkyl or unsubstituted 5 membered cycloalkyl. In embodiments, $R^2$ is unsubstituted 4 membered heterocycloalkyl, unsubstituted 5 membered heterocycloalkyl, unsubstituted 6 membered heterocycloalkyl, unsubstituted 5 membered aryl, unsubstituted 6 membered aryl, unsubstituted 5 membered heteroaryl, or unsubstituted 6 membered heteroaryl.

In embodiments, $R^2$ is $R^{2a}$-substituted or unsubstituted alkyl, $R^{2a}$-substituted or unsubstituted heteroalkyl, $R^{2a}$-substituted or unsubstituted cycloalkyl, $R^{2a}$-substituted or unsubstituted heterocycloalkyl, $R^{2a}$-substituted or unsubstituted aryl, or $R^{2a}$-substituted or unsubstituted heteroaryl. In embodiments, $R^2$ is $R^{2a}$-substituted or unsubstituted alkyl or $R^{2a}$-substituted or unsubstituted heteroalkyl.

In embodiments, $R^2$ is $R^{2a}$-substituted or unsubstituted $C_1$-$C_8$ alkyl, $R^{2a}$-substituted or unsubstituted 2 to 8 membered heteroalkyl, $R^{2a}$-substituted or unsubstituted 3 to 8 membered cycloalkyl, $R^{2a}$-substituted or unsubstituted 3 to 8 membered heterocycloalkyl, $R^{2a}$-substituted or unsubstituted 5 or 8 membered aryl, or $R^{2a}$-substituted or unsubstituted 5 or 8 membered heteroaryl. In embodiments, $R^2$ is $R^{2a}$-substituted or unsubstituted $C_1$-$C_8$ alkyl or $R^{2a}$-substituted or unsubstituted 2 to 8 membered heteroalkyl, $R^{2a}$-substituted or unsubstituted 3 to 8 membered cycloalkyl, $R^{2a}$-substituted or unsubstituted 3 to 8 membered heterocycloalkyl, $R^{2a}$-substituted or unsubstituted 5 to 8 membered aryl, or $R^{2a}$-substituted or unsubstituted 5 to 8 membered heteroaryl.

In embodiments, $R^2$ is $R^{2a}$-substituted or unsubstituted $C_1$-$C_5$ alkyl, $R^{2a}$-substituted or unsubstituted 2 to 5 membered heteroalkyl, $R^{2a}$-substituted or unsubstituted 3 to 5 membered cycloalkyl, $R^{2a}$-substituted or unsubstituted 3 to 6 membered heterocycloalkyl, $R^{2a}$-substituted or unsubstituted 5 or 6 membered aryl, or $R^{2a}$-substituted or unsubstituted 5 to 6 membered heteroaryl. In embodiments, $R^2$ is $R^{2a}$-substituted or unsubstituted $C_1$-$C_5$ alkyl or $R^{2a}$-substituted or unsubstituted 2 to 5 membered heteroalkyl.

In embodiments, $R^2$ is $R^{2a}$-substituted or unsubstituted $C_1$-$C_3$ alkyl or $R^{2a}$-substituted or unsubstituted 2 to 3 membered heteroalkyl. In embodiments, $R^2$ is $R^{2a}$-substituted or unsubstituted 3 membered cycloalkyl, $R^{2a}$-substituted or unsubstituted 4 membered cycloalkyl, or $R^{2a}$-substituted or unsubstituted 5 membered cycloalkyl. In embodiments, $R^2$ is $R^{2a}$-substituted or unsubstituted 4 membered heterocycloalkyl, $R^{2a}$-substituted or unsubstituted 5 membered heterocycloalkyl, $R^{2a}$-substituted or unsubstituted 6 membered heterocycloalkyl, $R^{2a}$-substituted or unsubstituted 5 membered aryl, $R^{2a}$-substituted or unsubstituted 6 membered aryl, $R^{2a}$-substituted or unsubstituted 5 membered heteroaryl, or $R^{2a}$-substituted or unsubstituted 6 membered heteroaryl.

In embodiments, $R^2$ is hydrogen, halogen (e.g. —F, —Cl, —Br, or —I), —$N_3$, —$CF_3$, —$CCl_3$, —$CBr_3$, —$CI_3$, —CN, —CHO, —$OR^{33B}$, —$NR^{34B}R^{35B}$, —$COOR^{33B}$, —$CONR^{34B}R^{35B}$, —$NO_2$, —$SR^{36B}$, —$SO_{n}R^{34B}$, —$SO_{n2}OR^{34B}$, —$SO_{n2}NR^{34B}R^{35B}$, —$NHNR^{34B}R^{35B}$, —$ONR^{34B}R^{35B}$, —NHC(O)NHNR$^{34B}$R$^{35B}$ (e.g., —OH, —$OCH_3$, —NH2, —$NHCH_3$, $NCH_3NCH_3$, —COOH, —$COOCH_3$, —$CONH_2$, —$CONHCH_3$, —$NO_2$, —SH, —$SCH_3$, —SOH, —$SOCH_3$, —$SO_2H$, —$SO_2CH_3$, —S(O) OH, —S(O)$OCH_3$, —S(O)$_2$H, S(O)$_2OCH_3$, —S(O)$NH_2$, —S(O)$NHCH_3$, —S(O)$_2NH_2$, S(O)$_2NHCH_3$, —$NHNH_2$, —$NHNHCH_3$, —$NHNCH_3CH_3$, —$ONH_2$, —$ONHCH_3$, —NHC(O)NHNH$_2$, or —NHC(O)NHNHCH$_3$), substituted or unsubstituted alkyl (e.g., $C_1$-$C_8$, $C_1$-$C_5$, or $C_1$-$C_3$), substituted or unsubstituted heteroalkyl (e.g., 2 to 8 membered, 2 to 5 membered, 2 to 3 membered), substituted or unsubstituted cycloalkyl (e.g., $C_3$-$C_8$, $C_3$-$C_5$, or $C_3$), substituted or unsubstituted heterocycloalkyl (e.g., 3 to 8 membered, 3 to 6 membered, or 4 membered), substituted or unsubstituted aryl (e.g., $C_5$-$C_8$, $C_5$-$C_6$, or phenyl), or substituted or unsubstituted heteroaryl (e.g., 5 to 8 membered, 5 to 6 membered, or 6 membered).

In embodiments, $R^2$ is hydrogen, halogen (e.g. —F, —Cl, —Br, or —I), —$N_3$, —$CF_3$, —$CCl_3$, —$CBr_3$, —$CI_3$, —CN, —CHO, —$OR^{33B}$, —$NR^{34B}R^{35B}$, —$COOR^{33B}$, —$CONR^{34B}R^{35B}$, —$NO_2$, —$SR^{36B}$, —$SO_{n2}R^{34B}$, —$SO_{n2}OR^{34B}$, —$SO_{n2}NR^{34B}R^{35B}$, —$NHNR^{34B}R^{35B}$, —$ONR^{34B}R^{35B}$, —NHC(O)$NHNR^{34B}R^{35B}$ (e.g., —OH, —$OCH_3$, —NH2, —$NHCH_3$, $NCH_3NCH_3$, —COOH, —$COOCH_3$, —$CONH_2$, —$CONHCH_3$, —$NO_2$, —SH, —$SCH_3$, —SOH, —$SOCH_3$, —$SO_2H$, —$SO_2CH_3$, —S(O)OH, —S(O)$OCH_3$, —S(O)$_2H$, S(O)$_2OCH_3$, —S(O)$NH_2$, —S(O)$NHCH_3$, —S(O)$_2NH_2$, S(O)$_2NHCH_3$, —$NHNH_2$, —$NHNHCH_3$, —$NHNCH_3CH_3$, —$ONH_2$, —$ONHCH_3$, —NHC(O)$NHNH_2$, or —NHC(O)$NHNHCH_3$), $R^{2a}$-substituted or unsubstituted alkyl (e.g., $C_1$-$C_8$, $C_1$-$C_5$, or $C_1$-$C_3$), $R^{2a}$-substituted or unsubstituted heteroalkyl (e.g., 2 to 8 membered, 2 to 5 membered, 2 to 3 membered), $R^{2a}$-substituted or unsubstituted cycloalkyl (e.g., $C_3$-$C_8$, $C_3$-$C_3$, or $C_3$), $R^{2a}$-substituted or unsubstituted heterocycloalkyl (e.g., 3 to 8 membered, 3 to 6 membered, or 4 membered), $R^{2a}$-substituted or unsubstituted aryl (e.g., $C_5$-$C_8$, $C_5$-$C_6$, or phenyl), or $R^{2a}$-substituted or unsubstituted heteroaryl (e.g., 5 to 8 membered, 5 to 6 membered, or 6 membered).

In embodiments, $R^2$ is hydrogen, halogen (e.g. —F, —Cl, —Br, or —I), —$N_3$, —$CF_3$, —$CCl_3$, —$CBr_3$, —$CI_3$, —CN, —CHO, —$OR^{33B}$, —$NR^{34B}R^{35B}$, —$COOR^{33B}$, —$CONR^{34B}R^{35B}$, —$NO_2$, —$SR^{36B}$, —$SO_{n2}R^{34B}$, —$SO_{n2}OR^{34B}$, —$SO_{n2}NR^{34B}R^{35B}$, —$NHNR^{34B}R^{35B}$, —$ONR^{34B}R^{35B}$, —NHC(O)$NHNR^{34B}R^{35B}$ (e.g., —OH, —$OCH_3$, —NH2, —$NHCH_3$, $NCH_3NCH_3$, —COOH, —$COOCH_3$, —$CONH_2$, —$CONHCH_3$, —$NO_2$, —SH, —$SCH_3$, —SOH, —$SOCH_3$, —$SO_2H$, —$SO_2CH_3$, —S(O)OH, —S(O)$OCH_3$, —S(O)$_2H$, S(O)$_2OCH_3$, —S(O)$NH_2$, —S(O)$NHCH_3$, —S(O)$_2NH_2$, S(O)$_2NHCH_3$, —$NHNH_2$, —$NHNHCH_3$, —$NHNCH_3CH_3$, —$ONH_2$, —$ONHCH_3$, —NHC(O)$NHNH_2$, or —NHC(O)$NHNHCH_3$), unsubstituted alkyl (e.g., $C_1$-$C_8$, $C_1$-$C_5$, or $C_1$-$C_3$), unsubstituted heteroalkyl (e.g., 2 to 8 membered, 2 to 5 membered, 2 to 3 membered), unsubstituted cycloalkyl (e.g., $C_3$-$C_8$, $C_3$-$C_3$, or $C_3$), unsubstituted heterocycloalkyl (e.g., 3 to 8 membered, 3 to 6 membered, or 4 membered), unsubstituted aryl (e.g., $C_5$-$C_8$, $C_5$-$C_6$, or phenyl), or unsubstituted heteroaryl (e.g., 5 to 8 membered, 5 to 6 membered, or 6 membered).

In embodiments, $R^2$ is hydrogen, halogen (e.g. —F, —Cl, —Br, or —I), —OH, —$OCH_3$, —NH2, —$NHCH_3$, $NCH_3NCH_3$, —COOH, —$COOCH_3$, —$CONH_2$, —$CONHCH_3$, —$NO_2$, —SH, —$SCH_3$, —SOH, —$SOCH_3$, —$SO_2H$, —$SO_2CH_3$, —S(O)OH, —S(O)$OCH_3$, —S(O)$_2H$, S(O)$_2OCH_3$, —S(O)$NH_2$, —S(O)$NHCH_3$, —S(O)$_2NH_2$, S(O)$_2NHCH_3$, —$NHNH_2$, —$NHNHCH_3$, —$NHNCH_3CH_3$, —$ONH_2$, —$ONHCH_3$, —NHC(O)$NHNH_2$, or —NHC(O)$NHNHCH_3$), $R^{2a}$-substituted or unsubstituted $C_1$-$C_3$ alkyl, $R^{2a}$-substituted or unsubstituted 2 to 3 membered heteroalkyl, $R^{2a}$-substituted or unsubstituted $C_3$-$C_5$ cycloalkyl, $R^{2a}$-substituted or unsubstituted 5 to 6 membered heterocycloalkyl, $R^{2a}$-substituted or unsubstituted phenyl, or $R^{2a}$-substituted or unsubstituted 5 to 6 membered heteroaryl.

In embodiments, $R^2$ is hydrogen, —F, —Cl, —Br, —I, —OH, —$OCH_3$, —NH2, —$NHCH_3$, $NCH_3NCH_3$, —COOH, —$COOCH_3$, —$CONH_2$, —$CONHCH_3$, —$NO_2$, —SH, —$SCH_3$, —SOH, —$SOCH_3$, —$SO_2H$, —$SO_2CH_3$, —S(O)OH, —S(O)$OCH_3$, —S(O)$_2H$, S(O)$_2OCH_3$, —S(O)$NH_2$, —S(O)$NHCH_3$, —S(O)$_2NH_2$, S(O)$_2NHCH_3$, —$NHNH_2$, —$NHNHCH_3$, —$NHNCH_3CH_3$, —$ONH_2$, —$ONHCH_3$, —NHC(O)$NHNH_2$, or —NHC(O)$NHNHCH_3$), unsubstituted $C_1$-$C_3$ alkyl, unsubstituted 2 to 3 membered heteroalkyl, unsubstituted $C_3$-$C_5$ cycloalkyl, unsubstituted 5 to 6 membered heterocycloalkyl, unsubstituted phenyl, or unsubstituted 5 to 6 membered heteroaryl.

$R^{2a}$ is halogen (e.g. —F, —Cl, —Br, or —I), —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC(O)$NHNH_2$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{12}$, $C_6$-$C_{10}$, or phenyl), or substituted or unsubstituted heteroaryl (e.g., 5 to 12 membered, 5 to 10 membered, 5 to 9 membered, or 5 to 6 membered). In embodiments, $R^{2a}$ is halogen (e.g. —F, —Cl, —Br, or —I), —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC(O)$NHNH_2$, $R^{2b}$-substituted or unsubstituted alkyl (e.g., $C_1$-$C_8$, $C_1$-$C_6$, $C_1$-$C_4$, or $C_1$-$C_2$), $R^{2b}$-substituted or unsubstituted heteroalkyl (e.g., 2 to 8 membered, 2 to 6 membered, 4 to 6 membered, 2 to 3 membered, or 4 to 5 membered), $R^{2b}$-substituted or unsubstituted cycloalkyl (e.g., $C_3$-$C_8$, $C_3$-$C_6$, $C_4$-$C_6$, or $C_5$-$C_6$), $R^{2b}$-substituted or unsubstituted heterocycloalkyl (e.g., 3 to 8 membered, 3 to 6 membered, 4 to 6 membered, 4 to 5 membered, or 5 to 6 membered), $R^{2b}$-substituted or unsubstituted aryl (e.g., $C_6$-$C_{12}$, $C_6$-$C_{10}$, or phenyl), or $R^{2b}$-substituted or unsubstituted heteroaryl (e.g., 5 to 12 membered, 5 to 10 membered, 5 to 9 membered, or 5 to 6 membered). In embodiments, $R^{2a}$ is halogen (e.g. —F, —Cl, —Br, or —I), —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC(O)$NHNH_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered).

$R^{2b}$ is halogen (e.g. —F, —Cl, —Br, or —I), —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC(O)$NHNH_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered).

In embodiments, $R^2$ is hydrogen, halogen (e.g. —F, —Cl, —Br, or —I), —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —ONH$_2$, —NHC(O)NHNH$_2$, R$^{2a}$-substituted or unsubstituted C$_1$-C$_8$ alkyl, R$^{2a}$-substituted or unsubstituted 2 to 8 membered heteroalkyl, R$^{2a}$-substituted or unsubstituted 3 to 8 membered cycloalkyl, R$^{2a}$-substituted or unsubstituted 3 to 6 membered heterocycloalkyl, R$^{2a}$-substituted or unsubstituted 5 or 6 membered aryl, or R$^{2a}$-substituted or unsubstituted 5 or 6 membered heteroaryl. In embodiments, R$^2$ is —N$_3$, —CF$_3$, —CCl$_3$, —CBr$_3$, —CI$_3$, —CN, —CHO, —OH, —NH$_2$, —COOH, —CONH$_2$, —NO$_2$, —SH, —SO$_2$Cl, —SO$_3$H, —SO$_4$H, —SO$_2$Ph, —SO$_2$NH$_2$, —NHNH$_2$, —ONH$_2$, R$^{2a}$-substituted or unsubstituted C$_1$-C$_3$ alkyl, or 1 to 3 membered R$^{2a}$-substituted or unsubstituted heteroalkyl. In embodiments, R$^2$ is unsubstituted C$_1$-C$_5$ alkyl or unsubstituted 2 to 5 membered heteroalkyl. In embodiments, R$^2$ is unsubstituted methyl. In embodiments, R$^2$ is unsubstituted methoxy (e.g. —OCH$_3$).

In embodiments, R$^2$ is R$^{2a}$-substituted or unsubstituted C$_1$-C$_5$ alkyl (e.g. R$^{2a}$-substituted or unsubstituted methylene). In embodiments, R$^2$ is R$^{2a}$-substituted C$_1$-C$_5$ alkyl. In embodiments, when R$^2$ is substituted or unsubstituted C$_1$-C$_5$ alkyl, R$^{2a}$ is unsubstituted heterocycloalkyl, unsubstituted aryl, or unsubstituted heteroaryl. In embodiments, R$^{2a}$ is unsubstituted or unsubstituted morpholino (e.g. R$^{2b}$-substituted or unsubstituted morpholino). In embodiments, R$^2$ is R$^{2a}$-substituted or unsubstituted 2 to 5 membered heteroalkyl. In embodiments, when R$^2$ is substituted or unsubstituted 2 to 5 membered heteroalkyl, R$^{2a}$ is is unsubstituted C$_1$-C$_5$ alkyl, unsubstituted heterocycloalkyl, unsubstituted aryl, or unsubstituted heteroaryl. In embodiments, R$^2$ is —OCH$_3$. In embodiments, R$^2$ is unsubstituted methyl. In embodiments, R$^2$ is —CN.

In embodiments, R$^1$ is halogen (e.g. —F, —Cl, —Br, or —I), —N$_3$, —NO$_2$, —CF$_3$, CCl$_3$, CBr$_3$, CI$_3$, —CN, —CHO, —CONH$_2$, or substituted or unsubstituted 2 to 8 membered heteroalkyl and R$^2$ is hydrogen, halogen (e.g. —F, —Cl, —Br, or —I), —N$_3$, —CF$_3$, —CCl$_3$, —CBr$_3$, —CI$_3$, —CN, —CHO, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC(O)NHNH$_2$, R$^{2a}$-substituted or unsubstituted C$_1$-C$_8$ alkyl, R$^{2a}$-substituted or unsubstituted 2 to 8 membered heteroalkyl, R$^{2a}$-substituted or unsubstituted 3 to 8 membered cycloalkyl, R$^{2a}$-substituted or unsubstituted 3 to 6 membered heterocycloalkyl, R$^{2a}$-substituted or unsubstituted 5 or 6 membered aryl, or R$^{2a}$-substituted or unsubstituted 5 or 6 membered heteroaryl heteroaryl. In embodiments, at least one of R$^1$ and R$^2$ is an electron withdrawing group (EWG) (e.g. halogen (e.g. —F, —Cl, —Br, or —I), —N$_3$, —NO$_2$, —CF$_3$, CCl$_3$, CBr$_3$, CI$_3$, —CN, —CHO, —CONH$_2$, or substituted or unsubstituted 2 to 8 membered heteroalkyl. In embodiments, when R$^1$ is CN, R$^2$ is —CN. In embodiments, when R$^1$ is halogen (e.g. —F, —Cl, —Br, or —I), R$^2$ is halogen (e.g. —F, —Cl, —Br, or —I). In embodiments, when R$^1$ is —CN, R$^2$ is unsubstituted C$_1$-C$_5$ alkyl. In embodiments, when R$^1$ is —CN, R$^2$ is unsubstituted methyl. In embodiments, when R$^1$ is unsubstituted 2 to 8 membered heteroalkyl (e.g. —COOCH$_3$), R$^2$ is unsubstituted C$_1$-C$_5$ alkyl. In embodiments, when R$^1$ is —CN, R$^2$ is R$^{2a}$-substituted or unsubstituted C$_1$-C$_5$ alkyl. In embodiments, when R$^1$ is —CN, R$^2$ is R$^{2a}$-substituted or unsubstituted C$_1$-C$_5$ heteroalkyl. In embodiments, R$^{2a}$ is unsubstituted alkyl, unsubstituted cycloalkyl, unsubstituted heterocycloalkyl, unsubstituted aryl, or unsubstituted heteroaryl.

In embodiments, R$^2$ is a polar substituent and provides polarity to the compounds provided herein (e.g. where R$^2$ is a substituted or unsubstituted 2 to 8 membered heteroalkyl). A "polar substituent" is understood by one skilled in the art to be a moiety that creates a dipole moment, thereby forming a positive or negative charge on a molecule. In embodiments, R$^2$ is an aqueous solubility enhancing substituent (e.g. a moiety that increases the water solubility of the compound), where germinal substitution at R$^2$ with a substituent other than methyl improves the solubility of the compound in an aqueous medium. Solubility enhancing substituents may include basic substituents or groups that add polarity.

In embodiments, R$^3$ is substituted or unsubstituted alkyl (e.g., C$_1$-C$_8$, C$_1$-C$_5$, or C$_1$-C$_3$), substituted or unsubstituted heteroalkyl (e.g., 2 to 8 membered, 2 to 5 membered, 2 to 3 membered), substituted or unsubstituted cycloalkyl (e.g., C$_3$-C$_8$, C$_3$-C$_5$, or C$_3$), substituted or unsubstituted heterocycloalkyl (e.g., 3 to 8 membered, 3 to 6 membered, or 4 membered), substituted or unsubstituted aryl (e.g., C$_5$-C$_8$, C$_5$-C$_6$, or phenyl), or substituted or unsubstituted heteroaryl (e.g., 5 to 8 membered, 5 to 6 membered, or 6 membered).

In embodiments, R$^3$ is R$^{3a}$-substituted or unsubstituted alkyl (e.g., C$_1$-C$_8$, C$_1$-C$_5$, or C$_1$-C$_3$), R$^{3a}$-substituted or unsubstituted heteroalkyl (e.g., 2 to 8 membered, 2 to 5 membered, 2 to 3 membered), R$^{3a}$-substituted or unsubstituted cycloalkyl (e.g., C$_3$-C$_8$, C$_3$-C$_5$, or C$_3$), R$^{3a}$-substituted or unsubstituted heterocycloalkyl (e.g., 3 to 8 membered, 3 to 6 membered, or 4 membered), R$^{3a}$-substituted or unsubstituted aryl (e.g., C$_5$-C$_8$, C$_5$-C$_6$, or phenyl), or R$^{3a}$-substituted or unsubstituted heteroaryl (e.g., 5 to 8 membered, 5 to 6 membered, or 6 membered). In embodiments, R$^3$ is unsubstituted alkyl (e.g., C$_1$-C$_8$, C$_1$-C$_5$, or C$_1$-C$_3$), unsubstituted heteroalkyl (e.g., 2 to 8 membered, 2 to 5 membered, 2 to 3 membered), unsubstituted cycloalkyl (e.g., C$_3$-C$_8$, C$_3$-C$_5$, or C$_3$), unsubstituted heterocycloalkyl (e.g., 3 to 8 membered, 3 to 6 membered, or 4 membered), unsubstituted aryl (e.g., C$_5$-C$_8$, C$_5$-C$_6$, or phenyl), or unsubstituted heteroaryl (e.g., 5 to 8 membered, 5 to 6 membered, or 6 membered).

In embodiments, R$^3$ is substituted or unsubstituted alkyl, substituted or unsubstituted C$_1$-C$_8$ alkyl, substituted or unsubstituted C$_1$-C$_5$ alkyl, substituted or unsubstituted C$_1$-C$_3$ alkyl. In embodiments, R$^3$ is R$^{3a}$-substituted or unsubstituted alkyl, R$^{3a}$-substituted or unsubstituted C$_1$-C$_8$ alkyl, R$^{3a}$-substituted or unsubstituted C$_1$-C$_5$ alkyl, or R$^{3a}$-substituted or unsubstituted C$_1$-C$_3$ alkyl. In embodiments, R$^3$ is unsubstituted alkyl, unsubstituted C$_1$-C$_8$ alkyl, unsubstituted C$_1$-C$_5$ alkyl, or unsubstituted C$_1$-C$_3$ alkyl.

In embodiments, R$^3$ is substituted or unsubstituted heteroalkyl, substituted or unsubstituted 2 to 8 membered heteroalkyl, substituted or unsubstituted 2 to 5 membered heteroalkyl, substituted or unsubstituted 2 to 3 membered heteroalkyl. In embodiments, R$^3$ is R$^{3a}$-substituted or unsubstituted heteroalkyl, R$^{3a}$-substituted or unsubstituted 2 to 8 membered heteroalkyl, R$^{3a}$-substituted or unsubstituted 2 to 5 membered heteroalkyl, or R$^{3a}$-substituted or unsubstituted 2 to 3 membered heteroalkyl. In embodiments, R$^3$ is independently unsubstituted heteroalkyl, unsubstituted 2 to 8 membered heteroalkyl, or unsubstituted 2 to 5 membered heteroalkyl, unsubstituted 2 to 3 membered heteroalkyl.

In embodiments, R$^3$ is substituted or unsubstituted cycloalkyl, substituted or unsubstituted 3 to 8 membered cycloalkyl, substituted or unsubstituted 3 to 5 membered cycloalkyl, substituted or unsubstituted 3 membered cycloalkyl, substituted or unsubstituted 4 membered cycloalkyl, or substituted or unsubstituted 5 membered cycloalkyl. In embodiments, R$^3$ is R$^{3a}$-substituted or unsubstituted cycloalkyl, R$^{3a}$-substituted or unsubstituted 3 to 8 membered cycloalkyl, R$^{3a}$-substituted or unsubstituted 3 to 5 membered cycloalkyl, R$^{3a}$-substituted or unsubstituted 3 membered cycloalkyl, R$^{3a}$-substituted or unsubstituted 4 membered cycloalkyl, or R$^{3a}$-substituted or unsubstituted 5 membered cycloalkyl. In embodiments, R$^3$ is unsubstituted cycloalkyl, unsubstituted 3 to 8 membered cycloalkyl, unsubstituted 3 to 5 membered cycloalkyl, unsubstituted 3 membered cycloalkyl, unsubstituted 4 membered cycloalkyl, or unsubstituted 5 membered cycloalkyl.

In embodiments, R$^3$ is substituted or unsubstituted heterocycloalkyl, substituted or unsubstituted 3 to 6 membered heterocycloalkyl, substituted or unsubstituted 4 membered heterocycloalkyl, substituted or unsubstituted 5 membered heterocycloalkyl, or substituted or unsubstituted 6 membered heterocycloalkyl. In embodiments, R$^3$ is R$^{3a}$-substituted or unsubstituted heterocycloalkyl, R$^{3a}$-substituted or unsubstituted 3 to 6 membered heterocycloalkyl, R$^{3a}$-substituted or unsubstituted 4 membered heterocycloalkyl, R$^{3a}$-substituted or unsubstituted 5 membered heterocycloalkyl, or R$^{3a}$-substituted or unsubstituted 6 membered heterocycloalkyl. In embodiments, R$^3$ is unsubstituted heterocycloalkyl, unsubstituted 3 to 6 membered heterocycloalkyl, unsubstituted 4 membered heterocycloalkyl, unsubstituted 5 membered heterocycloalkyl, or unsubstituted 6 membered heterocycloalkyl.

In embodiments, R$^3$ is substituted or unsubstituted aryl, substituted or unsubstituted 5 to 6 membered aryl, substituted or unsubstituted 5 membered aryl, or substituted or unsubstituted 6 membered aryl. In embodiments, R$^3$ is R$^{3a}$-substituted or unsubstituted aryl, R$^{3a}$-substituted or unsubstituted 5 to 6 membered aryl, R$^{3a}$-substituted or unsubstituted 5 membered aryl, or R$^{3a}$-substituted or unsubstituted 6 membered aryl. In embodiments, R$^3$ is unsubstituted aryl, unsubstituted 5 to 6 membered aryl, unsubstituted 5 membered aryl, or unsubstituted 6 membered aryl.

In embodiments, R$^3$ is substituted or unsubstituted heteroaryl, substituted or unsubstituted 5 to 6 membered heteroaryl, substituted or unsubstituted 5 membered heteroaryl, or substituted or unsubstituted 6 membered heteroaryl. In embodiments, R$^3$ is R$^{3a}$-substituted or unsubstituted heteroaryl, R$^{3a}$-substituted or unsubstituted 5 to 6 membered heteroaryl, R$^{3a}$-substituted or unsubstituted 5 membered heteroaryl, or R$^{3a}$-substituted or unsubstituted 6 membered heteroaryl. In embodiments, R$^3$ is unsubstituted heteroaryl, unsubstituted 5 to 6 membered heteroaryl, unsubstituted 5 membered heteroaryl, or unsubstituted 6 membered heteroaryl.

In embodiments, R$^3$ is hydrogen, halogen (e.g. —F, —Cl, —Br, or —I), substituted or unsubstituted $C_1$-$C_8$ alkyl, substituted or unsubstituted $C_1$-$C_5$ alkyl, or substituted or unsubstituted $C_1$-$C_3$ alkyl. In embodiments, R$^3$ is hydrogen, halogen (e.g. —F, —Cl, —Br, or —I), R$^{3a}$-substituted or unsubstituted $C_1$-$C_8$ alkyl, R$^{3a}$-substituted or unsubstituted $C_1$-$C_5$ alkyl, or R$^{3a}$-substituted or unsubstituted $C_1$-$C_3$ alkyl. In embodiments, R$^3$ is hydrogen, halogen (e.g. —F, —Cl, —Br, or —I), unsubstituted $C_1$-$C_8$ alkyl, unsubstituted $C_1$-$C_5$ alkyl, or unsubstituted $C_1$-$C_3$ alkyl. In embodiments, R$^3$ is hydrogen, halogen (e.g. —F, —Cl, —Br, or —I), or R$^{3a}$-substituted or unsubstituted $C_1$-$C_8$ alkyl. In embodiments, R$^3$ is hydrogen, halogen (e.g. —F, —Cl, —Br, or —I), or R$^{3a}$-substituted or unsubstituted $C_1$-$C_5$ alkyl. In embodiments, R$^3$ is hydrogen, halogen (e.g. —F, —Cl, —Br, or —I), or R$^{3a}$-substituted or unsubstituted $C_1$-$C_3$ alkyl. In embodiments, R$^3$ is hydrogen, halogen (e.g. —F, —Cl, —Br, or —I), or unsubstituted $C_1$-$C_3$ alkyl. In embodiments, R$^3$ is hydrogen, or unsubstituted $C_1$-$C_3$ alkyl. In embodiments, R$^3$ is hydrogen. In embodiments, R$^3$ is unsubstituted methyl, unsubstituted ethyl, or unsubstituted propyl.

In embodiments, R$^3$ is hydrogen, halogen (e.g. —F, —Cl, —Br, or —I), —N$_3$, —CF$_3$, —CCl$_3$, —CBr$_3$, —CI$_3$, —CN, —CHO, —OR$^{33C}$, —NR$^{34C}$R$^{35C}$, —COOR$^{33C}$, —CONR$^{34C}$R$^{35C}$, —NO$_2$, —SR$^{36C}$, —SO$_{n3}$R$^{34C}$, —SO$_{n3}$OR$^{34C}$, —SO$_{n3}$NR$^{34C}$R$^{35C}$, —NHNR$^{34C}$R$^{35C}$, —ONR$^{34C}$R$^{35C}$, —NHC(O)NHNR$^{34C}$R$^{35C}$ (e.g., —OH, —OCH$_3$, —NH2, —NHCH$_3$, NCH$_3$NCH$_3$, —COOH, —COOCH$_3$, —CONH$_2$, —CONHCH$_3$, —NO$_2$, —SH, —SCH$_3$, —SOH, —SOCH$_3$, —SO$_2$H, —SO$_2$CH$_3$, —S(O)OH, —S(O)OCH$_3$, —S(O)$_2$H, S(O)$_2$OCH$_3$, —S(O)NH$_2$, —S(O)NHCH$_3$, —S(O)$_2$NH$_2$, S(O)$_2$NHCH$_3$, —NHNH$_2$, —NHNHCH$_3$, —NHNCH$_3$CH$_3$, —ONH$_2$, —ONHCH$_3$, —NHC(O)NHNH$_2$, or —NHC(O)NHNHCH$_3$), substituted or unsubstituted alkyl (e.g., $C_1$-$C_8$, $C_1$-$C_5$, or $C_1$-$C_3$), substituted or unsubstituted heteroalkyl (e.g., 2 to 8 membered, 2 to 5 membered, 2 to 3 membered), substituted or unsubstituted cycloalkyl (e.g., $C_3$-$C_8$, $C_3$-$C_5$, or $C_3$), substituted or unsubstituted heterocycloalkyl (e.g., 3 to 8 membered, 3 to 6 membered, or 4 membered), substituted or unsubstituted aryl (e.g., $C_5$-$C_8$, $C_5$-$C_6$, or phenyl), or substituted or unsubstituted heteroaryl (e.g., 5 to 8 membered, 5 to 6 membered, or 6 membered).

In embodiments, R$^3$ is hydrogen, halogen (e.g. —F, —Cl, —Br, or —I), —N$_3$, —CF$_3$, —CCl$_3$, —CBr$_3$, —CI$_3$, —CN, —CHO, —OR$^{33C}$, —NR$^{34C}$R$^{35C}$, —COOR$^{33C}$, —CONR$^{34C}$R$^{35C}$, —NO$_2$, —SR$^{36C}$, —SO$_{n3}$R$^{34C}$, —SO$_{n3}$OR$^{34C}$, —SO$_{n3}$NR$^{34C}$R$^{35C}$, —NHNR$^{34C}$R$^{35C}$, —ONR$^{34C}$R$^{35C}$, —NHC(O)NHNR$^{34C}$R$^{35C}$ (e.g., —OH, —OCH$_3$, —NH2, —NHCH$_3$, NCH$_3$NCH$_3$, —COOH, —COOCH$_3$, —CONH$_2$, —CONHCH$_3$, —NO$_2$, —SH, —SCH$_3$, —SOH, —SOCH$_3$, —SO$_2$H, —SO$_2$CH$_3$, —S(O)OH, —S(O)OCH$_3$, —S(O)$_2$H, S(O)$_2$OCH$_3$, —S(O)NH$_2$, —S(O)NHCH$_3$, —S(O)$_2$NH$_2$, S(O)$_2$NHCH$_3$, —NHNH$_2$, —NHNHCH$_3$, —NHNCH$_3$CH$_3$, —ONH$_2$, —ONHCH$_3$, —NHC(O)NHNH$_2$, or —NHC(O)NHNHCH$_3$), R$^{3a}$-substituted or unsubstituted alkyl (e.g., $C_1$-$C_8$, $C_1$-$C_5$, or $C_1$-$C_3$), R$^{3a}$-substituted or unsubstituted heteroalkyl (e.g., 2 to 8 membered, 2 to 5 membered, 2 to 3 membered), R$^{3a}$-substituted or unsubstituted cycloalkyl (e.g., $C_3$-$C_8$, $C_3$-$C_3$, or $C_3$), R$^{3a}$-substituted or unsubstituted heterocycloalkyl (e.g., 3 to 8 membered, 3 to 6 membered, or 4 membered), R$^3$-substituted or unsubstituted aryl (e.g., $C_5$-$C_8$, $C_5$-$C_6$, or phenyl), or R$^{3a}$-substituted or unsubstituted heteroaryl (e.g., 5 to 8 membered, 5 to 6 membered, or 6 membered).

In embodiments, R$^3$ is hydrogen, halogen (e.g. —F, —Cl, —Br, or —I), —N$_3$, —CF$_3$, —CCl$_3$, —CBr$_3$, —CI$_3$, —CN, —CHO, —OR$^{33C}$, —NR$^{34C}$R$^{35C}$, —COOR$^{33C}$, —CONR$^{34C}$R$^{35C}$, —NO$_2$, —SR$^{36C}$, —SO$_{n3}$R$^{34C}$, —SO$_{n3}$OR$^{34C}$, —SO$_{n3}$NR$^{34C}$R$^{35C}$, —NHNR$^{34C}$R$^{35C}$, —ONR$^{34C}$R$^{35C}$, —NHC(O)NHNR$^{34C}$R$^{35C}$ (e.g., —OH, —OCH$_3$, —NH2, —NHCH$_3$, NCH$_3$NCH$_3$, —COOH, —COOCH$_3$, —CONH$_2$, —CONHCH$_3$, —NO$_2$, —SH, —SCH$_3$, —SOH, —SOCH$_3$, —SO$_2$H, —SO$_2$CH$_3$, —S(O)OH, —S(O)OCH$_3$, —S(O)$_2$H, S(O)$_2$OCH$_3$, —S(O)NH$_2$, —S(O)NHCH$_3$, —S(O)$_2$NH$_2$, S(O)$_2$NHCH$_3$, —NHNH$_2$, —NHNHCH$_3$, —NHNCH$_3$CH$_3$, —ONH$_2$, —ONHCH$_3$, —NHC(O)NHNH$_2$, or —NHC(O)NHNHCH$_3$), unsubstituted alkyl (e.g., $C_1$-$C_8$, $C_1$-$C_5$, or $C_1$-$C_3$), unsubstituted heteroalkyl (e.g., 2 to 8 membered, 2 to 5 membered, 2 to 3 membered), unsubstituted cycloalkyl (e.g., $C_3$-$C_8$, $C_3$-$C_3$, or $C_3$), unsubstituted heterocycloalkyl (e.g., 3 to 8 membered, 3 to 6 membered, or 4 membered), unsubstituted aryl (e.g., $C_5$-$C_8$, $C_5$-$C_6$, or phenyl), or unsubstituted heteroaryl (e.g., 5 to 8 membered, 5 to 6 membered, or 6 membered).

In embodiments, R$^3$ is hydrogen, halogen (e.g. —F, —Cl, —Br, or —I), —OH, —OCH$_3$, —NH2, —NHCH$_3$, NCH$_3$NCH$_3$, —COOH, —COOCH$_3$, —CONH$_2$, —CONHCH$_3$, —NO$_2$, —SH, —SCH$_3$, —SOH, —SOCH$_3$, —SO$_2$H, —SO$_2$CH$_3$, —S(O)OH, —S(O)OCH$_3$, —S(O)$_2$H, S(O)$_2$OCH$_3$, —S(O)NH$_2$, —S(O)NHCH$_3$, —S(O)$_2$NH$_2$, S(O)$_2$NHCH$_3$, —NHNH$_2$, —NHNHCH$_3$, —NHNCH$_3$CH$_3$, —ONH$_2$, —ONHCH$_3$, —NHC(O)NHNH$_2$, or —NHC(O)NHNHCH$_3$), R$^{3a}$-substituted or unsubstituted C$_1$-C$_3$ alkyl, R$^{3a}$-substituted or unsubstituted 2 to 3 membered heteroalkyl, R$^{3a}$-substituted or unsubstituted C$_3$-C$_5$ cycloalkyl, R$^{3a}$-substituted or unsubstituted 5 to 6 membered heterocycloalkyl, R$^{3a}$-substituted or unsubstituted phenyl, or R$^{3a}$-substituted or unsubstituted 5 to 6 membered heteroaryl.

In embodiments, R$^3$ is hydrogen, —F, —Cl, —Br, —I, —OH, —OCH$_3$, —NH2, —NHCH$_3$, NCH$_3$NCH$_3$, —COOH, —COOCH$_3$, —CONH$_2$, —CONHCH$_3$, —NO$_2$, —SH, —SCH$_3$, —SOH, —SOCH$_3$, —SO$_2$H, —SO$_2$CH$_3$, —S(O)OH, —S(O)OCH$_3$, —S(O)$_2$H, S(O)$_2$OCH$_3$, —S(O)NH$_2$, —S(O)NHCH$_3$, —S(O)$_2$NH$_2$, S(O)$_2$NHCH$_3$, —NHNH$_2$, —NHNHCH$_3$, —NHNCH$_3$CH$_3$, —ONH$_2$, —ONHCH$_3$, —NHC(O)NHNH$_2$, or —NHC(O)NHNHCH$_3$), unsubstituted C$_1$-C$_3$ alkyl, unsubstituted 2 to 3 membered heteroalkyl, unsubstituted C$_3$-C$_5$ cycloalkyl, unsubstituted 5 to 6 membered heterocycloalkyl, unsubstituted phenyl, or unsubstituted 5 to 6 membered heteroaryl.

R$^{3a}$ is halogen (e.g. —F, —Cl, —Br, or —I), —N$_3$, —CF$_3$, —CCl$_3$, —CBr$_3$, —CI$_3$, —CN, —CHO, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC(O)NHNH$_2$, substituted or unsubstituted alkyl (e.g., C$_1$-C$_8$, C$_1$-C$_6$, C$_1$-C$_4$, or C$_1$-C$_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., C$_3$-C$_8$, C$_3$-C$_6$, C$_4$-C$_6$, or C$_5$-C$_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., C$_6$-C$_{12}$, C$_6$-C$_{10}$, or phenyl), or substituted or unsubstituted heteroaryl (e.g., 5 to 12 membered, 5 to 10 membered, 5 to 9 membered, or 5 to 6 membered). In embodiments, R$^{3a}$ is halogen (e.g. —F, —Cl, —Br, or —I), —N$_3$, —CF$_3$, —CCl$_3$, —CBr$_3$, —CI$_3$, —CN, —CHO, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC(O)NHNH$_2$, R$^{3b}$-substituted or unsubstituted alkyl (e.g., C$_1$-C$_8$, C$_1$-C$_6$, C$_1$-C$_4$, or C$_1$-C$_2$), R$^{3b}$-substituted or unsubstituted heteroalkyl (e.g., 2 to 8 membered, 2 to 6 membered, 4 to 6 membered, 2 to 3 membered, or 4 to 5 membered), R$^{3b}$-substituted or unsubstituted cycloalkyl (e.g., C$_3$-C$_8$, C$_3$-C$_6$, C$_4$-C$_6$, or C$_5$-C$_6$), R$^{3b}$-substituted or unsubstituted heterocycloalkyl (e.g., 3 to 8 membered, 3 to 6 membered, 4 to 6 membered, 4 to 5 membered, or 5 to 6 membered), R$^{3b}$-substituted or unsubstituted aryl (e.g., C$_6$-C$_{12}$, C$_6$-C$_{10}$, or phenyl), or R$^{3b}$-substituted or unsubstituted heteroaryl (e.g., 5 to 12 membered, 5 to 10 membered, 5 to 9 membered, or 5 to 6 membered). In embodiments, R$^{3a}$ is halogen (e.g. —F, —Cl, —Br, or —I), —N$_3$, —CF$_3$, —CCl$_3$, —CBr$_3$, —CI$_3$, —CN, —CHO, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC(O)NHNH$_2$, unsubstituted alkyl (e.g., C$_1$-C$_8$, C$_1$-C$_6$, C$_1$-C$_4$, or C$_1$-C$_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., C$_3$-C$_8$, C$_3$-C$_6$, C$_4$-C$_6$, or C$_5$-C$_6$), unsubstituted heterocycloalkyl (e.g., 3 to 8 membered, 3 to 6 membered, 4 to 6 membered, 4 to 5 membered, or 5 to 6 membered), unsubstituted aryl (e.g., C$_6$-C$_{12}$, C$_6$-C$_{10}$, or phenyl), or unsubstituted heteroaryl (e.g., 5 to 12 membered, 5 to 10 membered, 5 to 9 membered, or 5 to 6 membered).

R$^{3b}$ is halogen (e.g. —F, —Cl, —Br, or —I), —N$_3$, —CF$_3$, —CCl$_3$, —CBr$_3$, —CI$_3$, —CN, —CHO, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC(O)NHNH$_2$, unsubstituted alkyl (e.g., C$_1$-C$_8$, C$_1$-C$_6$, C$_1$-C$_4$, or C$_1$-C$_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., C$_3$-C$_8$, C$_3$-C$_6$, C$_4$-C$_6$, or C$_5$-C$_6$), unsubstituted heterocycloalkyl (e.g., 3 to 8 membered, 3 to 6 membered, 4 to 6 membered, 4 to 5 membered, or 5 to 6 membered), unsubstituted aryl (e.g., C$_6$-C$_{12}$, C$_6$-C$_{10}$, or phenyl), or unsubstituted heteroaryl (e.g., 5 to 12 membered, 5 to 10 membered, 5 to 9 membered, or 5 to 6 membered).

In embodiments, R$^4$ is substituted or unsubstituted alkyl (e.g., C$_1$-C$_8$, C$_1$-C$_5$, or C$_1$-C$_3$), substituted or unsubstituted heteroalkyl (e.g., 2 to 8 membered, 2 to 5 membered, 2 to 3 membered), substituted or unsubstituted cycloalkyl (e.g., C$_3$-C$_8$, C$_3$-C$_5$, or C$_3$), substituted or unsubstituted heterocycloalkyl (e.g., 3 to 8 membered, 3 to 6 membered, or 4 membered), substituted or unsubstituted aryl (e.g., C$_5$-C$_8$, C$_5$-C$_6$, or phenyl), or substituted or unsubstituted heteroaryl (e.g., 5 to 8 membered, 5 to 6 membered, or 6 membered). In embodiments, R$^4$ is R$^{4a}$-substituted or unsubstituted alkyl (e.g., C$_1$-C$_8$, C$_1$-C$_5$, or C$_1$-C$_3$), R$^{4a}$-substituted or unsubstituted heteroalkyl (e.g., 2 to 8 membered, 2 to 5 membered, 2 to 3 membered), R$^{4a}$-substituted or unsubstituted cycloalkyl (e.g., C$_3$-C$_8$, C$_3$-C$_5$, or C$_3$), R$^{4a}$-substituted or unsubstituted heterocycloalkyl (e.g., 3 to 8 membered, 3 to 6 membered, or 4 membered), R$^{4a}$-substituted or unsubstituted aryl (e.g., C$_5$-C$_8$, C$_5$-C$_6$, or phenyl), or R$^{4a}$-substituted or unsubstituted heteroaryl (e.g., 5 to 8 membered, 5 to 6 membered, or 6 membered). In embodiments, R$^4$ is unsubstituted alkyl (e.g., C$_1$-C$_8$, C$_1$-C$_5$, or C$_1$-C$_3$), unsubstituted heteroalkyl (e.g., 2 to 8 membered, 2 to 5 membered, 2 to 3 membered), unsubstituted cycloalkyl (e.g., C$_3$-C$_8$, C$_3$-C$_5$, or C$_3$), unsubstituted heterocycloalkyl (e.g., 3 to 8 membered, 3 to 6 membered, or 4 membered), unsubstituted aryl (e.g., C$_5$-C$_8$, C$_5$-C$_6$, or phenyl), or unsubstituted heteroaryl (e.g., 5 to 8 membered, 5 to 6 membered, or 6 membered).

In embodiments, R$^4$ is substituted or unsubstituted alkyl, substituted or unsubstituted C$_1$-C$_8$ alkyl, substituted or unsubstituted C$_1$-C$_5$ alkyl, substituted or unsubstituted C$_1$-C$_3$ alkyl. In embodiments, R$^4$ is R$^{3a}$-substituted or unsubstituted alkyl, R$^{3a}$-substituted or unsubstituted C$_1$-C$_8$ alkyl, R$^{3a}$-substituted or unsubstituted C$_1$-C$_5$ alkyl, or R$^{3a}$-substituted or unsubstituted C$_1$-C$_3$ alkyl. In embodiments, R$^4$ is unsubstituted alkyl, unsubstituted C$_1$-C$_8$ alkyl, unsubstituted C$_1$-C$_5$ alkyl, or unsubstituted C$_1$-C$_3$ alkyl.

In embodiments, R$^4$ is substituted or unsubstituted heteroalkyl, substituted or unsubstituted 2 to 8 membered heteroalkyl, substituted or unsubstituted 2 to 5 membered heteroalkyl, substituted or unsubstituted 2 to 3 membered heteroalkyl. In embodiments, R$^4$ is R$^{4a}$-substituted or unsubstituted heteroalkyl, R$^{4a}$-substituted or unsubstituted 2 to 8 membered heteroalkyl, R$^{4a}$-substituted or unsubstituted 2 to 5 membered heteroalkyl, or R$^{4a}$-substituted or unsubstituted 2 to 3 membered heteroalkyl. In embodiments, R$^4$ is independently unsubstituted heteroalkyl, unsubstituted 2 to 8 membered heteroalkyl, unsubstituted 2 to 5 membered heteroalkyl, or unsubstituted 2 to 3 membered heteroalkyl.

In embodiments, R$^4$ is substituted or unsubstituted cycloalkyl, substituted or unsubstituted 3 to 8 membered cycloalkyl, substituted or unsubstituted 3 to 5 membered cycloalkyl, substituted or unsubstituted 3 membered cycloalkyl, substituted or unsubstituted 4 membered cycloalkyl, or substituted or unsubstituted 5 membered cycloalkyl. In embodiments, $R^4$ is $R^{4a}$-substituted or unsubstituted cycloalkyl, $R^{4a}$-substituted or unsubstituted 3 to 8 membered cycloalkyl, $R^{4a}$-substituted or unsubstituted 3 to 5 membered cycloalkyl, $R^{4a}$-substituted or unsubstituted 3 membered cycloalkyl, $R^{4a}$-substituted or unsubstituted 4 membered cycloalkyl, or $R^{4a}$-substituted or unsubstituted 5 membered cycloalkyl. In embodiments, $R^4$ is unsubstituted cycloalkyl, unsubstituted 3 to 8 membered cycloalkyl, unsubstituted 3 to 5 membered cycloalkyl, unsubstituted 3 membered cycloalkyl, unsubstituted 4 membered cycloalkyl, or unsubstituted 5 membered cycloalkyl.

In embodiments, $R^4$ is substituted or unsubstituted heterocycloalkyl, substituted or unsubstituted 3 to 6 membered heterocycloalkyl, substituted or unsubstituted 4 membered heterocycloalkyl, substituted or unsubstituted 5 membered heterocycloalkyl, or substituted or unsubstituted 6 membered heterocycloalkyl. In embodiments, $R^4$ is $R^{4a}$-substituted or unsubstituted heterocycloalkyl, $R^{4a}$-substituted or unsubstituted 3 to 6 membered heterocycloalkyl, $R^{4a}$-substituted or unsubstituted 4 membered heterocycloalkyl, $R^{4a}$-substituted or unsubstituted 5 membered heterocycloalkyl, or $R^{4a}$-substituted or unsubstituted 6 membered heterocycloalkyl. In embodiments, $R^4$ is unsubstituted heterocycloalkyl, unsubstituted 3 to 6 membered heterocycloalkyl, unsubstituted 4 membered heterocycloalkyl, unsubstituted 5 membered heterocycloalkyl, or unsubstituted 6 membered heterocycloalkyl.

In embodiments, $R^4$ is substituted or unsubstituted aryl, substituted or unsubstituted 5 to 6 membered aryl, substituted or unsubstituted 5 membered aryl, or substituted or unsubstituted 6 membered aryl. In embodiments, $R^4$ is $R^{4a}$-substituted or unsubstituted aryl, $R^{4a}$-substituted or unsubstituted 5 to 6 membered aryl, $R^{4a}$-substituted or unsubstituted 5 membered aryl, or $R^{4a}$-substituted or unsubstituted 6 membered aryl. In embodiments, $R^4$ is unsubstituted aryl, unsubstituted 5 to 6 membered aryl, unsubstituted 5 membered aryl, or unsubstituted 6 membered aryl.

In embodiments, $R^4$ is substituted or unsubstituted heteroaryl, substituted or unsubstituted 5 to 6 membered heteroaryl, substituted or unsubstituted 5 membered heteroaryl, or substituted or unsubstituted 6 membered heteroaryl. In embodiments, $R^4$ is $R^{4a}$-substituted or unsubstituted heteroaryl, $R^{4a}$-substituted or unsubstituted 5 to 6 membered heteroaryl, $R^{4a}$-substituted or unsubstituted 5 membered heteroaryl, or $R^{4a}$-substituted or unsubstituted 6 membered heteroaryl. In embodiments, $R^4$ is unsubstituted heteroaryl, unsubstituted 5 to 6 membered heteroaryl, unsubstituted 5 membered heteroaryl, or unsubstituted 6 membered heteroaryl.

In embodiments, $R^4$ is hydrogen, halogen (e.g. —F, —Cl, —Br, or —I), substituted or unsubstituted $C_1$-$C_8$ alkyl, substituted or unsubstituted $C_1$-$C_5$ alkyl, or substituted or unsubstituted $C_1$-$C_3$ alkyl. In embodiments, $R^4$ is hydrogen, halogen (e.g. —F, —Cl, —Br, or —I), $R^{4a}$-substituted or unsubstituted $C_1$-$C_8$ alkyl, $R^{4a}$-substituted or unsubstituted $C_1$-$C_5$ alkyl, or $R^{4a}$-substituted or unsubstituted $C_1$-$C_3$ alkyl. In embodiments, $R^4$ is hydrogen, halogen (e.g. —F, —Cl, —Br, or —I), unsubstituted $C_1$-$C_8$ alkyl, unsubstituted $C_1$-$C_5$ alkyl, or unsubstituted $C_1$-$C_3$ alkyl. In embodiments, $R^4$ is hydrogen, halogen (e.g. —F, —Cl, —Br, or —I), or $R^{4a}$-substituted or unsubstituted $C_1$-$C_8$ alkyl. In embodiments, $R^4$ is hydrogen, halogen (e.g. —F, —Cl, —Br, or —I), or $R^{4a}$-substituted or unsubstituted $C_1$-$C_5$ alkyl. In embodiments, $R^4$ is hydrogen, halogen (e.g. —F, —Cl, —Br, or —I), or $R^{4a}$-substituted or unsubstituted $C_1$-$C_3$ alkyl. In embodiments, $R^4$ is hydrogen, halogen (e.g. —F, —Cl, —Br, or —I), or unsubstituted $C_1$-$C_3$ alkyl. In embodiments, $R^4$ is hydrogen, or unsubstituted $C_1$-$C_3$ alkyl. In embodiments, $R^4$ is hydrogen. In embodiments, $R^4$ is unsubstituted methyl, unsubstituted ethyl, or unsubstituted propyl.

In embodiments, $R^4$ is hydrogen, halogen (e.g. —F, —Cl, —Br, or —I), —N$_3$, —CF$_3$, —CCl$_3$, —CBr$_3$, —CI$_3$, —CN, —CHO, —OR$^{33D}$, —NR$^{34D}$R$^{35D}$, —COOR$^{33D}$, —CONR$^{34D}$R$^{35D}$, —NO$_2$, —SR$^{36D}$, —SO$_{n4}$R$^{34D}$, —SO$_{n4}$OR$^{34D}$, —SO$_{n4}$NR$^{34D}$R$^{35D}$, —NHNR$^{34D}$R$^{35D}$, —ONR$^{34D}$R$^{35D}$, —NHC(O)NHNR$^{34D}$R$^{35D}$ (e.g., —OH, —OCH$_3$, —NH2, —NHCH$_3$, NCH$_3$NCH$_3$, —COOH, —COOCH$_3$, —CONH$_2$, —CONHCH$_3$, —NO$_2$, —SH, —SCH$_3$, —SOH, —SOCH$_3$, —SO$_2$H, —SO$_2$CH$_3$, —S(O)OH, —S(O)OCH$_3$, —S(O)$_2$H, S(O)$_2$OCH$_3$, —S(O)NH$_2$, —S(O)NHCH$_3$, —S(O)$_2$NH$_2$, S(O)$_2$NHCH$_3$, —NHNH$_2$, —NHNHCH$_3$, —NHNCH$_3$CH$_3$, —ONH$_2$, —ONHCH$_3$, —NHC(O)NHNH$_2$, or —NHC(O)NHNHCH$_3$, substituted or unsubstituted alkyl (e.g., $C_1$-$C_8$, $C_1$-$C_5$, or $C_1$-$C_3$), substituted or unsubstituted heteroalkyl (e.g., 2 to 8 membered, 2 to 5 membered, 2 to 3 membered), substituted or unsubstituted cycloalkyl (e.g., $C_3$-$C_8$, $C_3$-$C_5$, or $C_3$), substituted or unsubstituted heterocycloalkyl (e.g., 3 to 8 membered, 3 to 6 membered, or 4 membered), substituted or unsubstituted aryl (e.g., $C_5$-$C_8$, $C_5$-$C_6$, or phenyl), or substituted or unsubstituted heteroaryl (e.g., 5 to 8 membered, 5 to 6 membered, or 6 membered).

In embodiments, $R^4$ is hydrogen, halogen (e.g. —F, —Cl, —Br, or —I), —N$_3$, —CF$_3$, —CCl$_3$, —CBr$_3$, —CI$_3$, —CN, —CHO, —OR$^{33D}$, —NR$^{34D}$R$^{35D}$, —COOR$^{33D}$, —CONR$^{34D}$R$^{35D}$, —NO$_2$, —SR$^{36D}$, —SO$_{n4}$R$^{34D}$, —SO$_{n4}$OR$^{34D}$, —SO$_{n4}$NR$^{34D}$R$^{35D}$, —NHNR$^{34D}$R$^{35D}$, —ONR$^{34D}$R$^{35D}$, —NHC(O)NHNR$^{34D}$R$^{35D}$ (e.g., —OH, —OCH$_3$, —NH2, —NHCH$_3$, NCH$_3$NCH$_3$, —COOH, —COOCH$_3$, —CONH$_2$, —CONHCH$_3$, —NO$_2$, —SH, —SCH$_3$, —SOH, —SOCH$_3$, —SO$_2$H, —SO$_2$CH$_3$, —S(O)OH, —S(O)OCH$_3$, —S(O)$_2$H, S(O)$_2$OCH$_3$, —S(O)NH$_2$, —S(O)NHCH$_3$, —S(O)$_2$NH$_2$, S(O)$_2$NHCH$_3$, —NHNH$_2$, —NHNHCH$_3$, —NHNCH$_3$CH$_3$, —ONH$_2$, —ONHCH$_3$, —NHC(O)NHNH$_2$, or —NHC(O)NHNHCH$_3$), $R^{4a}$-substituted or unsubstituted alkyl (e.g., $C_1$-$C_8$, $C_1$-$C_5$, or $C_1$-$C_3$), $R^{4a}$-substituted or unsubstituted heteroalkyl (e.g., 2 to 8 membered, 2 to 5 membered, 2 to 3 membered), $R^{4a}$-substituted or unsubstituted cycloalkyl (e.g., $C_3$-$C_8$, $C_3$-$C_3$, or $C_3$), $R^{4a}$-substituted or unsubstituted heterocycloalkyl (e.g., 3 to 8 membered, 3 to 6 membered, or 4 membered), $R^{4a}$-substituted or unsubstituted aryl (e.g., $C_5$-$C_8$, $C_5$-$C_6$, or phenyl), or $R^{4a}$-substituted or unsubstituted heteroaryl (e.g., 5 to 8 membered, 5 to 6 membered, or 6 membered).

In embodiments, $R^4$ is hydrogen, halogen (e.g. —F, —Cl, —Br, or —I), —N$_3$, —CF$_3$, —CCl$_3$, —CBr$_3$, —CI$_3$, —CN, —CHO, —OR$^{33D}$, —NR$^{34D}$R$^{35D}$, —COOR$^{33D}$, —CONR$^{34D}$R$^{35D}$, —NO$_2$, —SR$^{36D}$, —SO$_{n4}$R$^{34D}$, —SO$_{n4}$OR$^{34D}$, —SO$_{n4}$NR$^{34D}$R$^{35D}$, —NHNR$^{34D}$R$^{35D}$, —ONR$^{34D}$R$^{35D}$, —NHC(O)NHNR$^{34D}$R$^{35D}$ (e.g., —OH, —OCH$_3$, —NH$_2$, —NHCH$_3$, NCH$_3$NCH$_3$, —COOH, —COOCH$_3$, —CONH$_2$, —CONHCH$_3$, —NO$_2$, —SH, —SCH$_3$, —SOH, —SOCH$_3$, —SO$_2$H, —SO$_2$CH$_3$, —S(O)OH, —S(O)OCH$_3$, —S(O)$_2$H, S(O)$_2$OCH$_3$, —S(O)NH$_2$, —S(O)NHCH$_3$, —S(O)$_2$NH$_2$, S(O)$_2$NHCH$_3$, —NHNH$_2$, —NHNHCH$_3$, —NHNCH$_3$CH$_3$, —ONH$_2$, —ONHCH$_3$, —NHC(O)NHNH$_2$, or —NHC(O)NHNHCH$_3$), unsubstituted alkyl (e.g., $C_1$-$C_8$, $C_1$-$C_5$, or $C_1$-$C_3$), unsubstituted heteroalkyl (e.g., 2 to 8 membered, 2 to 5 membered, 2 to 3 membered), unsubstituted cycloalkyl (e.g., $C_3$-$C_8$, $C_3$-$C_3$, or $C_3$), unsubstituted heterocycloalkyl (e.g., 3 to 8 membered, 3 to 6 membered, or 4 membered), unsubstituted aryl (e.g., $C_5$-$C_8$, $C_5$-$C_6$, or phenyl), or unsubstituted heteroaryl (e.g., 5 to 8 membered, 5 to 6 membered, or 6 membered).

In embodiments, $R^4$ is hydrogen, halogen (e.g. —F, —Cl, —Br, or —I), —OH, —OCH$_3$, —NH2, —NHCH$_3$, NCH$_3$NCH$_3$, —COOH, —COOCH$_3$, —CONH$_2$, —CONHCH$_3$, —NO$_2$, —SH, —SCH$_3$, —SOH, —SOCH$_3$, —SO$_2$H, —SO$_2$CH$_3$, —S(O)OH, —S(O)OCH$_3$, —S(O)$_2$H, S(O)$_2$OCH$_3$, —S(O)NH$_2$, —S(O)NHCH$_3$, —S(O)$_2$NH$_2$, S(O)$_2$NHCH$_3$, —NHNH$_2$, —NHNHCH$_3$, —NHNCH$_3$CH$_3$, —ONH$_2$, —ONHCH$_3$, —NHC(O)NHNH$_2$, or —NHC(O)NHNHCH$_3$), $R^{4a}$-substituted or unsubstituted $C_1$-$C_3$ alkyl, $R^{4a}$-substituted or unsubstituted 2 to 3 membered heteroalkyl, $R^{4a}$-substituted or unsubstituted $C_3$-$C_5$ cycloalkyl, $R^{4a}$-substituted or unsubstituted 5 to 6 membered heterocycloalkyl, $R^{4a}$-substituted or unsubstituted phenyl, or $R^{4a}$-substituted or unsubstituted 5 to 6 membered heteroaryl.

In embodiments, $R^4$ is hydrogen, —F, —Cl, —Br, —I, —OH, —OCH$_3$, —NH2, —NHCH$_3$, NCH$_3$NCH$_3$, —COOH, —COOCH$_3$, —CONH$_2$, —CONHCH$_3$, —NO$_2$, —SH, —SCH$_3$, —SOH, —SOCH$_3$, —SO$_2$H, —SO$_2$CH$_3$, —S(O)OH, —S(O)OCH$_3$, —S(O)$_2$H, S(O)$_2$OCH$_3$, —S(O)NH$_2$, —S(O)NHCH$_3$, —S(O)$_2$NH$_2$, S(O)$_2$NHCH$_3$, —NHNH$_2$, —NHNHCH$_3$, —NHNCH$_3$CH$_3$, —ONH$_2$, —ONHCH$_3$, —NHC(O)NHNH$_2$, or —NHC(O)NHNHCH$_3$), unsubstituted $C_1$-$C_3$ alkyl, unsubstituted 2 to 3 membered heteroalkyl, unsubstituted $C_3$-$C_5$ cycloalkyl, unsubstituted 5 to 6 membered heterocycloalkyl, unsubstituted phenyl, or unsubstituted 5 to 6 membered heteroaryl.

$R^{4a}$ is halogen (e.g. —F, —Cl, —Br, or —I), —N$_3$, —CF$_3$, —CCl$_3$, —CBr$_3$, —CI$_3$, —CN, —CHO, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC(O)NHNH$_2$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{12}$, $C_6$-$C_{10}$, or phenyl), or substituted or unsubstituted heteroaryl (e.g., 5 to 12 membered, 5 to 10 membered, 5 to 9 membered, or 5 to 6 membered). In embodiments, $R^{4a}$ is halogen (e.g. —F, —Cl, —Br, or —I), —N$_3$, —CF$_3$, —CCl$_3$, —CBr$_3$, —CI$_3$, —CN, —CHO, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC(O)NHNH$_2$, $R^{4b}$-substituted or unsubstituted alkyl (e.g., $C_1$-$C_8$, $C_1$-$C_6$, $C_1$-$C_4$, or $C_1$-$C_2$), $R^{4b}$-substituted or unsubstituted heteroalkyl (e.g., 2 to 8 membered, 2 to 6 membered, 4 to 6 membered, 2 to 3 membered, or 4 to 5 membered), $R^{4b}$-substituted or unsubstituted cycloalkyl (e.g., $C_3$-$C_8$, $C_3$-$C_6$, $C_4$-$C_6$, or $C_5$-$C_6$), $R^{4b}$-substituted or unsubstituted heterocycloalkyl (e.g., 3 to 8 membered, 3 to 6 membered, 4 to 6 membered, 4 to 5 membered, or 5 to 6 membered), $R^{4b}$-substituted or unsubstituted aryl (e.g., $C_6$-$C_{12}$, $C_6$-$C_{10}$, or phenyl), or $R^{4b}$-substituted or unsubstituted heteroaryl (e.g., 5 to 12 membered, 5 to 10 membered, 5 to 9 membered, or 5 to 6 membered). In embodiments, $R^{4a}$ is halogen (e.g. —F, —Cl, —Br, or —I), —N$_3$, —CF$_3$, —CCl$_3$, —CBr$_3$, —CI$_3$, —CN, —CHO, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC(O)NHNH$_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered).

$R^{4b}$ is halogen (e.g. —F, —Cl, —Br, or —I), —N$_3$, —CF$_3$, —CCl$_3$, —CBr$_3$, —CI$_3$, —CN, —CHO, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC(O)NHNH$_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered).

In embodiments, $R^3$ is hydrogen, halogen (e.g. —F, —Cl, —Br, or —I), or $R^{3a}$-substituted or unsubstituted $C_1$-$C_3$ alkyl, and $R^4$ is hydrogen, halogen (e.g. —F, —Cl, —Br, or —I), or $R^{4a}$-substituted or unsubstituted $C_1$-$C_3$ alkyl. In embodiments, $R^3$ is hydrogen, or unsubstituted $C_1$-$C_3$ alkyl, and $R^4$ is hydrogen, or unsubstituted $C_1$-$C_3$ alkyl. In embodiments, $R^3$ and $R^4$ are independently hydrogen, unsubstituted methyl, unsubstituted ethyl, or unsubstituted propyl. In embodiments, $R^3$ and $R^4$ are independently unsubstituted methyl, unsubstituted ethyl, or unsubstituted propyl. In embodiments, $R^3$ and $R^4$ are hydrogen.

In embodiments, $R^5$ is hydrogen, halogen (e.g. —F, —Cl, —Br, or —I), —N$_3$, —CF$_3$, —CCl$_3$, —CBr$_3$, —CI$_3$, —CN, —CHO, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC(O)NHNH$_2$. In embodiments, $R^5$ is halogen (e.g. —F, —Cl, —Br, or —I), —CHO, —COOH, —CONH$_2$, —SH, —NHNH$_2$, —ONH$_2$, —NHC(O)NHNH$_2$, substituted or unsubstituted alkyl (e.g., $C_1$-$C_8$, $C_1$-$C_5$, or $C_1$-$C_3$), or substituted or unsubstituted heteroalkyl (e.g., 2 to 8 membered, 2 to 5 membered, 2 to 3 membered). In embodiments, $R^5$ is halogen (e.g. —F, —Cl, —Br, or —I), —CHO, —COOH, —CONH$_2$, —SH, —NHNH$_2$, —ONH$_2$, —NHC(O)NHNH$_2$, $R^{5a}$-substituted or unsubstituted alkyl (e.g., $C_1$-$C_8$, $C_1$-$C_5$, or $C_1$-$C_3$), or $R^{5a}$-substituted or unsubstituted heteroalkyl (e.g., 2 to 8 membered, 2 to 5 membered, 2 to 3 membered).

In embodiments, $R^5$ is substituted or unsubstituted alkyl (e.g., $C_1$-$C_8$, $C_1$-$C_5$, or $C_1$-$C_3$), substituted or unsubstituted heteroalkyl (e.g., 2 to 8 membered, 2 to 5 membered, 2 to 3 membered), substituted or unsubstituted cycloalkyl (e.g., $C_3$-$C_8$, $C_3$-$C_5$, or $C_3$), substituted or unsubstituted heterocycloalkyl (e.g., 3 to 8 membered, 3 to 6 membered, or 4 membered), substituted or unsubstituted aryl (e.g., $C_5$-$C_8$, $C_5$-$C_6$, or phenyl), or substituted or unsubstituted heteroaryl (e.g., 5 to 8 membered, 5 to 6 membered, or 6 membered). In embodiments, $R^5$ is $R^{5a}$-substituted or unsubstituted alkyl (e.g., $C_1$-$C_8$, $C_1$-$C_5$, or $C_1$-$C_3$), $R^{5a}$-substituted or unsubstituted heteroalkyl (e.g., 2 to 8 membered, 2 to 5 membered, 2 to 3 membered), $R^{5a}$-substituted or unsubstituted cycloalkyl (e.g., $C_3$-$C_8$, $C_3$-$C_5$, or $C_3$), $R^{5a}$-substituted or unsubstituted heterocycloalkyl (e.g., 3 to 8 membered, 3 to 6 membered, or 4 membered), $R^{5a}$-substituted or unsubstituted aryl (e.g., $C_5$-$C_8$, $C_5$-$C_6$, or phenyl), or $R^{5a}$-substituted or unsubstituted heteroaryl (e.g., 5 to 8 membered, 5 to 6 membered, or 6 membered). In embodiments, $R^5$ is unsubstituted alkyl (e.g., $C_1$-$C_8$, $C_1$-$C_5$, or $C_1$-$C_3$), unsubstituted heteroalkyl (e.g., 2 to 8 membered, 2 to 5 membered, 2 to 3 membered), unsubstituted cycloalkyl (e.g., $C_3$-$C_8$, $C_3$-$C_5$, or C$_3$), unsubstituted heterocycloalkyl (e.g., 3 to 8 membered, 3 to 6 membered, or 4 membered), unsubstituted aryl (e.g., C$_5$-C$_8$, C$_5$-C$_6$, or phenyl), or unsubstituted heteroaryl (e.g., 5 to 8 membered, 5 to 6 membered, or 6 membered).

In embodiments, R$^5$ is substituted or unsubstituted C$_1$-C$_8$ alkyl, substituted or unsubstituted 2 to 8 membered heteroalkyl, substituted or unsubstituted 3 to 8 membered cycloalkyl, substituted or unsubstituted 3 to 8 membered heterocycloalkyl, substituted or unsubstituted 5 to 8 membered aryl, or substituted or unsubstituted 5 to 8 membered heteroaryl. In embodiments, R$^5$ is R$^{5a}$-substituted or unsubstituted C$_1$-C$_8$ alkyl, R$^{5a}$-substituted or unsubstituted 2 to 8 membered heteroalkyl, R$^{5a}$-substituted or unsubstituted 3 to 8 membered cycloalkyl, R$^{5a}$-substituted or unsubstituted 3 to 8 membered heterocycloalkyl, R$^{5a}$-substituted or unsubstituted 5 to 8 membered aryl, or R$^{5a}$-substituted or unsubstituted 5 to 8 membered heteroaryl. In embodiments, R$^5$ is unsubstituted C$_1$-C$_8$ alkyl, unsubstituted 2 to 8 membered heteroalkyl, unsubstituted 3 to 8 membered cycloalkyl, unsubstituted 3 to 8 membered heterocycloalkyl, unsubstituted 5 to 8 membered aryl, or unsubstituted 5 to 8 membered heteroaryl.

In embodiments, R$^5$ is substituted or unsubstituted C$_1$-C$_5$ alkyl, substituted or unsubstituted 2 to 5 membered heteroalkyl, substituted or unsubstituted 3 to 5 membered cycloalkyl, substituted or unsubstituted 3 to 6 membered heterocycloalkyl, substituted or unsubstituted 5 to 6 membered aryl, or substituted or unsubstituted 5 to 6 membered heteroaryl. In embodiments, R$^5$ is R$^{5a}$-substituted or unsubstituted C$_1$-C$_5$ alkyl, R$^{5a}$-substituted or unsubstituted 2 to 5 membered heteroalkyl, R$^{5a}$-substituted or unsubstituted 3 to 5 membered cycloalkyl, R$^{5a}$-substituted or unsubstituted 3 to 6 membered heterocycloalkyl, R$^{5a}$-substituted or unsubstituted 5 to 6 membered aryl, or R$^{5a}$-substituted or unsubstituted 5 to 6 membered heteroaryl. In embodiments, R$^5$ is unsubstituted C$_1$-C$_5$ alkyl, unsubstituted 2 to 5 membered heteroalkyl, unsubstituted 3 to 5 membered cycloalkyl, unsubstituted 3 to 6 membered heterocycloalkyl, unsubstituted 5 to 6 membered aryl, or unsubstituted 5 to 6 membered heteroaryl.

In embodiments, R$^5$ is substituted or unsubstituted C$_1$-C$_3$ alkyl or substituted or unsubstituted 2 to 3 membered heteroalkyl. In embodiments, R$^5$ is substituted or unsubstituted 3 membered cycloalkyl, substituted or unsubstituted 4 membered cycloalkyl, or substituted or unsubstituted 5 membered cycloalkyl. In embodiments, R$^5$ is substituted or unsubstituted 4 membered heterocycloalkyl, substituted or unsubstituted 5 membered heterocycloalkyl, or substituted or unsubstituted 6 membered heterocycloalkyl. In embodiments, R$^5$ is substituted or unsubstituted 5 membered aryl, substituted or unsubstituted 6 membered aryl, substituted or unsubstituted 5 membered heteroaryl, or substituted or unsubstituted 6 membered heteroaryl. In embodiments, R$^5$ is R$^{5a}$-substituted or unsubstituted C$_1$-C$_3$ alkyl or R$^{5a}$-substituted or unsubstituted 2 to 3 membered heteroalkyl. In embodiments, R$^5$ is R$^{5a}$-substituted or unsubstituted 3 membered cycloalkyl, R$^{5a}$-substituted or unsubstituted 4 membered cycloalkyl, or R$^{5a}$-substituted or unsubstituted 5 membered cycloalkyl. In embodiments, R$^5$ is R$^{5a}$-substituted or unsubstituted 4 membered heterocycloalkyl, R$^{5a}$-substituted or unsubstituted 5 membered heterocycloalkyl, or R$^{5a}$-substituted or unsubstituted 6 membered heterocycloalkyl. In embodiments, R$^5$ is R$^{5a}$-substituted or unsubstituted 5 membered aryl, R$^{5a}$-substituted or unsubstituted 6 membered aryl, R$^{5a}$-substituted or unsubstituted 5 membered heteroaryl, or R$^{5a}$-substituted or unsubstituted 6 membered heteroaryl. In embodiments, R$^5$ is unsubstituted C$_1$-C$_3$ alkyl or unsubstituted 2 to 3 membered heteroalkyl. In embodiments, R$^5$ is or unsubstituted 3 membered cycloalkyl, or unsubstituted 4 membered cycloalkyl, or unsubstituted 5 membered cycloalkyl. In embodiments, R$^5$ is or unsubstituted 4 membered heterocycloalkyl, or unsubstituted 5 membered heterocycloalkyl, or unsubstituted 6 membered heterocycloalkyl. In embodiments, R$^5$ is or unsubstituted 5 membered aryl, or unsubstituted 6 membered aryl, or unsubstituted 5 membered heteroaryl, or unsubstituted 6 membered heteroaryl.

In embodiments, R$^5$ is hydrogen, halogen (e.g. —F, —Cl, —Br, or —I), —N$_3$, —CF$_3$, —CCl$_3$, —CBr$_3$, —CI$_3$, —CN, —CHO, —OR$^{33E}$, —NR$^{34E}$R$^{35E}$, —COOR$^{33E}$, —CONR$^{34E}$R$^{35E}$, —NO$_2$, —SR$^{36E}$, —SO$_{n5}$R$^{34E}$, —SO$_{n5}$OR$^{34E}$, —SO$_{n5}$NR$^{34E}$R$^{35E}$, —NHNR$^{34E}$R$^{35E}$, —ONR$^{34E}$R$^{35E}$, —NHC(O)NHNR$^{34E}$R$^{35E}$ (e.g., —OH, —OCH$_3$, —NH2, —NHCH$_3$, NCH$_3$NCH$_3$, —COOH, —COOCH$_3$, —CONH$_2$, —CONHCH$_3$, —NO$_2$, —SH, —SCH$_3$, —SOH, —SOCH$_3$, —SO$_2$H, —SO$_2$CH$_3$, —S(O)OH, —S(O)OCH$_3$, —S(O)$_2$H, S(O)$_2$OCH$_3$, —S(O)NH$_2$, —S(O)NHCH$_3$, —S(O)$_2$NH$_2$, S(O)$_2$NHCH$_3$, —NHNH$_2$, —NHNHCH$_3$, —NHNCH$_3$CH$_3$, —ONH$_2$, —ONHCH$_3$, —NHC(O)NHNH$_2$, or —NHC(O)NHNHCH$_3$), substituted or unsubstituted alkyl (e.g., C$_1$-C$_8$, C$_1$-C$_5$, or C$_1$-C$_3$), substituted or unsubstituted heteroalkyl (e.g., 2 to 8 membered, 2 to 5 membered, 2 to 3 membered), substituted or unsubstituted cycloalkyl (e.g., C$_3$-C$_8$, C$_3$-C$_5$, or C$_3$), substituted or unsubstituted heterocycloalkyl (e.g., 3 to 8 membered, 3 to 6 membered, or 4 membered), substituted or unsubstituted aryl (e.g., C$_5$-C$_8$, C$_5$-C$_6$, or phenyl), or substituted or unsubstituted heteroaryl (e.g., 5 to 8 membered, 5 to 6 membered, or 6 membered).

In embodiments, R$^5$ is hydrogen, halogen (e.g. —F, —Cl, —Br, or —I), —N$_3$, —CF$_3$, —CCl$_3$, —CBr$_3$, —CI$_3$, —CN, —CHO, —OR$^{33E}$, —NR$^{34E}$R$^{35E}$, —COOR$^{33E}$, —CONR$^{34E}$R$^{35E}$, —NO$_2$, —SR$^{36E}$, —SO$_{n5}$R$^{34E}$, —SO$_{n5}$OR$^{34E}$, —SO$_{n5}$NR$^{34E}$R$^{35E}$, —NHNR$^{34E}$R$^{35E}$, —ONR$^{34E}$R$^{35E}$, —NHC(O)NHNR$^{34E}$R$^{35E}$ (e.g., —OH, —OCH$_3$, —NH2, —NHCH$_3$, NCH$_3$NCH$_3$, —COOH, —COOCH$_3$, —CONH$_2$, —CONHCH$_3$, —NO$_2$, —SH, —SCH$_3$, —SOH, —SOCH$_3$, —SO$_2$H, —SO$_2$CH$_3$, —S(O)OH, —S(O)OCH$_3$, —S(O)$_2$H, S(O)$_2$OCH$_3$, —S(O)NH$_2$, —S(O)NHCH$_3$, —S(O)$_2$NH$_2$, S(O)$_2$NHCH$_3$, —NHNH$_2$, —NHNHCH$_3$, —NHNCH$_3$CH$_3$, —ONH$_2$, —ONHCH$_3$, —NHC(O)NHNH$_2$, or —NHC(O)NHNHCH$_3$), R$^{5a}$-substituted or unsubstituted alkyl (e.g., C$_1$-C$_8$, C$_1$-C$_5$, or C$_1$-C$_3$), R$^{5a}$-substituted or unsubstituted heteroalkyl (e.g., 2 to 8 membered, 2 to 5 membered, 2 to 3 membered), R$^{5a}$-substituted or unsubstituted cycloalkyl (e.g., C$_3$-C$_8$, C$_3$-C$_5$, or C$_3$), R$^{5a}$-substituted or unsubstituted heterocycloalkyl (e.g., 3 to 8 membered, 3 to 6 membered, or 4 membered), R$^{5a}$-substituted or unsubstituted aryl (e.g., C$_5$-C$_8$, C$_5$-C$_6$, or phenyl), or R$^{5a}$-substituted or unsubstituted heteroaryl (e.g., 5 to 8 membered, 5 to 6 membered, or 6 membered).

In embodiments, R$^5$ is hydrogen, halogen (e.g. —F, —Cl, —Br, or —I), —N$_3$, —CF$_3$, —CCl$_3$, —CBr$_3$, —CI$_3$, —CN, —CHO, —OR$^{33E}$, —NR$^{34E}$R$^{35E}$, —COOR$^{33E}$, —CONR$^{34E}$R$^{35E}$, —NO$_2$, —SR$^{36E}$, —SO$_{n5}$R$^{34E}$, —SO$_{n5}$OR$^{34E}$, —SO$_{n5}$NR$^{34E}$R$^{35E}$, —NHNR$^{34E}$R$^{35E}$, —ONR$^{34E}$R$^{35E}$, —NHC(O)NHNR$^{34E}$R$^{35E}$ (e.g., —OH, —OCH$_3$, —NH2, —NHCH$_3$, NCH$_3$NCH$_3$, —COOH, —COOCH$_3$, —CONH$_2$, —CONHCH$_3$, —NO$_2$, —SH, —SCH$_3$, —SOH, —SOCH$_3$, —SO$_2$H, —SO$_2$CH$_3$, —S(O)OH, —S(O)OCH$_3$, —S(O)$_2$H, S(O)$_2$OCH$_3$, —S(O)NH$_2$, —S(O)NHCH$_3$, —S(O)$_2$NH$_2$, S(O)$_2$NHCH$_3$, —NHNH$_2$, —NHNHCH$_3$, —NHNCH$_3$CH$_3$, —ONH$_2$, —ONHCH$_3$, —NHC(O)NHNH$_2$, or —NHC(O)NHNHCH$_3$), unsubstituted alkyl (e.g., $C_1$-$C_8$, $C_1$-$C_5$, or $C_1$-$C_3$), unsubstituted heteroalkyl (e.g., 2 to 8 membered, 2 to 5 membered, 2 to 3 membered), unsubstituted cycloalkyl (e.g., $C_3$-$C_8$, $C_3$-$C_3$, or $C_3$), unsubstituted heterocycloalkyl (e.g., 3 to 8 membered, 3 to 6 membered, or 4 membered), unsubstituted aryl (e.g., $C_5$-$C_8$, $C_5$-$C_6$, or phenyl), or unsubstituted heteroaryl (e.g., 5 to 8 membered, 5 to 6 membered, or 6 membered).

In embodiments, $R^5$ is hydrogen, halogen (e.g. —F, —Cl, —Br, or —I), —OH, —OCH$_3$, —NH2, —NHCH$_3$, NCH$_3$NCH$_3$, —COOH, —COOCH$_3$, —CONH$_2$, —CONHCH$_3$, —NO$_2$, —SH, —SCH$_3$, —SOH, —SOCH$_3$, —SO$_2$H, —SO$_2$CH$_3$, —S(O)OH, —S(O)OCH$_3$, —S(O)$_2$H, S(O)$_2$OCH$_3$, —S(O)NH$_2$, —S(O)NHCH$_3$, —S(O)$_2$NH$_2$, S(O)$_2$NHCH$_3$, —NHNH$_2$, —NHNHCH$_3$, —NHNCH$_3$CH$_3$, —ONH$_2$, —ONHCH$_3$, —NHC(O)NHNH$_2$, or —NHC(O)NHNHCH$_3$), $R^{5a}$-substituted or unsubstituted $C_1$-$C_3$ alkyl, $R^{5a}$-substituted or unsubstituted 2 to 3 membered heteroalkyl, $R^5$-substituted or unsubstituted $C_3$-$C_5$ cycloalkyl, $R^{5a}$-substituted or unsubstituted 5 to 6 membered heterocycloalkyl, $R^{5a}$-substituted or unsubstituted phenyl, or $R^{5a}$-substituted or unsubstituted 5 to 6 membered heteroaryl.

In embodiments, $R^5$ is hydrogen, —F, —Cl, —Br, —I, —OH, —OCH$_3$, —NH2, —NHCH$_3$, NCH$_3$NCH$_3$, —COOH, —COOCH$_3$, —CONH$_2$, —CONHCH$_3$, —NO$_2$, —SH, —SCH$_3$, —SOH, —SOCH$_3$, —SO$_2$H, —SO$_2$CH$_3$, —S(O)OH, —S(O)OCH$_3$, —S(O)$_2$H, S(O)$_2$OCH$_3$, —S(O)NH$_2$, —S(O)NHCH$_3$, —S(O)$_2$NH$_2$, S(O)$_2$NHCH$_3$, —NHNH$_2$, —NHNHCH$_3$, —NHNCH$_3$CH$_3$, —ONH$_2$, —ONHCH$_3$, —NHC(O)NHNH$_2$, or —NHC(O)NHNHCH$_3$), unsubstituted $C_1$-$C_3$ alkyl, unsubstituted 2 to 3 membered heteroalkyl, unsubstituted $C_3$-$C_5$ cycloalkyl, unsubstituted 5 to 6 membered heterocycloalkyl, unsubstituted phenyl, or unsubstituted 5 to 6 membered heteroaryl.

$R^{5a}$ is halogen (e.g. —F, —Cl, —Br, or —I), —N$_3$, —CF$_3$, —CCl$_3$, —CBr$_3$, —CI$_3$, —CN, —CHO, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC(O)NHNH$_2$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{12}$, $C_6$-$C_{10}$, or phenyl), or substituted or unsubstituted heteroaryl (e.g., 5 to 12 membered, 5 to 10 membered, 5 to 9 membered, or 5 to 6 membered). In embodiments, $R^{5a}$ is halogen (e.g. —F, —Cl, —Br, or —I), —N$_3$, —CF$_3$, —CCl$_3$, —CBr$_3$, —CI$_3$, —CN, —CHO, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC(O)NHNH$_2$, $R^{5b}$-substituted or unsubstituted alkyl (e.g., $C_1$-$C_8$, $C_1$-$C_6$, $C_1$-$C_4$, or $C_1$-$C_2$), $R^{5b}$-substituted or unsubstituted heteroalkyl (e.g., 2 to 8 membered, 2 to 6 membered, 4 to 6 membered, 2 to 3 membered, or 4 to 5 membered), $R^{5b}$-substituted or unsubstituted cycloalkyl (e.g., $C_3$-$C_8$, $C_3$-$C_6$, $C_4$-$C_6$, or $C_5$-$C_6$), $R^{5b}$-substituted or unsubstituted heterocycloalkyl (e.g., 3 to 8 membered, 3 to 6 membered, 4 to 6 membered, 4 to 5 membered, or 5 to 6 membered), $R^{5b}$-substituted or unsubstituted aryl (e.g., $C_6$-$C_{12}$, $C_6$-$C_{10}$, or phenyl), or $R^{5b}$-substituted or unsubstituted heteroaryl (e.g., 5 to 12 membered, 5 to 10 membered, 5 to 9 membered, or 5 to 6 membered). In embodiments, $R^{5a}$ is halogen (e.g. —F, —Cl, —Br, or —I), —N$_3$, —CF$_3$, —CCl$_3$, —CBr$_3$, —CI$_3$, —CN, —CHO, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC(O)NHNH$_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered).

$R^{5b}$ is halogen (e.g. —F, —Cl, —Br, or —I), —N$_3$, —CF$_3$, —CCl$_3$, —CBr$_3$, —CI$_3$, —CN, —CHO, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC(O)NHNH$_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered).

In embodiments, $R^5$ is $R^{5a}$-substituted or unsubstituted $C_1$-$C_8$ alkyl, $R^{5a}$-substituted or unsubstituted 2 to 8 membered heteroalkyl, unsubstituted 3 to 5 membered cycloalkyl, or unsubstituted 3 to 5 membered heterocycloalkyl. In embodiments, $R^5$ is unsubstituted $C_1$-$C_8$ alkyl. In embodiments, $R^5$ is unsubstituted methyl, unsubstituted ethyl, or unsubstituted propyl. In embodiments, $R^5$ is methyl, ethyl, or propyl. In embodiments, $R^5$ is unsubstituted methyl. In embodiments, $R^5$ is unsubstituted ethyl. In embodiments, $R^5$ is unsubstituted propyl. In embodiments, $R^5$ is unsubstituted allyl. In embodiments, $R^5$ is $R^{5a}$-substituted alkyl. In embodiments, $R^{5a}$ is unsubstituted 5 or 6 membered heterocycloalkyl. In embodiments, $R^{5a}$ is unsubstituted morpholino. In embodiments, $R^5$ is substituted or unsubstituted 2 to 8 membered heteroalkyl. In embodiments, $R^5$ is —(CH$_2$)$_3$N(CH$_3$)$_3$. In embodiments, $R^5$ is unsubstituted 3 to 5 membered cycloalkyl. In embodiments, $R^5$ is unsubstituted cyclopropane.

In embodiments, $R^6$ is hydrogen, halogen (e.g. —F, —Cl, —Br, or —I), —N$_3$, —CF$_3$, —CCl$_3$, —CBr$_3$, —CI$_3$, —CN, —CHO, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC(O)NHNH$_2$. In embodiments, $R^6$ is hydrogen, halogen (e.g. —F, —Cl, —Br, or —I), —CF$_3$, —CCl$_3$, —CBr$_3$, —CI$_3$, —CN, —CHO, —OH, —NH$_2$, —COOH, —CONH$_2$, —NO$_2$, —SH, or substituted or unsubstituted alkyl (e.g., $C_1$-$C_8$, $C_1$-$C_5$, or $C_1$-$C_3$), or substituted or unsubstituted heteroalkyl (e.g., 2 to 8 membered, 2 to 5 membered, 2 to 3 membered). In embodiments, $R^6$ is halogen (e.g. —F, —Cl, —Br, or —I), —CHO, —COOH, —CONH$_2$, —SH, —NHNH$_2$, —ONH$_2$, —NHC(O)NHNH$_2$, $R^{6a}$-substituted or unsubstituted alkyl (e.g., $C_1$-$C_8$, $C_1$-$C_5$, or $C_1$-$C_3$), or $R^{6a}$-substituted or unsubstituted heteroalkyl (e.g., 2 to 8 membered, 2 to 5 membered, 2 to 3 membered).

In embodiments, $R^6$ is substituted or unsubstituted alkyl (e.g., $C_1$-$C_8$, $C_1$-$C_5$, or $C_1$-$C_3$), substituted or unsubstituted heteroalkyl (e.g., 2 to 8 membered, 2 to 5 membered, 2 to 3 membered), substituted or unsubstituted cycloalkyl (e.g., $C_3$-$C_8$, $C_3$-$C_5$, or $C_3$), substituted or unsubstituted heterocycloalkyl (e.g., 3 to 8 membered, 3 to 6 membered, or 4 membered), substituted or unsubstituted aryl (e.g., $C_5$-$C_8$, $C_5$-$C_6$, or phenyl), or substituted or unsubstituted heteroaryl (e.g., 5 to 8 membered, 5 to 6 membered, or 6 membered). In embodiments, $R^6$ is $R^{6a}$-substituted or unsubstituted alkyl (e.g., $C_1$-$C_8$, $C_1$-$C_5$, or $C_1$-$C_3$), $R^{6a}$-substituted or unsubstituted heteroalkyl (e.g., 2 to 8 membered, 2 to 5 membered, 2 to 3 membered), $R^{6a}$-substituted or unsubstituted cycloalkyl (e.g., $C_3$-$C_8$, $C_3$-$C_5$, or $C_3$), $R^{6a}$-substituted or unsubstituted heterocycloalkyl (e.g., 3 to 8 membered, 3 to 6 membered, or 4 membered), $R^{6a}$-substituted or unsubstituted aryl (e.g., $C_5$-$C_8$, $C_5$-$C_6$, or phenyl), or $R^{6a}$-substituted or unsubstituted heteroaryl (e.g., 5 to 8 membered, 5 to 6 membered, or 6 membered). In embodiments, $R^6$ is unsubstituted alkyl (e.g., $C_1$-$C_8$, $C_1$-$C_5$, or $C_1$-$C_3$), unsubstituted heteroalkyl (e.g., 2 to 8 membered, 2 to 5 membered, 2 to 3 membered), unsubstituted cycloalkyl (e.g., $C_3$-$C_8$, $C_3$-$C_5$, or $C_3$), unsubstituted heterocycloalkyl (e.g., 3 to 8 membered, 3 to 6 membered, or 4 membered), unsubstituted aryl (e.g., $C_5$-$C_8$, $C_5$-$C_6$, or phenyl), or unsubstituted heteroaryl (e.g., 5 to 8 membered, 5 to 6 membered, or 6 membered).

In embodiments, $R^6$ is substituted or unsubstituted $C_1$-$C_8$ alkyl, substituted or unsubstituted 2 to 8 membered heteroalkyl, substituted or unsubstituted 3 to 8 membered cycloalkyl, substituted or unsubstituted 3 to 8 membered heterocycloalkyl, substituted or unsubstituted 5 to 8 membered aryl, or substituted or unsubstituted 5 to 8 membered heteroaryl. In embodiments, $R^6$ is $R^{6a}$-substituted or unsubstituted $C_1$-$C_8$ alkyl, $R^{6a}$-substituted or unsubstituted 2 to 8 membered heteroalkyl, $R^{6a}$-substituted or unsubstituted 3 to 8 membered cycloalkyl, $R^{6a}$-substituted or unsubstituted 3 to 8 membered heterocycloalkyl, $R^{6a}$-substituted or unsubstituted 5 to 8 membered aryl, or $R^{6a}$-substituted or unsubstituted 5 to 8 membered heteroaryl. In embodiments, $R^6$ is unsubstituted $C_1$-$C_8$ alkyl, unsubstituted 2 to 8 membered heteroalkyl, unsubstituted 3 to 8 membered cycloalkyl, unsubstituted 3 to 8 membered heterocycloalkyl, unsubstituted 5 to 8 membered aryl, or unsubstituted 5 to 8 membered heteroaryl.

In embodiments, $R^6$ is substituted or unsubstituted $C_1$-$C_5$ alkyl, substituted or unsubstituted 2 to 5 membered heteroalkyl, substituted or unsubstituted 3 to 5 membered cycloalkyl, substituted or unsubstituted 3 to 6 membered heterocycloalkyl, substituted or unsubstituted 5 to 6 membered aryl, or substituted or unsubstituted 5 to 6 membered heteroaryl. In embodiments, $R^6$ is $R^{6a}$-substituted or unsubstituted $C_1$-$C_5$ alkyl, $R^{6a}$-substituted or unsubstituted 2 to 5 membered heteroalkyl, $R^{6a}$-substituted or unsubstituted 3 to 5 membered cycloalkyl, $R^{6a}$-substituted or unsubstituted 3 to 6 membered heterocycloalkyl, $R^{6a}$-substituted or unsubstituted 5 to 6 membered aryl, or $R^{6a}$-substituted or unsubstituted 5 to 6 membered heteroaryl. In embodiments, $R^6$ is unsubstituted $C_1$-$C_5$ alkyl, unsubstituted 2 to 5 membered heteroalkyl, unsubstituted 3 to 5 membered cycloalkyl, unsubstituted 3 to 6 membered heterocycloalkyl, unsubstituted 5 to 6 membered aryl, or unsubstituted 5 to 6 membered heteroaryl.

In embodiments, $R^6$ is substituted or unsubstituted $C_1$-$C_3$ alkyl or substituted or unsubstituted 2 to 3 membered heteroalkyl. In embodiments, $R^6$ is substituted or unsubstituted 3 membered cycloalkyl, substituted or unsubstituted 4 membered cycloalkyl, or substituted or unsubstituted 5 membered cycloalkyl. In embodiments, $R^6$ is substituted or unsubstituted 4 membered heterocycloalkyl, substituted or unsubstituted 5 membered heterocycloalkyl, or substituted or unsubstituted 6 membered heterocycloalkyl. In embodiments, $R^6$ is substituted or unsubstituted 5 membered aryl, substituted or unsubstituted 6 membered aryl, substituted or unsubstituted 5 membered heteroaryl, or substituted or unsubstituted 6 membered heteroaryl. In embodiments, $R^6$ is $R^{6a}$-substituted or unsubstituted $C_1$-$C_3$ alkyl or $R^{6a}$-substituted or unsubstituted 2 to 3 membered heteroalkyl. In embodiments, $R^6$ is $R^{6a}$-substituted or unsubstituted 3 membered cycloalkyl, $R^{6a}$-substituted or unsubstituted 4 membered cycloalkyl, or $R^{6a}$-substituted or unsubstituted 5 membered cycloalkyl. In embodiments, $R^6$ is $R^{6a}$-substituted or unsubstituted 4 membered heterocycloalkyl, $R^{6a}$-substituted or unsubstituted 5 membered heterocycloalkyl, or $R^{6a}$-substituted or unsubstituted 6 membered heterocycloalkyl. In embodiments, $R^6$ is $R^{6a}$-substituted or unsubstituted 5 membered aryl, $R^{6a}$-substituted or unsubstituted 6 membered aryl, $R^{6a}$-substituted or unsubstituted 5 membered heteroaryl, or $R^{6a}$-substituted or unsubstituted 6 membered heteroaryl. In embodiments, $R^6$ is unsubstituted $C_1$-$C_3$ alkyl or unsubstituted 2 to 3 membered heteroalkyl. In embodiments, $R^6$ is or unsubstituted 3 membered cycloalkyl, or unsubstituted 4 membered cycloalkyl, or unsubstituted 5 membered cycloalkyl. In embodiments, $R^6$ is or unsubstituted 4 membered heterocycloalkyl, or unsubstituted 5 membered heterocycloalkyl, or unsubstituted 6 membered heterocycloalkyl. In embodiments, $R^6$ is or unsubstituted 5 membered aryl, or unsubstituted 6 membered aryl, or unsubstituted 5 membered heteroaryl, or unsubstituted 6 membered heteroaryl.

In embodiments, $R^6$ is hydrogen, halogen (e.g. —F, —Cl, —Br, or —I), —$N_3$, —$CF_3$, —$CCl_3$, —$CBr_3$, —$CI_3$, —CN, —CHO, —$OR^{33F}$, —$NR^{34F}R^{35F}$, —$COOR^{33F}$, —$CONR^{34F}R^{35F}$, —$NO_2$, —$SR^{36F}$, —$SO_{n6}R^{34F}$, —$SO_{n6}OR^{34F}$, —$SO_{n6}NR^{34F}R^{35F}$, —$NHNR^{34F}R^{35F}$, —$ONR^{34F}R^{35F}$, —NHC(O)NHN$R^{34F}R^{35F}$ (e.g., —OH, —$OCH_3$, —$NH2$, —$NHCH_3$, $NCH_3NCH_3$, —COOH, —$COOCH_3$, —$CONH_2$, —$CONHCH_3$, —$NO_2$, —SH, —$SCH_3$, —SOH, —$SOCH_3$, —$SO_2H$, —$SO_2CH_3$, —S(O)OH, —S(O)$OCH_3$, —$S(O)_2H$, $S(O)_2OCH_3$, —$S(O)NH_2$, —$S(O)NHCH_3$, —$S(O)_2NH_2$, $S(O)_2NHCH_3$, —$NHNH_2$, —$NHNHCH_3$, —$NHNCH_3CH_3$, —$ONH_2$, —$ONHCH_3$, —NHC(O)$NHNH_2$, or —NHC(O)$NHNHCH_3$), substituted or unsubstituted alkyl (e.g., $C_1$-$C_8$, $C_1$-$C_5$, or $C_1$-$C_3$), substituted or unsubstituted heteroalkyl (e.g., 2 to 8 membered, 2 to 5 membered, 2 to 3 membered), substituted or unsubstituted cycloalkyl (e.g., $C_3$-$C_8$, $C_3$-$C_5$, or $C_3$), substituted or unsubstituted heterocycloalkyl (e.g., 3 to 8 membered, 3 to 6 membered, or 4 membered), substituted or unsubstituted aryl (e.g., $C_5$-$C_8$, $C_5$-$C_6$, or phenyl), or substituted or unsubstituted heteroaryl (e.g., 5 to 8 membered, 5 to 6 membered, or 6 membered).

In embodiments, $R^6$ is hydrogen, halogen (e.g. —F, —Cl, —Br, or —I), —$N_3$, —$CF_3$, —$CCl_3$, —$CBr_3$, —$CI_3$, —CN, —CHO, —$OR^{33F}$, —$NR^{34F}R^{35F}$, —$COOR^{33F}$, —$CONR^{34F}R^{35F}$, —$NO_2$, —$SR^{36F}$, —$SO_{n6}R^{34F}$, —$SO_{n6}OR^{34F}$, —$SO_{n6}NR^{34F}R^{35F}$, —$NHNR^{34F}R^{35F}$, —$ONR^{34F}R^{35F}$, —NHC(O)NHN$R^{34F}R^{35F}$ (e.g., —OH, —$OCH_3$, —$NH2$, —$NHCH_3$, $NCH_3NCH_3$, —COOH, —$COOCH_3$, —$CONH_2$, —$CONHCH_3$, —$NO_2$, —SH, —$SCH_3$, —SOH, —$SOCH_3$, —$SO_2H$, —$SO_2CH_3$, —S(O)OH, —S(O)$OCH_3$, —$S(O)_2H$, $S(O)_2OCH_3$, —$S(O)NH_2$, —$S(O)NHCH_3$, —$S(O)_2NH_2$, $S(O)_2NHCH_3$, —$NHNH_2$, —$NHNHCH_3$, —$NHNCH_3CH_3$, —$ONH_2$, —$ONHCH_3$, —NHC(O)$NHNH_2$, or —NHC(O)$NHNHCH_3$), $R^{6a}$-substituted or unsubstituted alkyl (e.g., $C_1$-$C_8$, $C_1$-$C_5$, or $C_1$-$C_3$), $R^{6a}$-substituted or unsubstituted heteroalkyl (e.g., 2 to 8 membered, 2 to 5 membered, 2 to 3 membered), $R^{6a}$-substituted or unsubstituted cycloalkyl (e.g., $C_3$-$C_8$, $C_3$-$C_5$, or $C_3$), $R^{6a}$-substituted or unsubstituted heterocycloalkyl (e.g., 3 to 8 membered, 3 to 6 membered, or 4 membered), $R^{6a}$-substituted or unsubstituted aryl (e.g., $C_5$-$C_8$, $C_5$-$C_6$, or phenyl), or $R^{6a}$-substituted or unsubstituted heteroaryl (e.g., 5 to 8 membered, 5 to 6 membered, or 6 membered).

In embodiments, $R^6$ is hydrogen, halogen (e.g. —F, —Cl, —Br, or —I), —$N_3$, —$CF_3$, —$CCl_3$, —$CBr_3$, —$CI_3$, —CN, —CHO, —$OR^{33F}$, —$NR^{34F}R^{35F}$, —$COOR^{33F}$, —$CONR^{34F}R^{35F}$, —$NO_2$, —$SR^{36F}$, —$SO_{n6}R^{34F}$, —$SO_{n6}OR^{34F}$, —$SO_{n6}NR^{34F}R^{35F}$, —$NHNR^{34F}R^{35F}$, —$ONR^{34F}R^{35F}$, —$NHC(O)NHNR^{34F}R^{35F}$ (e.g., —OH, —$OCH_3$, —$NH2$, —$NHCH_3$, $NCH_3NCH_3$, —COOH, —$COOCH_3$, —$CONH_2$, —$CONHCH_3$, —$NO_2$, —SH, —$SCH_3$, —SOH, —$SOCH_3$, —$SO_2H$, —$SO_2CH_3$, —$S(O)OH$, —$S(O)OCH_3$, —$S(O)_2H$, $S(O)_2OCH_3$, —$S(O)NH_2$, —$S(O)NHCH_3$, —$S(O)_2NH_2$, $S(O)_2NHCH_3$, —$NHNH_2$, —$NHNHCH_3$, —$NHNCH_3CH_3$, —$ONH_2$, —$ONHCH_3$, —$NHC(O)NHNH_2$, or —$NHC(O)NHNHCH_3$), unsubstituted alkyl (e.g., $C_1$-$C_8$, $C_1$-$C_5$, or $C_1$-$C_3$), unsubstituted heteroalkyl (e.g., 2 to 8 membered, 2 to 5 membered, 2 to 3 membered), unsubstituted cycloalkyl (e.g., $C_3$-$C_8$, $C_3$-$C_3$, or $C_3$), unsubstituted heterocycloalkyl (e.g., 3 to 8 membered, 3 to 6 membered, or 4 membered), unsubstituted aryl (e.g., $C_5$-$C_8$, $C_5$-$C_6$, or phenyl), or unsubstituted heteroaryl (e.g., 5 to 8 membered, 5 to 6 membered, or 6 membered).

In embodiments, $R^6$ is hydrogen, halogen (e.g. —F, —Cl, —Br, or —I), —OH, —$OCH_3$, —$NH2$, —$NHCH_3$, $NCH_3NCH_3$, —COOH, —$COOCH_3$, —$CONH_2$, —$CONHCH_3$, —$NO_2$, —SH, —$SCH_3$, —SOH, —$SOCH_3$, —$SO_2H$, —$SO_2CH_3$, —$S(O)OH$, —$S(O)OCH_3$, —$S(O)_2H$, $S(O)_2OCH_3$, —$S(O)NH_2$, —$S(O)NHCH_3$, —$S(O)_2NH_2$, $S(O)_2NHCH_3$, —$NHNH_2$, —$NHNHCH_3$, —$NHNCH_3CH_3$, —$ONH_2$, —$ONHCH_3$, —$NHC(O)NHNH_2$, or —$NHC(O)NHNHCH_3$), $R^{6a}$-substituted or unsubstituted $C_1$-$C_3$ alkyl, $R^{6a}$-substituted or unsubstituted 2 to 3 membered heteroalkyl, $R^{6a}$-substituted or unsubstituted $C_3$-$C_5$ cycloalkyl, $R^{6a}$-substituted or unsubstituted 5 to 6 membered heterocycloalkyl, $R^{6a}$-substituted or unsubstituted phenyl, or $R^{6a}$-substituted or unsubstituted 5 to 6 membered heteroaryl.

In embodiments, $R^6$ is hydrogen, —F, —Cl, —Br, —I, —OH, —OH, —$OCH_3$, —$NH2$, —$NHCH_3$, $NCH_3NCH_3$, —COOH, —$COOCH_3$, —$CONH_2$, —$CONHCH_3$, —$NO_2$, —SH, —$SCH_3$, —SOH, —$SOCH_3$, —$SO_2H$, —$SO_2CH_3$, —$S(O)OH$, —$S(O)OCH_3$, —$S(O)_2H$, $S(O)_2OCH_3$, —$S(O)NH_2$, —$S(O)NHCH_3$, —$S(O)_2NH_2$, $S(O)_2NHCH_3$, —$NHNH_2$, —$NHNHCH_3$, —$NHNCH_3CH_3$, —$ONH_2$, —$ONHCH_3$, —$NHC(O)NHNH_2$, or —$NHC(O)NHNHCH_3$), unsubstituted $C_1$-$C_3$ alkyl, unsubstituted 2 to 3 membered heteroalkyl, unsubstituted $C_3$-$C_5$ cycloalkyl, unsubstituted 5 to 6 membered heterocycloalkyl, unsubstituted phenyl, or unsubstituted 5 to 6 membered heteroaryl.

$R^{6a}$ is halogen (e.g. —F, —Cl, —Br, or —I), —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —$NHC(O)NHNH_2$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{12}$, $C_6$-$C_{10}$, or phenyl), or substituted or unsubstituted heteroaryl (e.g., 5 to 12 membered, 5 to 10 membered, 5 to 9 membered, or 5 to 6 membered). In embodiments, $R^{6a}$ is halogen (e.g. —F, —Cl, —Br, or —I), —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —$NHC(O)NHNH_2$, $R^{6b}$-substituted or unsubstituted alkyl (e.g., $C_1$-$C_8$, $C_1$-$C_6$, $C_1$-$C_4$, or $C_1$-$C_2$), $R^{6b}$-substituted or unsubstituted heteroalkyl (e.g., 2 to 8 membered, 2 to 6 membered, 4 to 6 membered, 2 to 3 membered, or 4 to 5 membered), $R^{6b}$-substituted or unsubstituted cycloalkyl (e.g., $C_3$-$C_8$, $C_3$-$C_6$, $C_4$-$C_6$, or $C_5$-$C_6$), $R^{6b}$-substituted or unsubstituted heterocycloalkyl (e.g., 3 to 8 membered, 3 to 6 membered, 4 to 6 membered, 4 to 5 membered, or 5 to 6 membered), $R^{6b}$-substituted or unsubstituted aryl (e.g., $C_6$-$C_{12}$, $C_6$-$C_{10}$, or phenyl), or $R^{6b}$-substituted or unsubstituted heteroaryl (e.g., 5 to 12 membered, 5 to 10 membered, 5 to 9 membered, or 5 to 6 membered). In embodiments, $R^{6a}$ is halogen (e.g. —F, —Cl, —Br, or —I), —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —$NHC(O)NHNH_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered).

$R^{6b}$ is halogen (e.g. —F, —Cl, —Br, or —I), —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —$NHC(O)NHNH_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered).

In embodiments, $R^6$ is hydrogen, halogen (e.g. —F, —Cl, —Br, or —I), $R^{6a}$-substituted or unsubstituted $C_1$-$C_8$ alkyl, or unsubstituted 5 or 6 membered aryl. In embodiments, $R^6$ is hydrogen. In embodiments, $R^6$ is halogen (e.g. —F, —Cl, —Br, or —I). In embodiments, $R^6$ is $R^{6a}$-substituted or unsubstituted $C_1$-$C_8$ alkyl. In embodiments, $R^6$ is $R^{6a}$-substituted or unsubstituted $C_1$-$C_5$ alkyl. In embodiments, $R^6$ is $R^{6a}$-substituted or unsubstituted $C_1$-$C_3$ alkyl. In embodiments, $R^6$ is unsubstituted $C_1$-$C_3$ alkyl. In embodiments, $R^6$ is unsubstituted methyl. In embodiments, $R^6$ is unsubstituted ethyl. In embodiments, $R^6$ is unsubstituted propyl. In embodiments, $R^6$ is unsubstituted $C_1$-$C_5$ allyl. In embodiments, $R^6$ is unsubstituted 5 to 6 membered aryl. In embodiments, $R^6$ is unsubstituted phenyl.

In embodiments, $R^5$ and $R^6$ are independently hydrogen, halogen (e.g. —F, —Cl, —Br, or —I), —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, unsubstituted alkyl, or unsubstituted cycloalkyl. In embodiments, $R^5$ and $R^6$ are independently hydrogen, $C_1$-$C_3$ unsubstituted alkyl or 3 to 5 membered cycloalkyl. In embodiments, $R^5$ and $R^6$ are independently hydrogen, unsubstituted methyl, unsubstituted ethyl, unsubstituted allyl, or unsubstituted cyclopropyl. In embodiments, $R^5$ and $R^6$ are independently hydrogen or halogen (e.g. —F, —Cl, —Br, or —I). In embodiments, $R^5$ and $R^6$ are independently $C_1$-$C_3$ substituted or unsubstituted alkyl. In embodiments, $R^5$ and $R^6$ are unsubstituted methyl. In embodiments, $R^5$ and $R^6$ are independently unsubstituted methyl or unsubstituted ethyl.

In embodiments, $R^{16}$ is hydrogen, halogen (e.g. —F, —Cl, —Br, or —I), —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC(O)$NHNH_2$. In embodiments, $R^{16}$ is substituted or unsubstituted alkyl (e.g., $C_1$-$C_8$, $C_1$-$C_5$, or $C_1$-$C_3$). $R^{16}$ is substituted or unsubstituted $C_1$-$C_5$ alkyl. In embodiments, $R^{16}$ is substituted or unsubstituted $C_1$-$C_5$ alkyl. In embodiments, $R^{16}$ is substituted or unsubstituted $C_1$-$C_3$ alkyl. In embodiments, $R^{16}$ is $R^{16a}$-substituted or unsubstituted alkyl (e.g., $C_1$-$C_8$, $C_1$-$C_5$, or $C_1$-$C_3$). In embodiments, $R^{16}$ is $R^{16a}$-substituted or unsubstituted $C_1$-$C_5$ alkyl. In embodiments, $R^{16}$ is $R^{16a}$-substituted or unsubstituted $C_1$-$C_5$ alkyl. In embodiments, $R^{16}$ is $R^{16a}$-substituted or unsubstituted $C_1$-$C_3$ alkyl. In embodiments, $R^{16}$ is unsubstituted alkyl (e.g., $C_1$-$C_8$, $C_1$-$C_5$, or $C_1$-$C_3$). In embodiments, $R^{16}$ is unsubstituted $C_1$-$C_5$ alkyl. In embodiments, $R^{16}$ is unsubstituted $C_1$-$C_5$ alkyl. In embodiments, $R^{16}$ is unsubstituted $C_1$-$C_3$ alkyl.

In embodiments, $R^{16}$ is substituted or unsubstituted alkyl (e.g., $C_1$-$C_8$, $C_1$-$C_5$, or $C_1$-$C_3$), substituted or unsubstituted heteroalkyl (e.g., 2 to 8 membered, 2 to 5 membered, 2 to 3 membered), substituted or unsubstituted cycloalkyl (e.g., $C_3$-$C_8$, $C_3$-$C_5$, or $C_3$), substituted or unsubstituted heterocycloalkyl (e.g., 3 to 8 membered, 3 to 6 membered, or 4 membered), substituted or unsubstituted aryl (e.g., $C_5$-$C_8$, $C_5$-$C_6$, or phenyl), or substituted or unsubstituted heteroaryl (e.g., 5 to 8 membered, 5 to 6 membered, or 6 membered). In embodiments, $R^{16}$ is $R^{16a}$-substituted or unsubstituted alkyl (e.g., $C_1$-$C_8$, $C_1$-$C_5$, or $C_1$-$C_3$), $R^{16a}$-substituted or unsubstituted heteroalkyl (e.g., 2 to 8 membered, 2 to 5 membered, 2 to 3 membered), $R^{16a}$-substituted or unsubstituted cycloalkyl (e.g., $C_3$-$C_8$, $C_3$-$C_5$, or $C_3$), $R^{16a}$-substituted or unsubstituted heterocycloalkyl (e.g., 3 to 8 membered, 3 to 6 membered, or 4 membered), $R^{16}$-substituted or unsubstituted aryl (e.g., $C_5$-$C_8$, $C_5$-$C_6$, or phenyl), or $R^{16a}$-substituted or unsubstituted heteroaryl (e.g., 5 to 8 membered, 5 to 6 membered, or 6 membered). In embodiments, $R^{16}$ is unsubstituted alkyl (e.g., $C_1$-$C_8$, $C_1$-$C_5$, or $C_1$-$C_3$), unsubstituted heteroalkyl (e.g., 2 to 8 membered, 2 to 5 membered, 2 to 3 membered), unsubstituted cycloalkyl (e.g., $C_3$-$C_8$, $C_3$-$C_5$, or $C_3$), unsubstituted heterocycloalkyl (e.g., 3 to 8 membered, 3 to 6 membered, or 4 membered), unsubstituted aryl (e.g., $C_5$-$C_8$, $C_5$-$C_6$, or phenyl), or unsubstituted heteroaryl (e.g., 5 to 8 membered, 5 to 6 membered, or 6 membered).

In embodiments, $R^{16}$ is substituted or unsubstituted alkyl, substituted or unsubstituted $C_1$-$C_8$ alkyl, substituted or unsubstituted $C_1$-$C_5$ alkyl, substituted or unsubstituted $C_1$-$C_3$ alkyl. In embodiments, $R^{16}$ is $R^{3a}$-substituted or unsubstituted alkyl, $R^{3a}$-substituted or unsubstituted $C_1$-$C_8$ alkyl, $R^{3a}$-substituted or unsubstituted $C_1$-$C_5$ alkyl, or $R^{3a}$-substituted or unsubstituted $C_1$-$C_3$ alkyl. In embodiments, $R^{16}$ is unsubstituted alkyl, unsubstituted $C_1$-$C_8$ alkyl, unsubstituted $C_1$-$C_5$ alkyl, or unsubstituted $C_1$-$C_3$ alkyl.

In embodiments, $R^{16}$ is substituted or unsubstituted heteroalkyl. $R^{16}$ is substituted or unsubstituted 2 to 8 membered heteroalkyl. In embodiments, $R^{16}$ is substituted or unsubstituted 2 to 5 membered heteroalkyl. In embodiments, $R^{16}$ is substituted or unsubstituted 2 to 3 membered heteroalkyl. In embodiments, $R^{16}$ is $R^{16a}$-substituted or unsubstituted heteroalkyl. In embodiments, $R^{16}$ is $R^{16a}$-substituted or unsubstituted 2 to 8 membered heteroalkyl. In embodiments, $R^{16}$ is $R^{16a}$-substituted or unsubstituted 2 to 5 membered heteroalkyl. In embodiments, $R^{16}$ is $R^{16a}$-substituted or unsubstituted 2 to 3 membered heteroalkyl. In embodiments, $R^{16}$ is unsubstituted heteroalkyl. In embodiments, $R^{16}$ is unsubstituted 2 to 8 membered heteroalkyl. In embodiments, $R^{16}$ is unsubstituted 2 to 5 membered heteroalkyl. In embodiments, $R^{16}$ is unsubstituted 2 to 3 membered heteroalkyl.

In embodiments, $R^{16}$ is substituted or unsubstituted cycloalkyl. $R^{16}$ is substituted or unsubstituted 3 to 8 membered cycloalkyl. In embodiments, $R^{16}$ is substituted or unsubstituted 3 to 5 membered cycloalkyl. In embodiments, $R^{16}$ is substituted or unsubstituted 3 membered cycloalkyl. In embodiments, $R^{16}$ is substituted or unsubstituted 4 membered cycloalkyl. In embodiments, $R^{16}$ is substituted or unsubstituted 5 membered cycloalkyl. In embodiments, $R^{16}$ is $R^{16a}$-substituted or unsubstituted cycloalkyl. In embodiments, $R^{16}$ is $R^{16a}$-substituted or unsubstituted 3 to 8 membered cycloalkyl. In embodiments, $R^{16}$ is $R^{16a}$-substituted or unsubstituted 3 to 5 membered cycloalkyl. In embodiments, $R^{16}$ is $R^{16a}$-substituted or unsubstituted 3 membered cycloalkyl. In embodiments, $R^{16}$ is $R^{16a}$-substituted or unsubstituted 4 membered cycloalkyl. In embodiments, $R^{16}$ is $R^{16a}$-substituted or unsubstituted 5 membered cycloalkyl. In embodiments, $R^{16}$ is unsubstituted cycloalkyl. In embodiments, $R^{16}$ is unsubstituted 3 to 8 membered cycloalkyl. In embodiments, $R^{16}$ is unsubstituted 3 to 5 membered cycloalkyl. In embodiments, $R^{16}$ is unsubstituted 3 membered cycloalkyl. In embodiments, $R^{16}$ is unsubstituted 4 membered cycloalkyl. In embodiments, $R^{16}$ is unsubstituted 5 membered cycloalkyl.

In embodiments, $R^{16}$ is substituted or unsubstituted heterocycloalkyl. In embodiments, $R^{16}$ is substituted or unsubstituted 3 to 6 membered heterocycloalkyl. In embodiments, $R^{16}$ is substituted or unsubstituted 4 membered heterocycloalkyl. In embodiments, $R^{16}$ is substituted or unsubstituted 5 membered heterocycloalkyl. In embodiments, $R^{16}$ is substituted or unsubstituted 6 membered heterocycloalkyl. In embodiments, $R^{16}$ is $R^{16a}$-substituted or unsubstituted heterocycloalkyl. In embodiments, $R^{16}$ is $R^{16a}$-substituted or unsubstituted 3 to 6 membered heterocycloalkyl. In embodiments, $R^{16}$ is $R^{16a}$-substituted or unsubstituted 4 membered heterocycloalkyl. In embodiments, $R^{16}$ is $R^{16a}$-substituted or unsubstituted 5 membered heterocycloalkyl. In embodiments, $R^{16}$ is $R^{16a}$-substituted or unsubstituted 6 membered heterocycloalkyl. In embodiments, $R^{16}$ is unsubstituted heterocycloalkyl. In embodiments, $R^{16}$ is unsubstituted 3 to 6 membered heterocycloalkyl. In embodiments, $R^{16}$ is unsubstituted 4 membered heterocycloalkyl. In embodiments, $R^{16}$ is unsubstituted 5 membered heterocycloalkyl. In embodiments, $R^{16}$ is unsubstituted 6 membered heterocycloalkyl.

In embodiments, $R^{16}$ is substituted or unsubstituted aryl. In embodiments, $R^{16}$ is substituted or unsubstituted 5 to 6 membered aryl. In embodiments, $R^{16}$ is substituted or unsubstituted 5 membered aryl. In embodiments, $R^{16}$ is substituted or unsubstituted 6 membered aryl. In embodiments, $R^{16}$ is $R^{16a}$-substituted or unsubstituted aryl. In embodiments, $R^{16}$ is $R^{16a}$-substituted or unsubstituted 5 to 6 membered aryl. In embodiments, $R^{16}$ is $R^{16a}$-substituted or unsubstituted 5 membered aryl. In embodiments, $R^{16}$ is $R^{16a}$-substituted or unsubstituted 6 membered aryl. In embodiments, $R^{16}$ is unsubstituted aryl. In embodiments, $R^{16}$ is unsubstituted 5 to 6 membered aryl. In embodiments, $R^{16}$ is unsubstituted 5 membered aryl. In embodiments, $R^{16}$ is unsubstituted 6 membered aryl.

In embodiments, $R^{16}$ is substituted or unsubstituted heteroaryl. In embodiments, $R^{16}$ is substituted or unsubstituted 5 to 6 membered heteroaryl. In embodiments, $R^{16}$ is substituted or unsubstituted 5 membered heteroaryl. In embodiments, $R^{16}$ is substituted or unsubstituted 6 membered heteroaryl. In embodiments, $R^{16}$ is $R^{16a}$-substituted or unsubstituted heteroaryl. In embodiments, $R^{16}$ is $R^{16a}$-substituted or unsubstituted 5 to 6 membered heteroaryl. In embodiments, $R^{16}$ is $R^{16a}$-substituted or unsubstituted 5 membered heteroaryl. In embodiments, $R^{16}$ is $R^{16a}$-substituted or unsubstituted 6 membered heteroaryl. In embodiments, $R^{16}$ is unsubstituted heteroaryl. In embodiments, $R^{16}$ is unsubstituted 5 to 6 membered heteroaryl. In embodiments, $R^{16}$ is unsubstituted 5 membered heteroaryl. In embodiments, $R^{16}$ is unsubstituted 6 membered heteroaryl.

In embodiments, $R^{16}$ is hydrogen, halogen (e.g. —F, —Cl, —Br, or —I), —N$_3$, —CF$_3$, —CCl$_3$, —CBr$_3$, —CI$_3$, —CN, —CHO, —OR$^{33G}$, —NR$^{34G}$R$^{35G}$, —COOR$^{33G}$, —CONR$^{34G}$R$^{35G}$, —NO$_2$, —SR$^{36G}$, —SO$_{n7}$R$^{34G}$, —SO$_{n7}$OR$^{34G}$, —SO$_{n7}$NR$^{34G}$R$^{35G}$, —NHNR$^{34G}$R$^{35G}$, —ONR$^{34G}$R$^{35G}$, —NHC(O)NHNR$^{34G}$R$^{35G}$ (e.g., —OH, —OCH$_3$, —NH2, —NHCH$_3$, NCH$_3$NCH$_3$, —COOH, —COOCH$_3$, —CONH$_2$, —CONHCH$_3$, —NO$_2$, —SH, —SCH$_3$, —SOH, —SOCH$_3$, —SO$_2$H, —SO$_2$CH$_3$, —S(O)OH, —S(O)OCH$_3$, —S(O)$_2$H, S(O)$_2$OCH$_3$, —S(O)NH$_2$, —S(O)NHCH$_3$, —S(O)$_2$NH$_2$, S(O)$_2$NHCH$_3$, —NHNH$_2$, —NHNHCH$_3$, —NHNCH$_3$CH$_3$, —ONH$_2$, —ONHCH$_3$, —NHC(O)NHNH$_2$, or —NHC(O)NHNHCH$_3$), substituted or unsubstituted alkyl (e.g., C$_1$-C$_8$, C$_1$-C$_5$, or C$_1$-C$_3$), substituted or unsubstituted heteroalkyl (e.g., 2 to 8 membered, 2 to 5 membered, 2 to 3 membered), substituted or unsubstituted cycloalkyl (e.g., C$_3$-C$_8$, C$_3$-C$_5$, or C$_3$), substituted or unsubstituted heterocycloalkyl (e.g., 3 to 8 membered, 3 to 6 membered, or 4 membered), substituted or unsubstituted aryl (e.g., C$_5$-C$_8$, C$_5$-C$_6$, or phenyl), or substituted or unsubstituted heteroaryl (e.g., 5 to 8 membered, 5 to 6 membered, or 6 membered). I In embodiments, $R^{16}$ is hydrogen, halogen (e.g. —F, —Cl, —Br, or —I), —N$_3$, —CF$_3$, —CCl$_3$, —CBr$_3$, —CI$_3$, —CN, —CHO, —OR$^{33G}$, —NR$^{34G}$R$^{35G}$, —COOR$^{33G}$, —CONR$^{34G}$R$^{35G}$, —NO$_2$, —SR$^{36G}$, —SO$_{n7}$R$^{34G}$, —SO$_{n7}$OR$^{34G}$, —SO$_{n7}$NR$^{34G}$R$^{35G}$, —NHNR$^{34G}$R$^{35G}$, —ONR$^{34G}$R$^{35G}$, —NHC(O)NHNR$^{34G}$R$^{35G}$ (e.g., —OH, —OCH$_3$, —NH2, —NHCH$_3$, NCH$_3$NCH$_3$, —COOH, —COOCH$_3$, —CONH$_2$, —CONHCH$_3$, —NO$_2$, —SH, —SCH$_3$, —SOH, —SOCH$_3$, —SO$_2$H, —SO$_2$CH$_3$, —S(O)OH, —S(O)OCH$_3$, —S(O)$_2$H, S(O)$_2$OCH$_3$, —S(O)NH$_2$, —S(O)NHCH$_3$, —S(O)$_2$NH$_2$, S(O)$_2$NHCH$_3$, —NHNH$_2$, —NHNHCH$_3$, —NHNCH$_3$CH$_3$, —ONH$_2$, —ONHCH$_3$, —NHC(O)NHNH$_2$, or —NHC(O)NHNHCH$_3$), $R^{16a}$-substituted or unsubstituted alkyl (e.g., C$_1$-C$_8$, C$_1$-C$_5$, or C$_1$-C$_3$), $R^{16a}$-substituted or unsubstituted heteroalkyl (e.g., 2 to 8 membered, 2 to 5 membered, 2 to 3 membered), $R^{16a}$-substituted or unsubstituted cycloalkyl (e.g., C$_3$-C$_8$, C$_3$-C$_3$, or C$_3$), $R^{16a}$-substituted or unsubstituted heterocycloalkyl (e.g., 3 to 8 membered, 3 to 6 membered, or 4 membered), $R^{16a}$-substituted or unsubstituted aryl (e.g., C$_5$-C$_8$, C$_5$-C$_6$, or phenyl), or $R^{16a}$-substituted or unsubstituted heteroaryl (e.g., 5 to 8 membered, 5 to 6 membered, or 6 membered).

In embodiments, $R^{16}$ is hydrogen, halogen (e.g. —F, —Cl, —Br, or —I), —N$_3$, —CF$_3$, —CCl$_3$, —CBr$_3$, —CI$_3$, —CN, —CHO, —OR$^{33G}$, —NR$^{34G}$R$^{35G}$, —COOR$^{33G}$, —CONR$^{34G}$R$^{35G}$, —NO$_2$, —SR$^{36G}$, —SO$_{n7}$R$^{34G}$, —SO$_{n7}$OR$^{34G}$, —SO$_{n7}$NR$^{34G}$R$^{35G}$, —NHNR$^{34G}$R$^{35G}$, —ONR$^{34G}$R$^{35G}$, —NHC(O)NHNR$^{34G}$R$^{35G}$ (e.g., —OH, —OCH$_3$, —NH2, —NHCH$_3$, NCH$_3$NCH$_3$, —COOH, —COOCH$_3$, —CONH$_2$, —CONHCH$_3$, —NO$_2$, —SH, —SCH$_3$, —SOH, —SOCH$_3$, —SO$_2$H, —SO$_2$CH$_3$, —S(O)OH, —S(O)OCH$_3$, —S(O)$_2$H, S(O)$_2$OCH$_3$, —S(O)NH$_2$, —S(O)NHCH$_3$, —S(O)$_2$NH$_2$, S(O)$_2$NHCH$_3$, —NHNH$_2$, —NHNHCH$_3$, —NHNCH$_3$CH$_3$, —ONH$_2$, —ONHCH$_3$, —NHC(O)NHNH$_2$, or —NHC(O)NHNHCH$_3$), unsubstituted alkyl (e.g., C$_1$-C$_8$, C$_1$-C$_5$, or C$_1$-C$_3$), unsubstituted heteroalkyl (e.g., 2 to 8 membered, 2 to 5 membered, 2 to 3 membered), unsubstituted cycloalkyl (e.g., C$_3$-C$_8$, C$_3$-C$_3$, or C$_3$), unsubstituted heterocycloalkyl (e.g., 3 to 8 membered, 3 to 6 membered, or 4 membered), unsubstituted aryl (e.g., C$_5$-C$_8$, C$_5$-C$_6$, or phenyl), or unsubstituted heteroaryl (e.g., 5 to 8 membered, 5 to 6 membered, or 6 membered).

In embodiments, $R^{16}$ is hydrogen, halogen (e.g. —F, —Cl, —Br, or —I), —OH, —OCH$_3$, —NH2, —NHCH$_3$, NCH$_3$NCH$_3$, —COOH, —COOCH$_3$, —CONH$_2$, —CONHCH$_3$, —NO$_2$, —SH, —SCH$_3$, —SOH, —SOCH$_3$, —SO$_2$H, —SO$_2$CH$_3$, —S(O)OH, —S(O)OCH$_3$, —S(O)$_2$H, S(O)$_2$OCH$_3$, —S(O)NH$_2$, —S(O)NHCH$_3$, —S(O)$_2$NH$_2$, S(O)$_2$NHCH$_3$, —NHNH$_2$, —NHNHCH$_3$, —NHNCH$_3$CH$_3$, —ONH$_2$, —ONHCH$_3$, —NHC(O)NHNH$_2$, or —NHC(O)NHNHCH$_3$), $R^{16a}$-substituted or unsubstituted C$_1$-C$_3$ alkyl, $R^{16a}$-substituted or unsubstituted 2 to 3 membered heteroalkyl, $R^{16a}$-substituted or unsubstituted C$_3$-C$_5$ cycloalkyl, $R^{16a}$-substituted or unsubstituted 5 to 6 membered heterocycloalkyl, $R^{16a}$-substituted or unsubstituted phenyl, or $R^{16a}$-substituted or unsubstituted 5 to 6 membered heteroaryl.

In embodiments, $R^{16}$ is hydrogen, —F, —Cl, —Br, —I, —OH, —OH, —OCH$_3$, —NH2, —NHCH$_3$, NCH$_3$NCH$_3$, —COOH, —COOCH$_3$, —CONH$_2$, —CONHCH$_3$, —NO$_2$, —SH, —SCH$_3$, —SOH, —SOCH$_3$, —SO$_2$H, —SO$_2$CH$_3$, —S(O)OH, —S(O)OCH$_3$, —S(O)$_2$H, S(O)$_2$OCH$_3$, —S(O)NH$_2$, —S(O)NHCH$_3$, —S(O)$_2$NH$_2$, S(O)$_2$NHCH$_3$, —NHNH$_2$, —NHNHCH$_3$, —NHNCH$_3$CH$_3$, —ONH$_2$, —ONHCH$_3$, —NHC(O)NHNH$_2$, or —NHC(O)NHNHCH$_3$), unsubstituted C$_1$-C$_3$ alkyl, unsubstituted 2 to 3 membered heteroalkyl, unsubstituted C$_3$-C$_5$ cycloalkyl, unsubstituted 5 to 6 membered heterocycloalkyl, unsubstituted phenyl, or unsubstituted 5 to 6 membered heteroaryl.

$R^{16a}$ is halogen (e.g. —F, —Cl, —Br, or —I), —N$_3$, —CF$_3$, —CCl$_3$, —CBr$_3$, —CI$_3$, —CN, —CHO, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC(O)NHNH$_2$, substituted or unsubstituted alkyl (e.g., C$_1$-C$_8$, C$_1$-C$_6$, C$_1$-C$_4$, or C$_1$-C$_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., C$_3$-C$_8$, C$_3$-C$_6$, C$_4$-C$_6$, or C$_5$-C$_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., C$_6$-C$_{12}$, C$_6$-C$_{10}$, or phenyl), or substituted or unsubstituted heteroaryl (e.g., 5 to 12 membered, 5 to 10 membered, 5 to 9 membered, or 5 to 6 membered). In embodiments, $R^{16a}$ is halogen (e.g. —F, —Cl, —Br, or —I), —N$_3$, —CF$_3$, —CCl$_3$, —CBr$_3$, —CI$_3$, —CN, —CHO, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC(O)NHNH$_2$, $R^{16b}$-substituted or unsubstituted alkyl (e.g., C$_1$-C$_8$, C$_1$-C$_6$, C$_1$-C$_4$, or C$_1$-C$_2$), $R^{16b}$-substituted or unsubstituted heteroalkyl (e.g., 2 to 8 membered, 2 to 6 membered, 4 to 6 membered, 2 to 3 membered, or 4 to 5 membered), $R^{16b}$-substituted or unsubstituted cycloalkyl (e.g., C$_3$-C$_8$, C$_3$-C$_6$, C$_4$-C$_6$, or C$_5$-C$_6$), $R^{16b}$-substituted or unsubstituted heterocycloalkyl (e.g., 3 to 8 membered, 3 to 6 membered, 4 to 6 membered, 4 to 5 membered, or 5 to 6 membered), $R^{16b}$-substituted or unsubstituted aryl (e.g., C$_6$-C$_{12}$, C$_6$-C$_{10}$, or phenyl), or $R^{16b}$-substituted or unsubstituted heteroaryl (e.g., 5 to 12 membered, 5 to 10 membered, 5 to 9 membered, or 5 to 6 membered). In embodiments, $R^{16a}$ is halogen (e.g. —F, —Cl, —Br, or —I), —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —$NHC(O)NHNH_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered).

$R^{16b}$ is halogen (e.g. —F, —Cl, —Br, or —I), —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —$NHC(O)NHNH_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered).

In embodiments, $R^{16}$ is hydrogen, halogen (e.g. —F, —Cl, —Br, or —I) or substituted or unsubstituted alkyl (e.g., $C_1$-$C_8$, $C_1$-$C_5$, or $C_1$-$C_3$). In embodiments, $R^{16}$ is hydrogen. In embodiments, $R^{16}$ is halogen (e.g. —F, —Cl, —Br, or —I). In embodiments, $R^{16}$ is substituted or unsubstituted alkyl (e.g., $C_1$-$C_8$, $C_1$-$C_5$, or $C_1$-$C_3$). In embodiments, $R^{16}$ is $R^{16a}$-substituted or unsubstituted $C_1$-$C_8$ alkyl. In embodiments, $R^{16}$ is $R^{16a}$-substituted or unsubstituted $C_1$-$C_5$ alkyl. In embodiments, $R^{16}$ is $R^{16a}$-substituted or unsubstituted $C_1$-$C_3$ alkyl. In embodiments, $R^{16}$ is unsubstituted $C_1$-$C_3$ alkyl. In embodiments, $R^{16}$ is unsubstituted methyl or ethyl. In embodiments, $R^3$, $R^4$, and $R^{16}$ are hydrogen.

In embodiments, $R^{18}$ is halogen (e.g. —F, —Cl, —Br, or —I), substituted or unsubstituted alkyl (e.g., $C_1$-$C_8$, $C_1$-$C_5$, or $C_1$-$C_3$), substituted or unsubstituted heteroalkyl (e.g., 2 to 8 membered, 2 to 5 membered, 2 to 3 membered), substituted or unsubstituted cycloalkyl (e.g., $C_3$-$C_8$, $C_3$-$C_5$, or $C_3$), substituted or unsubstituted heterocycloalkyl (e.g., 3 to 8 membered, 3 to 6 membered, or 4 membered), substituted or unsubstituted aryl (e.g., $C_5$-$C_8$, $C_5$-$C_6$, or phenyl), or substituted or unsubstituted heteroaryl (e.g., 5 to 8 membered, 5 to 6 membered, or 6 membered).

In embodiments, $R^{18}$ is substituted or unsubstituted alkyl (e.g., $C_1$-$C_8$, $C_1$-$C_5$, or $C_1$-$C_3$), substituted or unsubstituted heteroalkyl (e.g., 2 to 8 membered, 2 to 5 membered, 2 to 3 membered), substituted or unsubstituted cycloalkyl (e.g., $C_3$-$C_8$, $C_3$-$C_5$, or $C_3$), substituted or unsubstituted heterocycloalkyl (e.g., 3 to 8 membered, 3 to 6 membered, or 4 membered), substituted or unsubstituted aryl (e.g., $C_5$-$C_8$, $C_5$-$C_6$, or phenyl), or substituted or unsubstituted heteroaryl (e.g., 5 to 8 membered, 5 to 6 membered, or 6 membered).

In embodiments, $R^{18}$ is $R^{18a}$-substituted or unsubstituted alkyl (e.g., $C_1$-$C_8$, $C_1$-$C_5$, or $C_1$-$C_3$), $R^{18a}$-substituted or unsubstituted heteroalkyl (e.g., 2 to 8 membered, 2 to 5 membered, 2 to 3 membered), $R^{18a}$-substituted or unsubstituted cycloalkyl (e.g., $C_3$-$C_8$, $C_3$-$C_5$, or $C_3$), $R^{18a}$-substituted or unsubstituted heterocycloalkyl (e.g., 3 to 8 membered, 3 to 6 membered, or 4 membered), $R^{18a}$-substituted or unsubstituted aryl (e.g., $C_5$-$C_8$, $C_5$-$C_6$, or phenyl), or $R^{18a}$-substituted or unsubstituted heteroaryl (e.g., 5 to 8 membered, 5 to 6 membered, or 6 membered). In embodiments, $R^{18}$ is unsubstituted alkyl (e.g., $C_1$-$C_8$, $C_1$-$C_5$, or $C_1$-$C_3$), unsubstituted heteroalkyl (e.g., 2 to 8 membered, 2 to 5 membered, 2 to 3 membered), unsubstituted cycloalkyl (e.g., $C_3$-$C_8$, $C_3$-$C_5$, or $C_3$), unsubstituted heterocycloalkyl (e.g., 3 to 8 membered, 3 to 6 membered, or 4 membered), unsubstituted aryl (e.g., $C_5$-$C_8$, $C_5$-$C_6$, or phenyl), or unsubstituted heteroaryl (e.g., 5 to 8 membered, 5 to 6 membered, or 6 membered).

In embodiments, $R^{18}$ is substituted or unsubstituted $C_1$-$C_8$ alkyl, substituted or unsubstituted 2 to 8 membered heteroalkyl, substituted or unsubstituted 3 to 8 membered cycloalkyl, substituted or unsubstituted 3 to 8 membered heterocycloalkyl, substituted or unsubstituted 5 to 8 membered aryl, or substituted or unsubstituted 5 or 8 membered heteroaryl. In embodiments, $R^{18}$ is $R^{18a}$-substituted or unsubstituted $C_1$-$C_8$ alkyl, $R^{18a}$-substituted or unsubstituted 2 to 8 membered heteroalkyl, $R^{18a}$-substituted or unsubstituted 3 to 8 membered cycloalkyl, $R^{18a}$-substituted or unsubstituted 3 to 8 membered heterocycloalkyl, $R^{18a}$-substituted or unsubstituted 5 to 8 membered aryl, or $R^{18a}$-substituted or unsubstituted 5 to 8 membered heteroaryl. In embodiments, $R^{18}$ is unsubstituted $C_1$-$C_8$ alkyl, unsubstituted 2 to 8 membered heteroalkyl, unsubstituted 3 to 8 membered cycloalkyl, unsubstituted 3 to 8 membered heterocycloalkyl, unsubstituted 5 to 8 membered aryl, or unsubstituted 5 or 8 membered heteroaryl.

In embodiments, $R^{18}$ is substituted or unsubstituted $C_1$-$C_5$ alkyl, substituted or unsubstituted 2 to 5 membered heteroalkyl, substituted or unsubstituted 3 to 5 membered cycloalkyl, substituted or unsubstituted 3 to 6 membered heterocycloalkyl, substituted or unsubstituted 5 to 6 membered aryl, or substituted or unsubstituted 5 or 6 membered heteroaryl. In embodiments, $R^{18}$ is $R^{18a}$-substituted or unsubstituted $C_1$-$C_5$ alkyl, $R^{18a}$-substituted or unsubstituted 2 to 5 membered heteroalkyl, $R^{18a}$-substituted or unsubstituted 3 to 5 membered cycloalkyl, $R^{18a}$-substituted or unsubstituted 3-6 membered heterocycloalkyl, $R^{18a}$-substituted or unsubstituted 5 to 6 membered aryl, or $R^{18a}$-substituted or unsubstituted 5 to 6 membered heteroaryl. In embodiments, $R^{18}$ is unsubstituted $C_1$-$C_5$ alkyl, unsubstituted 2 to 5 membered heteroalkyl, unsubstituted 3 to 5 membered cycloalkyl, unsubstituted 3 to 6 membered heterocycloalkyl, unsubstituted 5 to 6 membered aryl, or unsubstituted 5 or 6 membered heteroaryl.

In embodiments, $R^{18}$ is substituted or unsubstituted $C_1$-$C_3$ alkyl, substituted or unsubstituted 2 to 3 membered heteroalkyl. In embodiments, $R^{18}$ is substituted or unsubstituted 3 membered cycloalkyl, substituted or unsubstituted 4 membered cycloalkyl, or substituted or unsubstituted 5 membered cycloalkyl. In embodiments, $R^{18}$ is $R^{18a}$-substituted or unsubstituted $C_1$-$C_3$ alkyl or $R^{18a}$-substituted or unsubstituted 2 to 3 membered heteroalkyl. In embodiments, $R^{18}$ is $R^{18a}$-substituted or unsubstituted 3 membered cycloalkyl, $R^{18a}$-substituted or unsubstituted 4 membered cycloalkyl, or $R^{18a}$-substituted or unsubstituted 5 membered cycloalkyl. In embodiments, $R^{18}$ is unsubstituted $C_1$-$C_3$ alkyl or unsubstituted 2 to 3 membered heteroalkyl. In embodiments, $R^{18}$ is unsubstituted 3 membered cycloalkyl, unsubstituted 4 membered cycloalkyl, or unsubstituted 5 membered cycloalkyl. In embodiments, $R^{18}$ is substituted or unsubstituted 4 membered heterocycloalkyl, substituted or unsubstituted 5 membered heterocycloalkyl, or substituted or unsubstituted 6 membered heterocycloalkyl. In embodiments, $R^{18}$ is $R^{18a}$-substituted or unsubstituted 4 membered heterocycloalkyl, $R^{18a}$-substituted or unsubstituted 5 membered heterocycloalkyl, or $R^{18a}$-substituted or unsubstituted 6 membered heterocycloalkyl. In embodiments, $R^{18}$ is unsubstituted 4 membered heterocycloalkyl, unsubstituted 5 membered heterocycloalkyl, or unsubstituted 6 membered heterocycloalkyl. In embodiments, $R^{18}$ is substituted or unsubstituted 5 membered aryl, substituted or unsubstituted 6 membered aryl or phenyl, substituted or unsubstituted 5 membered heteroaryl, or substituted or unsubstituted 6 membered heteroaryl. In embodiments, $R^{18}$ is $R^{18a}$-substituted or unsubstituted 5 membered aryl, $R^{18a}$-substituted or unsubstituted 6 membered aryl or phenyl, $R^{18a}$-substituted or unsubstituted 5 membered heteroaryl, or $R^{18a}$-substituted or unsubstituted 6 membered heteroaryl. In embodiments, $R^{18}$ is unsubstituted 5 membered aryl, unsubstituted 6 membered aryl or phenyl, unsubstituted 5 membered heteroaryl, or unsubstituted 6 membered heteroaryl.

In embodiments, $R^{18}$ is hydrogen, halogen (e.g. —F, —Cl, —Br, or —I), —N$_3$, —CF$_3$, —CCl$_3$, —CBr$_3$, —CI$_3$, —CN, —CHO, —OR$^{33H}$, —NR$^{34H}$R$^{35H}$, —COOR$^{33H}$, —CONR$^{34H}$R$^{35H}$, —NO$_2$, —SR$^{36H}$, —SO$_{n8}$R$^{34H}$, —SO$_{n8}$OR$^{34H}$, —SO$_{n8}$NR$^{34H}$R$^{35H}$, —NHNR$^{34H}$R$^{35H}$, —ONR$^{34H}$R$^{35H}$, —NHC(O)NHNR$^{34H}$R$^{35H}$ (e.g., —OH, —OCH$_3$, —NH2, —NHCH$_3$, NCH$_3$NCH$_3$, —COOH, —COOCH$_3$, —CONH$_2$, —CONHCH$_3$, —NO$_2$, —SH, —SCH$_3$, —SOH, —SOCH$_3$, —SO$_2$H, —SO$_2$CH$_3$, —S(O)OH, —S(O)OCH$_3$, —S(O)$_2$H, S(O)$_2$OCH$_3$, —S(O)NH$_2$, —S(O)NHCH$_3$, —S(O)$_2$NH$_2$, S(O)$_2$NHCH$_3$, —NHNH$_2$, —NHNHCH$_3$, —NHNCH$_3$CH$_3$, —ONH$_2$, —ONHCH$_3$, —NHC(O)NHNH$_2$, or —NHC(O)NHNHCH$_3$), substituted or unsubstituted alkyl (e.g., $C_1$-$C_8$, $C_1$-$C_5$, or $C_1$-$C_3$), substituted or unsubstituted heteroalkyl (e.g., 2 to 8 membered, 2 to 5 membered, 2 to 3 membered), substituted or unsubstituted cycloalkyl (e.g., $C_3$-$C_8$, $C_3$-$C_5$, or $C_3$), substituted or unsubstituted heterocycloalkyl (e.g., 3 to 8 membered, 3 to 6 membered, or 4 membered), substituted or unsubstituted aryl (e.g., $C_5$-$C_8$, $C_5$-$C_6$, or phenyl), or substituted or unsubstituted heteroaryl (e.g., 5 to 8 membered, 5 to 6 membered, or 6 membered).

In embodiments, $R^{18}$ is hydrogen, halogen (e.g. —F, —Cl, —Br, or —I), —N$_3$, —CF$_3$, —CCl$_3$, —CBr$_3$, —CI$_3$, —CN, —CHO, —OR$^{33H}$, —NR$^{34H}$R$^{35H}$, —COOR$^{33H}$, —CONR$^{34H}$R$^{35H}$, —NO$_2$, —SR$^{36H}$, —SO$_{n8}$R$^{34H}$, —SO$_{n8}$OR$^{34H}$, —SO$_{n8}$NR$^{34H}$R$^{35H}$, —NHNR$^{34H}$R$^{35H}$, —ONR$^{34H}$R$^{35H}$, —NHC(O)NHNR$^{34H}$R$^{35H}$ (e.g., —OH, —OCH$_3$, —NH2, —NHCH$_3$, NCH$_3$NCH$_3$, —COOH, —COOCH$_3$, —CONH$_2$, —CONHCH$_3$, —NO$_2$, —SH, —SCH$_3$, —SOH, —SOCH$_3$, —SO$_2$H, —SO$_2$CH$_3$, —S(O)OH, —S(O)OCH$_3$, —S(O)$_2$H, S(O)$_2$OCH$_3$, —S(O)NH$_2$, —S(O)NHCH$_3$, —S(O)$_2$NH$_2$, S(O)$_2$NHCH$_3$, —NHNH$_2$, —NHNHCH$_3$, —NHNCH$_3$CH$_3$, —ONH$_2$, —ONHCH$_3$, —NHC(O)NHNH$_2$, or —NHC(O)NHNHCH$_3$), $R^{18a}$-substituted or unsubstituted alkyl (e.g., $C_1$-$C_8$, $C_1$-$C_5$, or $C_1$-$C_3$), $R^{18a}$-substituted or unsubstituted heteroalkyl (e.g., 2 to 8 membered, 2 to 5 membered, 2 to 3 membered), $R^{18a}$-substituted or unsubstituted cycloalkyl (e.g., $C_3$-$C_8$, $C_3$-$C_3$, or $C_3$), $R^{18a}$-substituted or unsubstituted heterocycloalkyl (e.g., 3 to 8 membered, 3 to 6 membered, or 4 membered), $R^{18a}$-substituted or unsubstituted aryl (e.g., $C_5$-$C_8$, $C_5$-$C_6$, or phenyl), or $R^{18a}$-substituted or unsubstituted heteroaryl (e.g., 5 to 8 membered, 5 to 6 membered, or 6 membered).

In embodiments, $R^{18}$ is hydrogen, halogen (e.g. —F, —Cl, —Br, or —I), —OH, —OCH$_3$, —NH2, —NHCH$_3$, NCH$_3$NCH$_3$, —COOH, —COOCH$_3$, —CONH$_2$, —CONHCH$_3$, —NO$_2$, —SH, —SCH$_3$, —SOH, —SOCH$_3$, —SO$_2$H, —SO$_2$CH$_3$, —S(O)OH, —S(O)OCH$_3$, —S(O)$_2$H, S(O)$_2$OCH$_3$, —S(O)NH$_2$, —S(O)NHCH$_3$, —S(O)$_2$NH$_2$, S(O)$_2$NHCH$_3$, —NHNH$_2$, —NHNHCH$_3$, —NHNCH$_3$CH$_3$, —ONH$_2$, —ONHCH$_3$, —NHC(O)NHNH$_2$, or —NHC(O)NHNHCH$_3$), $R^{18a}$-substituted or unsubstituted $C_1$-$C_3$ alkyl, $R^{18a}$-substituted or unsubstituted 2 to 3 membered heteroalkyl, $R^{18a}$-substituted or unsubstituted $C_3$-$C_5$ cycloalkyl, $R^{18a}$-substituted or unsubstituted 5 to 6 membered heterocycloalkyl, $R^{18a}$-substituted or unsubstituted phenyl, or $R^{18a}$-substituted or unsubstituted 5 to 6 membered heteroaryl.

In embodiments, $R^{18}$ is hydrogen, —F, —Cl, —Br, —I, —OH, —OH, —OCH$_3$, —NH2, —NHCH$_3$, NCH$_3$NCH$_3$, —COOH, —COOCH$_3$, —CONH$_2$, —CONHCH$_3$, —NO$_2$, —SH, —SCH$_3$, —SOH, —SOCH$_3$, —SO$_2$H, —SO$_2$CH$_3$, —S(O)OH, —S(O)OCH$_3$, —S(O)$_2$H, S(O)$_2$OCH$_3$, —S(O)NH$_2$, —S(O)NHCH$_3$, —S(O)$_2$NH$_2$, S(O)$_2$NHCH$_3$, —NHNH$_2$, —NHNHCH$_3$, —NHNCH$_3$CH$_3$, —ONH$_2$, —ONHCH$_3$, —NHC(O)NHNH$_2$, or —NHC(O)NHNHCH$_3$), unsubstituted $C_1$-$C_3$ alkyl, unsubstituted 2 to 3 membered heteroalkyl, unsubstituted $C_3$-$C_5$ cycloalkyl, unsubstituted 5 to 6 membered heterocycloalkyl, unsubstituted phenyl, or unsubstituted 5 to 6 membered heteroaryl.

$R^{18a}$ is halogen (e.g. —F, —Cl, —Br, or —I), —N$_3$, —CF$_3$, —CCl$_3$, —CBr$_3$, —CI$_3$, —CN, —CHO, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC(O)NHNH$_2$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{12}$, $C_6$-$C_{10}$, or phenyl), or substituted or unsubstituted heteroaryl (e.g., 5 to 12 membered, 5 to 10 membered, 5 to 9 membered, or 5 to 6 membered). In embodiments, $R^{18a}$ is halogen (e.g. —F, —Cl, —Br, or —I), —N$_3$, —CF$_3$, —CCl$_3$, —CBr$_3$, —CI$_3$, —CN, —CHO, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC(O)NHNH$_2$, $R^{18b}$-substituted or unsubstituted alkyl (e.g., $C_1$-$C_8$, $C_1$-$C_6$, $C_1$-$C_4$, or $C_1$-$C_2$), $R^{18b}$-substituted or unsubstituted heteroalkyl (e.g., 2 to 8 membered, 2 to 6 membered, 4 to 6 membered, 2 to 3 membered, or 4 to 5 membered), $R^{18b}$-substituted or unsubstituted cycloalkyl (e.g., $C_3$-$C_8$, $C_3$-$C_6$, $C_4$-$C_6$, or $C_5$-$C_6$), $R^{18b}$-substituted or unsubstituted heterocycloalkyl (e.g., 3 to 8 membered, 3 to 6 membered, 4 to 6 membered, 4 to 5 membered, or 5 to 6 membered), $R^{18b}$-substituted or unsubstituted aryl (e.g., $C_6$-$C_{12}$, $C_6$-$C_{10}$, or phenyl), or $R^{18b}$-substituted or unsubstituted heteroaryl (e.g., 5 to 12 membered, 5 to 10 membered, 5 to 9 membered, or 5 to 6 membered). In embodiments, $R^{18a}$ is halogen (e.g. —F, —Cl, —Br, or —I), —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —$NHC(O)NHNH_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered).

$R^{18b}$ is halogen (e.g. —F, —Cl, —Br, or —I), —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —$NHC(O)NHNH_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered).

In embodiments, $R^{18}$ is substituted or unsubstituted heterocycloalkyl (e.g., 3 to 8 membered, 3 to 6 membered, or 4 membered), substituted or unsubstituted aryl (e.g., $C_5$-$C_8$, $C_5$-$C_6$, or phenyl), or substituted or unsubstituted heteroaryl (e.g., 5 to 8 membered, 5 to 6 membered, or 6 membered). In embodiments, $R^{18}$ is substituted or unsubstituted 5-membered heterocycloalkyl, substituted or unsubstituted 6 membered aryl or phenyl, or substituted or unsubstituted 6 membered heteroaryl. In embodiments, $R^{18}$ is $R^{18a}$-substituted or unsubstituted 5 membered heterocycloalkyl, $R^{18a}$-substituted or unsubstituted 6 membered aryl, $R^{18a}$-substituted or unsubstituted 6 membered heteroaryl, $R^{18a}$-substituted or unsubstituted 6,6 fused ring aryl-heterocycloalkyl, $R^{18a}$-substituted or unsubstituted 6,5 fused ring aryl-heterocycloalkyl, $R^{18a}$-substituted or unsubstituted 5,6 fused ring aryl-heterocycloalkyl, where $R^{18a}$ and $R^{18b}$ are as described herein, including embodiments thereof.

In embodiments, $R^{18}$ is $R^{18a}$-substituted or unsubstituted 5 membered heterocycloalkyl, $R^{18a}$-substituted 6 membered aryl, $R^{18a}$-substituted or unsubstituted 6 membered heteroaryl, $R^{18a}$-substituted or unsubstituted 6,6 fused ring aryl, $R^{18a}$-substituted or unsubstituted 6,6 fused ring heteroaryl, $R^{18a}$-substituted or unsubstituted 6,5 fused ring aryl, $R^{18a}$-substituted or unsubstituted 6,5 fused ring heteroaryl, $R^{18a}$-substituted or unsubstituted 5,6 fused ring aryl, $R^{18a}$-substituted or unsubstituted 5,6 fused ring heteroaryl, $R^{18a}$-substituted or unsubstituted 6,6 fused ring aryl-heterocycloalkyl, $R^{18a}$-substituted or unsubstituted 6,5 fused ring aryl-heterocycloalkyl, or $R^{18a}$-substituted or unsubstituted 5,6 fused ring aryl-heterocycloalkyl.

In embodiments, $R^{18}$ is $R^{18a}$-substituted or unsubstituted 3 to 6 membered heterocycloalkyl. In embodiments, the $R^{18a}$-substituted or unsubstituted 3 to 6 membered heterocycloalkyl is $R^{18a}$-substituted or unsubstituted thiophenyl, $R^{18a}$-substituted or unsubstituted thiazolyl, $R^{18a}$-substituted or unsubstituted oxazolyl, $R^{18a}$-substituted or unsubstituted imidazolyl, or derivatives thereof. In embodiments, $R^{18}$ is $R^{18a}$-substituted or unsubstituted 6 membered aryl or phenyl. In embodiments, $R^{18}$ is $R^{18a}$-substituted or unsubstituted 6 membered heteroaryl. In embodiments, $R^{18}$ is $R^{18a}$-substituted or unsubstituted 6,6 fused ring aryl-heterocycloalkyl. In embodiments, the $R^{18a}$-substituted or unsubstituted 6,6 fused ring aryl-heteroaryl is $R^{18a}$-substituted or unsubstituted dihydrobenzo[1,4]dioxinyl. In embodiments, $R^{18}$ is $R^{18a}$-substituted or unsubstituted 6,5 fused ring aryl-heterocycloalkyl or $R^{18a}$-substituted or unsubstituted 5,6 fused ring aryl-heterocycloalkyl. In embodiments, the $R^{18a}$-substituted or unsubstituted 6,5 or 5,6 fused ring aryl-heterocycloalkyl is dihydro-indenyl, benzo[1,3]dioxolyl, or indolyl. In embodiments, $R^{18a}$ is halogen (e.g. —F, —Cl, —Br, or —I), $SO_2Ph$, $C_1$-$C_5$ $R^{18b}$-substituted or unsubstituted alkyl, or 2 to 5 membered $R^{18b}$-substituted or unsubstituted heteroalkyl.

In embodiments, $R^1$ and $R^{18}$ are not joined to form a substituted or unsubstituted cycloalkyl, substituted or unsubstituted heterocycloalkyl, substituted or unsubstituted aryl (including fused cycloalkyl-aryl, heterocycloalkyl-aryl and aryl rings) or substituted or unsubstituted heteroaryl (including fused cycloalkyl-heteroaryl, heterocycloalkyl-heteroaryl and heteroaryl rings). In embodiments, $R^1$ and $R^{16}$ are not joined to form a substituted or unsubstituted cycloalkyl, substituted or unsubstituted heterocycloalkyl, substituted or unsubstituted aryl (including fused cycloalkyl-aryl, heterocycloalkyl-aryl and aryl rings) or substituted or unsubstituted heteroaryl (including fused cycloalkyl-heteroaryl, heterocycloalkyl-heteroaryl and heteroaryl rings).

In embodiments, $R^2$ and $R^{18}$ are not joined to form a substituted or unsubstituted cycloalkyl, substituted or unsubstituted heterocycloalkyl, substituted or unsubstituted aryl (including fused cycloalkyl-aryl, heterocycloalkyl-aryl and aryl rings) or substituted or unsubstituted heteroaryl (including fused cycloalkyl-heteroaryl, heterocycloalkyl-heteroaryl and heteroaryl rings). In embodiments, $R^2$ and $R^{16}$ are not joined to form a substituted or unsubstituted cycloalkyl, substituted or unsubstituted heterocycloalkyl, substituted or unsubstituted aryl (including fused cycloalkyl-aryl, heterocycloalkyl-aryl and aryl rings) or substituted or unsubstituted heteroaryl (including fused cycloalkyl-heteroaryl, heterocycloalkyl-heteroaryl and heteroaryl rings).

In embodiments, $R^1$ and $R^{18}$ are not hydrogen. In embodiments, the compound of formula (I) does not have the formula (3R,8S,8aR)-8-hydroxy-2-methyltetrahydro-1H-3,8a-epidithiopyrrolo[1,2-a]pyrazine-1,4(6H)-dione. In embodiments, the compound of formula (I) does not have the formula (3R,8S,8aR)-2-methyl-1,4-dioxohexahydro-1H-3,8a-epidithiopyrrolo[1,2-a]pyrazin-8-yl acetate. In embodiments, the compound of formula (I) does not have the formula (3R,6R,8S,8aR)-6-(((tert-butyldiphenylsilyl)oxy)methyl)-8-hydroxy-2-methyltetrahydro-1H-3,8a-epidithiopyrrolo[1,2-a]pyrazine-1,4(6H)-dione. In embodiments, the compound does not have the formula 2,3-dimethyltetrahydro-1H-3,8a-epidithiopyrrolo[1,2-a]pyrazine-1,4(6H)-dione. In embodiments, the compound does not have the formula 3-(hydroxymethyl)-2-methyltetrahydro-1H-3,8a-epidithiopyrrolo[1,2-a]pyrazine-1,4(6H)-dione.

The compound of formula (II) may have the formula:

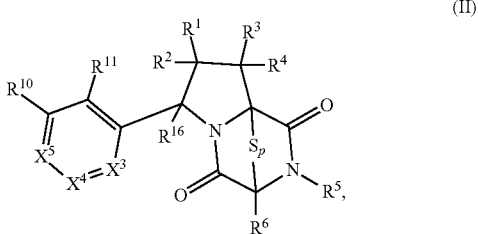

(II)

wherein p, $R^1$, $R^2$, $R^3$, $R^4$, $R^5$, $R^6$ and $R^{16}$ are as described herein, including embodiments thereof.

$X^3$ is N or $CR^7$. $X^4$ is N or $CR^8$. $X^5$ is N or $CR^9$. $R^7$ is hydrogen, halogen (e.g. —F, —Cl, —Br, or —I), —N$_3$, —CF$_3$, —CCl$_3$, —CBr$_3$, —CI$_3$, —CN, —CHO, —OR$^{33I}$, —NR$^{34I}$R$^{35I}$, —COOR$^{33I}$, —CONR$^{34I}$R$^{35I}$, —NO$_2$, —SR$^{36I}$, —SO$_{n9}$R$^{34I}$, —SO$_{n9}$OR$^{34I}$, —SO$_{n9}$NR$^{34I}$R$^{35I}$, —NHNR$^{34I}$R$^{35I}$, —ONR$^{34I}$R$^{35I}$, —NHC(O)NHNR$^{34I}$R$^{35I}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^8$ is hydrogen, halogen (e.g. —F, —Cl, —Br, or —I), —N$_3$, —CF$_3$, —CCl$_3$, —CBr$_3$, —CI$_3$, —CN, —CHO, —OR$^{33J}$, —NR$^{34J}$R$^{35J}$, —COOR$^{33J}$, —CONR$^{34J}$R$^{35J}$, —NO$_2$, —SR$^{36J}$, —SO$_{n10}$R$^{34J}$, —SO$_{n10}$OR$^{34J}$, —SO$_{n10}$NR$^{34J}$R$^{35J}$, —NHNR$^{34J}$R$^{35J}$, —ONR$^{34J}$R$^{35J}$, —NHC(O)NHNR$^{34J}$R$^{35J}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^9$ is hydrogen, halogen (e.g. —F, —Cl, —Br, or —I), —N$_3$, —CF$_3$, —CCl$_3$, —CBr$_3$, —CI$_3$, —CN, —CHO, —OR$^{33K}$, —NR$^{34K}$R$^{35K}$, —COOR$^{33K}$, —CONR$^{34K}$R$^{35K}$, —NO$_2$, —SR$^{36K}$, —SO$_{n11}$R$^{34K}$, —SO$_{n11}$OR$^{34K}$, —SO$_{n11}$NR$^{34K}$R$^{35K}$, —NHNR$^{34K}$R$^{35K}$, —ONR$^{34K}$R$^{35K}$, —NHC(O)NHNR$^{34K}$R$^{35K}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{10}$ and $R^{11}$ are independently hydrogen, halogen (e.g. —F, —Cl, —Br, or —I), —N$_3$, —CF$_3$, —CCl$_3$, —CBr$_3$, —CI$_3$, —CN, —CHO, —OR$^{33L}$, —NR$^{34L}$R$^{35L}$, —COOR$^{33L}$, —CONR$^{34L}$R$^{35L}$, —NO$_2$, —SR$^{36L}$, —SO$_{n12}$R$^{34L}$, —SO$_{n12}$OR$^{34L}$, —SO$_{n12}$NR$^{34L}$R$^{35L}$, —NHNR$^{34L}$R$^{35L}$, —ONR$^{34L}$R$^{35L}$, —NHC(O)NHNR$^{34L}$R$^{35L}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, or are optionally joined together to form a substituted or unsubstituted cycloalkyl, a substituted or unsubstituted heterocycloalkyl, a substituted or unsubstituted aryl, or a substituted or unsubstituted heteroaryl. $R^{33I}$, $R^{34I}$, $R^{35I}$, $R^{36I}$, $R^{33J}$, $R^{34J}$, $R^{35J}$, $R^{36J}$, $R^{33K}$, $R^{34K}$, $R^{35K}$, $R^{36K}$, $R^{33L}$, $R^{34L}$, $R^{35L}$, and $R^{36L}$, are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^{33I}$, $R^{34I}$, $R^{35I}$, $R^{36I}$, $R^{33J}$, $R^{34J}$, $R^{35J}$, $R^{36J}$, $R^{33K}$, $R^{34K}$, $R^{35K}$, $R^{36K}$, $R^{33L}$, $R^{34L}$, $R^{35L}$, and $R^{36L}$, are independently hydrogen, $R^{44a}$-substituted or unsubstituted alkyl, $R^{44a}$-substituted or unsubstituted heteroalkyl, $R^{44a}$-substituted or unsubstituted cycloalkyl, $R^{44a}$-substituted or unsubstituted heterocycloalkyl, $R^{44a}$-substituted or unsubstituted aryl, or $R^{44a}$-substituted or unsubstituted heteroaryl. In embodiments, $R^{33I}$, $R^{34I}$, $R^{35I}$, $R^{36I}$, $R^{33J}$, $R^{34J}$, $R^{35J}$, $R^{36J}$, $R^{33K}$, $R^{34K}$, $R^{35K}$, $R^{36K}$, $R^{33L}$, $R^{34L}$, $R^{35L}$, and $R^{36L}$, are independently hydrogen, unsubstituted alkyl, unsubstituted heteroalkyl, unsubstituted cycloalkyl, unsubstituted heterocycloalkyl, unsubstituted aryl, or unsubstituted heteroaryl. The symbols n9, n10, n11, and n12 are independently 1 or 2.

The symbols n9, n10, n11, and n12 are independently 1 or 2. In embodiments, n9 is 1. In embodiments, n9 is 2. In embodiments, n10 is 1. In embodiments, n10 is 2. In embodiments, n11 is 1. In embodiments, n11 is 2. In embodiments, n12 is 1. In embodiments, n12 is 2.

In embodiments, $R^{10}$ and $R^{11}$ are optionally joined together to form substituted or unsubstituted cycloalkyl, substituted or unsubstituted heterocycloalkyl, substituted or unsubstituted aryl, or substituted or unsubstituted heteroaryl. In embodiments, $R^{10}$ and $R^{11}$ are optionally joined together to form $R^{40a}$-substituted or unsubstituted cycloalkyl, a $R^{40a}$-substituted or unsubstituted heterocycloalkyl, a $R^{40a}$-substituted or unsubstituted aryl, or a $R^{40a}$-substituted or unsubstituted heteroaryl. In embodiments, $R^{10}$ and $R^{11}$ are optionally joined together to form unsubstituted cycloalkyl, unsubstituted heterocycloalkyl, unsubstituted aryl, or unsubstituted heteroaryl.

$R^{40a}$ is halogen (e.g. —F, —Cl, —Br, or —I), —N$_3$, —CF$_3$, —CCl$_3$, —CBr$_3$, —CI$_3$, —CN, —CHO, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC(O)NHNH$_2$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{12}$, $C_6$-$C_{10}$, or phenyl), or substituted or unsubstituted heteroaryl (e.g., 5 to 12 membered, 5 to 10 membered, 5 to 9 membered, or 5 to 6 membered). In embodiments, $R^{40a}$ is halogen (e.g. —F, —Cl, —Br, or —I), —N$_3$, —CF$_3$, —CCl$_3$, —CBr$_3$, —CI$_3$, —CN, —CHO, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC(O)NHNH$_2$, $R^{40b}$-substituted or unsubstituted alkyl (e.g., $C_1$-$C_8$, $C_1$-$C_6$, $C_1$-$C_4$, or $C_1$-$C_2$), $R^{4b}$-substituted or unsubstituted heteroalkyl (e.g., 2 to 8 membered, 2 to 6 membered, 4 to 6 membered, 2 to 3 membered, or 4 to 5 membered), $R^{40b}$-substituted or unsubstituted cycloalkyl (e.g., $C_3$-$C_8$, $C_3$-$C_6$, $C_4$-$C_6$, or $C_5$-$C_6$), $R^{40b}$-substituted or unsubstituted heterocycloalkyl (e.g., 3 to 8 membered, 3 to 6 membered, 4 to 6 membered, 4 to 5 membered, or 5 to 6 membered), $R^{40b}$-substituted or unsubstituted aryl (e.g., $C_6$-$C_{12}$, $C_6$-$C_{10}$, or phenyl), or $R^{40b}$-substituted or unsubstituted heteroaryl (e.g., 5 to 12 membered, 5 to 10 membered, 5 to 9 membered, or 5 to 6 membered). In embodiments, $R^{40a}$ is halogen (e.g. —F, —Cl, —Br, or —I), —N$_3$, —CF$_3$, —CCl$_3$, —CBr$_3$, —CI$_3$, —CN, —CHO, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC(O)NHNH$_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered).

$R^{40b}$ is halogen (e.g. —F, —Cl, —Br, or —I), —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC(O)$NHNH_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered).

In embodiments, $R^7$ and $R^8$ are optionally joined together to form substituted or unsubstituted cycloalkyl, substituted or unsubstituted heterocycloalkyl, substituted or unsubstituted aryl, or a substituted or unsubstituted heteroaryl. In embodiments, $R^7$ and $R^8$ are optionally joined together to form $R^{41a}$-substituted or unsubstituted cycloalkyl, $R^{41a}$-substituted or unsubstituted heterocycloalkyl, $R^{41a}$-substituted or unsubstituted aryl, or $R^{41a}$-substituted or unsubstituted heteroaryl. In embodiments, $R^7$ and $R^8$ are optionally joined together to form a unsubstituted cycloalkyl, unsubstituted heterocycloalkyl, unsubstituted aryl, or unsubstituted heteroaryl.

$R^{41a}$ is halogen (e.g. —F, —Cl, —Br, or —I), —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC(O)$NHNH_2$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{12}$, $C_6$-$C_{10}$, or phenyl), or substituted or unsubstituted heteroaryl (e.g., 5 to 12 membered, 5 to 10 membered, 5 to 9 membered, or 5 to 6 membered). In embodiments, $R^{41a}$ is halogen (e.g. —F, —Cl, —Br, or —I), —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC(O)$NHNH_2$, $R^{41b}$-substituted or unsubstituted alkyl (e.g., $C_1$-$C_8$, $C_1$-$C_6$, $C_1$-$C_4$, or $C_1$-$C_2$), $R^{41b}$-substituted or unsubstituted heteroalkyl (e.g., 2 to 8 membered, 2 to 6 membered, 4 to 6 membered, 2 to 3 membered, or 4 to 5 membered), $R^{41b}$-substituted or unsubstituted cycloalkyl (e.g., $C_3$-$C_8$, $C_3$-$C_6$, $C_4$-$C_6$, or $C_5$-$C_6$), $R^{41b}$-substituted or unsubstituted heterocycloalkyl (e.g., 3 to 8 membered, 3 to 6 membered, 4 to 6 membered, 4 to 5 membered, or 5 to 6 membered), $R^{41b}$-substituted or unsubstituted aryl (e.g., $C_6$-$C_{12}$, $C_6$-$C_{10}$, or phenyl), or $R^{41b}$-substituted or unsubstituted heteroaryl (e.g., 5 to 12 membered, 5 to 10 membered, 5 to 9 membered, or 5 to 6 membered). In embodiments, $R^{41a}$ is halogen (e.g. —F, —Cl, —Br, or —I), —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC(O)$NHNH_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered).

$R^{41b}$ is halogen (e.g. —F, —Cl, —Br, or —I), —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC(O)$NHNH_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered).

In embodiments, $R^8$ and $R^9$ are optionally joined together to form substituted or unsubstituted cycloalkyl, substituted or unsubstituted heterocycloalkyl, substituted or unsubstituted aryl, or substituted or unsubstituted heteroaryl. In embodiments, $R^8$ and $R^9$ are optionally joined together to form $R^{42a}$-substituted or unsubstituted cycloalkyl, $R^{42a}$-substituted or unsubstituted heterocycloalkyl, $R^{42a}$-substituted or unsubstituted aryl, or $R^{42a}$-substituted or unsubstituted heteroaryl. In embodiments, $R^8$ and $R^9$ are optionally joined together to form unsubstituted cycloalkyl, unsubstituted heterocycloalkyl, unsubstituted aryl, or unsubstituted heteroaryl.

$R^{42a}$ is halogen (e.g. —F, —Cl, —Br, or —I), —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC(O)$NHNH_2$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{12}$, $C_6$-$C_{10}$, or phenyl), or substituted or unsubstituted heteroaryl (e.g., 5 to 12 membered, 5 to 10 membered, 5 to 9 membered, or 5 to 6 membered). In embodiments, $R^{42a}$ is halogen (e.g. —F, —Cl, —Br, or —I), —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC(O)$NHNH_2$, $R^{42b}$-substituted or unsubstituted alkyl (e.g., $C_1$-$C_8$, $C_1$-$C_6$, $C_1$-$C_4$, or $C_1$-$C_2$), $R^{42b}$-substituted or unsubstituted heteroalkyl (e.g., 2 to 8 membered, 2 to 6 membered, 4 to 6 membered, 2 to 3 membered, or 4 to 5 membered), $R^{42b}$-substituted or unsubstituted cycloalkyl (e.g., $C_3$-$C_8$, $C_3$-$C_6$, $C_4$-$C_6$, or $C_5$-$C_6$), $R^{42b}$-substituted or unsubstituted heterocycloalkyl (e.g., 3 to 8 membered, 3 to 6 membered, 4 to 6 membered, 4 to 5 membered, or 5 to 6 membered), $R^{42b}$-substituted or unsubstituted aryl (e.g., $C_6$-$C_{12}$, $C_6$-$C_{10}$, or phenyl), or $R^{42b}$-substituted or unsubstituted heteroaryl (e.g., 5 to 12 membered, 5 to 10 membered, 5 to 9 membered, or 5 to 6 membered). In embodiments, $R^{42a}$ is halogen (e.g. —F, —Cl, —Br, or —I), —N$_3$, —CF$_3$, —CCl$_3$, —CBr$_3$, —CI$_3$, —CN, —CHO, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC(O)NHNH$_2$, unsubstituted alkyl (e.g., C$_1$-C$_8$, C$_1$-C$_6$, C$_1$-C$_4$, or C$_1$-C$_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., C$_3$-C$_8$, C$_3$-C$_6$, C$_4$-C$_6$, or C$_5$-C$_6$), unsubstituted heterocycloalkyl (e.g., 3 to 8 membered, 3 to 6 membered, 4 to 6 membered, 4 to 5 membered, or 5 to 6 membered), unsubstituted aryl (e.g., C$_6$-C$_{12}$, C$_6$-C$_{10}$, or phenyl), or unsubstituted heteroaryl (e.g., 5 to 12 membered, 5 to 10 membered, 5 to 9 membered, or 5 to 6 membered).

R$^{42b}$ is halogen (e.g. —F, —Cl, —Br, or —I), —N$_3$, —CF$_3$, —CCl$_3$, —CBr$_3$, —CI$_3$, —CN, —CHO, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC(O)NHNH$_2$, unsubstituted alkyl (e.g., C$_1$-C$_8$, C$_1$-C$_6$, C$_1$-C$_4$, or C$_1$-C$_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., C$_3$-C$_8$, C$_3$-C$_6$, C$_4$-C$_6$, or C$_5$-C$_6$), unsubstituted heterocycloalkyl (e.g., 3 to 8 membered, 3 to 6 membered, 4 to 6 membered, 4 to 5 membered, or 5 to 6 membered), unsubstituted aryl (e.g., C$_6$-C$_{12}$, C$_6$-C$_{10}$, or phenyl), or unsubstituted heteroaryl (e.g., 5 to 12 membered, 5 to 10 membered, 5 to 9 membered, or 5 to 6 membered).

In embodiments, R$^9$ and R$^{10}$ are optionally joined together to form substituted or unsubstituted cycloalkyl, substituted or unsubstituted heterocycloalkyl, substituted or unsubstituted aryl, or substituted or unsubstituted heteroaryl. In embodiments, R$^9$ and R$^{10}$ are optionally joined together to form R$^{43a}$-substituted or unsubstituted cycloalkyl, R$^{43a}$-substituted or unsubstituted heterocycloalkyl, R$^{43a}$-substituted or unsubstituted aryl, or R$^{43a}$-substituted or unsubstituted heteroaryl. In embodiments, R$^9$ and R$^{10}$ are optionally joined together to form unsubstituted cycloalkyl, unsubstituted heterocycloalkyl, unsubstituted aryl, or unsubstituted heteroaryl.

R$^{43a}$ is halogen (e.g. —F, —Cl, —Br, or —I), —N$_3$, —CF$_3$, —CCl$_3$, —CBr$_3$, —CI$_3$, —CN, —CHO, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC(O)NHNH$_2$, substituted or unsubstituted alkyl (e.g., C$_1$-C$_8$, C$_1$-C$_6$, C$_1$-C$_4$, or C$_1$-C$_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., C$_3$-C$_8$, C$_3$-C$_6$, C$_4$-C$_6$, or C$_5$-C$_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., C$_6$-C$_{12}$, C$_6$-C$_{10}$, or phenyl), or substituted or unsubstituted heteroaryl (e.g., 5 to 12 membered, 5 to 10 membered, 5 to 9 membered, or 5 to 6 membered). In embodiments, R$^{43a}$ is halogen (e.g. —F, —Cl, —Br, or —I), —N$_3$, —CF$_3$, —CCl$_3$, —CBr$_3$, —CI$_3$, —CN, —CHO, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC(O)NHNH$_2$, R$^{43b}$-substituted or unsubstituted alkyl (e.g., C$_1$-C$_8$, C$_1$-C$_6$, C$_1$-C$_4$, or C$_1$-C$_2$), R$^{43b}$-substituted or unsubstituted heteroalkyl (e.g., 2 to 8 membered, 2 to 6 membered, 4 to 6 membered, 2 to 3 membered, or 4 to 5 membered), R$^{43b}$-substituted or unsubstituted cycloalkyl (e.g., C$_3$-C$_8$, C$_3$-C$_6$, C$_4$-C$_6$, or C$_5$-C$_6$), R$^{43b}$-substituted or unsubstituted heterocycloalkyl (e.g., 3 to 8 membered, 3 to 6 membered, 4 to 6 membered, 4 to 5 membered, or 5 to 6 membered), R$^{43b}$-substituted or unsubstituted aryl (e.g., C$_6$-C$_{12}$, C$_6$-C$_{10}$, or phenyl), or R$^{43b}$-substituted or unsubstituted heteroaryl (e.g., 5 to 12 membered, 5 to 10 membered, 5 to 9 membered, or 5 to 6 membered). In embodiments, R$^{43a}$ is halogen (e.g. —F, —Cl, —Br, or —I), —N$_3$, —CF$_3$, —CCl$_3$, —CBr$_3$, —CI$_3$, —CN, —CHO, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC(O)NHNH$_2$, unsubstituted alkyl (e.g., C$_1$-C$_8$, C$_1$-C$_6$, C$_1$-C$_4$, or C$_1$-C$_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., C$_3$-C$_8$, C$_3$-C$_6$, C$_4$-C$_6$, or C$_5$-C$_6$), unsubstituted heterocycloalkyl (e.g., 3 to 8 membered, 3 to 6 membered, 4 to 6 membered, 4 to 5 membered, or 5 to 6 membered), unsubstituted aryl (e.g., C$_6$-C$_{12}$, C$_6$-C$_{10}$, or phenyl), or unsubstituted heteroaryl (e.g., 5 to 12 membered, 5 to 10 membered, 5 to 9 membered, or 5 to 6 membered).

R$^{43b}$ is halogen (e.g. —F, —Cl, —Br, or —I), —N$_3$, —CF$_3$, —CCl$_3$, —CBr$_3$, —CI$_3$, —CN, —CHO, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC(O)NHNH$_2$, unsubstituted alkyl (e.g., C$_1$-C$_8$, C$_1$-C$_6$, C$_1$-C$_4$, or C$_1$-C$_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., C$_3$-C$_8$, C$_3$-C$_6$, C$_4$-C$_6$, or C$_5$-C$_6$), unsubstituted heterocycloalkyl (e.g., 3 to 8 membered, 3 to 6 membered, 4 to 6 membered, 4 to 5 membered, or 5 to 6 membered), unsubstituted aryl (e.g., C$_6$-C$_{12}$, C$_6$-C$_{10}$, or phenyl), or unsubstituted heteroaryl (e.g., 5 to 12 membered, 5 to 10 membered, 5 to 9 membered, or 5 to 6 membered).

In embodiments, p is 2 or 3. In embodiments, p is 2. In embodiments, p is 3.

In embodiments, when X$^3$ is N, X$^4$ is CR$^8$ and X$^5$ is CR$^9$. In embodiments, when X$^4$ is N, X$^3$ is CR$^7$ and X$^5$ is CR$^9$. In embodiments, when X$^5$ is N, X$^3$ is CR$^7$ and X$^4$ is CR$^8$. In embodiments, X$^3$, X$^4$, and X$^5$ are CR$^7$, CR$^8$, and CR$^9$ respectively.

R$^7$ is hydrogen, halogen (e.g. —F, —Cl, —Br, or —I), —N$_3$, —CF$_3$, —CCl$_3$, —CBr$_3$, —CI$_3$, —CN, —CHO, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC(O)NHNH$_2$, substituted or unsubstituted alkyl (e.g., C$_1$-C$_8$, C$_1$-C$_5$, or C$_1$-C$_3$), or substituted or unsubstituted heteroalkyl (e.g., 2 to 8 membered, 2 to 5 membered, 2 to 3 membered). In embodiments, R$^7$ is hydrogen, halogen (e.g. —F, —Cl, —Br, or —I), —N$_3$, —CF$_3$, —CCl$_3$, —CBr$_3$, —CI$_3$, —CN, —CHO, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC(O)NHNH$_2$, R$^{7a}$-substituted or unsubstituted alkyl (e.g., C$_1$-C$_8$, C$_1$-C$_5$, or C$_1$-C$_3$), or R$^{7a}$-substituted or unsubstituted heteroalkyl (e.g., 2 to 8 membered, 2 to 5 membered, 2 to 3 membered). In embodiments, R$^7$ is halogen (e.g. —F, —Cl, —Br, or —I), —CF$_3$, —CCl$_3$, —CBr$_3$, —CI$_3$, —CN, substituted or unsubstituted alkyl, or substituted or unsubstituted heteroalkyl. In embodiments, R$^7$ is halogen (e.g. —F, —Cl, —Br, or —I), R$^{7a}$-substituted or unsubstituted C$_1$-C$_5$ alkyl, or R$^{7a}$-substituted or unsubstituted 2 to 5 membered heteroalkyl. In embodiments, R$^7$ is halogen (e.g. —F, —Cl, —Br, or —I), unsubstituted C$_1$-C$_5$ alkyl, or unsubstituted 2 to 5 membered heteroalkyl. In embodiments, R$^7$ is halogen (e.g. —F, —Cl, —Br, or —I) or R$^{7a}$-substituted or unsubstituted C$_1$-C$_5$ alkyl. In embodiments, R$^7$ is halogen (e.g. —F, —Cl, —Br, or —I) or unsubstituted C$_1$-C$_5$ alkyl. In embodiments, R$^7$ is halogen (e.g. —F, —Cl, —Br, or —I) or unsubstituted C$_1$-C$_3$ alkyl. In embodiments, R$^7$ is unsubstituted $C_1$-$C_3$ alkyl. In embodiments, $R^7$ is unsubstituted methyl or ethyl. In embodiments, $R^7$ is halogen (e.g. —F, —Cl, —Br, or —I), or unsubstituted 2 to 5 membered heteroalkyl. In embodiments, $R^7$ is halogen (e.g. —F, —Cl, —Br, or —I), halogen (e.g. —F, —Cl, —Br, or —I), —CF$_3$, —CCl$_3$, —CBr$_3$, or —CI$_3$.

In embodiments, $R^7$ is substituted or unsubstituted alkyl (e.g., $C_1$-$C_8$, $C_1$-$C_5$, or $C_1$-$C_3$), substituted or unsubstituted heteroalkyl (e.g., 2 to 8 membered, 2 to 5 membered, 2 to 3 membered), substituted or unsubstituted cycloalkyl (e.g., $C_3$-$C_8$, $C_3$-$C_5$, or $C_3$), substituted or unsubstituted heterocycloalkyl (e.g., 3 to 8 membered, 3 to 6 membered, or 4 membered), substituted or unsubstituted aryl (e.g., $C_5$-$C_8$, $C_5$-$C_6$, or phenyl), or substituted or unsubstituted heteroaryl (e.g., 5 to 8 membered, 5 to 6 membered, or 6 membered). In embodiments, $R^7$ is $R^{7a}$-substituted or unsubstituted alkyl (e.g., $C_1$-$C_8$, $C_1$-$C_5$, or $C_1$-$C_3$), $R^{7a}$-substituted or unsubstituted heteroalkyl (e.g., 2 to 8 membered, 2 to 5 membered, 2 to 3 membered), $R^{7a}$-substituted or unsubstituted cycloalkyl (e.g., $C_3$-$C_8$, $C_3$-$C_5$, or $C_3$), $R^{7a}$-substituted or unsubstituted heterocycloalkyl (e.g., 3 to 8 membered, 3 to 6 membered, or 4 membered), $R^{7a}$-substituted or unsubstituted aryl (e.g., $C_5$-$C_8$, $C_5$-$C_6$, or phenyl), or $R^{7a}$-substituted or unsubstituted heteroaryl (e.g., 5 to 8 membered, 5 to 6 membered, or 6 membered). In embodiments, $R^7$ is unsubstituted alkyl (e.g., $C_1$-$C_8$, $C_1$-$C_5$, or $C_1$-$C_3$), unsubstituted heteroalkyl (e.g., 2 to 8 membered, 2 to 5 membered, 2 to 3 membered), unsubstituted cycloalkyl (e.g., $C_3$-$C_8$, $C_3$-$C_5$, or $C_3$), unsubstituted heterocycloalkyl (e.g., 3 to 8 membered, 3 to 6 membered, or 4 membered), unsubstituted aryl (e.g., $C_5$-$C_8$, $C_5$-$C_6$, or phenyl), or unsubstituted heteroaryl (e.g., 5 to 8 membered, 5 to 6 membered, or 6 membered).

In embodiments, $R^7$ is substituted or unsubstituted $C_1$-$C_8$ alkyl, substituted or unsubstituted 2 to 8 membered heteroalkyl, substituted or unsubstituted 3 to 8 membered cycloalkyl, substituted or unsubstituted 3 to 8 membered heterocycloalkyl, substituted or unsubstituted 5 to 8 membered aryl, or substituted or unsubstituted 5 to 8 membered heteroaryl. In embodiments, $R^7$ is $R^{7a}$-substituted or unsubstituted $C_1$-$C_8$ alkyl, $R^{7a}$-substituted or unsubstituted 2 to 8 membered heteroalkyl, $R^{7a}$-substituted or unsubstituted 3 to 8 membered cycloalkyl, $R^{7a}$-substituted or unsubstituted 3 to 8 membered heterocycloalkyl, $R^{7a}$-substituted or unsubstituted 5 to 8 membered aryl, or $R^{7a}$-substituted or unsubstituted 5 to 8 membered heteroaryl. In embodiments, $R^7$ is unsubstituted $C_1$-$C_8$ alkyl, unsubstituted 2 to 8 membered heteroalkyl, unsubstituted 3 to 8 membered cycloalkyl, unsubstituted 3 to 8 membered heterocycloalkyl, unsubstituted 5 to 8 membered aryl, or unsubstituted 5 to 8 membered heteroaryl.

In embodiments, $R^7$ is substituted or unsubstituted $C_1$-$C_5$ alkyl, substituted or unsubstituted 2 to 5 membered heteroalkyl, substituted or unsubstituted 3 to 5 membered cycloalkyl, substituted or unsubstituted 3 to 6 membered heterocycloalkyl, substituted or unsubstituted 5 to 6 membered aryl, or substituted or unsubstituted 5 to 6 membered heteroaryl. In embodiments, $R^7$ is $R^{7a}$-substituted or unsubstituted $C_1$-$C_5$ alkyl, $R^{7a}$-substituted or unsubstituted 2 to 5 membered heteroalkyl, $R^{7a}$-substituted or unsubstituted 3 to 5 membered cycloalkyl, $R^{7a}$-substituted or unsubstituted 3 to 6 membered heterocycloalkyl, $R^{7a}$-substituted or unsubstituted 5 to 6 membered aryl, or $R^{7a}$-substituted or unsubstituted 5 to 6 membered heteroaryl. In embodiments, $R^7$ is unsubstituted $C_1$-$C_5$ alkyl, unsubstituted 2 to 5 membered heteroalkyl, unsubstituted 3 to 5 membered cycloalkyl, unsubstituted 3 to 6 membered heterocycloalkyl, unsubstituted 5 to 6 membered aryl, or unsubstituted 5 to 6 membered heteroaryl.

In embodiments, $R^7$ is substituted or unsubstituted $C_1$-$C_3$ alkyl or substituted or unsubstituted 2 to 3 membered heteroalkyl. In embodiments, $R^7$ is substituted or unsubstituted 3 membered cycloalkyl, substituted or unsubstituted 4 membered cycloalkyl, or substituted or unsubstituted 5 membered cycloalkyl. In embodiments, $R^7$ is substituted or unsubstituted 4 membered heterocycloalkyl, substituted or unsubstituted 5 membered heterocycloalkyl, or substituted or unsubstituted 6 membered heterocycloalkyl. In embodiments, $R^7$ is substituted or unsubstituted 5 membered aryl, substituted or unsubstituted 6 membered aryl, substituted or unsubstituted 5 membered heteroaryl, or substituted or unsubstituted 6 membered heteroaryl. In embodiments, $R^7$ is $R^{7a}$-substituted or unsubstituted $C_1$-$C_3$ alkyl or $R^{7a}$-substituted or unsubstituted 2 to 3 membered heteroalkyl. In embodiments, $R^7$ is $R^{7a}$-substituted or unsubstituted 3 membered cycloalkyl, $R^{7a}$-substituted or unsubstituted 4 membered cycloalkyl, or $R^{7a}$-substituted or unsubstituted 5 membered cycloalkyl. In embodiments, $R^7$ is $R^{7a}$-substituted or unsubstituted 4 membered heterocycloalkyl, $R^{7a}$-substituted or unsubstituted 5 membered heterocycloalkyl, or $R^{7a}$-substituted or unsubstituted 6 membered heterocycloalkyl. In embodiments, $R^7$ is $R^{7a}$-substituted or unsubstituted 5 membered aryl, $R^{7a}$-substituted or unsubstituted 6 membered aryl, $R^{7a}$-substituted or unsubstituted 5 membered heteroaryl, or $R^{7a}$-substituted or unsubstituted 6 membered heteroaryl. In embodiments, $R^7$ is unsubstituted $C_1$-$C_3$ alkyl or unsubstituted 2 to 3 membered heteroalkyl. In embodiments, $R^7$ is or unsubstituted 3 membered cycloalkyl, or unsubstituted 4 membered cycloalkyl, or unsubstituted 5 membered cycloalkyl. In embodiments, $R^7$ is or unsubstituted 4 membered heterocycloalkyl, or unsubstituted 5 membered heterocycloalkyl, or unsubstituted 6 membered heterocycloalkyl. In embodiments, $R^7$ is or unsubstituted 5 membered aryl, or unsubstituted 6 membered aryl, or unsubstituted 5 membered heteroaryl, or unsubstituted 6 membered heteroaryl.

In embodiments, $R^7$ is hydrogen, halogen (e.g. —F, —Cl, —Br, or —I), —N$_3$, —CF$_3$, —CCl$_3$, —CBr$_3$, —CI$_3$, —CN, —CHO, —OR$^{33I}$, —NR$^{34I}$R$^{35I}$, —COOR$^{33I}$, —CONR$^{34I}$R$^{35I}$, —NO$_2$, —SR$^{36I}$, —SO$_{n9}$R$^{34I}$, —SO$_{n9}$OR$^{34I}$, —SO$_{n9}$NR$^{34I}$R$^{35I}$, —NHNR$^{34I}$R$^{35I}$, —ONR$^{34I}$R$^{35I}$, —NHC(O)NHNR$^{34I}$R$^{35I}$ (e.g., —OH, —OCH$_3$, —NH2, —NHCH$_3$, NCH$_3$NCH$_3$, —COOH, —COOCH$_3$, —CONH$_2$, —CONHCH$_3$, —NO$_2$, —SH, —SCH$_3$, —SOH, —SOCH$_3$, —SO$_2$H, —SO$_2$CH$_3$, —S(O)OH, —S(O)OCH$_3$, —S(O)$_2$H, S(O)$_2$OCH$_3$, —S(O)NH$_2$, —S(O)NHCH$_3$, —S(O)$_2$NH$_2$, S(O)$_2$NHCH$_3$, —NHNH$_2$, —NHNHCH$_3$, —NHNCH$_3$CH$_3$, —ONH$_2$, —ONHCH$_3$, —NHC(O)NHNH$_2$, or —NHC(O)NHNHCH$_3$), substituted or unsubstituted alkyl (e.g., $C_1$-$C_8$, $C_1$-$C_5$, or $C_1$-$C_3$), substituted or unsubstituted heteroalkyl (e.g., 2 to 8 membered, 2 to 5 membered, 2 to 3 membered), substituted or unsubstituted cycloalkyl (e.g., $C_3$-$C_8$, $C_3$-$C_5$, or $C_3$), substituted or unsubstituted heterocycloalkyl (e.g., 3 to 8 membered, 3 to 6 membered, or 4 membered), substituted or unsubstituted aryl (e.g., $C_5$-$C_8$, $C_5$-$C_6$, or phenyl), or substituted or unsubstituted heteroaryl (e.g., 5 to 8 membered, 5 to 6 membered, or 6 membered).

In embodiments, $R^7$ is hydrogen, halogen (e.g. —F, —Cl, —Br, or —I), —N$_3$, —CF$_3$, —CCl$_3$, —CBr$_3$, —CI$_3$, —CN, —CHO, —OR$^{33I}$, —NR$^{34I}$R$^{35I}$, —COOR$^{33I}$, —CONR$^{34I}$R$^{35I}$, —NO$_2$, —SR$^{36I}$, —SO$_{n9}$R$^{34I}$, —SO$_{n9}$OR$^{34I}$, —SO$_{n9}$NR$^{34I}$R$^{35I}$, —NHNR$^{34I}$R$^{35I}$, —ONR$^{34I}$R$^{35I}$, —NHC(O)NHNR$^{34I}$R$^{35I}$ (e.g., —OH, —OCH$_3$, —NH2, —NHCH$_3$, NCH$_3$NCH$_3$, —COOH, —COOCH$_3$, —CONH$_2$, —CONHCH$_3$, —NO$_2$, —SH, —SCH$_3$, —SOH, —SOCH$_3$, —SO$_2$H, —SO$_2$CH$_3$, —S(O) OH, —S(O)OCH$_3$, —S(O)$_2$H, S(O)$_2$OCH$_3$, —S(O)NH$_2$, —S(O)NHCH$_3$, —S(O)$_2$NH$_2$, S(O)$_2$NHCH$_3$, —NHNH$_2$, —NHNHCH$_3$, —NHNCH$_3$CH$_3$, —ONH$_2$, —ONHCH$_3$, —NHC(O)NHNH$_2$, or —NHC(O)NHNHCH$_3$), R$^{7a}$-substituted or unsubstituted alkyl (e.g., C$_1$-C$_8$, C$_1$-C$_5$, or C$_1$-C$_3$), R$^{7a}$-substituted or unsubstituted heteroalkyl (e.g., 2 to 8 membered, 2 to 5 membered, 2 to 3 membered), R$^{7a}$-substituted or unsubstituted cycloalkyl (e.g., C$_3$-C$_8$, C$_3$-C$_3$, or C$_3$), R$^{7a}$-substituted or unsubstituted heterocycloalkyl (e.g., 3 to 8 membered, 3 to 6 membered, or 4 membered), R$^7$-substituted or unsubstituted aryl (e.g., C$_5$-C$_8$, C$_5$-C$_6$, or phenyl), or R$^7$-substituted or unsubstituted heteroaryl (e.g., 5 to 8 membered, 5 to 6 membered, or 6 membered).

In embodiments, R$^7$ is hydrogen, halogen (e.g. —F, —Cl, —Br, or —I), —N$_3$, —CF$_3$, —CCl$_3$, —CBr$_3$, —CI$_3$, —CN, —CHO, —OR$^{33I}$, —NR$^{34I}$R$^{35I}$, —COOR$^{33I}$, —CONR$^{34I}$R$^{35I}$, —NO$_2$, —SR$^{36I}$, —SO$_{n9}$R$^{34I}$, —SO$_{n9}$OR$^{34I}$, —SO$_{n9}$NR$^{34I}$R$^{35I}$, —NHNR$^{34I}$R$^{35I}$, —ONR$^{34I}$R$^{35I}$, —NHC(O)NHNR$^{34I}$R$^{35I}$ (e.g., —OH, —OCH$_3$, —NH2, —NHCH$_3$, NCH$_3$NCH$_3$, —COOH, —COOCH$_3$, —CONH$_2$, —CONHCH$_3$, —NO$_2$, —SH, —SCH$_3$, —SOH, —SOCH$_3$, —SO$_2$H, —SO$_2$CH$_3$, —S(O) OH, —S(O)OCH$_3$, —S(O)$_2$H, S(O)$_2$OCH$_3$, —S(O)NH$_2$, —S(O)NHCH$_3$, —S(O)$_2$NH$_2$, S(O)$_2$NHCH$_3$, —NHNH$_2$, —NHNHCH$_3$, —NHNCH$_3$CH$_3$, —ONH$_2$, —ONHCH$_3$, —NHC(O)NHNH$_2$, or —NHC(O)NHNHCH$_3$), unsubstituted alkyl (e.g., C$_1$-C$_8$, C$_1$-C$_5$, or C$_1$-C$_3$), unsubstituted heteroalkyl (e.g., 2 to 8 membered, 2 to 5 membered, 2 to 3 membered), unsubstituted cycloalkyl (e.g., C$_3$-C$_8$, C$_3$-C$_3$, or C$_3$), unsubstituted heterocycloalkyl (e.g., 3 to 8 membered, 3 to 6 membered, or 4 membered), unsubstituted aryl (e.g., C$_5$-C$_8$, C$_5$-C$_6$, or phenyl), or unsubstituted heteroaryl (e.g., 5 to 8 membered, 5 to 6 membered, or 6 membered).

In embodiments, R$^7$ is hydrogen, halogen (e.g. —F, —Cl, —Br, or —I), —OH, —OCH$_3$, —NH2, —NHCH$_3$, NCH$_3$NCH$_3$, —COOH, —COOCH$_3$, —CONH$_2$, —CONHCH$_3$, —NO$_2$, —SH, —SCH$_3$, —SOH, —SOCH$_3$, —SO$_2$H, —SO$_2$CH$_3$, —S(O)OH, —S(O)OCH$_3$, —S(O)$_2$H, S(O)$_2$OCH$_3$, —S(O)NH$_2$, —S(O)NHCH$_3$, —S(O)$_2$NH$_2$, S(O)$_2$NHCH$_3$, —NHNH$_2$, —NHNHCH$_3$, —NHNCH$_3$CH$_3$, —ONH$_2$, —ONHCH$_3$, —NHC(O)NHNH$_2$, or —NHC(O) NHNHCH$_3$), R$^{7a}$-substituted or unsubstituted C$_1$-C$_3$ alkyl, R$^{7a}$-substituted or unsubstituted 2 to 3 membered heteroalkyl, R$^{7a}$-substituted or unsubstituted C$_3$-C$_5$ cycloalkyl, R$^{7a}$-substituted or unsubstituted 5 to 6 membered heterocycloalkyl, R$^{7a}$-substituted or unsubstituted phenyl, or R$^{7a}$-substituted or unsubstituted 5 to 6 membered heteroaryl. In embodiments, R$^7$ is hydrogen, —F, —Cl, —Br, —I, —OH, —OH, —OCH$_3$, —NH2, —NHCH$_3$, NCH$_3$NCH$_3$, —COOH, —COOCH$_3$, —CONH$_2$, —CONHCH$_3$, —NO$_2$, —SH, —SCH$_3$, —SOH, —SOCH$_3$, —SO$_2$H, —SO$_2$CH$_3$, —S(O)OH, —S(O)OCH$_3$, —S(O)$_2$H, S(O)$_2$OCH$_3$, —S(O) NH$_2$, —S(O)NHCH$_3$, —S(O)$_2$NH$_2$, S(O)$_2$NHCH$_3$, —NHNH$_2$, —NHNHCH$_3$, —NHNCH$_3$CH$_3$, —ONH$_2$, —ONHCH$_3$, —NHC(O)NHNH$_2$, or —NHC(O) NHNHCH$_3$), unsubstituted C$_1$-C$_3$ alkyl, unsubstituted 2 to 3 membered heteroalkyl, unsubstituted C$_3$-C$_5$ cycloalkyl, unsubstituted 5 to 6 membered heterocycloalkyl, unsubstituted phenyl, or unsubstituted 5 to 6 membered heteroaryl.

R$^{7a}$ is halogen (e.g. —F, —Cl, —Br, or —I), —N$_3$, —CF$_3$, —CCl$_3$, —CBr$_3$, —CI$_3$, —CN, —CHO, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC(O)NHNH$_2$, substituted or unsubstituted alkyl (e.g., C$_1$-C$_8$, C$_1$-C$_6$, C$_1$-C$_4$, or C$_1$-C$_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., C$_3$-C$_8$, C$_3$-C$_6$, C$_4$-C$_6$, or C$_5$-C$_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., C$_6$-C$_{12}$, C$_6$-C$_{10}$, or phenyl), or substituted or unsubstituted heteroaryl (e.g., 5 to 12 membered, 5 to 10 membered, 5 to 9 membered, or 5 to 6 membered). In embodiments, R$^{7a}$ is halogen (e.g. —F, —Cl, —Br, or —I), —N$_3$, —CF$_3$, —CCl$_3$, —CBr$_3$, —CI$_3$, —CN, —CHO, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC(O)NHNH$_2$, R$^{7b}$-substituted or unsubstituted alkyl (e.g., C$_1$-C$_8$, C$_1$-C$_6$, C$_1$-C$_4$, or C$_1$-C$_2$), R$^{7b}$-substituted or unsubstituted heteroalkyl (e.g., 2 to 8 membered, 2 to 6 membered, 4 to 6 membered, 2 to 3 membered, or 4 to 5 membered), R$^{7b}$-substituted or unsubstituted cycloalkyl (e.g., C$_3$-C$_8$, C$_3$-C$_6$, C$_4$-C$_6$, or C$_5$-C$_6$), R$^{7b}$-substituted or unsubstituted heterocycloalkyl (e.g., 3 to 8 membered, 3 to 6 membered, 4 to 6 membered, 4 to 5 membered, or 5 to 6 membered), R$^{7b}$-substituted or unsubstituted aryl (e.g., C$_6$-C$_{12}$, C$_6$-C$_{10}$, or phenyl), or R$^{7b}$-substituted or unsubstituted heteroaryl (e.g., 5 to 12 membered, 5 to 10 membered, 5 to 9 membered, or 5 to 6 membered). In embodiments, R$^{7a}$ is halogen (e.g. —F, —Cl, —Br, or —I), —N$_3$, —CF$_3$, —CCl$_3$, —CBr$_3$, —CI$_3$, —CN, —CHO, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC(O)NHNH$_2$, unsubstituted alkyl (e.g., C$_1$-C$_8$, C$_1$-C$_6$, C$_1$-C$_4$, or C$_1$-C$_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., C$_3$-C$_8$, C$_3$-C$_6$, C$_4$-C$_6$, or C$_5$-C$_6$), unsubstituted heterocycloalkyl (e.g., 3 to 8 membered, 3 to 6 membered, 4 to 6 membered, 4 to 5 membered, or 5 to 6 membered), unsubstituted aryl (e.g., C$_6$-C$_{12}$, C$_6$-C$_{10}$, or phenyl), or unsubstituted heteroaryl (e.g., 5 to 12 membered, 5 to 10 membered, 5 to 9 membered, or 5 to 6 membered).

R$^{7b}$ is halogen (e.g. —F, —Cl, —Br, or —I), —N$_3$, —CF$_3$, —CCl$_3$, —CBr$_3$, —CI$_3$, —CN, —CHO, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC(O)NHNH$_2$, unsubstituted alkyl (e.g., C$_1$-C$_8$, C$_1$-C$_6$, C$_1$-C$_4$, or C$_1$-C$_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., C$_3$-C$_8$, C$_3$-C$_6$, C$_4$-C$_6$, or C$_5$-C$_6$), unsubstituted heterocycloalkyl (e.g., 3 to 8 membered, 3 to 6 membered, 4 to 6 membered, 4 to 5 membered, or 5 to 6 membered), unsubstituted aryl (e.g., C$_6$-C$_{12}$, C$_6$-C$_{10}$, or phenyl), or unsubstituted heteroaryl (e.g., 5 to 12 membered, 5 to 10 membered, 5 to 9 membered, or 5 to 6 membered).

In embodiments, R$^8$ is hydrogen, halogen (e.g. —F, —Cl, —Br, or —I), —N$_3$, —CF$_3$, —CCl$_3$, —CBr$_3$, —CI$_3$, —CN, —CHO, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC(O)NHNH$_2$. In embodiments, R$^8$ is hydrogen, halogen (e.g. —F, —Cl, —Br, or —I), —N$_3$, —CF$_3$, —CCl$_3$, —CBr$_3$, —CI$_3$, —OH, —NH$_2$, —COOH, —CONH$_2$, —NO$_2$, —SH, or —SO$_2$. In embodiments, R$^8$ is hydrogen, halogen (e.g. —F, —Cl, —Br, or —I), —CF$_3$, —CCl$_3$, —CBr$_3$, —CI$_3$, —OH, or —NH$_2$.

In embodiments, R$^8$ is hydrogen, halogen (e.g. —F, —Cl, —Br, or —I), —N$_3$, —CF$_3$, —CCl$_3$, —CBr$_3$, —CI$_3$, —CN, —CHO, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC(O)NHNH$_2$, substituted or unsubstituted alkyl (e.g., $C_1$-$C_8$, $C_1$-$C_5$, or $C_1$-$C_3$), or substituted or unsubstituted heteroalkyl (e.g., 2 to 8 membered, 2 to 5 membered, 2 to 3 membered). In embodiments, $R^8$ is hydrogen, halogen (e.g. —F, —Cl, —Br, or —I), —N$_3$, —CF$_3$, —CCl$_3$, —CBr$_3$, —CI$_3$, —CN, —CHO, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC(O)NHNH$_2$, $R^{8a}$-substituted or unsubstituted alkyl (e.g., $C_1$-$C_8$, $C_1$-$C_5$, or $C_1$-$C_3$), or $R^{8a}$-substituted or unsubstituted heteroalkyl (e.g., 2 to 8 membered, 2 to 5 membered, 2 to 3 membered).

In embodiments, $R^8$ is substituted or unsubstituted alkyl (e.g., $C_1$-$C_8$, $C_1$-$C_5$, or $C_1$-$C_3$), substituted or unsubstituted heteroalkyl (e.g., 2 to 8 membered, 2 to 5 membered, 2 to 3 membered), substituted or unsubstituted cycloalkyl (e.g., $C_3$-$C_8$, $C_3$-$C_5$, or $C_3$), substituted or unsubstituted heterocycloalkyl (e.g., 3 to 8 membered, 3 to 6 membered, or 4 membered), substituted or unsubstituted aryl (e.g., $C_5$-$C_8$, $C_5$-$C_6$, or phenyl), or substituted or unsubstituted heteroaryl (e.g., 5 to 8 membered, 5 to 6 membered, or 6 membered). In embodiments, $R^8$ is $R^{8a}$-substituted or unsubstituted alkyl (e.g., $C_1$-$C_8$, $C_1$-$C_5$, or $C_1$-$C_3$), $R^{8a}$-substituted or unsubstituted heteroalkyl (e.g., 2 to 8 membered, 2 to 5 membered, 2 to 3 membered), $R^{8a}$-substituted or unsubstituted cycloalkyl (e.g., $C_3$-$C_8$, $C_3$-$C_5$, or $C_3$), $R^{8a}$-substituted or unsubstituted heterocycloalkyl (e.g., 3 to 8 membered, 3 to 6 membered, or 4 membered), $R^{8a}$-substituted or unsubstituted aryl (e.g., $C_5$-$C_8$, $C_5$-$C_6$, or phenyl), or $R^{8a}$-substituted or unsubstituted heteroaryl (e.g., 5 to 8 membered, 5 to 6 membered, or 6 membered). In embodiments, $R^8$ is unsubstituted alkyl (e.g., $C_1$-$C_8$, $C_1$-$C_5$, or $C_1$-$C_3$), unsubstituted heteroalkyl (e.g., 2 to 8 membered, 2 to 5 membered, 2 to 3 membered), unsubstituted cycloalkyl (e.g., $C_3$-$C_8$, $C_3$-$C_5$, or $C_3$), unsubstituted heterocycloalkyl (e.g., 3 to 8 membered, 3 to 6 membered, or 4 membered), unsubstituted aryl (e.g., $C_5$-$C_8$, $C_5$-$C_6$, or phenyl), or unsubstituted heteroaryl (e.g., 5 to 8 membered, 5 to 6 membered, or 6 membered).

In embodiments, $R^8$ is substituted or unsubstituted $C_1$-$C_8$ alkyl, substituted or unsubstituted 3 to 8 membered heteroalkyl, substituted or unsubstituted 3 to 8 membered cycloalkyl, substituted or unsubstituted 3 to 8 membered heterocycloalkyl, substituted or unsubstituted 5 to 8 membered aryl, or substituted or unsubstituted 5 to 8 membered heteroaryl. In embodiments, $R^8$ is $R^{8a}$-substituted or unsubstituted $C_1$-$C_8$ alkyl, $R^{8a}$-substituted or unsubstituted 3 to 8 membered heteroalkyl, $R^{8a}$-substituted or unsubstituted 3 to 8 membered cycloalkyl, $R^{8a}$-substituted or unsubstituted 3 to 8 membered heterocycloalkyl, $R^{8a}$-substituted or unsubstituted 5 to 8 membered aryl, or $R^{8a}$-substituted or unsubstituted 5 to 8 membered heteroaryl. In embodiments, $R^8$ is unsubstituted $C_1$-$C_8$ alkyl, unsubstituted 3 to 8 membered heteroalkyl, unsubstituted 3 to 8 membered cycloalkyl, unsubstituted 3 to 8 membered heterocycloalkyl, unsubstituted 5 to 8 membered aryl, or unsubstituted 5 to 8 membered heteroaryl.

In embodiments, $R^8$ is substituted or unsubstituted $C_1$-$C_5$ alkyl, substituted or unsubstituted 2 to 5 membered heteroalkyl, substituted or unsubstituted 3 to 5 membered cycloalkyl, substituted or unsubstituted 3 to 6 membered heterocycloalkyl, substituted or unsubstituted 5 to 6 membered aryl, or substituted or unsubstituted 5 to 6 membered heteroaryl. In embodiments, $R^8$ is $R^{8a}$-substituted or unsubstituted $C_1$-$C_5$ alkyl, $R^{8a}$-substituted or unsubstituted 2 to 5 membered heteroalkyl, $R^{8a}$-substituted or unsubstituted 3 to 5 membered cycloalkyl, $R^{8a}$-substituted or unsubstituted 3 to 6 membered heterocycloalkyl, $R^{8a}$-substituted or unsubstituted 5 to 6 membered aryl, or $R^{8a}$-substituted or unsubstituted 5 to 6 membered heteroaryl. In embodiments, $R^8$ is unsubstituted $C_1$-$C_5$ alkyl, unsubstituted 2 to 5 membered heteroalkyl, unsubstituted 3 to 5 membered cycloalkyl, unsubstituted 3 to 6 membered heterocycloalkyl, unsubstituted 5 to 6 membered aryl, or unsubstituted 5 to 6 membered heteroaryl.

In embodiments, $R^8$ is substituted or unsubstituted $C_1$-$C_3$ alkyl or substituted or unsubstituted 2 to 3 membered heteroalkyl. In embodiments, $R^8$ is substituted or unsubstituted 3 membered cycloalkyl, substituted or unsubstituted 4 membered cycloalkyl, or substituted or unsubstituted 5 membered cycloalkyl. In embodiments, $R^8$ is substituted or unsubstituted 4 membered heterocycloalkyl, substituted or unsubstituted 5 membered heterocycloalkyl, or substituted or unsubstituted 6 membered heterocycloalkyl. In embodiments, $R^8$ is substituted or unsubstituted 5 membered aryl, substituted or unsubstituted 6 membered aryl, substituted or unsubstituted 5 membered heteroaryl, or substituted or unsubstituted 6 membered heteroaryl. In embodiments, $R^8$ is $R^{8a}$-substituted or unsubstituted $C_1$-$C_3$ alkyl or $R^{8a}$-substituted or unsubstituted 2 to 3 membered heteroalkyl. In embodiments, $R^8$ is $R^{8a}$-substituted or unsubstituted 3 membered cycloalkyl, $R^{8a}$-substituted or unsubstituted 4 membered cycloalkyl, or $R^{8a}$-substituted or unsubstituted 5 membered cycloalkyl. In embodiments, $R^8$ is $R^{8a}$-substituted or unsubstituted 4 membered heterocycloalkyl, $R^{8a}$-substituted or unsubstituted 5 membered heterocycloalkyl, or $R^{8a}$-substituted or unsubstituted 6 membered heterocycloalkyl. In embodiments, $R^8$ is $R^{8a}$-substituted or unsubstituted 5 membered aryl, $R^{8a}$-substituted or unsubstituted 6 membered aryl, $R^{8a}$-substituted or unsubstituted 5 membered heteroaryl, or $R^8$ substituted or unsubstituted 6 membered heteroaryl. In embodiments, $R^8$ is unsubstituted $C_1$-$C_3$ alkyl or unsubstituted 2 to 3 membered heteroalkyl. In embodiments, $R^8$ is or unsubstituted 3 membered cycloalkyl, or unsubstituted 4 membered cycloalkyl, or unsubstituted 5 membered cycloalkyl. In embodiments, $R^8$ is or unsubstituted 4 membered heterocycloalkyl, or unsubstituted 5 membered heterocycloalkyl, or unsubstituted 6 membered heterocycloalkyl. In embodiments, $R^8$ is or unsubstituted 5 membered aryl, or unsubstituted 6 membered aryl, or unsubstituted 5 membered heteroaryl, or unsubstituted 6 membered heteroaryl.

In embodiments, $R^8$ is hydrogen, halogen (e.g. —F, —Cl, —Br, or —I), —N$_3$, —CF$_3$, —CCl$_3$, —CBr$_3$, —CI$_3$, —CN, —CHO, —OR$^{33J}$, —NR$^{34J}$R$^{35J}$, —COOR$^{33J}$, —CONR$^{34J}$R$^{35J}$, —NO$_2$, —SR$^{36J}$, —SO$_{n10}$R$^{34J}$, —SO$_{n10}$OR$^{34J}$, —SO$_{n10}$NR$^{34J}$R$^{35J}$, —NHNR$^{34J}$R$^{35J}$, —ONR$^{34J}$R$^{35J}$, —NHC(O)NHNR$^{34J}$R$^{35J}$ (e.g., —OH, —OCH$_3$, —NH2, —NHCH$_3$, NCH$_3$NCH$_3$, —COOH, —COOCH$_3$, —CONH$_2$, —CONHCH$_3$, —NO$_2$, —SH, —SCH$_3$, —SOH, —SOCH$_3$, —SO$_2$H, —SO$_2$CH$_3$, —S(O)OH, —S(O)OCH$_3$, —S(O)$_2$H, S(O)$_2$OCH$_3$, —S(O)NH$_2$, —S(O)NHCH$_3$, —S(O)$_2$NH$_2$, S(O)$_2$NHCH$_3$, —NHNH$_2$, —NHNHCH$_3$, —NHNCH$_3$CH$_3$, —ONH$_2$, —ONHCH$_3$, —NHC(O)NHNH$_2$, or —NHC(O)NHNHCH$_3$), substituted or unsubstituted alkyl (e.g., $C_1$-$C_8$, $C_1$-$C_5$, or $C_1$-$C_3$), substituted or unsubstituted heteroalkyl (e.g., 2 to 8 membered, 2 to 5 membered, 2 to 3 membered), substituted or unsubstituted cycloalkyl (e.g., $C_3$-$C_8$, $C_3$-$C_5$, or $C_3$), substituted or unsubstituted heterocycloalkyl (e.g., 3 to 8 membered, 3 to 6 membered, or 4 membered), substituted or unsubstituted aryl (e.g., $C_5$-$C_8$, $C_5$-$C_6$, or phenyl), or substituted or unsubstituted heteroaryl (e.g., 5 to 8 membered, 5 to 6 membered, or 6 membered).

In embodiments, $R^8$ is hydrogen, halogen (e.g. —F, —Cl, —Br, or —I), —$N_3$, —$CF_3$, —$CCl_3$, —$CBr_3$, —$CI_3$, —CN, —CHO, —$OR^{33.J}$, —$NR^{34.J}R^{35.J}$, —$COOR^{33.J}$, —$CONR^{34.J}R^{35.J}$, —$NO_2$, —$SR^{36.J}$, —$SO_{n10}R^{34.J}$, —$SO_{n10}OR^{34.J}$, —$SO_{n10}NR^{34.J}R^{35.J}$, —$NHNR^{34.J}R^{35.J}$, —$ONR^{34.J}R^{35.J}$, —$NHC(O)NHNR^{34.J}R^{35.J}$ (e.g., —OH, —$OCH_3$, —NH2, —$NHCH_3$, $NCH_3NCH_3$, —COOH, —$COOCH_3$, —$CONH_2$, —$CONHCH_3$, —$NO_2$, —SH, —$SCH_3$, —SOH, —$SOCH_3$, —$SO_2H$, —$SO_2CH_3$, —S(O) OH, —S(O)$OCH_3$, —S(O)$_2H$, S(O)$_2OCH_3$, —S(O)$NH_2$, —S(O)$NHCH_3$, —S(O)$_2NH_2$, S(O)$_2NHCH_3$, —$NHNH_2$, —$NHNHCH_3$, —$NHNCH_3CH_3$, —$ONH_2$, —$ONHCH_3$, —$NHC(O)NHNH_2$, or —$NHC(O)NHNHCH_3$), $R^{8a}$-substituted or unsubstituted alkyl (e.g., $C_1$-$C_8$, $C_1$-$C_5$, or $C_1$-$C_3$), $R^{8a}$-substituted or unsubstituted heteroalkyl (e.g., 2 to 8 membered, 2 to 5 membered, 2 to 3 membered), $R^{8a}$-substituted or unsubstituted cycloalkyl (e.g., $C_3$-$C_8$, $C_3$-$C_3$, or $C_3$), $R^{8a}$-substituted or unsubstituted heterocycloalkyl (e.g., 3 to 8 membered, 3 to 6 membered, or 4 membered), $R^{8a}$-substituted or unsubstituted aryl (e.g., $C_5$-$C_8$, $C_5$-$C_6$, or phenyl), or $R^{8a}$-substituted or unsubstituted heteroaryl (e.g., 5 to 8 membered, 5 to 6 membered, or 6 membered).

In embodiments, $R^8$ is hydrogen, halogen (e.g. —F, —Cl, —Br, or —I), —$N_3$, —$CF_3$, —$CCl_3$, —$CBr_3$, —$CI_3$, —CN, —CHO, —$OR^{33.J}$, —$NR^{34.J}R^{35.J}$, —$COOR^{33.J}$, —$CONR^{34.J}R^{35.J}$, —$NO_2$, —$SR^{36.J}$, —$SO_{n10}R^{34.J}$, —$SO_{n10}OR^{34.J}$, —$SO_{n10}NR^{34.J}R^{35.J}$, —$NHNR^{34.J}R^{35.J}$, —$ONR^{34.J}R^{35.J}$, —$NHC(O)NHNR^{34.J}R^{35.J}$ (e.g., —OH, —$OCH_3$, —NH2, —$NHCH_3$, $NCH_3NCH_3$, —COOH, —$COOCH_3$, —$CONH_2$, —$CONHCH_3$, —$NO_2$, —SH, —$SCH_3$, —SOH, —$SOCH_3$, —$SO_2H$, —$SO_2CH_3$, —S(O) OH, —S(O)$OCH_3$, —S(O)$_2H$, S(O)$_2OCH_3$, —S(O)$NH_2$, —S(O)$NHCH_3$, —S(O)$_2NH_2$, S(O)$_2NHCH_3$, —$NHNH_2$, —$NHNHCH_3$, —$NHNCH_3CH_3$, —$ONH_2$, —$ONHCH_3$, —$NHC(O)NHNH_2$, or —$NHC(O)NHNHCH_3$), unsubstituted alkyl (e.g., $C_1$-$C_8$, $C_1$-$C_5$, or $C_1$-$C_3$), unsubstituted heteroalkyl (e.g., 2 to 8 membered, 2 to 5 membered, 2 to 3 membered), unsubstituted cycloalkyl (e.g., $C_3$-$C_8$, $C_3$-$C_3$, or $C_3$), unsubstituted heterocycloalkyl (e.g., 3 to 8 membered, 3 to 6 membered, or 4 membered), unsubstituted aryl (e.g., $C_5$-$C_8$, $C_5$-$C_6$, or phenyl), or unsubstituted heteroaryl (e.g., 5 to 8 membered, 5 to 6 membered, or 6 membered).

In embodiments, $R^8$ is hydrogen, halogen (e.g. —F, —Cl, —Br, or —I), —OH, —$OCH_3$, —NH2, —$NHCH_3$, $NCH_3NCH_3$, —COOH, —$COOCH_3$, —$CONH_2$, —$CONHCH_3$, —$NO_2$, —SH, —$SCH_3$, —SOH, —$SOCH_3$, —$SO_2H$, —$SO_2CH_3$, —S(O)OH, —S(O)$OCH_3$, —S(O)$_2H$, S(O)$_2OCH_3$, —S(O)$NH_2$, —S(O)$NHCH_3$, —S(O)$_2NH_2$, S(O)$_2NHCH_3$, —$NHNH_2$, —$NHNHCH_3$, —$NHNCH_3CH_3$, —$ONH_2$, —$ONHCH_3$, —$NHC(O)NHNH_2$, or —$NHC(O)NHNHCH_3$), $R^{8a}$-substituted or unsubstituted $C_1$-$C_3$ alkyl, $R^{8a}$-substituted or unsubstituted 2 to 3 membered heteroalkyl, $R^{8a}$-substituted or unsubstituted $C_3$-$C_5$ cycloalkyl, $R^{8a}$-substituted or unsubstituted 5 to 6 membered heterocycloalkyl, $R^{8a}$-substituted or unsubstituted phenyl, or $R^{8a}$-substituted or unsubstituted 5 to 6 membered heteroaryl. In embodiments, $R^8$ is hydrogen, —F, —Cl, —Br, —I, —OH, —OH, —$OCH_3$, —NH2, —$NHCH_3$, $NCH_3NCH_3$, —COOH, —$COOCH_3$, —$CONH_2$, —$CONHCH_3$, —$NO_2$, —SH, —$SCH_3$, —SOH, —$SOCH_3$, —$SO_2H$, —$SO_2CH_3$, —S(O)OH, —S(O)$OCH_3$, —S(O)$_2H$, S(O)$_2OCH_3$, —S(O)$NH_2$, —S(O)$NH_2$, S(O)$_2NHCH_3$, —$NHNH_2$, —$NHNHCH_3$, —$NHNCH_3CH_3$, —$ONH_2$, —$ONHCH_3$, —$NHC(O)NHNH_2$, or —$NHC(O)$NHNHCH_3$), unsubstituted $C_1$-$C_3$ alkyl, unsubstituted 2 to 3 membered heteroalkyl, unsubstituted $C_3$-$C_5$ cycloalkyl, unsubstituted 5 to 6 membered heterocycloalkyl, unsubstituted phenyl, or unsubstituted 5 to 6 membered heteroaryl.

$R^{8a}$ is halogen (e.g. —F, —Cl, —Br, or —I), —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —$NHC(O)NHNH_2$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{12}$, $C_6$-$C_{10}$, or phenyl), or substituted or unsubstituted heteroaryl (e.g., 5 to 12 membered, 5 to 10 membered, 5 to 9 membered, or 5 to 6 membered). In embodiments, $R^{5a}$ is halogen (e.g. —F, —Cl, —Br, or —I), —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —$NHC(O)NHNH_2$, $R^{8b}$-substituted or unsubstituted alkyl (e.g., $C_1$-$C_8$, $C_1$-$C_6$, $C_1$-$C_4$, or $C_1$-$C_2$), $R^{8b}$-substituted or unsubstituted heteroalkyl (e.g., 2 to 8 membered, 2 to 6 membered, 4 to 6 membered, 2 to 3 membered, or 4 to 5 membered), $R^{8b}$-substituted or unsubstituted cycloalkyl (e.g., $C_3$-$C_8$, $C_3$-$C_6$, $C_4$-$C_6$, or $C_5$-$C_6$), $R^{8b}$-substituted or unsubstituted heterocycloalkyl (e.g., 3 to 8 membered, 3 to 6 membered, 4 to 6 membered, 4 to 5 membered, or 5 to 6 membered), $R^{8b}$-substituted or unsubstituted aryl (e.g., $C_6$-$C_{12}$, $C_6$-$C_{10}$, or phenyl), or $R^{8b}$-substituted or unsubstituted heteroaryl (e.g., 5 to 12 membered, 5 to 10 membered, 5 to 9 membered, or 5 to 6 membered). In embodiments, $R^{5a}$ is halogen (e.g. —F, —Cl, —Br, or —I), —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —$NHC(O)NHNH_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered).

$R^{8b}$ is halogen (e.g. —F, —Cl, —Br, or —I), —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —$NHC(O)NHNH_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered).

In embodiments, $R^8$ is hydrogen, halogen (e.g. —F, —Cl, —Br, or —I) or substituted or unsubstituted alkyl (e.g., $C_1$-$C_8$, $C_1$-$C_5$, or $C_1$-$C_3$). In embodiments, $R^8$ is hydrogen. In embodiments, $R^8$ is halogen (e.g. —F, —Cl, —Br, or —I).

In embodiments, $R^8$ is substituted or unsubstituted alkyl (e.g., $C_1$-$C_8$, $C_1$-$C_5$, or $C_1$-$C_3$). In embodiments, $R^8$ is substituted or unsubstituted $C_1$-$C_5$ alkyl. In embodiments, $R^8$ is $R^{5a}$-substituted $C_1$-$C_3$ alkyl. In embodiments, $R^8$ is unsubstituted $C_1$-$C_5$ alkyl. In embodiments, $R^8$ is unsubstituted $C_1$-$C_3$ alkyl.

In embodiments, $R^8$ is hydrogen, halogen (e.g. —F, —Cl, —Br, or —I), —$OR^{33J}$, —$NR^{34J}R^{35J}$, —$COOR^{33J}$, —$CONR^{34J}R^{35J}$, —$NO_2$, —$SR^{36J}$, —$SO_{n10}R^{34J}$, —$SO_{n10}OR^{34J}$, —$SO_{n10}NR^{34J}R^{35J}$, —$NHNR^{34J}R^{35J}$, —$ONR^{34J}R^{35J}$, —$NHC(O)NHNR^{34J}R^{35J}$. In embodiments, $R^8$ is hydrogen, halogen (e.g. —F, —Cl, —Br, or —I), $OR^{33J}$, —$NR^{34J}R^{35J}$, —$COOR^{33J}$, —$CONR^{34J}R^{35J}$, —$NO_2$, —$SR^{36J}$, —$SO_{n10}R^{34J}$, —$SO_{n10}OR^{34J}$, or —$SO_{n10}NR^{34J}R^{35J}$. In embodiments, $R^8$ is hydrogen, halogen (e.g. —F, —Cl, —Br, or —I), $OR^{33J}$, —$NR^{34J}R^{35J}$, —$COOR^{33J}$, —$CONR^{34J}R^{35J}$, or —$NO_2$. In embodiments, $R^8$ is hydrogen, halogen (e.g. —F, —Cl, —Br, or —I), $OR^{33J}$, or —$COOR^{33J}$. In embodiments, $R^8$ is hydrogen or —$OR^{33J}$. In embodiments, $R^8$ is $OR^{33J}$. In embodiments, $R^{33J}$ is hydrogen, or unsubstituted $C_1$-$C_3$ alkyl. In embodiments, $R^{33J}$ is hydrogen, unsubstituted methyl or unsubstituted ethyl. In embodiments, $R^8$ is hydrogen or —$OR^{33J}$ and $R^9$ is hydrogen or halogen (e.g. —F, —Cl, —Br, or —I), wherein $R^{33J}$ is hydrogen, or unsubstituted alkyl or $C_1$-$C_3$ alkyl.

In embodiments, $R^9$ is hydrogen, halogen (e.g. —F, —Cl, —Br, or —I), —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —$NHC(O)NHNH_2$. In embodiments, $R^9$ is hydrogen, halogen (e.g. —F, —Cl, —Br, or —I), —$N_3$, —$CF_3$, —$CCl_3$, —$CBr_3$, —$CI_3$, —OH, —$NH_2$, —COOH, —$CONH_2$, —$NO_2$, —SH, or —$SO_2$. In embodiments, $R^9$ is hydrogen, halogen (e.g. —F, —Cl, —Br, or —I), —$CF_3$, —$CCl_3$, —$CBr_3$, —$CI_3$, —OH, or —$NH_2$.

In embodiments, $R^9$ is hydrogen, halogen (e.g. —F, —Cl, —Br, or —I), —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —$NHC(O)NHNH_2$, substituted or unsubstituted alkyl (e.g., $C_1$-$C_8$, $C_1$-$C_5$, or $C_1$-$C_3$), or substituted or unsubstituted heteroalkyl (e.g., 2 to 8 membered, 2 to 5 membered, 2 to 3 membered). In embodiments, $R^9$ is hydrogen, halogen (e.g. —F, —Cl, —Br, or —I), —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —$NHC(O)NHNH_2$, $R^{9a}$-substituted or unsubstituted alkyl (e.g., $C_1$-$C_8$, $C_1$-$C_5$, or $C_1$-$C_3$), or $R^{9a}$-substituted or unsubstituted heteroalkyl (e.g., 2 to 8 membered, 2 to 5 membered, 2 to 3 membered).

In embodiments, $R^9$ is substituted or unsubstituted alkyl (e.g., $C_1$-$C_8$, $C_1$-$C_5$, or $C_1$-$C_3$), substituted or unsubstituted heteroalkyl (e.g., 2 to 8 membered, 2 to 5 membered, 2 to 3 membered), substituted or unsubstituted cycloalkyl (e.g., $C_3$-$C_8$, $C_3$-$C_5$, or $C_3$), substituted or unsubstituted heterocycloalkyl (e.g., 3 to 8 membered, 3 to 6 membered, or 4 membered), substituted or unsubstituted aryl (e.g., $C_5$-$C_8$, $C_5$-$C_6$, or phenyl), or substituted or unsubstituted heteroaryl (e.g., 5 to 8 membered, 5 to 6 membered, or 6 membered). In embodiments, $R^9$ is $R^{9a}$-substituted or unsubstituted alkyl (e.g., $C_1$-$C_8$, $C_1$-$C_5$, or $C_1$-$C_3$), $R^{9a}$-substituted or unsubstituted heteroalkyl (e.g., 2 to 8 membered, 2 to 5 membered, 2 to 3 membered), $R^{9a}$-substituted or unsubstituted cycloalkyl (e.g., $C_3$-$C_8$, $C_3$-$C_5$, or $C_3$), $R^{9a}$-substituted or unsubstituted heterocycloalkyl (e.g., 3 to 8 membered, 3 to 6 membered, or 4 membered), $R^{9a}$-substituted or unsubstituted aryl (e.g., $C_5$-$C_8$, $C_5$-$C_6$, or phenyl), or $R^{9a}$-substituted or unsubstituted heteroaryl (e.g., 5 to 8 membered, 5 to 6 membered, or 6 membered). In embodiments, $R^9$ is unsubstituted alkyl (e.g., $C_1$-$C_8$, $C_1$-$C_5$, or $C_1$-$C_3$), unsubstituted heteroalkyl (e.g., 2 to 8 membered, 2 to 5 membered, 2 to 3 membered), unsubstituted cycloalkyl (e.g., $C_3$-$C_8$, $C_3$-$C_5$, or $C_3$), unsubstituted heterocycloalkyl (e.g., 3 to 8 membered, 3 to 6 membered, or 4 membered), unsubstituted aryl (e.g., $C_5$-$C_8$, $C_5$-$C_6$, or phenyl), or unsubstituted heteroaryl (e.g., 5 to 8 membered, 5 to 6 membered, or 6 membered).

In embodiments, $R^9$ is substituted or unsubstituted $C_1$-$C_8$ alkyl, substituted or unsubstituted 3 to 8 membered heteroalkyl, substituted or unsubstituted 3 to 8 membered cycloalkyl, substituted or unsubstituted 3 to 8 membered heterocycloalkyl, substituted or unsubstituted 5 to 8 membered aryl, or substituted or unsubstituted 5 to 8 membered heteroaryl. In embodiments, $R^9$ is $R^{9a}$-substituted or unsubstituted $C_1$-$C_8$ alkyl, $R^{9a}$-substituted or unsubstituted 3 to 8 membered heteroalkyl, $R^{9a}$-substituted or unsubstituted 3 to 8 membered cycloalkyl, $R^{9a}$-substituted or unsubstituted 3 to 8 membered heterocycloalkyl, $R^{9a}$-substituted or unsubstituted 5 to 8 membered aryl, or $R^{9a}$-substituted or unsubstituted 5 to 8 membered heteroaryl. In embodiments, $R^9$ is unsubstituted $C_1$-$C_8$ alkyl, unsubstituted 3 to 8 membered heteroalkyl, unsubstituted 3 to 8 membered cycloalkyl, unsubstituted 3 to 8 membered heterocycloalkyl, unsubstituted 5 to 8 membered aryl, or unsubstituted 5 to 8 membered heteroaryl.

In embodiments, $R^9$ is substituted or unsubstituted $C_1$-$C_5$ alkyl, substituted or unsubstituted 2 to 5 membered heteroalkyl, substituted or unsubstituted 3 to 5 membered cycloalkyl, substituted or unsubstituted 3 to 6 membered heterocycloalkyl, substituted or unsubstituted 5 to 6 membered aryl, or substituted or unsubstituted 5 to 6 membered heteroaryl. In embodiments, $R^9$ is $R^{9a}$-substituted or unsubstituted $C_1$-$C_5$ alkyl, $R^{9a}$-substituted or unsubstituted 2 to 5 membered heteroalkyl, $R^{9a}$-substituted or unsubstituted 3 to 5 membered cycloalkyl, $R^{9a}$-substituted or unsubstituted 3 to 6 membered heterocycloalkyl, $R^{9a}$-substituted or unsubstituted 5 to 6 membered aryl, or $R^{9a}$-substituted or unsubstituted 5 to 6 membered heteroaryl. In embodiments, $R^9$ is unsubstituted $C_1$-$C_5$ alkyl, unsubstituted 2 to 5 membered heteroalkyl, unsubstituted 3 to 5 membered cycloalkyl, unsubstituted 3 to 6 membered heterocycloalkyl, unsubstituted 5 to 6 membered aryl, or unsubstituted 5 to 6 membered heteroaryl.

In embodiments, $R^9$ is substituted or unsubstituted $C_1$-$C_3$ alkyl or substituted or unsubstituted 2 to 3 membered heteroalkyl. In embodiments, $R^9$ is substituted or unsubstituted 3 membered cycloalkyl, substituted or unsubstituted 4 membered cycloalkyl, or substituted or unsubstituted 5 membered cycloalkyl. In embodiments, $R^9$ is substituted or unsubstituted 4 membered heterocycloalkyl, substituted or unsubstituted 5 membered heterocycloalkyl, or substituted or unsubstituted 6 membered heterocycloalkyl. In embodiments, $R^9$ is substituted or unsubstituted 5 membered aryl, substituted or unsubstituted 6 membered aryl, substituted or unsubstituted 5 membered heteroaryl, or substituted or unsubstituted 6 membered heteroaryl. In embodiments, $R^9$ is $R^{9a}$-substituted or unsubstituted $C_1$-$C_3$ alkyl or $R^{9a}$-substituted or unsubstituted 2 to 3 membered heteroalkyl. In embodiments, $R^9$ is $R^{9a}$-substituted or unsubstituted 3 membered cycloalkyl, $R^{9a}$-substituted or unsubstituted 4 membered cycloalkyl, or $R^{9a}$-substituted or unsubstituted 5 membered cycloalkyl. In embodiments, $R^9$ is $R^{9a}$-substituted or unsubstituted 4 membered heterocycloalkyl, $R^{9a}$-substituted or unsubstituted 5 membered heterocycloalkyl, or $R^{9a}$-substituted or unsubstituted 6 membered heterocycloalkyl. In embodiments, $R^9$ is $R^{9a}$-substituted or unsubstituted 5 membered aryl, $R^{9a}$-substituted or unsubstituted 6 membered aryl, $R^{9a}$-substituted or unsubstituted 5 membered heteroaryl, or $R^{9a}$-substituted or unsubstituted 6 membered heteroaryl. In embodiments, $R^9$ is unsubstituted $C_1$-$C_3$ alkyl or unsubstituted 2 to 3 membered heteroalkyl. In embodiments, $R^9$ is or unsubstituted 3 membered cycloalkyl, or unsubstituted 4 membered cycloalkyl, or unsubstituted 5 membered cycloalkyl. In embodiments, $R^9$ is or unsubstituted 4 membered heterocycloalkyl, or unsubstituted 5 membered heterocycloalkyl, or unsubstituted 6 membered heterocycloalkyl. In embodiments, $R^9$ is or unsubstituted 5 membered aryl, or unsubstituted 6 membered aryl, or unsubstituted 5 membered heteroaryl, or unsubstituted 6 membered heteroaryl.

In embodiments, $R^9$ is hydrogen, halogen (e.g. —F, —Cl, —Br, or —I), —$N_3$, —$CF_3$, —$CCl_3$, —$CBr_3$, —$CI_3$, —CN, —CHO, —$OR^{33K}$, —$NR^{34K}R^{35K}$, —$COOR^{33K}$, —$CONR^{34K}R^{35K}$, —$NO_2$, —$SR^{36K}$, —$SO_{n11}R^{34K}$, —$SO_{n11}OR^{34K}$, —$SO_{n11}NR^{34K}R^{35K}$, —$NHNR^{34K}R^{35K}$, —$ONR^{34K}R^{35K}$, —$NHC(O)NHNR^{34K}R^{35K}$ (e.g., —OH, —$OCH_3$, —$NH2$, —$NHCH_3$, $NCH_3NCH_3$, —COOH, —$COOCH_3$, —$CONH_2$, —$CONHCH_3$, —$NO_2$, —SH, —$SCH_3$, —SOH, —$SOCH_3$, —$SO_2H$, —$SO_2CH_3$, —S(O)OH, —S(O)$OCH_3$, —S(O)$_2$H, S(O)$_2OCH_3$, —S(O)$NH_2$, —S(O)$NHCH_3$, —S(O)$_2NH_2$, S(O)$_2NHCH_3$, —$NHNH_2$, —$NHNHCH_3$, —$NHNCH_3CH_3$, —$ONH_2$, —$ONHCH_3$, —$NHC(O)NHNH_2$, or —$NHC(O)NHNHCH_3$), substituted or unsubstituted alkyl (e.g., $C_1$-$C_8$, $C_1$-$C_5$, or $C_1$-$C_3$), substituted or unsubstituted heteroalkyl (e.g., 2 to 8 membered, 2 to 5 membered, 2 to 3 membered), substituted or unsubstituted cycloalkyl (e.g., $C_3$-$C_8$, $C_3$-$C_5$, or $C_3$), substituted or unsubstituted heterocycloalkyl (e.g., 3 to 8 membered, 3 to 6 membered, or 4 membered), substituted or unsubstituted aryl (e.g., $C_5$-$C_8$, $C_5$-$C_6$, or phenyl), or substituted or unsubstituted heteroaryl (e.g., 5 to 8 membered, 5 to 6 membered, or 6 membered).

In embodiments, $R^9$ is hydrogen, halogen (e.g. —F, —Cl, —Br, or —I), —$N_3$, —$CF_3$, —$CCl_3$, —$CBr_3$, —$CI_3$, —CN, —CHO, —$OR^{33K}$, —$NR^{34K}R^{35K}$, —$COOR^{33K}$, —$CONR^{34K}R^{35K}$, —$NO_2$, —$SR^{36K}$, —$SO_{n11}R^{34K}$, —$SO_{n11}OR^{34K}$, —$SO_{n11}NR^{34K}R^{35K}$, —$NHNR^{34K}R^{35K}$, —$ONR^{34K}R^{35K}$, —$NHC(O)NHNR^{34K}R^{35K}$ (e.g., —OH, —$OCH_3$, —$NH2$, —$NHCH_3$, $NCH_3NCH_3$, —COOH, —$COOCH_3$, —$CONH_2$, —$CONHCH_3$, —$NO_2$, —SH, —$SCH_3$, —SOH, —$SOCH_3$, —$SO_2H$, —$SO_2CH_3$, —S(O)OH, —S(O)$OCH_3$, —S(O)$_2$H, S(O)$_2OCH_3$, —S(O)$NH_2$, —S(O)$NHCH_3$, —S(O)$_2NH_2$, S(O)$_2NHCH_3$, —$NHNH_2$, —$NHNHCH_3$, —$NHNCH_3CH_3$, —$ONH_2$, —$ONHCH_3$, —$NHC(O)NHNH_2$, or —$NHC(O)NHNHCH_3$), $R^{9a}$-substituted or unsubstituted alkyl (e.g., $C_1$-$C_8$, $C_1$-$C_5$, or $C_1$-$C_3$), $R^{9a}$-substituted or unsubstituted heteroalkyl (e.g., 2 to 8 membered, 2 to 5 membered, 2 to 3 membered), $R^{9a}$-substituted or unsubstituted cycloalkyl (e.g., $C_3$-$C_8$, $C_3$-$C_3$, or $C_3$), $R^{9a}$-substituted or unsubstituted heterocycloalkyl (e.g., 3 to 8 membered, 3 to 6 membered, or 4 membered), $R^{9a}$-substituted or unsubstituted aryl (e.g., $C_5$-$C_8$, $C_5$-$C_6$, or phenyl), or $R^{9a}$-substituted or unsubstituted heteroaryl (e.g., 5 to 8 membered, 5 to 6 membered, or 6 membered).

In embodiments, $R^9$ is hydrogen, halogen (e.g. —F, —Cl, —Br, or —I), —OH, —$OCH_3$, —$NH2$, —$NHCH_3$, $NCH_3NCH_3$, —COOH, —$COOCH_3$, —$CONH_2$, —$CONHCH_3$, —$NO_2$, —SH, —$SCH_3$, —SOH, —$SOCH_3$, —$SO_2H$, —$SO_2CH_3$, —S(O)OH, —S(O)$OCH_3$, —S(O)$_2$H, S(O)$_2OCH_3$, —S(O)$NH_2$, —S(O)$NHCH_3$, —S(O)$_2NH_2$, S(O)$_2NHCH_3$, —$NHNH_2$, —$NHNHCH_3$, —$NHNCH_3CH_3$, —$ONH_2$, —$ONHCH_3$, —$NHC(O)NHNH_2$, or —$NHC(O)NHNHCH_3$), unsubstituted alkyl (e.g., $C_1$-$C_8$, $C_1$-$C_5$, or $C_1$-$C_3$), unsubstituted heteroalkyl (e.g., 2 to 8 membered, 2 to 5 membered, 2 to 3 membered), unsubstituted cycloalkyl (e.g., $C_3$-$C_8$, $C_3$-$C_3$, or $C_3$), unsubstituted heterocycloalkyl (e.g., 3 to 8 membered, 3 to 6 membered, or 4 membered), unsubstituted aryl (e.g., $C_5$-$C_8$, $C_5$-$C_6$, or phenyl), or unsubstituted heteroaryl (e.g., 5 to 8 membered, 5 to 6 membered, or 6 membered).

In embodiments, $R^9$ is hydrogen, halogen (e.g. —F, —Cl, —Br, or —I), —OH, —$OCH_3$, —$NH2$, —$NHCH_3$, $NCH_3NCH_3$, —COOH, —$COOCH_3$, —$CONH_2$, —$CONHCH_3$, —$NO_2$, —SH, —$SCH_3$, —SOH, —$SOCH_3$, —$SO_2H$, —$SO_2CH_3$, —S(O)OH, —S(O)$OCH_3$, —S(O)$_2$H, S(O)$_2OCH_3$, —S(O)$NH_2$, —S(O)$NHCH_3$, —S(O)$_2NH_2$, S(O)$_2NHCH_3$, —$NHNH_2$, —$NHNHCH_3$, —$NHNCH_3CH_3$, —$ONH_2$, —$ONHCH_3$, —$NHC(O)NHNH_2$, or —$NHC(O)NHNHCH_3$), $R^{9a}$-substituted or unsubstituted $C_1$-$C_3$ alkyl, $R^{9a}$-substituted or unsubstituted 2 to 3 membered heteroalkyl, $R^{9a}$-substituted or unsubstituted $C_3$-$C_5$ cycloalkyl, $R^{9a}$-substituted or unsubstituted 5 to 6 membered heterocycloalkyl, $R^{9a}$-substituted or unsubstituted phenyl, or $R^{9a}$-substituted or unsubstituted 5 to 6 membered heteroaryl. In embodiments, $R^9$ is hydrogen, —F, —Cl, —Br, —I, —OH, —OH, —$OCH_3$, —$NH2$, —$NHCH_3$, $NCH_3NCH_3$, —COOH, —$COOCH_3$, —$CONH_2$, —$CONHCH_3$, —$NO_2$, —SH, —$SCH_3$, —SOH, —$SOCH_3$, —$SO_2H$, —$SO_2CH_3$, —S(O)OH, —S(O)$OCH_3$, —S(O)$_2$H, S(O)$_2OCH_3$, —S(O)$NH_2$, —S(O)$NHCH_3$, —S(O)$_2NH_2$, S(O)$_2NHCH_3$, —$NHNH_2$, —$NHNHCH_3$, —$NHNCH_3CH_3$, —$ONH_2$, —$ONHCH_3$, —$NHC(O)NHNH_2$, or —$NHC(O)NHNHCH_3$), unsubstituted $C_1$-$C_3$ alkyl, unsubstituted 2 to 3 membered heteroalkyl, unsubstituted $C_3$-$C_5$ cycloalkyl, unsubstituted 5 to 6 membered heterocycloalkyl, unsubstituted phenyl, or unsubstituted 5 to 6 membered heteroaryl.

$R^{9a}$ is halogen (e.g. —F, —Cl, —Br, or —I), —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —$NHC(O)NHNH_2$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{12}$, $C_6$-$C_{10}$, or phenyl), or substituted or unsubstituted heteroaryl (e.g., 5 to 12 membered, 5 to 10 membered, 5 to 9 membered, or 5 to 6 membered). In embodiments, $R^{9a}$ is halogen (e.g. —F, —Cl, —Br, or —I), —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —$NHC(O)NHNH_2$, $R^{9b}$-substituted or unsubstituted alkyl (e.g., $C_1$-$C_8$, $C_1$-$C_6$, $C_1$-$C_4$, or $C_1$-$C_2$), $R^{9b}$-substituted or unsubstituted heteroalkyl (e.g., 2 to 8 membered, 2 to 6 membered, 4 to 6 membered, 2 to 3 membered, or 4 to 5 membered), $R^{9b}$-substituted or unsubstituted cycloalkyl (e.g., $C_3$-$C_8$, $C_3$-$C_6$, $C_4$-$C_6$, or $C_5$-$C_6$), $R^{9b}$-substituted or unsubstituted heterocycloalkyl (e.g., 3 to 8 membered, 3 to 6 membered, 4 to 6 membered, 4 to 5 membered, or 5 to 6 membered), $R^{9b}$-substituted or unsubstituted aryl (e.g., $C_6$-$C_{12}$, $C_6$-$C_{10}$, or phenyl), or $R^{9b}$-substituted or unsubstituted heteroaryl (e.g., 5 to 12 membered, 5 to 10 membered, 5 to 9 membered, or 5 to 6 membered). In embodiments, $R^{9a}$ is halogen (e.g. —F, —Cl, —Br, or —I), —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —$NHC(O)NHNH_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered).

$R^{9b}$ is halogen (e.g. —F, —Cl, —Br, or —I), —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —$NHC(O)NHNH_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered).

In embodiments, $R^9$ is hydrogen, halogen (e.g. —F, —Cl, —Br, or —I), substituted or unsubstituted alkyl (e.g., $C_1$-$C_8$, $C_1$-$C_5$, or $C_1$-$C_3$), or substituted or unsubstituted heteroalkyl (e.g., 2 to 8 membered, 2 to 5 membered, 2 to 3 membered). In embodiments, $R^9$ is hydrogen, halogen (e.g. —F, —Cl, —Br, or —I), $R^{9a}$-substituted or unsubstituted alkyl (e.g., $C_1$-$C_8$, $C_1$-$C_5$, or $C_1$-$C_3$), or $R^{9a}$-substituted or unsubstituted heteroalkyl (e.g., 2 to 8 membered, 2 to 5 membered, 2 to 3 membered). In embodiments, $R^9$ is $R^{9a}$-substituted or unsubstituted $C_1$-$C_5$ alkyl. In embodiments, $R^9$ is unsubstituted $C_1$-$C_5$ alkyl. In embodiments, $R^9$ is $R^{9a}$-substituted or unsubstituted $C_1$-$C_3$ alkyl. In embodiments, $R^9$ unsubstituted $C_1$-$C_3$ alkyl. In embodiments, $R^9$ is unsubstituted methyl, unsubstituted ethyl or unsubstituted propyl. In embodiments, $R^9$ is $R^{9a}$-substituted or unsubstituted 2 to 5 membered heteroalkyl. In embodiments, $R^9$ is unsubstituted 2 to 5 membered heteroalkyl.

In embodiments, $R^8$ and $R^9$ are joined together to form a substituted or unsubstituted cycloalkyl (e.g. 3 to 8 membered cycloalkyl). In embodiments, $R^8$ and $R^9$ are joined together to form $R^{42a}$-substituted or unsubstituted cycloalkyl (e.g. 3 to 8 membered cycloalkyl). In embodiments, $R^8$ and $R^9$ are joined together to form substituted or unsubstituted heterocycloalkyl (e.g. 3 to 8 membered heterocycloalkyl). In embodiments, $R^8$ and $R^9$ are joined together to form $R^{42a}$-substituted or unsubstituted heterocycloalkyl (e.g. 3 to 8 membered heterocycloalkyl). In embodiments, $R^8$ and $R^9$ are joined together to form substituted or unsubstituted aryl (e.g. 3 to 8 membered aryl). In embodiments, $R^8$ and $R^9$ are joined together to form $R^{42a}$-substituted or unsubstituted aryl (e.g. 3 to 8 membered aryl). In embodiments, $R^8$ and $R^9$ are joined together to form substituted or unsubstituted heteroaryl (e.g. 3 to 8 membered heteroaryl). In embodiments, $R^8$ and $R^9$ are joined together to form $R^{42a}$-substituted or unsubstituted heteroaryl (e.g. 3 to 8 membered heteroaryl).

In embodiments, $R^7$ and $R^8$ are joined together to form substituted or unsubstituted cycloalkyl (e.g. 3 to 8 membered cycloalkyl). In embodiments, $R^7$ and $R^8$ are joined together to form $R^{41a}$-substituted or unsubstituted cycloalkyl (e.g. 3 to 8 membered cycloalkyl). In embodiments, $R^7$ and $R^8$ are joined together to form substituted or unsubstituted heterocycloalkyl (e.g. 3 to 8 membered heterocycloalkyl). In embodiments, $R^7$ and $R^8$ are joined together to form $R^{41a}$-substituted or unsubstituted heterocycloalkyl (e.g. 3 to 8 membered heterocycloalkyl). In embodiments, $R^7$ and $R^8$ are joined together to form substituted or unsubstituted aryl (e.g. 3 to 8 membered aryl). In embodiments, $R^7$ and $R^8$ are joined together to form $R^{41a}$-substituted or unsubstituted aryl (e.g. 3 to 8 membered aryl). In embodiments, $R^7$ and $R^8$ are joined together to form substituted or unsubstituted heteroaryl (e.g. 3 to 8 membered heteroaryl). In embodiments, $R^7$ and $R^8$ are joined together to form $R^{41a}$-substituted or unsubstituted heteroaryl (e.g. 3 to 8 membered heteroaryl).

In embodiments, $R^{10}$ is hydrogen, halogen (e.g. —F, —Cl, —Br, or —I), —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —$NHC(O)NHNH_2$. In embodiments, $R^{10}$ is hydrogen, halogen (e.g. —F, —Cl, —Br, or —I), —$N_3$, —$CF_3$, —$CCl_3$, —$CBr_3$, —$CI_3$, —OH, —$NH_2$, —COOH, —$CONH_2$, —$NO_2$, —SH, or —$SO_2$. In embodiments, $R^{10}$ is hydrogen, halogen (e.g. —F, —Cl, —Br, or —I), —$CF_3$, —$CCl_3$, —$CBr_3$, —$CI_3$, —OH, or —$NH_2$.

In embodiments, $R^{10}$ is hydrogen, halogen (e.g. —F, —Cl, —Br, or —I), —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —$NHC(O)NHNH_2$, substituted or unsubstituted alkyl (e.g., $C_1$-$C_8$, $C_1$-$C_5$, or $C_1$-$C_3$), or substituted or unsubstituted heteroalkyl (e.g., 2 to 8 membered, 2 to 5 membered, 2 to 3 membered). In embodiments, $R^{10}$ is hydrogen, halogen (e.g. —F, —Cl, —Br, or —I), —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —$NHC(O)NHNH_2$, $R^{10a}$-substituted or unsubstituted alkyl (e.g., $C_1$-$C_8$, $C_1$-$C_5$, or $C_1$-$C_3$), or $R^{10a}$-substituted or unsubstituted heteroalkyl (e.g., 2 to 8 membered, 2 to 5 membered, 2 to 3 membered).

In embodiments, $R^{10}$ is substituted or unsubstituted alkyl (e.g., $C_1$-$C_8$, $C_1$-$C_5$, or $C_1$-$C_3$), substituted or unsubstituted heteroalkyl (e.g., 2 to 8 membered, 2 to 5 membered, 2 to 3 membered), substituted or unsubstituted cycloalkyl (e.g., $C_3$-$C_8$, $C_3$-$C_5$, or $C_3$), substituted or unsubstituted heterocycloalkyl (e.g., 3 to 8 membered, 3 to 6 membered, or 4 membered), substituted or unsubstituted aryl (e.g., $C_5$-$C_8$, $C_5$-$C_6$, or phenyl), or substituted or unsubstituted heteroaryl (e.g., 5 to 8 membered, 5 to 6 membered, or 6 membered). In embodiments, $R^{10}$ is $R^{10a}$-substituted or unsubstituted alkyl (e.g., $C_1$-$C_8$, $C_1$-$C_5$, or $C_1$-$C_3$), $R^{10a}$-substituted or unsubstituted heteroalkyl (e.g., 2 to 8 membered, 2 to 5 membered, 2 to 3 membered), $R^{10a}$-substituted or unsubstituted cycloalkyl (e.g., $C_3$-$C_8$, $C_3$-$C_5$, or $C_3$), $R^{10a}$-substituted or unsubstituted heterocycloalkyl (e.g., 3 to 8 membered, 3 to 6 membered, or 4 membered), $R^{10a}$-substituted or unsubstituted aryl (e.g., $C_5$-$C_8$, $C_5$-$C_6$, or phenyl), or $R^{10a}$-substituted or unsubstituted heteroaryl (e.g., 5 to 8 membered, 5 to 6 membered, or 6 membered). In embodiments, $R^{10}$ is unsubstituted alkyl (e.g., $C_1$-$C_8$, $C_1$-$C_5$, or $C_1$-$C_3$), unsubstituted heteroalkyl (e.g., 2 to 8 membered, 2 to 5 membered, 2 to 3 membered), unsubstituted cycloalkyl (e.g., $C_3$-$C_8$, $C_3$-$C_5$, or $C_3$), unsubstituted heterocycloalkyl (e.g., 3 to 8 membered, 3 to 6 membered, or 4 membered), unsubstituted aryl (e.g., $C_5$-$C_8$, $C_5$-$C_6$, or phenyl), or unsubstituted heteroaryl (e.g., 5 to 8 membered, 5 to 6 membered, or 6 membered).

In embodiments, $R^{10}$ is substituted or unsubstituted $C_1$-$C_8$ alkyl, substituted or unsubstituted 3 to 8 membered heteroalkyl, substituted or unsubstituted 3 to 8 membered cycloalkyl, substituted or unsubstituted 3 to 8 membered heterocycloalkyl, substituted or unsubstituted 5 to 8 membered aryl, or substituted or unsubstituted 5 to 8 membered heteroaryl. In embodiments, $R^{10}$ is $R^{10a}$-substituted or unsubstituted $C_1$-$C_8$ alkyl, $R^{10a}$-substituted or unsubstituted 3 to 8 membered heteroalkyl, $R^{10a}$-substituted or unsubstituted 3 to 8 membered cycloalkyl, $R^{10a}$-substituted or unsubstituted 3 to 8 membered heterocycloalkyl, $R^{10a}$-substituted or unsubstituted 5 to 8 membered aryl, or $R^{10a}$-substituted or unsubstituted 5 to 8 membered heteroaryl. In embodiments, $R^{10}$ is unsubstituted $C_1$-$C_8$ alkyl, unsubstituted 3 to 8 membered heteroalkyl, unsubstituted 3 to 8 membered cycloalkyl, unsubstituted 3 to 8 membered heterocycloalkyl, unsubstituted 5 to 8 membered aryl, or unsubstituted 5 to 8 membered heteroaryl.

In embodiments, $R^{10}$ is substituted or unsubstituted $C_1$-$C_5$ alkyl, substituted or unsubstituted 2 to 5 membered heteroalkyl, substituted or unsubstituted 3 to 5 membered cycloalkyl, substituted or unsubstituted 3 to 6 membered heterocycloalkyl, substituted or unsubstituted 5 to 6 membered aryl, or substituted or unsubstituted 5 to 6 membered heteroaryl. In embodiments, $R^{10}$ is $R^{10a}$-substituted or unsubstituted $C_1$-$C_5$ alkyl, $R^{10a}$-substituted or unsubstituted 2 to 5 membered heteroalkyl, $R^{10a}$-substituted or unsubstituted 3 to 5 membered cycloalkyl, $R^{10a}$-substituted or unsubstituted 3 to 6 membered heterocycloalkyl, $R^{10a}$-substituted or unsubstituted 5 to 6 membered aryl, or $R^{10a}$-substituted or unsubstituted 5 to 6 membered heteroaryl. In embodiments, $R^{10}$ is unsubstituted $C_1$-$C_5$ alkyl, unsubstituted 2 to 5 membered heteroalkyl, unsubstituted 3 to 5 membered cycloalkyl, unsubstituted 3 to 6 membered heterocycloalkyl, unsubstituted 5 to 6 membered aryl, or unsubstituted 5 to 6 membered heteroaryl.

In embodiments, $R^{10}$ is substituted or unsubstituted $C_1$-$C_3$ alkyl or substituted or unsubstituted 2 to 3 membered heteroalkyl. In embodiments, $R^{10}$ is substituted or unsubstituted 3 membered cycloalkyl, substituted or unsubstituted 4 membered cycloalkyl, or substituted or unsubstituted 5 membered cycloalkyl. In embodiments, $R^{10}$ is substituted or unsubstituted 4 membered heterocycloalkyl, substituted or unsubstituted 5 membered heterocycloalkyl, or substituted or unsubstituted 6 membered heterocycloalkyl. In embodiments, $R^{10}$ is substituted or unsubstituted 5 membered aryl, substituted or unsubstituted 6 membered aryl, substituted or unsubstituted 5 membered heteroaryl, or unsubstituted 6 membered heteroaryl. In embodiments, $R^{10}$ is $R^{10a}$-substituted or unsubstituted $C_1$-$C_3$ alkyl or $R^{10a}$-substituted or unsubstituted 2 to 3 membered heteroalkyl. In embodiments, $R^{10}$ is $R^{10a}$-substituted or unsubstituted 3 membered cycloalkyl, $R^{10a}$-substituted or unsubstituted 4 membered cycloalkyl, or $R^{10a}$-substituted or unsubstituted 5 membered cycloalkyl. In embodiments, $R^{10}$ is $R^{10a}$-substituted or unsubstituted 4 membered heterocycloalkyl, $R^{10a}$-substituted or unsubstituted 5 membered heterocycloalkyl, or $R^{10a}$-substituted or unsubstituted 6 membered heterocycloalkyl. In embodiments, $R^{10}$ is $R^{10a}$-substituted or unsubstituted 5 membered aryl, $R^{10a}$-substituted or unsubstituted 6 membered aryl, $R^{10a}$-substituted or unsubstituted 5 membered heteroaryl, or $R^{10a}$-substituted or unsubstituted 6 membered heteroaryl. In embodiments, $R^{10}$ is unsubstituted $C_1$-$C_3$ alkyl or unsubstituted 2 to 3 membered heteroalkyl. In embodiments, $R^{10}$ is or unsubstituted 3 membered cycloalkyl, or unsubstituted 4 membered cycloalkyl, or unsubstituted 5 membered cycloalkyl. In embodiments, $R^{10}$ is or unsubstituted 4 membered heterocycloalkyl, or unsubstituted 5 membered heterocycloalkyl, or unsubstituted 6 membered heterocycloalkyl. In embodiments, $R^{10}$ is or unsubstituted 5 membered aryl, or unsubstituted 6 membered aryl, or unsubstituted 5 membered heteroaryl, or unsubstituted 6 membered heteroaryl.

In embodiments, $R^{10}$ is hydrogen, halogen (e.g. —F, —Cl, —Br, or —I), —$N_3$, —$CF_3$, —$CCl_3$, —$CBr_3$, —$CI_3$, —CN, —CHO, —$OR^{33L}$, —$NR^{34L}R^{35L}$, —$COOR^{33L}$, —$CONR^{34L}R^{35L}$, —$NO_2$, —$SR^{36L}$, —$SO_{n2}R^{34L}$, —$SO_{n12}OR^{34L}$, —$SO_{n12}NR^{34L}R^{35L}$, —$NHNR^{34L}R^{35L}$, —$ONR^{34L}R^{35L}$, —$NHC(O)NHNR^{34L}R^{35L}$ (e.g., —OH, —$OCH_3$, —NH2, —$NHCH_3$, $NCH_3NCH_3$, —COOH, —$COOCH_3$, —$CONH_2$, —$CONHCH_3$, —$NO_2$, —SH, —$SCH_3$, —SOH, —$SOCH_3$, —$SO_2H$, —$SO_2CH_3$, —S(O)OH, —S(O)$OCH_3$, —S(O)$_2H$, S(O)$_2OCH_3$, —S(O)$NH_2$, —S(O)$NHCH_3$, —S(O)$_2NH_2$, S(O)$_2NHCH_3$, —$NHNH_2$, —$NHNHCH_3$, —$NHNCH_3CH_3$, —$ONH_2$, —$ONHCH_3$, —$NHC(O)NHNH_2$, or —$NHC(O)NHNHCH_3$), substituted or unsubstituted alkyl (e.g., $C_1$-$C_8$, $C_1$-$C_5$, or $C_1$-$C_3$), substituted or unsubstituted heteroalkyl (e.g., 2 to 8 membered, 2 to 5 membered, 2 to 3 membered), substituted or unsubstituted cycloalkyl (e.g., $C_3$-$C_8$, $C_3$-$C_5$, or $C_3$), substituted or unsubstituted heterocycloalkyl (e.g., 3 to 8 membered, 3 to 6 membered, or 4 membered), substituted or unsubstituted aryl (e.g., $C_5$-$C_8$, $C_5$-$C_6$, or phenyl), or substituted or unsubstituted heteroaryl (e.g., 5 to 8 membered, 5 to 6 membered, or 6 membered).

In embodiments, $R^{10}$ is hydrogen, halogen (e.g. —F, —Cl, —Br, or —I), —$N_3$, —$CF_3$, —$CCl_3$, —$CBr_3$, —$CI_3$, —CN, —CHO, —$OR^{33L}$, —$NR^{34L}R^{35L}$, —$COOR^{33L}$, —$CONR^{34L}R^{35L}$, —$NO_2$, —$SR^{36L}$, —$SO_{n2}R^{34L}$, —$SO_{n12}OR^{34L}$, —$SO_{n12}NR^{34L}R^{35L}$, —$NHNR^{34L}R^{35L}$, —$ONR^{34L}R^{35L}$, —$NHC(O)NHNR^{34L}R^{35L}$ (e.g., —OH, —$OCH_3$, —NH2, —$NHCH_3$, $NCH_3NCH_3$, —COOH, —$COOCH_3$, —$CONH_2$, —$CONHCH_3$, —$NO_2$, —SH, —$SCH_3$, —SOH, —$SOCH_3$, —$SO_2H$, —$SO_2CH_3$, —S(O)OH, —S(O)$OCH_3$, —S(O)$_2H$, S(O)$_2OCH_3$, —S(O)$NH_2$, —S(O)$NHCH_3$, —S(O)$_2NH_2$, S(O)$_2NHCH_3$, —$NHNH_2$, —$NHNHCH_3$, —$NHNCH_3CH_3$, —$ONH_2$, —$ONHCH_3$, —$NHC(O)NHNH_2$, or —$NHC(O)NHNHCH_3$), $R^{10a}$-substituted or unsubstituted alkyl (e.g., $C_1$-$C_8$, $C_1$-$C_5$, or $C_1$-$C_3$), $R^{10a}$-substituted or unsubstituted heteroalkyl (e.g., 2 to 8 membered, 2 to 5 membered, 2 to 3 membered), $R^{10}$ substituted or unsubstituted cycloalkyl (e.g., $C_3$-$C_8$, $C_3$-$C_3$, or $C_3$), $R^{10a}$-substituted or unsubstituted heterocycloalkyl (e.g., 3 to 8 membered, 3 to 6 membered, or 4 membered), $R^{10a}$-substituted or unsubstituted aryl (e.g., $C_5$-$C_8$, $C_5$-$C_6$, or phenyl), or $R^{10a}$-substituted or unsubstituted heteroaryl (e.g., 5 to 8 membered, 5 to 6 membered, or 6 membered).

In embodiments, $R^{10}$ is hydrogen, halogen (e.g. —F, —Cl, —Br, or —I), —$N_3$, —$CF_3$, —$CCl_3$, —$CBr_3$, —$CI_3$, —CN, —CHO, —$OR^{33L}$, —$NR^{34L}R^{35L}$, —$COOR^{33L}$, —$CONR^{34L}R^{35L}$, —$NO_2$, —$SR^{36L}$, —$SO_{n2}R^{34L}$, —$SO_{n12}OR^{34L}$, —$SO_{n12}NR^{34L}R^{35L}$, —$NHNR^{34L}R^{35L}$, —$ONR^{34L}R^{35L}$, —$NHC(O)NHNR^{34L}R^{35L}$ (e.g., —OH, —$OCH_3$, —NH2, —$NHCH_3$, $NCH_3NCH_3$, —COOH, —$COOCH_3$, —$CONH_2$, —$CONHCH_3$, —$NO_2$, —SH, —$SCH_3$, —SOH, —$SOCH_3$, —$SO_2H$, —$SO_2CH_3$, —S(O)

OH, —S(O)OCH$_3$, —S(O)$_2$H, S(O)$_2$OCH$_3$, —S(O)NH$_2$, —S(O)NHCH$_3$, —S(O)$_2$NH$_2$, S(O)$_2$NHCH$_3$, —NHNH$_2$, —NHNHCH$_3$, —NHNCH$_3$CH$_3$, —ONH$_2$, —ONHCH$_3$, —NHC(O)NHNH$_2$, or —NHC(O)NHNHCH$_3$), unsubstituted alkyl (e.g., C$_1$-C$_8$, C$_1$-C$_5$, or C$_1$-C$_3$), unsubstituted heteroalkyl (e.g., 2 to 8 membered, 2 to 5 membered, 2 to 3 membered), unsubstituted cycloalkyl (e.g., C$_3$-C$_8$, C$_3$-C$_5$, or C$_3$), unsubstituted heterocycloalkyl (e.g., 3 to 8 membered, 3 to 6 membered, or 4 membered), unsubstituted aryl (e.g., C$_5$-C$_8$, C$_5$-C$_6$, or phenyl), or unsubstituted heteroaryl (e.g., 5 to 8 membered, 5 to 6 membered, or 6 membered).

In embodiments, R$^{10}$ is hydrogen, halogen (e.g. —F, —Cl, —Br, or —I), —OH, —OCH$_3$, —NH2, —NHCH$_3$, NCH$_3$NCH$_3$, —COOH, —COOCH$_3$, —CONH$_2$, —CONHCH$_3$, —NO$_2$, —SH, —SCH$_3$, —SOH, —SOCH$_3$, —SO$_2$H, —SO$_2$CH$_3$, —S(O)OH, —S(O)OCH$_3$, —S(O)$_2$H, S(O)$_2$OCH$_3$, —S(O)NH$_2$, —S(O)NHCH$_3$, —S(O)$_2$NH$_2$, S(O)$_2$NHCH$_3$, —NHNH$_2$, —NHNHCH$_3$, —NHNCH$_3$CH$_3$, —ONH$_2$, —ONHCH$_3$, —NHC(O)NHNH$_2$, or —NHC(O)NHNHCH$_3$), R$^{10a}$-substituted or unsubstituted C$_1$-C$_3$ alkyl, R$^{10a}$-substituted or unsubstituted 2 to 3 membered heteroalkyl, R$^{10a}$-substituted or unsubstituted C$_3$-C$_5$ cycloalkyl, R$^{10a}$-substituted or unsubstituted 5 to 6 membered heterocycloalkyl, R$^{10a}$-substituted or unsubstituted phenyl, or R$^{10a}$-substituted or unsubstituted 5 to 6 membered heteroaryl.

In embodiments, R$^{10}$ is hydrogen, —F, —Cl, —Br, —I, —OH, —OH, —OCH$_3$, —NH2, —NHCH$_3$, NCH$_3$NCH$_3$, —COOH, —COOCH$_3$, —CONH$_2$, —CONHCH$_3$, —NO$_2$, —SH, —SCH$_3$, —SOH, —SOCH$_3$, —SO$_2$H, —SO$_2$CH$_3$, —S(O)OH, —S(O)OCH$_3$, —S(O)$_2$H, S(O)$_2$OCH$_3$, —S(O)NH$_2$, —S(O)NHCH$_3$, —S(O)$_2$NH$_2$, S(O)$_2$NHCH$_3$, —NHNH$_2$, —NHNHCH$_3$, —NHNCH$_3$CH$_3$, —ONH$_2$, —ONHCH$_3$, —NHC(O)NHNH$_2$, or —NHC(O)NHNHCH$_3$), unsubstituted C$_1$-C$_3$ alkyl, unsubstituted 2 to 3 membered heteroalkyl, unsubstituted C$_3$-C$_5$ cycloalkyl, unsubstituted 5 to 6 membered heterocycloalkyl, unsubstituted phenyl, or unsubstituted 5 to 6 membered heteroaryl.

R$^{10a}$ is halogen (e.g. —F, —Cl, —Br, or —I), —N$_3$, —CF$_3$, —CCl$_3$, —CBr$_3$, —CI$_3$, —CN, —CHO, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC(O)NHNH$_2$, substituted or unsubstituted alkyl (e.g., C$_1$-C$_8$, C$_1$-C$_6$, C$_1$-C$_4$, or C$_1$-C$_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., C$_3$-C$_8$, C$_3$-C$_6$, C$_4$-C$_6$, or C$_5$-C$_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., C$_6$-C$_{12}$, C$_6$-C$_{10}$, or phenyl), or substituted or unsubstituted heteroaryl (e.g., 5 to 12 membered, 5 to 10 membered, 5 to 9 membered, or 5 to 6 membered). In embodiments, R$^{10}$ is halogen (e.g. —F, —Cl, —Br, or —I), —N$_3$, —CF$_3$, —CCl$_3$, —CBr$_3$, —CI$_3$, —CN, —CHO, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC(O)NHNH$_2$, R$^{10b}$-substituted or unsubstituted alkyl (e.g., C$_1$-C$_8$, C$_1$-C$_6$, C$_1$-C$_4$, or C$_1$-C$_2$), R$^{10b}$-substituted or unsubstituted heteroalkyl (e.g., 2 to 8 membered, 2 to 6 membered, 4 to 6 membered, 2 to 3 membered, or 4 to 5 membered), R$^{10b}$-substituted or unsubstituted cycloalkyl (e.g., C$_3$-C$_8$, C$_3$-C$_6$, C$_4$-C$_6$, or C$_5$-C$_6$), R$^{10b}$-substituted or unsubstituted heterocycloalkyl (e.g., 3 to 8 membered, 3 to 6 membered, 4 to 6 membered, 4 to 5 membered, or 5 to 6 membered), R$^{10b}$-substituted or unsubstituted aryl (e.g., C$_6$-C$_{12}$, C$_6$-C$_{10}$, or phenyl), or R$^{10b}$-substituted or unsubstituted heteroaryl (e.g., 5 to 12 membered, 5 to 10 membered, 5 to 9 membered, or 5 to 6 membered). In embodiments, R$^{10}$ is halogen (e.g. —F, —Cl, —Br, or —I), —N$_3$, —CF$_3$, —CCl$_3$, —CBr$_3$, —CI$_3$, —CN, —CHO, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC(O)NHNH$_2$, unsubstituted alkyl (e.g., C$_1$-C$_8$, C$_1$-C$_6$, C$_1$-C$_4$, or C$_1$-C$_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., C$_3$-C$_8$, C$_3$-C$_6$, C$_4$-C$_6$, or C$_5$-C$_6$), unsubstituted heterocycloalkyl (e.g., 3 to 8 membered, 3 to 6 membered, 4 to 6 membered, 4 to 5 membered, or 5 to 6 membered), unsubstituted aryl (e.g., C$_6$-C$_{12}$, C$_6$-C$_{10}$, or phenyl), or unsubstituted heteroaryl (e.g., 5 to 12 membered, 5 to 10 membered, 5 to 9 membered, or 5 to 6 membered).

R$^{10b}$ is halogen (e.g. —F, —Cl, —Br, or —I), —N$_3$, —CF$_3$, —CCl$_3$, —CBr$_3$, —CI$_3$, —CN, —CHO, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC(O)NHNH$_2$, unsubstituted alkyl (e.g., C$_1$-C$_8$, C$_1$-C$_6$, C$_1$-C$_4$, or C$_1$-C$_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., C$_3$-C$_8$, C$_3$-C$_6$, C$_4$-C$_6$, or C$_5$-C$_6$), unsubstituted heterocycloalkyl (e.g., 3 to 8 membered, 3 to 6 membered, 4 to 6 membered, 4 to 5 membered, or 5 to 6 membered), unsubstituted aryl (e.g., C$_6$-C$_{12}$, C$_6$-C$_{10}$, or phenyl), or unsubstituted heteroaryl (e.g., 5 to 12 membered, 5 to 10 membered, 5 to 9 membered, or 5 to 6 membered).

In embodiments, R$^{11}$ is hydrogen, halogen (e.g. —F, —Cl, —Br, or —I), —N$_3$, —CF$_3$, —CCl$_3$, —CBr$_3$, —CI$_3$, —CN, —CHO, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC(O)NHNH$_2$. In embodiments, R$^{11}$ is hydrogen, halogen (e.g. —F, —Cl, —Br, or —I), —N$_3$, —CF$_3$, —CCl$_3$, —CBr$_3$, —CI$_3$, —OH, —NH$_2$, —COOH, —CONH$_2$, —NO$_2$, —SH, or —SO$_2$. In embodiments, R$^{11}$ is hydrogen, halogen (e.g. —F, —Cl, —Br, or —I), —CF$_3$, —CCl$_3$, —CBr$_3$, —CI$_3$, —OH, or —NH$_2$.

In embodiments, R$^{11}$ is hydrogen, halogen (e.g. —F, —Cl, —Br, or —I), —N$_3$, —CF$_3$, —CCl$_3$, —CBr$_3$, —CI$_3$, —CN, —CHO, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC(O)NHNH$_2$, substituted or unsubstituted alkyl (e.g., C$_1$-C$_8$, C$_1$-C$_5$, or C$_1$-C$_3$), or substituted or unsubstituted heteroalkyl (e.g., 2 to 8 membered, 2 to 5 membered, 2 to 3 membered). In embodiments, R$^{11}$ is hydrogen, halogen (e.g. —F, —Cl, —Br, or —I), —N$_3$, —CF$_3$, —CCl$_3$, —CBr$_3$, —CI$_3$, —CN, —CHO, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC(O)NHNH$_2$, R$^{11a}$-substituted or unsubstituted alkyl (e.g., C$_1$-C$_8$, C$_1$-C$_5$, or C$_1$-C$_3$), or R$^{11a}$-substituted or unsubstituted heteroalkyl (e.g., 2 to 8 membered, 2 to 5 membered, 2 to 3 membered).

In embodiments, R$^{11}$ is substituted or unsubstituted alkyl (e.g., C$_1$-C$_8$, C$_1$-C$_5$, or C$_1$-C$_3$), substituted or unsubstituted heteroalkyl (e.g., 2 to 8 membered, 2 to 5 membered, 2 to 3 membered), substituted or unsubstituted cycloalkyl (e.g., C$_3$-C$_8$, C$_3$-C$_5$, or C$_3$), substituted or unsubstituted heterocycloalkyl (e.g., 3 to 8 membered, 3 to 6 membered, or 4 membered), substituted or unsubstituted aryl (e.g., C$_5$-C$_8$, C$_5$-C$_6$, or phenyl), or substituted or unsubstituted heteroaryl (e.g., 5 to 8 membered, 5 to 6 membered, or 6 membered). In embodiments, R$^{11}$ is R$^{11a}$-substituted or unsubstituted alkyl (e.g., C$_1$-C$_8$, C$_1$-C$_5$, or C$_1$-C$_3$), R$^{11a}$-substituted or unsubstituted heteroalkyl (e.g., 2 to 8 membered, 2 to 5 membered, 2 to 3 membered), $R^{11}$-substituted or unsubstituted cycloalkyl (e.g., $C_3$-$C_8$, $C_3$-$C_5$, or $C_3$), $R^{11a}$-substituted or unsubstituted heterocycloalkyl (e.g., 3 to 8 membered, 3 to 6 membered, or 4 membered), $R^{11a}$-substituted or unsubstituted aryl (e.g., $C_5$-$C_8$, $C_5$-$C_6$, or phenyl), or $R^{11a}$-substituted or unsubstituted heteroaryl (e.g., 5 to 8 membered, 5 to 6 membered, or 6 membered). In embodiments, $R^{11}$ is unsubstituted alkyl (e.g., $C_1$-$C_8$, $C_1$-$C_5$, or $C_1$-$C_3$), unsubstituted heteroalkyl (e.g., 2 to 8 membered, 2 to 5 membered, 2 to 3 membered), unsubstituted cycloalkyl (e.g., $C_3$-$C_8$, $C_3$-$C_5$, or $C_3$), unsubstituted heterocycloalkyl (e.g., 3 to 8 membered, 3 to 6 membered, or 4 membered), unsubstituted aryl (e.g., $C_5$-$C_8$, $C_5$-$C_6$, or phenyl), or unsubstituted heteroaryl (e.g., 5 to 8 membered, 5 to 6 membered, or 6 membered).

In embodiments, $R^{11}$ is substituted or unsubstituted $C_1$-$C_8$ alkyl, substituted or unsubstituted 3 to 8 membered heteroalkyl, substituted or unsubstituted 3 to 8 membered cycloalkyl, substituted or unsubstituted 3 to 8 membered heterocycloalkyl, substituted or unsubstituted 5 to 8 membered aryl, or substituted or unsubstituted 5 to 8 membered heteroaryl. In embodiments, $R^{11}$ is $R^{11a}$-substituted or unsubstituted $C_1$-$C_8$ alkyl, $R^{11a}$-substituted or unsubstituted 3 to 8 membered heteroalkyl, $R^{11a}$-substituted or unsubstituted 3 to 8 membered cycloalkyl, $R^{11a}$-substituted or unsubstituted 3 to 8 membered heterocycloalkyl, $R^{11a}$-substituted or unsubstituted 5 to 8 membered aryl, or $R^{11a}$-substituted or unsubstituted 5 to 8 membered heteroaryl. In embodiments, $R^{11}$ is unsubstituted $C_1$-$C_8$ alkyl, unsubstituted 3 to 8 membered heteroalkyl, unsubstituted 3 to 8 membered cycloalkyl, unsubstituted 3 to 8 membered heterocycloalkyl, unsubstituted 5 to 8 membered aryl, or unsubstituted 5 to 8 membered heteroaryl.

In embodiments, $R^{11}$ is substituted or unsubstituted $C_1$-$C_5$ alkyl, substituted or unsubstituted 2 to 5 membered heteroalkyl, substituted or unsubstituted 3 to 5 membered cycloalkyl, substituted or unsubstituted 3 to 6 membered heterocycloalkyl, substituted or unsubstituted 5 to 6 membered aryl, or substituted or unsubstituted 5 to 6 membered heteroaryl. In embodiments, $R^{11}$ is $R^{11a}$-substituted or unsubstituted $C_1$-$C_8$ alkyl, $R^{11a}$-substituted or unsubstituted 2 to 5 membered heteroalkyl, $R^{11a}$-substituted or unsubstituted 3 to 5 membered cycloalkyl, $R^{11a}$-substituted or unsubstituted 3 to 6 membered heterocycloalkyl, $R^{11a}$-substituted or unsubstituted 5 to 6 membered aryl, or $R^{11a}$-substituted or unsubstituted 5 to 6 membered heteroaryl. In embodiments, $R^{11}$ is unsubstituted $C_1$-$C_5$ alkyl, unsubstituted 2 to 5 membered heteroalkyl, unsubstituted 3 to 5 membered cycloalkyl, unsubstituted 3 to 6 membered heterocycloalkyl, unsubstituted 5 to 6 membered aryl, or unsubstituted 5 to 6 membered heteroaryl.

In embodiments, $R^{11}$ is substituted or unsubstituted $C_1$-$C_3$ alkyl or substituted or unsubstituted 2 to 3 membered heteroalkyl. In embodiments, $R^{11}$ is substituted or unsubstituted 3 membered cycloalkyl, substituted or unsubstituted 4 membered cycloalkyl, or substituted or unsubstituted 5 membered cycloalkyl. In embodiments, $R^{11}$ is substituted or unsubstituted 4 membered heterocycloalkyl, substituted or unsubstituted 5 membered heterocycloalkyl, or substituted or unsubstituted 6 membered heterocycloalkyl. In embodiments, $R^{11}$ is substituted or unsubstituted 5 membered aryl, substituted or unsubstituted 6 membered aryl, substituted or unsubstituted 5 membered heteroaryl, or substituted or unsubstituted 6 membered heteroaryl. In embodiments, $R^{11}$ is $R^{11a}$-substituted or unsubstituted $C_1$-$C_3$ alkyl or $R^{11a}$-substituted or unsubstituted 2 to 3 membered heteroalkyl. In embodiments, $R^{11}$ is $R^{11a}$-substituted or unsubstituted 3 membered cycloalkyl, $R^{11a}$-substituted or unsubstituted 4 membered cycloalkyl, or $R^{11a}$-substituted or unsubstituted 5 membered cycloalkyl. In embodiments, $R^{11}$ is $R^{11a}$-substituted or unsubstituted 4 membered heterocycloalkyl, $R^{11a}$-substituted or unsubstituted 5 membered heterocycloalkyl, or $R^{11a}$-substituted or unsubstituted 6 membered heterocycloalkyl. In embodiments, $R^{11}$ is $R^{11a}$-substituted or unsubstituted 5 membered aryl, $R^{11a}$-substituted or unsubstituted 6 membered aryl, $R^{11a}$-substituted or unsubstituted 5 membered heteroaryl, or $R^{11a}$-substituted or unsubstituted 6 membered heteroaryl. In embodiments, $R^{11}$ is unsubstituted $C_1$-$C_3$ alkyl or unsubstituted 2 to 3 membered heteroalkyl. In embodiments, $R^{11}$ is or unsubstituted 3 membered cycloalkyl, or unsubstituted 4 membered cycloalkyl, or unsubstituted 5 membered cycloalkyl. In embodiments, $R^{11}$ is or unsubstituted 4 membered heterocycloalkyl, or unsubstituted 5 membered heterocycloalkyl, or unsubstituted 6 membered heterocycloalkyl. In embodiments, $R^{11}$ is or unsubstituted 5 membered aryl, or unsubstituted 6 membered aryl, or unsubstituted 5 membered heteroaryl, or unsubstituted 6 membered heteroaryl.

In embodiments, $R^{11}$ is hydrogen, halogen (e.g. —F, —Cl, —Br, or —I), —$N_3$, —$CF_3$, —$CCl_3$, —$CBr_3$, —$CI_3$, —CN, —CHO, —$OR^{33L}$, —$NR^{34L}R^{35L}$, —$COOR^{33L}$, —$CONR^{34L}R^{35L}$, —$NO_2$, —$SR^{36L}$, —$SO_{n12}R^{34L}$, —$SO_{n12}OR^{34L}$, —$SO_{n12}NR^{34L}R^{35L}$, —$NHNR^{34L}R^{35L}$, —$ONR^{34L}R^{35L}$, —$NHC(O)NHNR^{34L}R^{35L}$ (e.g., —OH, —$OCH_3$, —$NH2$, —$NHCH_3$, $NCH_3NCH_3$, —COOH, —$COOCH_3$, —$CONH_2$, —$CONHCH_3$, —$NO_2$, —SH, —$SCH_3$, —SOH, —$SOCH_3$, —$SO_2H$, —$SO_2CH_3$, —S(O)OH, —$S(O)OCH_3$, —$S(O)_2H$, $S(O)_2OCH_3$, —$S(O)NH_2$, —$S(O)NHCH_3$, —$S(O)_2NH_2$, $S(O)_2NHCH_3$, —$NHNH_2$, —$NHNHCH_3$, —$NHNCH_3CH_3$, —$ONH_2$, —$ONHCH_3$, —$NHC(O)NHNH_2$, or —$NHC(O)NHNHCH_3$), substituted or unsubstituted alkyl (e.g., $C_1$-$C_8$, $C_1$-$C_5$, or $C_1$-$C_3$), substituted or unsubstituted heteroalkyl (e.g., 2 to 8 membered, 2 to 5 membered, 2 to 3 membered), substituted or unsubstituted cycloalkyl (e.g., $C_3$-$C_8$, $C_3$-$C_5$, or $C_3$), substituted or unsubstituted heterocycloalkyl (e.g., 3 to 8 membered, 3 to 6 membered, or 4 membered), substituted or unsubstituted aryl (e.g., $C_5$-$C_8$, $C_5$-$C_6$, or phenyl), or substituted or unsubstituted heteroaryl (e.g., 5 to 8 membered, 5 to 6 membered, or 6 membered).

In embodiments, $R^{11}$ is hydrogen, halogen (e.g. —F, —Cl, —Br, or —I), —$N_3$, —$CF_3$, —$CCl_3$, —$CBr_3$, —$CI_3$, —CN, —CHO, —$OR^{33L}$, —$NR^{34L}R^{35L}$, —$COOR^{33L}$, —$CONR^{34L}R^{35L}$, —$NO_2$, —$SR^{36L}$, —$SO_{n12}R^{34L}$, —$SO_{n12}OR^{34L}$, —$SO_{n12}NR^{34L}R^{35L}$, —$NHNR^{34L}R^{35L}$, —$ONR^{34L}R^{35L}$, —$NHC(O)NHNR^{34L}R^{35L}$ (e.g., —OH, —$OCH_3$, —$NH2$, —$NHCH_3$, $NCH_3NCH_3$, —COOH, —$COOCH_3$, —$CONH_2$, —$CONHCH_3$, —$NO_2$, —SH, —$SCH_3$, —SOH, —$SOCH_3$, —$SO_2H$, —$SO_2CH_3$, —S(O)OH, —$S(O)OCH_3$, —$S(O)_2H$, $S(O)_2OCH_3$, —$S(O)NH_2$, —$S(O)NHCH_3$, —$S(O)_2NH_2$, $S(O)_2NHCH_3$, —$NHNH_2$, —$NHNHCH_3$, —$NHNCH_3CH_3$, —$ONH_2$, —$ONHCH_3$, —$NHC(O)NHNH_2$, or —$NHC(O)NHNHCH_3$), $R^{11a}$-substituted or unsubstituted alkyl (e.g., $C_1$-$C_8$, $C_1$-$C_5$, or $C_1$-$C_3$), $R^{11a}$-substituted or unsubstituted heteroalkyl (e.g., 2 to 8 membered, 2 to 5 membered, 2 to 3 membered), $R^{11}$-substituted or unsubstituted cycloalkyl (e.g., $C_3$-$C_8$, $C_3$-$C_3$, or $C_3$), $R^{11a}$-substituted or unsubstituted heterocycloalkyl (e.g., 3 to 8 membered, 3 to 6 membered, or 4 membered), $R^{11a}$-substituted or unsubstituted aryl (e.g., $C_5$-$C_8$, $C_5$-$C_6$, or phenyl), or $R^{11}$-substituted or unsubstituted heteroaryl (e.g., 5 to 8 membered, 5 to 6 membered, or 6 membered).

In embodiments, $R^{11}$ is hydrogen, halogen (e.g. —F, —Cl, —Br, or —I), —N$_3$, —CF$_3$, —CCl$_3$, —CBr$_3$, —CI$_3$, —CN, —CHO, —OR$^{33L}$, —NR$^{34L}$R$^{35L}$, —COOR$^{33L}$, —CONR$^{34L}$R$^{35L}$, —NO$_2$, —SR$^{36L}$, —SO$_{n12}$R$^{34L}$, —SO$_{n12}$OR$^{34L}$, —SO$_{n12}$NR$^{34L}$R$^{35L}$, —NHNR$^{34L}$R$^{35L}$, —ONR$^{34L}$R$^{35L}$, —NHC(O)NHNR$^{34L}$R$^{35L}$ (e.g., —OH, —OCH$_3$, —NH2, —NHCH$_3$, NCH$_3$NCH$_3$, —COOH, —COOCH$_3$, —CONH$_2$, —CONHCH$_3$, —NO$_2$, —SH, —SCH$_3$, —SOH, —SOCH$_3$, —SO$_2$H, —SO$_2$CH$_3$, —S(O)OH, —S(O)OCH$_3$, —S(O)$_2$H, S(O)$_2$OCH$_3$, —S(O)NH$_2$, —S(O)NHCH$_3$, —S(O)$_2$NH$_2$, S(O)$_2$NHCH$_3$, —NHNH$_2$, —NHNHCH$_3$, —NHNCH$_3$CH$_3$, —ONH$_2$, —ONHCH$_3$, —NHC(O)NHNH$_2$, or —NHC(O)NHNHCH$_3$), unsubstituted alkyl (e.g., C$_1$-C$_8$, C$_1$-C$_5$, or C$_1$-C$_3$), unsubstituted heteroalkyl (e.g., 2 to 8 membered, 2 to 5 membered, 2 to 3 membered), unsubstituted cycloalkyl (e.g., C$_3$-C$_8$, C$_3$-C$_3$, or C$_3$), unsubstituted heterocycloalkyl (e.g., 3 to 8 membered, 3 to 6 membered, or 4 membered), unsubstituted aryl (e.g., C$_5$-C$_8$, C$_5$-C$_6$, or phenyl), or unsubstituted heteroaryl (e.g., 5 to 8 membered, 5 to 6 membered, or 6 membered).

In embodiments, $R^{11}$ is hydrogen, halogen (e.g. —F, —Cl, —Br, or —I), —OH, —OCH$_3$, —NH2, —NHCH$_3$, NCH$_3$NCH$_3$, —COOH, —COOCH$_3$, —CONH$_2$, —CONHCH$_3$, —NO$_2$, —SH, —SCH$_3$, —SOH, —SOCH$_3$, —SO$_2$H, —SO$_2$CH$_3$, —S(O)OH, —S(O)OCH$_3$, —S(O)$_2$H, S(O)$_2$OCH$_3$, —S(O)$_2$H, S(O)$_2$OCH$_3$, —S(O)NH$_2$, —S(O)NHCH$_3$, —S(O)$_2$NH$_2$, S(O)$_2$NHCH$_3$, —NHNH$_2$, —NHNHCH$_3$, —NHNCH$_3$CH$_3$, —ONH$_2$, —ONHCH$_3$, —NHC(O)NHNH$_2$, or —NHC(O)NHNHCH$_3$), $R^{11a}$-substituted or unsubstituted $C_1$-$C_3$ alkyl, $R^{11a}$-substituted or unsubstituted 2 to 3 membered heteroalkyl, $R^{11a}$-substituted or unsubstituted $C_3$-$C_5$ cycloalkyl, $R^{11a}$-substituted or unsubstituted 5 to 6 membered heterocycloalkyl, $R^{11a}$-substituted or unsubstituted phenyl, or $R^{11a}$-substituted or unsubstituted 5 to 6 membered heteroaryl.

In embodiments, $R^{11}$ is hydrogen, —F, —Cl, —Br, —I, —OH, —OH, —OCH$_3$, —NH2, —NHCH$_3$, NCH$_3$NCH$_3$, —COOH, —COOCH$_3$, —CONH$_2$, —CONHCH$_3$, —NO$_2$, —SH, —SCH$_3$, —SOH, —SOCH$_3$, —SO$_2$H, —SO$_2$CH$_3$, —S(O)OH, —S(O)OCH$_3$, —S(O)$_2$H, S(O)$_2$OCH$_3$, —S(O)NH$_2$, —S(O)NHCH$_3$, —S(O)$_2$NH$_2$, S(O)$_2$NHCH$_3$, —NHNH$_2$, —NHNHCH$_3$, —NHNCH$_3$CH$_3$, —ONH$_2$, —ONHCH$_3$, —NHC(O)NHNH$_2$, or —NHC(O)NHNHCH$_3$), unsubstituted $C_1$-$C_3$ alkyl, unsubstituted 2 to 3 membered heteroalkyl, unsubstituted $C_3$-$C_5$ cycloalkyl, unsubstituted 5 to 6 membered heterocycloalkyl, unsubstituted phenyl, or unsubstituted 5 to 6 membered heteroaryl.

$R^{11a}$ is halogen (e.g. —F, —Cl, —Br, or —I), —N$_3$, —CF$_3$, —CCl$_3$, —CBr$_3$, —CI$_3$, —CN, —CHO, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC(O)NHNH$_2$, substituted or unsubstituted alkyl (e.g., C$_1$-C$_8$, C$_1$-C$_6$, C$_1$-C$_4$, or C$_1$-C$_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., C$_3$-C$_8$, C$_3$-C$_6$, C$_4$-C$_6$, or C$_5$-C$_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., C$_6$-C$_{12}$, C$_6$-C$_{10}$, or phenyl), or substituted or unsubstituted heteroaryl (e.g., 5 to 12 membered, 5 to 10 membered, 5 to 9 membered, or 5 to 6 membered). In embodiments, $R^{11}$ is halogen (e.g. —F, —Cl, —Br, or —I), —N$_3$, —CF$_3$, —CCl$_3$, —CBr$_3$, —CI$_3$, —CN, —CHO, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC(O)NHNH$_2$, $R^{11b}$-substituted or unsubstituted alkyl (e.g., C$_1$-C$_8$, C$_1$-C$_6$, C$_1$-C$_4$, or C$_1$-C$_2$), $R^{11b}$-substituted or unsubstituted heteroalkyl (e.g., 2 to 8 membered, 2 to 6 membered, 4 to 6 membered, 2 to 3 membered, or 4 to 5 membered), $R^{11b}$-substituted or unsubstituted cycloalkyl (e.g., C$_3$-C$_8$, C$_3$-C$_6$, C$_4$-C$_6$, or C$_5$-C$_6$), $R^{11b}$-substituted or unsubstituted heterocycloalkyl (e.g., 3 to 8 membered, 3 to 6 membered, 4 to 6 membered, 4 to 5 membered, or 5 to 6 membered), $R^{11b}$-substituted or unsubstituted aryl (e.g., C$_6$-C$_{12}$, C$_6$-C$_{10}$, or phenyl), or $R^{11b}$-substituted or unsubstituted heteroaryl (e.g., 5 to 12 membered, 5 to 10 membered, 5 to 9 membered, or 5 to 6 membered). In embodiments, $R^{11a}$ is halogen (e.g. —F, —Cl, —Br, or —I), —N$_3$, —CF$_3$, —CCl$_3$, —CBr$_3$, —CI$_3$, —CN, —CHO, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC(O)NHNH$_2$, unsubstituted alkyl (e.g., C$_1$-C$_8$, C$_1$-C$_6$, C$_1$-C$_4$, or C$_1$-C$_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., C$_3$-C$_8$, C$_3$-C$_6$, C$_4$-C$_6$, or C$_5$-C$_6$), unsubstituted heterocycloalkyl (e.g., 3 to 8 membered, 3 to 6 membered, 4 to 6 membered, 4 to 5 membered, or 5 to 6 membered), unsubstituted aryl (e.g., C$_6$-C$_{12}$, C$_6$-C$_{10}$, or phenyl), or unsubstituted heteroaryl (e.g., 5 to 12 membered, 5 to 10 membered, 5 to 9 membered, or 5 to 6 membered).

$R^{11b}$ is halogen (e.g. —F, —Cl, —Br, or —I), —N$_3$, —CF$_3$, —CCl$_3$, —CBr$_3$, —CI$_3$, —CN, —CHO, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC(O)NHNH$_2$, unsubstituted alkyl (e.g., C$_1$-C$_8$, C$_1$-C$_6$, C$_1$-C$_4$, or C$_1$-C$_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., C$_3$-C$_8$, C$_3$-C$_6$, C$_4$-C$_6$, or C$_5$-C$_6$), unsubstituted heterocycloalkyl (e.g., 3 to 8 membered, 3 to 6 membered, 4 to 6 membered, 4 to 5 membered, or 5 to 6 membered), unsubstituted aryl (e.g., C$_6$-C$_{12}$, C$_6$-C$_{10}$, or phenyl), or unsubstituted heteroaryl (e.g., 5 to 12 membered, 5 to 10 membered, 5 to 9 membered, or 5 to 6 membered).

In embodiments, $R^9$ and $R^{10}$ are joined together to form substituted or unsubstituted 3 to 8 membered cycloalkyl. In embodiments, $R^9$ and $R^{10}$ are joined together to form $R^{43a}$-substituted or unsubstituted 3 to 8 membered cycloalkyl. In embodiments, $R^9$ and $R^{10}$ are joined together to form substituted or unsubstituted 3 to 8 membered heterocycloalkyl. In embodiments, $R^9$ and $R^{10}$ are joined together to form $R^{43a}$-substituted or unsubstituted 3 to 8 membered heterocycloalkyl. In embodiments, $R^9$ and $R^{10}$ are joined together to form substituted or unsubstituted 3 to 8 membered aryl. In embodiments, $R^9$ and $R^{10}$ are joined together to form $R^{43a}$-substituted or unsubstituted 3 to 8 membered aryl. In embodiments, $R^9$ and $R^{10}$ are joined together to form substituted or unsubstituted 3 to 8 membered heteroaryl. In embodiments, $R^9$ and $R^{10}$ are joined together to form $R^{43a}$-substituted or unsubstituted 3 to 8 membered heteroaryl.

In embodiments, $R^{10}$ and $R^{11}$ are joined together to form substituted or unsubstituted 3 to 8 membered cycloalkyl. In embodiments, $R^{10}$ and $R^{11}$ are joined together to form $R^{40a}$-substituted or unsubstituted 3 to 8 membered cycloalkyl. In embodiments, $R^{10}$ and $R^{11}$ are joined together to form substituted or unsubstituted 3 to 8 membered heterocycloalkyl. In embodiments, $R^{10}$ and $R^{11}$ are joined together to form $R^{40a}$-substituted or unsubstituted 3 to 8 membered heterocycloalkyl. In embodiments, $R^{10}$ and $R^{11}$ are joined together to form substituted or unsubstituted 3 to 8 membered aryl. In embodiments, $R^{10}$ and $R^{11}$ are joined together to form $R^{40a}$-substituted or unsubstituted 3 to 8 membered aryl. In embodiments, $R^{10}$ and $R^{11}$ are joined together to form substituted or unsubstituted 3 to 8 membered heteroaryl. In embodiments, $R^{10}$ and $R^{11}$ are joined together to form $R^{40a}$-substituted or unsubstituted 3 to 8 membered heteroaryl.

In embodiments, $R^8$ is hydrogen or $—OR^{33J}$ and $R^9$, $R^{10}$, and $R^{11}$ are independently hydrogen or halogen (e.g. —F, —Cl, —Br, or —I). In embodiments, $R^{33J}$ is hydrogen, or unsubstituted $C_1$-$C_3$ alkyl. In embodiments, $R^{33J}$ is hydrogen, unsubstituted methyl or unsubstituted ethyl.

In embodiments, $R^7$, $R^8$, $R^9$, $R^{10}$ and $R^{11}$ are independently hydrogen, halogen (e.g. —F, —Cl, —Br, or —I), $C_1$-$C_5$ unsubstituted alkyl, 2 to 5 membered unsubstituted heteroalkyl. In embodiments, $R^7$, $R^8$, $R^9$, $R^{10}$ and $R^{11}$ are independently hydrogen, halogen (e.g. —F, —Cl, —Br, or —I), unsubstituted methyl, —OCH$_3$ or —O(CH$_2$)$_2$=CH$_2$. In embodiments, $R^{10}$ and $R^{11}$ are hydrogen.

The compound of formula (II) has the formula:

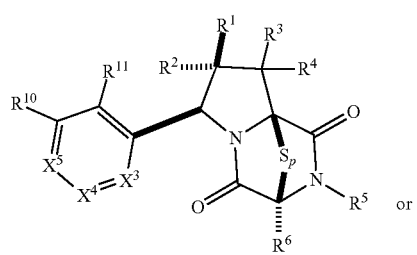

(II(S))

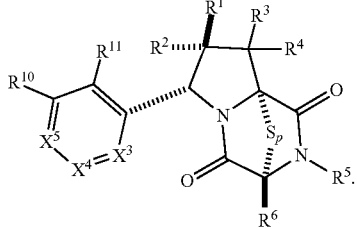

(II(R))

The symbol p, $X^3$, $X^4$, $X^5$, $R^1$, $R^2$, $R^3$, $R^4$, $R^5$, $R^6$, $R^7$, $R^8$, $R^9$, $R^{10}$, and $R^{11}$ are as described herein, including embodiments thereof. $R^5$ and $R^6$ may independently be unsubstituted $C_1$-$C_3$ alkyl or unsubstituted 3 to 5 membered cycloalkyl. $R^7$, $R^8$, $R^9$, and $R^{10}$ may independently be hydrogen, halogen (e.g. —F, —Cl, —Br, or —I), unsubstituted methyl, —OCH$_3$ or —O(CH$_2$)$_2$=CH$_2$. $R^1$ may be —CN or unsubstituted 2 to 5 membered heteroalkyl. $R^1$ may be —CN. $R^1$ may be —COOCH$_3$. $R^1$ may be unsubstituted methyl. $R^2$ may be $C_1$-$C_3$ unsubstituted alkyl. When $R^1$ is —CN, $R^2$ may be unsubstituted methyl. $R^3$ and $R^4$ are hydrogen. $R^{10}$ and $R^{11}$ are hydrogen.

In embodiments, the compound of formula (II) has the following formula:

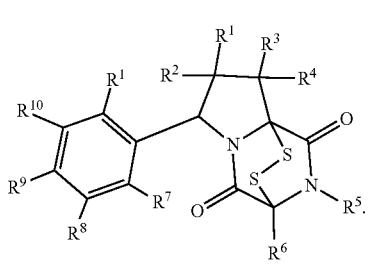

(II1)

In embodiments, $R^8$ is hydrogen or $—OR^{33J}$. In embodiments, $R^9$, $R^{10}$, and $R^{11}$ are independently hydrogen or halogen (e.g. —F, —Cl, —Br, or —I). In embodiments, $R^{33J}$ is hydrogen, or unsubstituted alkyl (e.g. unsubstituted methyl, unsubstituted ethyl, or unsubstituted propyl).

In embodiments, the compound of formula (II) has the following formula:

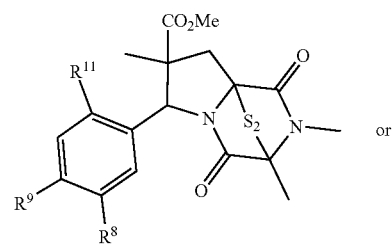

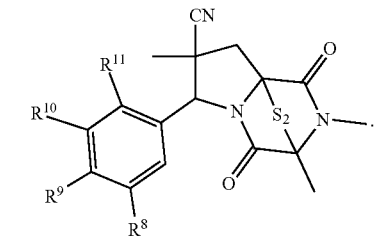

In embodiments, $R^8$ is hydrogen or $—OR^{33J}$. In embodiments, $R^9$, $R^{10}$, and $R^{11}$ are independently hydrogen or halogen (e.g. —F, —Cl, —Br, or —I). In embodiments, $R^{33J}$ may be hydrogen, or unsubstituted alkyl (e.g. unsubstituted methyl, unsubstituted ethyl, or unsubstituted propyl).

In embodiments, the compound of formula (III) has the following formula:

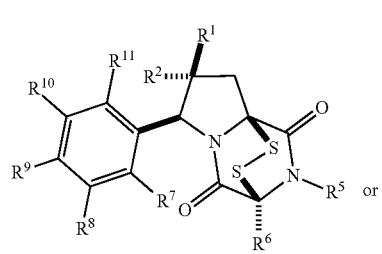

(III(S))

-continued

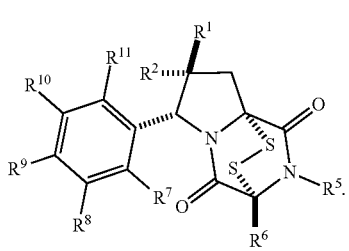
(II1(R))

In embodiments, the compound of formula (II) has the following formula:

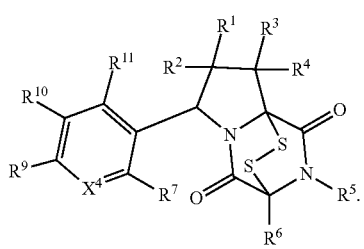
(II2)

In embodiments, the compound of formula (II2) has the following formula:

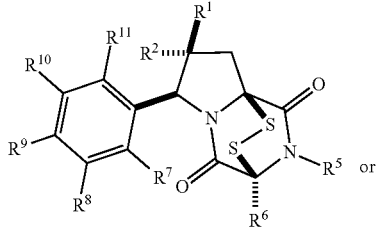
(II2(S))

or

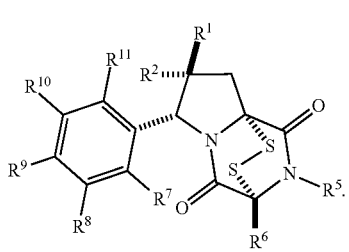
(II2(R))

In embodiments, the compound of formula (II) has the following formula:

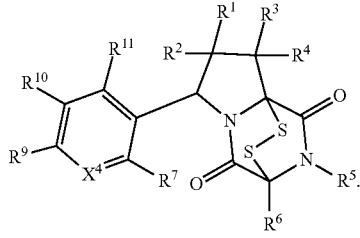
(II3)

In embodiments, the compound of formula (II3) has the following formula:

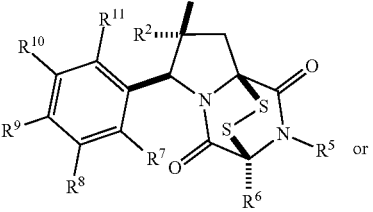
(II3(S))

or

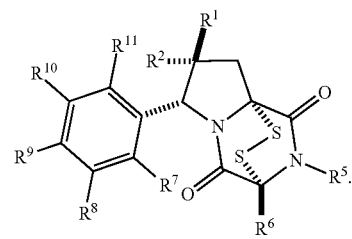
(II3(R))

In embodiments, the compound of formula (II) has the following formula:

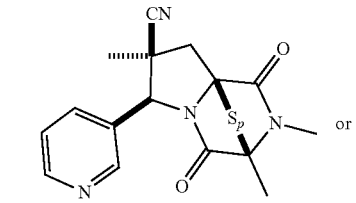
(II4)

or

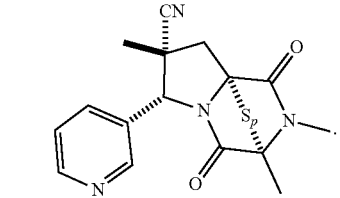
(II5)

In embodiments, the compound of formula (I) has the following formula:

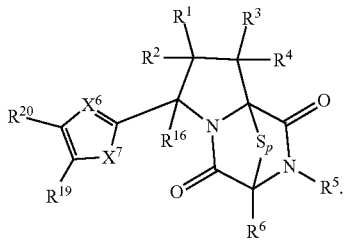
(III)

The symbol p, $R^1$, $R^2$, $R^3$, $R^4$, $R^5$, $R^6$, and $R^{16}$ are as described herein, including embodiments thereof. In embodiments, $R^5$ and $R^6$ are independently unsubstituted $C_1$-$C_3$ alkyl or unsubstituted 3 to 5 membered cycloalkyl. In embodiments, $R^7$, $R^8$, $R^9$, and $R^{10}$ are independently hydrogen, halogen (e.g. —F, —Cl, —Br, or —I), unsubstituted methyl, —OCH$_3$ or —O(CH$_2$)$_2$=CH$_2$. In embodiments, R$^1$ is —CN or unsubstituted 2 to 5 membered heteroalkyl. In embodiments, R$^1$ is —CN. R$^1$ may be —COOCH$_3$. In embodiments, R$^1$ is unsubstituted methyl. In embodiments, R$^2$ is C$_1$-C$_3$ unsubstituted alkyl. In embodiments, when R$^1$ is —CN, R$^2$ is unsubstituted methyl. In embodiments, R$^3$ and R$^4$ are hydrogen. In embodiments, R$^{10}$ and R$^{11}$ are hydrogen.

X$^6$ is CR$^{23}$ or N. X$^7$ is CR$^{24}$R$^{24A}$, S, O, or NR$^{24A}$. In embodiments, X$^6$ is CR$^{23}$. In embodiments, X$^6$ is N. In embodiments, X$^7$ is CR$^{24}$R$^{24A}$. In embodiments, X$^7$ is S or O. In embodiments, X$^7$ is NR$^{24A}$. In embodiments, X$^7$ is O. In embodiments, X$^7$ is S.

In embodiments, R$^{19}$, R$^{20}$, R$^{23}$, R$^{24}$ and R$^{24A}$ are independently hydrogen, halogen (e.g. —F, —Cl, —Br, or —I), —N$_3$, —CF$_3$, —CCl$_3$, —CBr$_3$, —CI$_3$, —CN, —CHO, —OR$^{33M}$, —NR$^{34M}$R$^{35M}$, —COOR$^{33M}$, —CONR$^{34M}$R$^{35M}$, —NO$_2$, —SR$^{36M}$, —SO$_{n13}$R$^{34M}$, —SO$_{n13}$OR$^{34M}$, —SO$_{n13}$NR$^{34M}$R$^{35M}$, —NHNR$^{34M}$R$^{35M}$, —ONR$^{34M}$R$^{35M}$, —NHC(O)NHNR$^{34M}$R$^{35M}$ (e.g., —OH, —OCH$_3$, —NH2, —NHCH$_3$, NCH$_3$NCH$_3$, —COOH, —COOCH$_3$, —CONH$_2$, —CONHCH$_3$, —NO$_2$, —SH, —SCH$_3$, —SOH, —SOCH$_3$, —SO$_2$H, —SO$_2$CH$_3$, —S(O)OH, —S(O)OCH$_3$, —S(O)$_2$H, S(O)$_2$OCH$_3$, —S(O)NH$_2$, —S(O)NHCH$_3$, —S(O)$_2$NH$_2$, S(O)$_2$NHCH$_3$, —NHNH$_2$, —NHNHCH$_3$, —NHNCH$_3$CH$_3$, —ONH$_2$, —ONHCH$_3$, —NHC(O)NHNH$_2$, or —NHC(O)NHNHCH$_3$), substituted or unsubstituted alkyl (e.g., C$_1$-C$_8$, C$_1$-C$_5$, or C$_1$-C$_3$), substituted or unsubstituted heteroalkyl (e.g., 2 to 8 membered, 2 to 5 membered, 2 to 3 membered), substituted or unsubstituted cycloalkyl (e.g., C$_3$-C$_8$, C$_3$-C$_5$, or C$_3$), substituted or unsubstituted heterocycloalkyl (e.g., 3 to 8 membered, 3 to 6 membered, or 4 membered), substituted or unsubstituted aryl (e.g., C$_5$-C$_8$, C$_5$-C$_6$, or phenyl), or substituted or unsubstituted heteroaryl (e.g., 5 to 8 membered, 5 to 6 membered, or 6 membered).

In embodiments, R$^{19}$, R$^{20}$, R$^{23}$, R$^{24}$ and R$^{24A}$ are independently hydrogen, halogen (e.g. —F, —Cl, —Br, or —I), —N$_3$, —CF$_3$, —CCl$_3$, —CBr$_3$, —CI$_3$, —CN, —CHO, —OR$^{33M}$, —NR$^{34M}$R$^{35M}$, —COOR$^{33M}$, —CONR$^{34M}$R$^{35M}$, —NO$_2$, —SR$^{36M}$, —SO$_{n13}$R$^{34M}$, —SO$_{n13}$OR$^{34M}$, —SO$_{n13}$NR$^{34M}$R$^{35M}$, —NHNR$^{34M}$R$^{35M}$, —ONR$^{34M}$R$^{35M}$, —NHC(O)NHNR$^{34M}$R$^{35M}$ (e.g., —OH, —OCH$_3$, —NH2, —NHCH$_3$, NCH$_3$NCH$_3$, —COOH, —COOCH$_3$, —CONH$_2$, —CONHCH$_3$, —NO$_2$, —SH, —SCH$_3$, —SOH, —SOCH$_3$, —SO$_2$H, —SO$_2$CH$_3$, —S(O)OH, —S(O)OCH$_3$, —S(O)$_2$H, S(O)$_2$OCH$_3$, —S(O)NH$_2$, —S(O)NHCH$_3$, —S(O)$_2$NH$_2$, S(O)$_2$NHCH$_3$, —NHNH$_2$, —NHNHCH$_3$, —NHNCH$_3$CH$_3$, —ONH$_2$, —ONHCH$_3$, —NHC(O)NHNH$_2$, or —NHC(O)NHNHCH$_3$), R$^{45a}$-substituted or unsubstituted alkyl (e.g., C$_1$-C$_8$, C$_1$-C$_5$, or C$_1$-C$_3$), R$^{45a}$-substituted or unsubstituted heteroalkyl (e.g., 2 to 8 membered, 2 to 5 membered, 2 to 3 membered), R$^{45a}$-substituted or unsubstituted cycloalkyl (e.g., C$_3$-C$_8$, C$_3$-C$_3$, or C$_3$), R$^{45a}$-substituted or unsubstituted heterocycloalkyl (e.g., 3 to 8 membered, 3 to 6 membered, or 4 membered), R$^{45a}$-substituted or unsubstituted aryl (e.g., C$_5$-C$_8$, C$_5$-C$_6$, or phenyl), or R$^{45a}$-substituted or unsubstituted heteroaryl (e.g., 5 to 8 membered, 5 to 6 membered, or 6 membered).

In embodiments, R$^{19}$, R$^{20}$, R$^{23}$, R$^{24}$ and R$^{24A}$ are independently hydrogen, halogen (e.g. —F, —Cl, —Br, or —I), —N$_3$, —CF$_3$, —CCl$_3$, —CBr$_3$, —CI$_3$, —CN, —CHO, —OR$^{33M}$, —NR$^{34M}$R$^{35M}$, —COOR$^{33M}$, —CONR$^{34M}$R$^{35M}$, —NO$_2$, —SR$^{36M}$, —SO$_{n13}$R$^{34M}$, —SO$_{n13}$OR$^{34M}$, —SO$_{n13}$NR$^{34M}$R$^{35M}$, —NHNR$^{34M}$R$^{35M}$, —ONR$^{34M}$R$^{35M}$, —NHC(O)NHNR$^{34M}$R$^{35M}$ (e.g., —OH, —OCH$_3$, —NH2, —NHCH$_3$, NCH$_3$NCH$_3$, —COOH, —COOCH$_3$, —CONH$_2$, —CONHCH$_3$, —NO$_2$, —SH, —SCH$_3$, —SOH, —SOCH$_3$, —SO$_2$H, —SO$_2$CH$_3$, —S(O)OH, —S(O)OCH$_3$, —S(O)$_2$H, S(O)$_2$OCH$_3$, —S(O)NH$_2$, —S(O)NHCH$_3$, —S(O)$_2$NH$_2$, S(O)$_2$NHCH$_3$, —NHNH$_2$, —NHNHCH$_3$, —NHNCH$_3$CH$_3$, —ONH$_2$, —ONHCH$_3$, —NHC(O)NHNH$_2$, or —NHC(O)NHNHCH$_3$), unsubstituted alkyl (e.g., C$_1$-C$_8$, C$_1$-C$_5$, or C$_1$-C$_3$), unsubstituted heteroalkyl (e.g., 2 to 8 membered, 2 to 5 membered, 2 to 3 membered), unsubstituted cycloalkyl (e.g., C$_3$-C$_8$, C$_3$-C$_3$, or C$_3$), unsubstituted heterocycloalkyl (e.g., 3 to 8 membered, 3 to 6 membered, or 4 membered), unsubstituted aryl (e.g., C$_5$-C$_8$, C$_5$-C$_6$, or phenyl), or unsubstituted heteroaryl (e.g., 5 to 8 membered, 5 to 6 membered, or 6 membered).

In embodiments, R$^{19}$, R$^{20}$, R$^{23}$, R$^{24}$ and R$^{24A}$ are independently hydrogen, halogen (e.g. —F, —Cl, —Br, or —I), —OH, —OCH$_3$, —NH2, —NHCH$_3$, NCH$_3$NCH$_3$, —COOH, —COOCH$_3$, —CONH$_2$, —CONHCH$_3$, —NO$_2$, —SH, —SCH$_3$, —SOH, —SOCH$_3$, —SO$_2$H, —SO$_2$CH$_3$, —S(O)OH, —S(O)OCH$_3$, —S(O)$_2$H, S(O)$_2$OCH$_3$, —S(O)NH$_2$, —S(O)NHCH$_3$, —S(O)$_2$NH$_2$, S(O)$_2$NHCH$_3$, —NHNH$_2$, —NHNHCH$_3$, —NHNCH$_3$CH$_3$, —ONH$_2$, —ONHCH$_3$, —NHC(O)NHNH$_2$, or —NHC(O)NHNHCH$_3$), R$^{45a}$-substituted or unsubstituted C$_1$-C$_3$ alkyl, R$^{45a}$-substituted or unsubstituted 2 to 3 membered heteroalkyl, R$^{45a}$-substituted or unsubstituted C$_3$-C$_5$ cycloalkyl, R$^{45a}$-substituted or unsubstituted 5 to 6 membered heterocycloalkyl, R$^{45a}$-substituted or unsubstituted phenyl, or R$^{45a}$-substituted or unsubstituted 5 to 6 membered heteroaryl.

In embodiments, R$^{19}$, R$^{20}$, R$^{23}$, R$^{24}$ and R$^{24A}$ are independently hydrogen, —F, —Cl, —Br, —I, —OH, —OH, —OCH$_3$, —NH2, —NHCH$_3$, NCH$_3$NCH$_3$, —COOH, —COOCH$_3$, —CONH$_2$, —CONHCH$_3$, —NO$_2$, —SH, —SCH$_3$, —SOH, —SOCH$_3$, —SO$_2$H, —SO$_2$CH$_3$, —S(O)OH, —S(O)OCH$_3$, —S(O)$_2$H, S(O)$_2$OCH$_3$, —S(O)NH$_2$, —S(O)NHCH$_3$, —S(O)$_2$NH$_2$, S(O)$_2$NHCH$_3$, —NHNH$_2$, —NHNHCH$_3$, —NHNCH$_3$CH$_3$, —ONH$_2$, —ONHCH$_3$, —NHC(O)NHNH$_2$, or —NHC(O)NHNHCH$_3$), unsubstituted C$_1$-C$_3$ alkyl, unsubstituted 2 to 3 membered heteroalkyl, unsubstituted C$_3$-C$_5$ cycloalkyl, unsubstituted 5 to 6 membered heterocycloalkyl, unsubstituted phenyl, or unsubstituted 5 to 6 membered heteroaryl.

R$^{45a}$ is halogen (e.g. —F, —Cl, —Br, or —I), —N$_3$, —CF$_3$, —CCl$_3$, —CBr$_3$, —CI$_3$, —CN, —CHO, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC(O)NHNH$_2$, substituted or unsubstituted alkyl (e.g., C$_1$-C$_8$, C$_1$-C$_6$, C$_1$-C$_4$, or C$_1$-C$_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., C$_3$-C$_8$, C$_3$-C$_6$, C$_4$-C$_6$, or C$_5$-C$_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., C$_6$-C$_{12}$, C$_6$-C$_{10}$, or phenyl), or substituted or unsubstituted heteroaryl (e.g., 5 to 12 membered, 5 to 10 membered, 5 to 9 membered, or 5 to 6 membered). In embodiments, R$^{45a}$ is halogen (e.g. —F, —Cl, —Br, or —I), —N$_3$, —CF$_3$, —CCl$_3$, —CBr$_3$, —CI$_3$, —CN, —CHO, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC(O)NHNH$_2$, R$^{45b}$-substituted or unsubstituted alkyl (e.g., C$_1$-C$_8$, C$_1$-C$_6$, C$_1$-C$_4$, or C$_1$-C$_2$), R$^{45b}$-substituted or unsubstituted heteroalkyl (e.g., 2 to 8 membered, 2 to 6 membered, 4 to 6 membered, 2 to 3 membered, or 4 to 5 membered), R$^{45b}$-substituted or unsubstituted cycloalkyl (e.g., C$_3$-C$_8$, C$_3$-C$_6$, C$_4$-C$_6$, or C$_5$-C$_6$), $R^{45b}$-substituted or unsubstituted heterocycloalkyl (e.g., 3 to 8 membered, 3 to 6 membered, 4 to 6 membered, 4 to 5 membered, or 5 to 6 membered), $R^{45b}$-substituted or unsubstituted aryl (e.g., $C_6$-$C_{12}$, $C_6$-$C_{10}$, or phenyl), or $R^{45b}$-substituted or unsubstituted heteroaryl (e.g., 5 to 12 membered, 5 to 10 membered, 5 to 9 membered, or 5 to 6 membered). In embodiments, $R^{45a}$ is halogen (e.g. —F, —Cl, —Br, or —I), —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —$NHC(O)NHNH_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered).

$R^{45b}$ is halogen (e.g. —F, —Cl, —Br, or —I), —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —$NHC(O)NHNH_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered).

In embodiments, $R^{33M}$, $R^{34M}$, $R^{35M}$, and $R^{36M}$ are independently hydrogen, substituted or unsubstituted alkyl (e.g., $C_1$-$C_8$, $C_1$-$C_5$, or $C_1$-$C_3$), substituted or unsubstituted heteroalkyl (e.g., 2 to 8 membered, 2 to 5 membered, 2 to 3 membered), substituted or unsubstituted cycloalkyl (e.g., $C_3$-$C_8$, $C_3$-$C_5$, or $C_3$), substituted or unsubstituted heterocycloalkyl (e.g., 3 to 8 membered, 3 to 6 membered, or 4 membered), substituted or unsubstituted aryl (e.g., $C_5$-$C_8$, $C_5$-$C_6$, or phenyl), or substituted or unsubstituted heteroaryl (e.g., 5 to 8 membered, 5 to 6 membered, or 6 membered). In embodiments, $R^{33M}$, $R^{34M}$, $R^{35M}$, and $R^{36M}$ are independently hydrogen, $R^{44a}$-substituted or unsubstituted alkyl (e.g., $C_1$-$C_8$, $C_1$-$C_5$, or $C_1$-$C_3$), $R^{44a}$-substituted or unsubstituted heteroalkyl (e.g., 2 to 8 membered, 2 to 5 membered, 2 to 3 membered), $R^{44a}$-substituted or unsubstituted cycloalkyl (e.g., $C_3$-$C_8$, $C_3$-$C_5$, or $C_3$), $R^{44a}$-substituted or unsubstituted heterocycloalkyl (e.g., 3 to 8 membered, 3 to 6 membered, or 4 membered), $R^{44a}$-substituted or unsubstituted aryl (e.g., $C_5$-$C_8$, $C_5$-$C_6$, or phenyl), or $R^{44a}$-substituted or unsubstituted heteroaryl (e.g., 5 to 8 membered, 5 to 6 membered, or 6 membered). In embodiments, $R^{33M}$, $R^{34M}$, $R^{35M}$, and $R^{36M}$ are independently hydrogen, unsubstituted alkyl (e.g., $C_1$-$C_8$, $C_1$-$C_5$, or $C_1$-$C_3$), unsubstituted heteroalkyl (e.g., 2 to 8 membered, 2 to 5 membered, 2 to 3 membered), unsubstituted cycloalkyl (e.g., $C_3$-$C_8$, $C_3$-$C_5$, or $C_3$), unsubstituted heterocycloalkyl (e.g., 3 to 8 membered, 3 to 6 membered, or 4 membered), unsubstituted aryl (e.g., $C_5$-$C_8$, $C_5$-$C_6$, or phenyl), or unsubstituted heteroaryl (e.g., 5 to 8 membered, 5 to 6 membered, or 6 membered). In embodiments, $R^{44a}$ is as described herein, including embodiments thereof.

The symbol n13 is 1 or 2. In embodiments, n13 is 1. In embodiments, n13 is 1.

In embodiments, $R^{19}$, $R^{20}$, $R^{23}$, $R^{24}$ and $R^{24A}$ are independently hydrogen, halogen (e.g. —F, —Cl, —Br, or —I), —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —$NHC(O)NHNH_2$. In embodiments, $R^{19}$, $R^{20}$, $R^{23}$, $R^{24}$ and $R^{24A}$ are independently substituted or unsubstituted $C_1$-$C_8$ alkyl, substituted or unsubstituted 2 to 8 membered heteroalkyl, substituted or unsubstituted 3 to 6 membered cycloalkyl, substituted or unsubstituted 3 to 6 membered heterocycloalkyl, substituted or unsubstituted 5 to 6 membered aryl, substituted or unsubstituted 5 to 6 membered heteroaryl. In embodiments, $R^{19}$, $R^{20}$, $R^{23}$, $R^{24}$ and $R^{24A}$ are independently $R^{45a}$-substituted or unsubstituted $C_1$-$C_5$ alkyl, $R^{45a}$-substituted or unsubstituted 2 to 8 membered heteroalkyl, $R^{45a}$-substituted or unsubstituted 3 to 6 membered cycloalkyl, $R^{45a}$-substituted or unsubstituted 3 to 6 membered heterocycloalkyl, $R^{45a}$-substituted or unsubstituted 5 to 6 membered aryl, $R^{45}$-substituted or unsubstituted 5 to 6 membered heteroaryl. In embodiments, $R^{19}$, $R^{20}$, $R^{23}$, $R^{24}$ and $R^{24A}$ are independently unsubstituted $C_1$-$C_8$ alkyl, unsubstituted 2 to 8 membered heteroalkyl, unsubstituted 3 to 6 membered cycloalkyl, unsubstituted 3 to 6 membered heterocycloalkyl, unsubstituted 5 to 6 membered aryl, unsubstituted 5 to 6 membered heteroaryl.

In embodiments, $R^{19}$, $R^{20}$, $R^{23}$, $R^{24}$ and $R^{24A}$ are fused to form substituted or unsubstituted 5 or 6 membered heterocycloalkyl, substituted or unsubstituted 5 or 6 membered aryl, or substituted or unsubstituted 5 or 6 membered heteroaryl. In embodiments, $R^{19}$, $R^{20}$, $R^{23}$, $R^{24}$ and $R^{24A}$ are fused to form $R^{45a}$-substituted or unsubstituted 5 or 6 membered heterocycloalkyl, $R^{45a}$-substituted or unsubstituted 5 or 6 membered aryl, or $R^{45a}$-substituted or unsubstituted 5 or 6 membered heteroaryl. In embodiments, $R^{19}$, $R^{20}$, $R^{23}$, $R^{24}$ and $R^{24A}$ are fused to form unsubstituted 5 or 6 membered heterocycloalkyl, unsubstituted 5 or 6 membered aryl, or unsubstituted 5 or 6 membered heteroaryl. In embodiments, $R^{45a}$ is as described herein, including embodiments thereof.

In embodiments, $R^{19}$, $R^{20}$, $R^{23}$, $R^{24}$ and $R^{24A}$ are independently substituted or unsubstituted alkyl (e.g., $C_1$-$C_8$, $C_1$-$C_5$, or $C_1$-$C_3$). In embodiments, $R^{19}$, $R^{20}$, $R^{23}$, $R^{24}$ and $R^{24A}$ are independently substituted or unsubstituted $C_1$-$C_8$ alkyl. In embodiments, $R^{19}$, $R^{20}$, $R^{23}$, $R^{24}$ and $R^{24A}$ are independently substituted or unsubstituted $C_1$-$C_5$ alkyl. In embodiments, $R^{19}$, $R^{20}$, $R^{23}$, $R^{24}$ and $R^{24A}$ are independently substituted or unsubstituted $C_1$-$C_3$ alkyl. In embodiments, $R^{19}$, $R^{20}$, $R^{23}$, $R^{24}$ and $R^{24A}$ are independently $R^{45a}$-substituted or unsubstituted alkyl (e.g., $C_1$-$C_8$, $C_1$-$C_5$, or $C_1$-$C_3$). In embodiments, $R^{19}$, $R^{20}$, $R^{23}$, $R^{24}$ and $R^{24A}$ are independently $R^{45a}$-substituted or unsubstituted $C_1$-$C_8$ alkyl. In embodiments, $R^{19}$, $R^{20}$, $R^{23}$, $R^{24}$ and $R^{24A}$ are independently $R^{45a}$-substituted or unsubstituted $C_1$-$C_5$ alkyl. In embodiments, $R^{19}$, $R^{20}$, $R^{23}$, $R^{24}$ and $R^{24A}$ are independently $R^{45a}$-substituted or unsubstituted $C_1$-$C_3$ alkyl. In embodiments, $R^{19}$, $R^{20}$, $R^{23}$, $R^{24}$ and $R^{24A}$ are independently unsubstituted alkyl (e.g., $C_1$-$C_8$, $C_1$-$C_5$, or $C_1$-$C_3$). In embodiments, $R^{19}$, $R^{20}$, $R^{23}$, $R^{24}$ and $R^{24A}$ are independently unsubstituted $C_1$-$C_8$ alkyl. In embodiments, $R^{19}$, $R^{20}$, $R^{23}$, $R^{24}$ and $R^{24A}$ are independently unsubstituted $C_1$-$C_5$ alkyl. In embodiments, $R^{19}$, $R^{20}$, $R^{23}$, $R^{24}$ and $R^{24A}$ are independently unsubstituted $C_1$-$C_3$ alkyl. In embodiments, $R^{45a}$ is as described herein, including embodiments thereof.

In embodiments, $R^{19}$, $R^{20}$, $R^{23}$, $R^{24}$ and $R^{24A}$ are independently substituted or unsubstituted heteroalkyl (e.g., 2 to 8 membered, 2 to 5 membered, 2 to 3 membered). In embodiments, $R^{19}$, $R^{20}$, $R^{23}$, $R^{24}$ and $R^{24A}$ are independently substituted or unsubstituted 2 to 8 membered heteroalkyl. In embodiments, $R^{19}, R^{20}, R^{23}, R^{24}$ and $R^{24A}$ are independently substituted or unsubstituted 2 to 5 membered heteroalkyl. In embodiments, $R^{19}, R^{20}, R^{23}, R^{24}$ and $R^{24A}$ are independently substituted or unsubstituted 2 to 3 membered heteroalkyl. In embodiments, $R^{19}, R^{20}, R^{23}, R^{24}$ and $R^{24A}$ are independently be $R^{45a}$-substituted or unsubstituted heteroalkyl. In embodiments, $R^{19}, R^{20}, R^{23}, R^{24}$ and $R^{24A}$ are independently $R^{45a}$-substituted or unsubstituted 2 to 8 membered heteroalkyl. In embodiments, $R^{19}, R^{20}, R^{23}, R^{24}$ and $R^{24A}$ are independently $R^{45a}$-substituted or unsubstituted 2 to 5 membered heteroalkyl. In embodiments, $R^{19}, R^{20}, R^{23}, R^{24}$ and $R^{24A}$ are independently $R^{45a}$-substituted or unsubstituted 2 to 3 membered heteroalkyl. In embodiments, $R^{19}, R^{20}, R^{23}, R^{24}$ and $R^{24A}$ are independently unsubstituted heteroalkyl (e.g., 2 to 8 membered, 2 to 5 membered, 2 to 3 membered). In embodiments, $R^{19}, R^{20}, R^{23}, R^{24}$ and $R^{24A}$ are independently unsubstituted 2 to 8 membered heteroalkyl. In embodiments, $R^{19}, R^{20}, R^{23}, R^{24}$ and $R^{24A}$ are independently unsubstituted 2 to 5 membered heteroalkyl. In embodiments, $R^{45a}$ is as described herein, including embodiments thereof.

In embodiments, $R^{19}, R^{20}, R^{23}, R^{24}$ and $R^{24A}$ are independently substituted or unsubstituted cycloalkyl (e.g., $C_3$-$C_8$, $C_3$-$C_5$, or $C_3$). In embodiments, $R^{19}, R^{20}, R^{23}, R^{24}$ and $R^{24A}$ are independently substituted or unsubstituted 3 to 8 membered cycloalkyl. In embodiments, $R^{19}, R^{20}, R^{23}, R^{24}$ and $R^{24A}$ are independently substituted or unsubstituted 3 to 5 membered cycloalkyl. In embodiments, $R^{19}, R^{20}, R^{23}, R^{24}$ and $R^{24A}$ are independently substituted or unsubstituted 3 membered cycloalkyl. In embodiments, $R^{19}, R^{20}, R^{23}, R^{24}$ and $R^{24A}$ are independently substituted or unsubstituted 4 membered cycloalkyl. In embodiments, $R^{19}, R^{20}, R^{23}, R^{24}$ and $R^{24A}$ are independently substituted or unsubstituted 5 membered cycloalkyl. In embodiments, $R^{19}, R^{20}, R^{23}, R^{24}$ and $R^{24A}$ are independently $R^{45a}$-substituted or unsubstituted cycloalkyl. In embodiments, $R^{19}, R^{20}, R^{23}, R^{24}$ and $R^{24A}$ are independently $R^{45a}$-substituted or unsubstituted 3 to 8 membered cycloalkyl. In embodiments, $R^{19}, R^{20}, R^{23}, R^{24}$ and $R^{24A}$ are independently $R^{45a}$-substituted or unsubstituted 3 to 5 membered cycloalkyl. In embodiments, $R^{19}, R^{20}, R^{23}, R^{24}$ and $R^{24A}$ independently $R^{45a}$-substituted or unsubstituted 3 membered cycloalkyl. In embodiments, $R^{19}, R^{20}, R^{23}, R^{24}$ and $R^{24A}$ are independently $R^{45a}$-substituted or unsubstituted 4 membered cycloalkyl. In embodiments, $R^{19}, R^{20}, R^{23}, R^{24}$ and $R^{24A}$ are independently $R^{45a}$-substituted or unsubstituted 5 membered cycloalkyl. In embodiments, $R^{19}, R^{20}, R^{23}, R^{24}$ and $R^{24A}$ are independently unsubstituted cycloalkyl (e.g., $C_3$-$C_8$, $C_3$-$C_5$, or $C_3$). In embodiments, $R^{19}, R^{20}, R^{23}, R^{24}$ and $R^{24A}$ are independently unsubstituted 3 to 8 membered cycloalkyl. In embodiments, $R^{19}, R^{20}, R^{23}, R^{24}$ and $R^{24A}$ are independently unsubstituted 3 to 5 membered cycloalkyl. In embodiments, $R^{19}, R^{20}, R^{23}, R^{24}$ and $R^{24A}$ are independently unsubstituted 3 membered cycloalkyl. In embodiments, $R^{19}, R^{20}, R^{23}, R^{24}$ and $R^{24A}$ are independently unsubstituted 4 membered cycloalkyl. In embodiments, $R^{19}, R^{20}, R^{23}, R^{24}$ and $R^{24A}$ are independently unsubstituted 5 membered cycloalkyl. In embodiments, $R^{45a}$ is as described herein, including embodiments thereof.

In embodiments, $R^{19}, R^{20}, R^{23}, R^{24}$ and $R^{24A}$ are independently substituted or unsubstituted heterocycloalkyl (e.g., 3 to 8 membered, 3 to 6 membered, or 4 membered). In embodiments, $R^{19}, R^{20}, R^{23}, R^{24}$ and $R^{24A}$ are independently substituted or unsubstituted 3 to 6 membered heterocycloalkyl. In embodiments, $R^{19}, R^{20}, R^{23}, R^{24}$ and $R^{24A}$ are independently substituted or unsubstituted 4 membered heterocycloalkyl. In embodiments, $R^{19}, R^{20}, R^{23}, R^{24}$ and $R^{24A}$ are independently substituted or unsubstituted 5 membered heterocycloalkyl. In embodiments, $R^{19}, R^{20}, R^{23}, R^{24}$ and $R^{24A}$ are independently substituted or unsubstituted 6 membered heterocycloalkyl. In embodiments, $R^{19}, R^{20}, R^{23}, R^{24}$ and $R^{24A}$ are independently $R^{45a}$-substituted or unsubstituted heterocycloalkyl. In embodiments, $R^{19}, R^{20}, R^{23}, R^{24}$ and $R^{24A}$ are independently $R^{45a}$-substituted or unsubstituted 3 to 6 membered heterocycloalkyl. In embodiments, $R^{19}, R^{20}, R^{23}, R^{24}$ and $R^{24A}$ are independently $R^{45a}$-substituted or unsubstituted 4 membered heterocycloalkyl. In embodiments, $R^{19}, R^{19}, R^{20}, R^{23}, R^{24}$ and $R^{24A}$ independently be $R^{45a}$-substituted or unsubstituted 5 membered heterocycloalkyl. In embodiments, $R^{19}, R^{20}, R^{23}, R^{24}$ and $R^{24A}$ are independently $R^{45a}$-substituted or unsubstituted 6 membered heterocycloalkyl. In embodiments, $R^{19}, R^{20}, R^{23}, R^{24}$ and $R^{24A}$ are independently unsubstituted heterocycloalkyl (e.g., 3 to 8 membered, 3 to 6 membered, or 4 membered). In embodiments, $R^{19}, R^{20}, R^{23}, R^{24}$ and $R^{24A}$ are independently unsubstituted 3 to 6 membered heterocycloalkyl. In embodiments, $R^{19}, R^{20}, R^{23}, R^{24}$ and $R^{24A}$ are independently unsubstituted 4 membered heterocycloalkyl. In embodiments, $R^{19}, R^{20}, R^{23}, R^{24}$ and $R^{24A}$ are independently unsubstituted 5 membered heterocycloalkyl. In embodiments, $R^{19}, R^{20}, R^{23}, R^{24}$ and $R^{24A}$ are independently unsubstituted 6 membered heterocycloalkyl. In embodiments, $R^{45a}$ is as described herein, including embodiments thereof.

In embodiments, $R^{19}, R^{20}, R^{23}, R^{24}$ and $R^{24A}$ are independently substituted or unsubstituted aryl (e.g., $C_5$-$C_8$, $C_5$-$C_6$, or phenyl). In embodiments, $R^{19}, R^{20}, R^{23}, R^{24}$ and $R^{24A}$ are independently substituted or unsubstituted 5 to 6 membered aryl. In embodiments, $R^{19}, R^{20}, R^{23}, R^{24}$ and $R^{24A}$ are independently substituted or unsubstituted 5 membered aryl. In embodiments, $R^{19}, R^{20}, R^{23}, R^{24}$ and $R^{24A}$ are independently substituted or unsubstituted 6 membered aryl or phenyl. In embodiments, $R^{19}, R^{20}, R^{23}, R^{24}$ and $R^{24A}$ are independently $R^{45a}$-substituted or unsubstituted aryl. In embodiments, $R^{19}, R^{20}, R^{23}, R^{24}$ and $R^{24A}$ are independently $R^{45a}$-substituted or unsubstituted 5 to 6 membered aryl. In embodiments, $R^{19}, R^{20}, R^{23}, R^{24}$ and $R^{24A}$ are independently $R^{45a}$-substituted or unsubstituted 5 membered aryl. In embodiments, $R^{19}, R^{20}, R^{23}, R^{24}$ and $R^{24A}$ are independently $R^{45a}$-substituted or unsubstituted 6 membered aryl or phenyl. In embodiments, $R^{19}, R^{20}, R^{23}, R^{24}$ and $R^{24A}$ are independently unsubstituted aryl (e.g., $C_5$-$C_8$, $C_5$-$C_6$, or phenyl). In embodiments, $R^{19}, R^{20}, R^{23}, R^{24}$ and $R^{24A}$ are independently unsubstituted 5 to 6 membered aryl. In embodiments, $R^{19}, R^{20}, R^{23}, R^{24}$ and $R^{24A}$ are independently unsubstituted 5 membered aryl. In embodiments, $R^{19}, R^{20}, R^{23}, R^{24}$ and $R^{24A}$ are independently unsubstituted 6 membered aryl or phenyl. In embodiments, $R^{45}$ is as described herein, including embodiments thereof.

In embodiments, $R^{19}, R^{20}, R^{23}, R^{24}$ and $R^{24A}$ are independently substituted or unsubstituted heteroaryl (e.g., 5 to 8 membered, 5 to 6 membered, or 6 membered). In embodiments, $R^{19}, R^{20}, R^{23}, R^{24}$ and $R^{24A}$ are independently substituted or unsubstituted 5 to 6 membered heteroaryl. In embodiments, $R^{19}, R^{20}, R^{23}, R^{24}$ and $R^{24A}$ are independently substituted or unsubstituted 5 membered heteroaryl. In embodiments, $R^{19}, R^{20}, R^{23}, R^{24}$ and $R^{24A}$ are independently substituted or unsubstituted 6 membered heteroaryl. In embodiments, $R^{19}, R^{20}, R^{23}, R^{24}$ and $R^{24A}$ are independently $R^{45a}$-substituted or unsubstituted heteroaryl (e.g., 5 to 8 membered, 5 to 6 membered, or 6 membered). In embodiments, $R^{19}, R^{20}, R^{23}, R^{24}$ and $R^{24A}$ are independently $R^{45a}$-substituted or unsubstituted 5 to 6 membered heteroaryl. In embodiments, $R^{19}, R^{20}, R^{23}, R^{24}$ and $R^{24A}$ are independently $R^{45a}$-substituted or unsubstituted 5 membered heteroaryl. In embodiments, $R^{19}$, $R^{20}$, $R^{23}$, $R^{24}$ and $R^{24A}$ are independently $R^{45a}$-substituted or unsubstituted 6 membered heteroaryl. In embodiments, $R^{19}$, $R^{20}$, $R^{21}$, $R^{22}$, $R^{23}$ and $R^{23A}$ are independently unsubstituted heteroaryl (e.g., 5 to 8 membered, 5 to 6 membered, or 6 membered). In embodiments, $R^{19}$, $R^{20}$, $R^{21}$, $R^{22}$, $R^{23}$ and $R^{23A}$ are independently unsubstituted 5 to 6 membered heteroaryl. In embodiments, $R^{19}$, $R^{20}$, $R^{21}$, $R^{22}$, $R^{23}$ and $R^{23A}$ are independently unsubstituted 5 membered heteroaryl. In embodiments, $R^{19}$, $R^{20}$, $R^{21}$, $R^{22}$, $R^{23}$ and $R^{23A}$ are independently unsubstituted 6 membered heteroaryl. In embodiments, $R^{45a}$ is as described herein, including embodiments thereof.

In embodiments, $R^{19}$ and $R^{20}$ are optionally bonded together to form substituted or unsubstituted 3 to 6 membered cycloalkyl, substituted or unsubstituted 3 to 6 membered heterocycloalkyl, substituted or unsubstituted 5 to 6 membered aryl, or substituted or unsubstituted 5 to 6 membered heteroaryl. In embodiments, $R^{19}$ and $R^{20}$ are optionally bonded together to form $R^{45a}$-substituted or unsubstituted 3 to 6 membered cycloalkyl, $R^{45a}$-substituted or unsubstituted 3 to 6 membered heterocycloalkyl, $R^{45a}$-substituted or unsubstituted 5 to 6 membered aryl, or $R^{45a}$-substituted or unsubstituted 5 to 6 membered heteroaryl. In embodiments, $R^{19}$ and $R^{20}$ are optionally bonded together to form unsubstituted 3 to 6 membered cycloalkyl, unsubstituted 3 to 6 membered heterocycloalkyl, unsubstituted 5 to 6 membered aryl, or unsubstituted 5 to 6 membered heteroaryl. In embodiments, $R^{45}$ is as described herein, including embodiments thereof.

In embodiments, $R^{19}$ and $R^{20}$ are optionally bonded together to form substituted or unsubstituted 3 to 6 membered cycloalkyl, substituted or unsubstituted 3 to 6 membered heterocycloalkyl, substituted or unsubstituted 5 to 6 membered aryl, or substituted or unsubstituted 5 to 6 membered heteroaryl. In embodiments, $R^{19}$ and $R^{22}$ are optionally bonded together to form $R^{45a}$-substituted or unsubstituted 3 to 6 membered cycloalkyl, $R^{45a}$-substituted or unsubstituted 3 to 6 membered heterocycloalkyl, $R^{45a}$-substituted or unsubstituted 5 to 6 membered aryl, or $R^{45a}$-substituted or unsubstituted 5 to 6 membered heteroaryl. In embodiments, $R^{19}$ and $R^{22}$ are optionally bonded together to form unsubstituted 3 to 6 membered cycloalkyl, unsubstituted 3 to 6 membered heterocycloalkyl, unsubstituted 5 to 6 membered aryl, or unsubstituted 5 to 6 membered heteroaryl. In embodiments, $R^{45a}$ is as described herein, including embodiments thereof.

In embodiments, $R^{19}$ and $R^{20}$ are optionally bonded together to form substituted or unsubstituted 3 to 6 membered cycloalkyl, substituted or unsubstituted 3 to 6 membered heterocycloalkyl, substituted or unsubstituted 5 to 6 membered aryl, or substituted or unsubstituted 5 to 6 membered heteroaryl. In embodiments, $R^{20}$ and $R^{21}$ are optionally bonded together to form $R^{45a}$-substituted or unsubstituted 3 to 6 membered cycloalkyl, $R^{45a}$-substituted or unsubstituted 3 to 6 membered heterocycloalkyl, $R^{45a}$-substituted or unsubstituted 5 to 6 membered aryl, or $R^{45a}$-substituted or unsubstituted 5 to 6 membered heteroaryl. In embodiments, $R^{20}$ and $R^{21}$ are optionally bonded together to form unsubstituted 3 to 6 membered cycloalkyl, unsubstituted 3 to 6 membered heterocycloalkyl, unsubstituted 5 to 6 membered aryl, or unsubstituted 5 to 6 membered heteroaryl. In embodiments, $R^{45a}$ is as described herein, including embodiments thereof.

In embodiments, when $X^7$ is S, $X^6$ is N or $CR^{23}$. In embodiments, when $X^7$ is NH, $X^6$ is N or $CR^{23}$. In embodiments, when $X^7$ is $NR^{24A}$, $X^6$ is $CR^{23}$ or N. In embodiments, when $X^7$ is O, $X^6$ is N, CH, or $CR^{23}$. In embodiments, $X^7$ is S and $X^6$ is CH. In embodiments, p is 2, 3, or 4. In embodiments, p is 2. In embodiments, p is 3. In embodiments, p is 4.

In embodiments, the compound of formula (III) has the following formula:

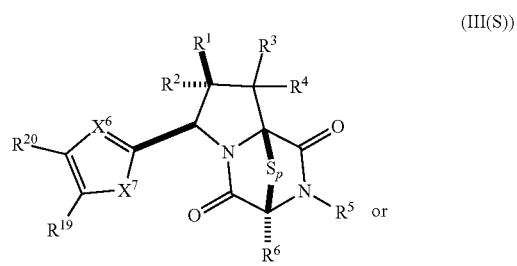

(III(S))

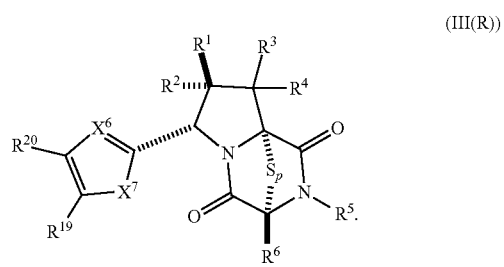

(III(R))

In embodiments, the compound of formula (III) has the following formula:

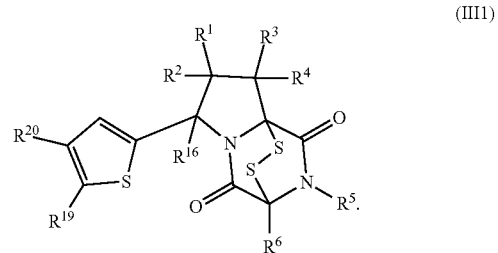

(III1)

In embodiments, the compound of formula (III1) has the following formula:

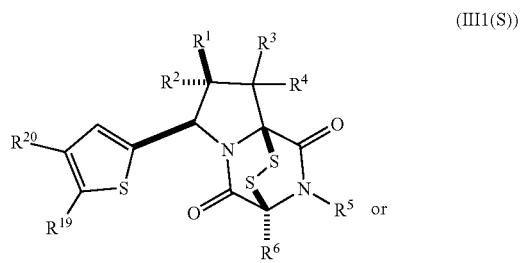

(III1(S))

-continued

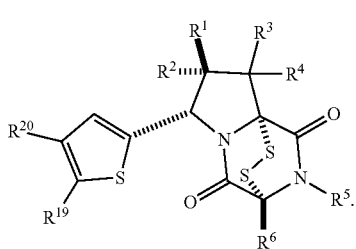
(III1(R))

In embodiments, the compound of formula (III) has the following formula:

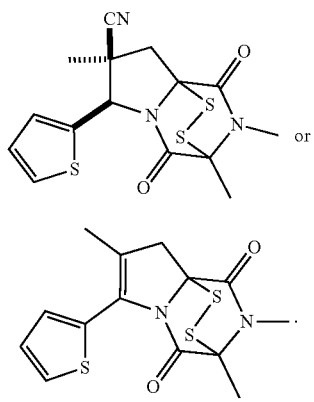
(ETP204)

or (ETP206)

In embodiments, the compound of formula (I) has the following formula:

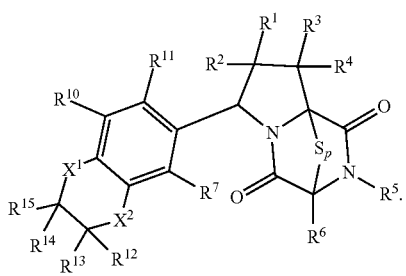
(IV)

The symbol p, $R^1$, $R^2$, $R^3$, $R^4$, $R^5$, $R^6$, $R^7$, $R^{10}$, and $R^{11}$ are as described herein, including embodiments thereof.

In embodiments, $R^{12}$, $R^{13}$, $R^{14}$, and $R^{15}$ are independently hydrogen, halogen (e.g. —F, —Cl, —Br, or —I), —N$_3$, —CF$_3$, —CCl$_3$, —CBr$_3$, —CI$_3$, —CN, —CHO, —OR$^{33M}$, —NR$^{34M}$R$^{35M}$, —COOR$^{33M}$, —CONR$^{34M}$R$^{35M}$, —NO$_2$, —SR$^{36M}$, —SO$_{n13}$R$^{34M}$, —SO$_{n13}$OR$^{34M}$, —SO$_{n13}$NR$^{34M}$R$^{35M}$, —NHNR$^{34M}$R$^{35M}$, —ONR$^{34M}$R$^{35M}$, —NHC(O)NHNR$^{34M}$R$^{35M}$ (e.g., —OH, —OCH$_3$, —NH2, —NHCH$_3$, NCH$_3$NCH$_3$, —COOH, —COOCH$_3$, —CONH$_2$, —CONHCH$_3$, —NO$_2$, —SH, —SCH$_3$, —SOH, —SOCH$_3$, —SO$_2$H, —SO$_2$CH$_3$, —S(O)OH, —S(O)OCH$_3$, —S(O)$_2$H, S(O)$_2$OCH$_3$, —S(O)NH$_2$, —S(O)NHCH$_3$, —S(O)$_2$NH$_2$, S(O)$_2$NHCH$_3$, —NHNH$_2$, —NHNHCH$_3$, —NHNCH$_3$CH$_3$, —ONH$_2$, —ONHCH$_3$, —NHC(O)NHNH$_2$, or —NHC(O)NHNHCH$_3$), substituted or unsubstituted alkyl (e.g., C$_1$-C$_8$, C$_1$-C$_5$, or C$_1$-C$_3$), substituted or unsubstituted heteroalkyl (e.g., 2 to 8 membered, 2 to 5 membered, 2 to 3 membered), substituted or unsubstituted cycloalkyl (e.g., C$_3$-C$_8$, C$_3$-C$_5$, or C$_3$), substituted or unsubstituted heterocycloalkyl (e.g., 3 to 8 membered, 3 to 6 membered, or 4 membered), substituted or unsubstituted aryl (e.g., C$_5$-C$_8$, C$_5$-C$_6$, or phenyl), or substituted or unsubstituted heteroaryl (e.g., 5 to 8 membered, 5 to 6 membered, or 6 membered).

In embodiments, $R^{12}$, $R^{13}$, $R^{14}$, and $R^{15}$ are independently hydrogen, halogen (e.g. —F, —Cl, —Br, or —I), —N$_3$, —CF$_3$, —CCl$_3$, —CBr$_3$, —CI$_3$, —CN, —CHO, —OR$^{33M}$, —NR$^{34M}$R$^{35M}$, —COOR$^{33M}$, —CONR$^{34M}$R$^{35M}$, —NO$_2$, —SR$^{36M}$, —SO$_{n13}$R$^{34M}$, —SO$_{n13}$OR$^{34M}$, —SO$_{n13}$NR$^{34M}$R$^{35M}$, —NHNR$^{34M}$R$^{35M}$, —ONR$^{34M}$R$^{35M}$, —NHC(O)NHNR$^{34M}$R$^{35M}$ (e.g., —OH, —OCH$_3$, —NH2, —NHCH$_3$, NCH$_3$NCH$_3$, —COOH, —COOCH$_3$, —CONH$_2$, —CONHCH$_3$, —NO$_2$, —SH, —SCH$_3$, —SOH, —SOCH$_3$, —SO$_2$H, —SO$_2$CH$_3$, —S(O)OH, —S(O)OCH$_3$, —S(O)$_2$H, S(O)$_2$OCH$_3$, —S(O)NH$_2$, —S(O)NHCH$_3$, —S(O)$_2$NH$_2$, S(O)$_2$NHCH$_3$, —NHNH$_2$, —NHNHCH$_3$, —NHNCH$_3$CH$_3$, —ONH$_2$, —ONHCH$_3$, —NHC(O)NHNH$_2$, or —NHC(O)NHNHCH$_3$), $R^{45a}$-substituted or unsubstituted alkyl (e.g., C$_1$-C$_8$, C$_1$-C$_5$, or C$_1$-C$_3$), $R^{45a}$-substituted or unsubstituted heteroalkyl (e.g., 2 to 8 membered, 2 to 5 membered, 2 to 3 membered), $R^{45a}$-substituted or unsubstituted cycloalkyl (e.g., C$_3$-C$_8$, C$_3$-C$_3$, or C$_3$), $R^{45a}$-substituted or unsubstituted heterocycloalkyl (e.g., 3 to 8 membered, 3 to 6 membered, or 4 membered), $R^{45a}$-substituted or unsubstituted aryl (e.g., C$_5$-C$_8$, C$_5$-C$_6$, or phenyl), or $R^{45a}$-substituted or unsubstituted heteroaryl (e.g., 5 to 8 membered, 5 to 6 membered, or 6 membered).

In embodiments, $R^{12}$, $R^{13}$, $R^{14}$, and $R^{15}$ are independently hydrogen, halogen (e.g. —F, —Cl, —Br, or —I), —N$_3$, —CF$_3$, —CCl$_3$, —CBr$_3$, —CI$_3$, —CN, —CHO, —OR$^{33M}$, —NR$^{34M}$R$^{35M}$, —COOR$^{33M}$, —CONR$^{34M}$R$^{35M}$, —NO$_2$, —SR$^{36M}$, —SO$_{n13}$R$^{34M}$, —SO$_{n13}$OR$^{34M}$, —SO$_{n13}$NR$^{34M}$R$^{35M}$, —NHNR$^{34M}$R$^{35M}$, —ONR$^{34M}$R$^{35M}$, —NHC(O)NHNR$^{34M}$R$^{35M}$ (e.g., —OH, —OCH$_3$, —NH2, —NHCH$_3$, NCH$_3$NCH$_3$, —COOH, —COOCH$_3$, —CONH$_2$, —CONHCH$_3$, —NO$_2$, —SH, —SCH$_3$, —SOH, —SOCH$_3$, —SO$_2$H, —SO$_2$CH$_3$, —S(O)OH, —S(O)OCH$_3$, —S(O)$_2$H, S(O)$_2$OCH$_3$, —S(O)NH$_2$, —S(O)NHCH$_3$, —S(O)$_2$NH$_2$, S(O)$_2$NHCH$_3$, —NHNH$_2$, —NHNHCH$_3$, —NHNCH$_3$CH$_3$, —ONH$_2$, —ONHCH$_3$, —NHC(O)NHNH$_2$, or —NHC(O)NHNHCH$_3$), unsubstituted alkyl (e.g., C$_1$-C$_8$, C$_1$-C$_5$, or C$_1$-C$_3$), unsubstituted heteroalkyl (e.g., 2 to 8 membered, 2 to 5 membered, 2 to 3 membered), unsubstituted cycloalkyl (e.g., C$_3$-C$_8$, C$_3$-C$_3$, or C$_3$), unsubstituted heterocycloalkyl (e.g., 3 to 8 membered, 3 to 6 membered, or 4 membered), unsubstituted aryl (e.g., C$_5$-C$_8$, C$_5$-C$_6$, or phenyl), or unsubstituted heteroaryl (e.g., 5 to 8 membered, 5 to 6 membered, or 6 membered).

In embodiments, $R^{12}$, $R^{13}$, $R^{14}$, and $R^{15}$ are independently hydrogen, halogen (e.g. —F, —Cl, —Br, or —I), —OH, —OCH$_3$, —NH2, —NHCH$_3$, NCH$_3$NCH$_3$, —COOH, —COOCH$_3$, —CONH$_2$, —CONHCH$_3$, —NO$_2$, —SH, —SCH$_3$, —SOH, —SOCH$_3$, —SO$_2$H, —SO$_2$CH$_3$, —S(O)OH, —S(O)OCH$_3$, —S(O)$_2$H, S(O)$_2$OCH$_3$, —S(O)NH$_2$, —S(O)NHCH$_3$, —S(O)$_2$NH$_2$, S(O)$_2$NHCH$_3$, —NHNH$_2$, —NHNHCH$_3$, —NHNCH$_3$CH$_3$, —ONH$_2$, —ONHCH$_3$, —NHC(O)NHNH$_2$, or —NHC(O)NHNHCH$_3$), $R^{45a}$-substituted or unsubstituted C$_1$-C$_3$ alkyl, $R^{45a}$-substituted or unsubstituted 2 to 3 membered heteroalkyl, $R^{45a}$-substituted or unsubstituted C$_3$-C$_5$ cycloalkyl, $R^{45a}$-substituted or unsubstituted 5 to 6 membered heterocycloalkyl, $R^{45a}$-substituted or unsubstituted phenyl, or $R^{45a}$-substituted or unsubstituted 5 to 6 membered heteroaryl. In embodiments, $R^{12}$, $R^{13}$, $R^{14}$, and $R^5$ are independently hydrogen, —F, —Cl, —Br, —I, —OH, —OH, —OCH$_3$, —NH2, —NHCH$_3$, NCH$_3$NCH$_3$, —COOH, —COOCH$_3$, —CONH$_2$, —CONHCH$_3$, —NO$_2$, —SH, —SCH$_3$, —SOH, —SOCH$_3$, —SO$_2$H, —SO$_2$CH$_3$, —S(O)OH, —S(O)OCH$_3$, —S(O)$_2$H, S(O)$_2$OCH$_3$, —S(O)NH$_2$, —S(O)NHCH$_3$, —S(O)$_2$NH$_2$, S(O)$_2$NHCH$_3$, —NHNH$_2$, —NHNHCH$_3$, —NHNCH$_3$CH$_3$, —ONH$_2$, —ONHCH$_3$, —NHC(O)NHNH$_2$, or —NHC(O)NHNHCH$_3$), unsubstituted $C_1$-$C_3$ alkyl, unsubstituted 2 to 3 membered heteroalkyl, unsubstituted $C_3$-$C_5$ cycloalkyl, unsubstituted 5 to 6 membered heterocycloalkyl, unsubstituted phenyl, or unsubstituted 5 to 6 membered heteroaryl. In embodiments, $R^{45a}$ is as described herein, including embodiments thereof.

In embodiments, $R^{33M}$, $R^{34M}$, $R^{35M}$, and $R^{36M}$ are independently hydrogen, substituted or unsubstituted alkyl (e.g., $C_1$-$C_8$, $C_1$-$C_5$, or $C_1$-$C_3$), substituted or unsubstituted heteroalkyl (e.g., 2 to 8 membered, 2 to 5 membered, 2 to 3 membered), substituted or unsubstituted cycloalkyl (e.g., $C_3$-$C_8$, $C_3$-$C_5$, or $C_3$), substituted or unsubstituted heterocycloalkyl (e.g., 3 to 8 membered, 3 to 6 membered, or 4 membered), substituted or unsubstituted aryl (e.g., $C_5$-$C_8$, $C_5$-$C_6$, or phenyl), or substituted or unsubstituted heteroaryl (e.g., 5 to 8 membered, 5 to 6 membered, or 6 membered). In embodiments, $R^{33M}$, $R^{34M}$, $R^{35M}$, and $R^{36M}$ are independently hydrogen, $R^{44a}$-substituted or unsubstituted alkyl (e.g., $C_1$-$C_8$, $C_1$-$C_5$, or $C_1$-$C_3$), $R^{44a}$-substituted or unsubstituted heteroalkyl (e.g., 2 to 8 membered, 2 to 5 membered, 2 to 3 membered), $R^{44a}$-substituted or unsubstituted cycloalkyl (e.g., $C_3$-$C_8$, $C_3$-$C_5$, or $C_3$), $R^{44a}$-substituted or unsubstituted heterocycloalkyl (e.g., 3 to 8 membered, 3 to 6 membered, or 4 membered), $R^{44a}$-substituted or unsubstituted aryl (e.g., $C_5$-$C_8$, $C_5$-$C_6$, or phenyl), or $R^{44a}$-substituted or unsubstituted heteroaryl (e.g., 5 to 8 membered, 5 to 6 membered, or 6 membered). In embodiments, $R^{33M}$, $R^{34M}$, $R^{35M}$, and $R^{36M}$ are independently hydrogen, unsubstituted alkyl (e.g., $C_1$-$C_8$, $C_1$-$C_5$, or $C_1$-$C_3$), unsubstituted heteroalkyl (e.g., 2 to 8 membered, 2 to 5 membered, 2 to 3 membered), unsubstituted cycloalkyl (e.g., $C_3$-$C_8$, $C_3$-$C_5$, or $C_3$), unsubstituted heterocycloalkyl (e.g., 3 to 8 membered, 3 to 6 membered, or 4 membered), unsubstituted aryl (e.g., $C_5$-$C_8$, $C_5$-$C_6$, or phenyl), or unsubstituted heteroaryl (e.g., 5 to 8 membered, 5 to 6 membered, or 6 membered). In embodiments, $R^{44a}$ is as described herein, including embodiments thereof.

The symbol n13 is 1 or 2. In embodiments, n13 is 1. In embodiments, n13 is 1.

$X^1$ is $CR^{21}R^{21A}$, O, $NR^{21A}$, or S. $X^2$ is $CR^{22}R^{22A}$, O, $NR^{22A}$, or S. In embodiments, $X^1$ is $CR^{21}R^{21A}$. In embodiments, $X^1$ is O or S. In embodiments, $X^1$ is $NR^{21A}$. In embodiments, $X^1$ is S. In embodiments, $X^1$ is O. In embodiments, $X^2$ is $CR^{22}R^{22A}$, O, $NR^{22A}$, or S. In embodiments, $X^2$ is $CR^{22}R^{22A}$. In embodiments, $X^2$ is O or S. In embodiments, $X^2$ is $NR^{22A}$. In embodiment, In embodiments, $X^2$ is O. In embodiments, $X^2$ is S.

In embodiments, $R^5$ and $R^6$ are independently unsubstituted $C_1$-$C_3$ alkyl or unsubstituted 3 to 5 membered cycloalkyl. In embodiments, $R^7$, $R^8$, $R^9$, and $R^{10}$ are independently be hydrogen, halogen (e.g. —F, —Cl, —Br, or —I), unsubstituted methyl, —OCH$_3$ or —O(CH$_2$)$_2$=CH$_2$. In embodiments, $R^1$ is —CN or unsubstituted 2 to 5 membered heteroalkyl. In embodiments, $R^1$ is —CN. In embodiments, $R^1$ is —COOCH$_3$. In embodiments, $R^1$ is unsubstituted methyl. In embodiments, $R^2$ is $C_1$-$C_3$ unsubstituted alkyl. In embodiments, when $R^1$ is —CN, $R^2$ is unsubstituted methyl.

In embodiments, $R^3$ and $R^4$ are hydrogen. In embodiments, $R^{10}$ and $R^{11}$ are hydrogen. In embodiments, $R^{12}$, $R^{13}$, $R^{14}$, and $R^{15}$ are hydrogen.

In embodiments, $R^{12}$, $R^{13}$, $R^{14}$, $R^{15}$ $R^{21}$, $R^{21A}$, $R^{22}$, and $R^{22A}$ are independently hydrogen, halogen (e.g. —F, —Cl, —Br, or —I), —N$_3$, —CF$_3$, —CCl$_3$, —CBr$_3$, —CI$_3$, —CN, —CHO, —OR$^{33M}$, —NR$^{34M}$R$^{35M}$, —COOR$^{33M}$, —CONR$^{34M}$R$^{35M}$, —NO$_2$, —SR$^{36M}$, —SO$_{n13}$R$^{34M}$, —SO$_{n13}$OR$^{34M}$, —SO$_{n13}$NR$^{34M}$R$^{35M}$, —NHNR$^{34M}$R$^{35M}$, —ONR$^{34M}$R$^{35M}$, —NHC(O)NHNR$^{34M}$R$^{35M}$ (e.g., —OH, —OCH$_3$, —NH2, —NHCH$_3$, NCH$_3$NCH$_3$, —COOH, —COOCH$_3$, —CONH$_2$, —CONHCH$_3$, —NO$_2$, —SH, —SCH$_3$, —SOH, —SOCH$_3$, —SO$_2$H, —SO$_2$CH$_3$, —S(O)OH, —S(O)OCH$_3$, —S(O)$_2$H, S(O)$_2$OCH$_3$, —S(O)NH$_2$, —S(O)NHCH$_3$, —S(O)$_2$NH$_2$, S(O)$_2$NHCH$_3$, —NHNH$_2$, —NHNHCH$_3$, —NHNCH$_3$CH$_3$, —ONH$_2$, —ONHCH$_3$, —NHC(O)NHNH$_2$, or —NHC(O)NHNHCH$_3$), substituted or unsubstituted alkyl (e.g., $C_1$-$C_8$, $C_1$-$C_5$, or $C_1$-$C_3$), substituted or unsubstituted heteroalkyl (e.g., 2 to 8 membered, 2 to 5 membered, 2 to 3 membered), substituted or unsubstituted cycloalkyl (e.g., $C_3$-$C_8$, $C_3$-$C_5$, or $C_3$), substituted or unsubstituted heterocycloalkyl (e.g., 3 to 8 membered, 3 to 6 membered, or 4 membered), substituted or unsubstituted aryl (e.g., $C_5$-$C_8$, $C_5$-$C_6$, or phenyl), or substituted or unsubstituted heteroaryl (e.g., 5 to 8 membered, 5 to 6 membered, or 6 membered).

In embodiments, $R^{12}$, $R^{13}$, $R^{14}$, $R^{15}$ $R^{21}$, $R^{21A}$, $R^{22}$, and $R^{22A}$ are independently hydrogen, halogen (e.g. —F, —Cl, —Br, or —I), —N$_3$, —CF$_3$, —CCl$_3$, —CBr$_3$, —CI$_3$, —CN, —CHO, —OR$^{33M}$, —NR$^{34M}$R$^{35M}$, —COOR$^{33M}$, —CONR$^{34M}$R$^{35M}$, —NO$_2$, —SR$^{36M}$, —SO$_{n13}$R$^{34M}$, —SO$_{n13}$OR$^{34M}$, —SO$_{n13}$NR$^{34M}$R$^{35M}$, —NHNR$^{34M}$R$^{35M}$, —ONR$^{34M}$R$^{35M}$, —NHC(O)NHNR$^{34M}$R$^{35M}$ (e.g., —OH, —OCH$_3$, —NH2, —NHCH$_3$, NCH$_3$NCH$_3$, —COOH, —COOCH$_3$, —CONH$_2$, —CONHCH$_3$, —NO$_2$, —SH, —SCH$_3$, —SOH, —SOCH$_3$, —SO$_2$H, —SO$_2$CH$_3$, —S(O)OH, —S(O)OCH$_3$, —S(O)$_2$H, S(O)$_2$OCH$_3$, —S(O)NH$_2$, —S(O)NHCH$_3$, —S(O)$_2$NH$_2$, S(O)$_2$NHCH$_3$, —NHNH$_2$, —NHNHCH$_3$, —NHNCH$_3$CH$_3$, —ONH$_2$, —ONHCH$_3$, —NHC(O)NHNH$_2$, or —NHC(O)NHNHCH$_3$), $R^{45a}$-substituted or unsubstituted alkyl (e.g., $C_1$-$C_8$, $C_1$-$C_5$, or $C_1$-$C_3$), $R^{45a}$-substituted or unsubstituted heteroalkyl (e.g., 2 to 8 membered, 2 to 5 membered, 2 to 3 membered), $R^{45a}$-substituted or unsubstituted cycloalkyl (e.g., $C_3$-$C_8$, $C_3$-$C_3$, or $C_3$), $R^{45a}$-substituted or unsubstituted heterocycloalkyl (e.g., 3 to 8 membered, 3 to 6 membered, or 4 membered), $R^{45a}$-substituted or unsubstituted aryl (e.g., $C_5$-$C_6$, $C_5$-$C_6$, or phenyl), or $R^{45a}$-substituted or unsubstituted heteroaryl (e.g., 5 to 8 membered, 5 to 6 membered, or 6 membered).

In embodiments, $R^{12}$, $R^{13}$, $R^{14}$, $R^{15}$ $R^{21}$, $R^{21A}$, $R^{22}$, and $R^{22A}$ are independently hydrogen, halogen (e.g. —F, —Cl, —Br, or —I), —N$_3$, —CF$_3$, —CCl$_3$, —CBr$_3$, —CI$_3$, —CN, —CHO, —OR$^{33M}$, —NR$^{34M}$R$^{35M}$, —COOR$^{33M}$, —CONR$^{34M}$R$^{35M}$, —NO$_2$, —SR$^{36M}$, —SO$_{n13}$R$^{34M}$, —SO$_{n13}$OR$^{34M}$, —SO$_{n13}$NR$^{34M}$R$^{35M}$, —NHNR$^{34M}$R$^{35M}$, —ONR$^{34M}$R$^{35M}$, —NHC(O)NHNR$^{34M}$R$^{35M}$ (e.g., —OH, —OCH$_3$, —NH2, —NHCH$_3$, NCH$_3$NCH$_3$, —COOH, —COOCH$_3$, —CONH$_2$, —CONHCH$_3$, —NO$_2$, —SH, —SCH$_3$, —SOH, —SOCH$_3$, —SO$_2$H, —SO$_2$CH$_3$, —S(O)OH, —S(O)OCH$_3$, —S(O)$_2$H, S(O)$_2$OCH$_3$, —S(O)NH$_2$, —S(O)NHCH$_3$, —S(O)$_2$NH$_2$, S(O)$_2$NHCH$_3$, —NHNH$_2$, —NHNHCH$_3$, —NHNCH$_3$CH$_3$, —ONH$_2$, —ONHCH$_3$, —NHC(O)NHNH$_2$, or —NHC(O)NHNHCH$_3$), unsubstituted alkyl (e.g., $C_1$-$C_8$, $C_1$-$C_5$, or $C_1$-$C_3$), unsubstituted heteroalkyl (e.g., 2 to 8 membered, 2 to 5 membered, 2 to 3 membered), unsubstituted cycloalkyl (e.g., $C_3$-$C_8$, $C_3$-$C_3$, or $C_3$), unsubstituted heterocycloalkyl (e.g., 3 to 8 membered, 3 to 6 membered, or 4 membered), unsubstituted aryl (e.g., $C_5$-$C_8$, $C_5$-$C_6$, or phenyl), or unsubstituted heteroaryl (e.g., 5 to 8 membered, 5 to 6 membered, or 6 membered).

In embodiments, $R^{12}$, $R^{13}$, $R^{14}$, $R^{15}$ $R^{21}$, $R^{21A}$, $R^{22}$, and $R^{22A}$ are independently hydrogen, halogen (e.g. —F, —Cl, —Br, or —I), —OH, —$OCH_3$, —NH2, —$NHCH_3$, $NCH_3NCH_3$, —COOH, —$COOCH_3$, —$CONH_2$, —$CONHCH_3$, —$NO_2$, —SH, —$SCH_3$, —SOH, —$SOCH_3$, —$SO_2H$, —$SO_2CH_3$, —S(O)OH, —S(O)$OCH_3$, —S(O)$_2$H, S(O)$_2OCH_3$, —S(O)$NH_2$, —S(O)$NHCH_3$, —S(O)$_2NH_2$, S(O)$_2NHCH_3$, —$NHNH_2$, —$NHNHCH_3$, —$NHNCH_3CH_3$, —$ONH_2$, —$ONHCH_3$, —NHC(O)$NHNH_2$, or —NHC(O)$NHNHCH_3$), $R^{45a}$-substituted or unsubstituted $C_1$-$C_3$ alkyl, $R^{45a}$-substituted or unsubstituted 2 to 3 membered heteroalkyl, $R^{45a}$-substituted or unsubstituted $C_3$-$C_5$ cycloalkyl, $R^{45a}$-substituted or unsubstituted 5 to 6 membered heterocycloalkyl, $R^{45a}$-substituted or unsubstituted phenyl, or $R^{45a}$-substituted or unsubstituted 5 to 6 membered heteroaryl.

In embodiments, $R^{12}$, $R^{13}$, $R^{14}$, $R^{15}$ $R^{21}$, $R^{21A}$, $R^{22}$, and $R^{22A}$ are independently hydrogen, —F, —Cl, —Br, —I, —OH, —OH, —$OCH_3$, —NH2, —$NHCH_3$, $NCH_3NCH_3$, —COOH, —$COOCH_3$, —$CONH_2$, —$CONHCH_3$, —$NO_2$, —SH, —$SCH_3$, —SOH, —$SOCH_3$, —$SO_2H$, —$SO_2CH_3$, —S(O)OH, —S(O)$OCH_3$, —S(O)$_2$H, S(O)$_2OCH_3$, —S(O)$NH_2$, —S(O)$NHCH_3$, —S(O)$_2NH_2$, S(O)$_2NHCH_3$, —$NHNH_2$, —$NHNHCH_3$, —$NHNCH_3CH_3$, —$ONH_2$, —$ONHCH_3$, —NHC(O)$NHNH_2$, or —NHC(O)$NHNHCH_3$), unsubstituted $C_1$-$C_3$ alkyl, unsubstituted 2 to 3 membered heteroalkyl, unsubstituted $C_3$-$C_5$ cycloalkyl, unsubstituted 5 to 6 membered heterocycloalkyl, unsubstituted phenyl, or unsubstituted 5 to 6 membered heteroaryl.

In embodiments, $R^{12}$, $R^{13}$, $R^{14}$, $R^{15}$ $R^{21}$, $R^{21A}$, $R^{22}$, and $R^{22A}$ are fused to form substituted or unsubstituted 5 or 6 membered heterocycloalkyl, substituted or unsubstituted 5 or 6 membered aryl, or substituted or unsubstituted 5 or 6 membered heteroaryl. In embodiments, $R^{12}$, $R^{13}$, $R^{14}$, $R^{15}$ $R^{21}$, $R^{21A}$, $R^{22}$, and $R^{22A}$ are fused to form $R^{45a}$-substituted or unsubstituted 5 or 6 membered heterocycloalkyl, $R^{45a}$-substituted or unsubstituted 5 or 6 membered aryl, or $R^{45a}$-substituted or unsubstituted 5 or 6 membered heteroaryl. In embodiments, $R^{12}$, $R^{13}$, $R^{14}$, $R^{15}$ $R^{21}$, $R^{21A}$, $R^{22}$, and $R^{22A}$ are fused to form unsubstituted 5 or 6 membered heterocycloalkyl, unsubstituted 5 or 6 membered aryl, or unsubstituted 5 or 6 membered heteroaryl. In embodiments, $R^{45a}$ is as described herein, including embodiments thereof.

In embodiments, $R^{12}$, $R^{13}$, $R^{14}$, and $R^{15}$ are independently substituted or unsubstituted alkyl (e.g., $C_1$-$C_8$, $C_1$-$C_5$, or $C_1$-$C_3$). In embodiments, $R^{12}$, $R^{13}$, $R^{14}$, $R^{15}$ $R^{21}$, $R^{21A}$, $R^{22}$, and $R^{22A}$ are independently substituted or unsubstituted $C_1$-$C_8$ alkyl. In embodiments, $R^{12}$, $R^{13}$, $R^{14}$, $R^{15}$ $R^{21}$, $R^{21A}$, $R^{22}$, and $R^{22A}$ are independently substituted or unsubstituted $C_1$-$C_5$ alkyl. In embodiments, $R^{12}$, $R^{13}$, $R^{14}$, $R^{15}$ $R^{21}$, $R^{21A}$, $R^{22}$, and $R^{22A}$ are independently substituted or unsubstituted $C_1$-$C_3$ alkyl. In embodiments, $R^{12}$, $R^{13}$, $R^{14}$, $R^{15}$ $R^{21}$, $R^{21A}$, $R^{22}$, and $R^{22A}$ are independently $R^{45a}$-substituted or unsubstituted alkyl (e.g., $C_1$-$C_8$, $C_1$-$C_5$, or $C_1$-$C_3$). In embodiments, $R^{12}$, $R^{13}$, $R^{14}$, $R^{15}$ $R^{21}$, $R^{21A}$, $R^{22}$, and $R^{22A}$ are independently $R^{45a}$-substituted or unsubstituted $C_1$-$C_8$ alkyl. In embodiments, $R^{12}$, $R^{13}$, $R^{14}$, $R^{15}$ $R^{21}$, $R^{21A}$, $R^{22}$, and $R^{22A}$ are independently $R^{45a}$-substituted or unsubstituted $C_1$-$C_5$ alkyl. In embodiments, $R^{12}$, $R^{13}$, $R^{14}$, $R^{15}$ $R^{21}$, $R^{21A}$, $R^{22}$, and $R^{22A}$ are independently $R^{45a}$-substituted or unsubstituted $C_1$-$C_3$ alkyl. In embodiments, $R^{12}$, $R^{13}$, $R^{14}$, and $R^{15}$ are independently unsubstituted alkyl (e.g., $C_1$-$C_8$, $C_1$-$C_5$, or $C_1$-$C_3$). In embodiments, $R^{12}$, $R^{13}$, $R^{14}$, $R^{15}$ $R^{21}$, $R^{21A}$, $R^{22}$, and $R^{22A}$ are independently unsubstituted $C_1$-$C_5$ alkyl. In embodiments, $R^{12}$, $R^{13}$, $R^{14}$, $R^{15}$ $R^{21}$, $R^{21A}$, $R^{22}$, and $R^{22A}$ are independently unsubstituted $C_1$-$C_5$ alkyl. In embodiments, $R^{12}$, $R^{13}$, $R^{14}$, $R^{15}$ $R^{21}$, $R^{21A}$, $R^{22}$, and $R^{22A}$ are independently unsubstituted $C_1$-$C_3$ alkyl. In embodiments, $R^{45a}$ is as described herein, including embodiments thereof.

In embodiments, $R^{12}$, $R^{13}$, $R^{14}$, $R^{15}$ $R^{21}$, $R^{21A}$, $R^{22}$, and $R^{22A}$ are independently substituted or unsubstituted heteroalkyl (e.g., 2 to 8 membered, 2 to 5 membered, 2 to 3 membered). In embodiments, $R^{12}$, $R^{13}$, $R^{14}$, $R^{15}$ $R^{21}$, $R^{21A}$, $R^{22}$, and $R^{22A}$ are independently substituted or unsubstituted 2 to 8 membered heteroalkyl. In embodiments, $R^{12}$, $R^{13}$, $R^{14}$, $R^{15}$ $R^{21}$, $R^{21A}$, $R^{22}$, and $R^{22A}$ are independently substituted or unsubstituted 2 to 5 membered heteroalkyl. In embodiments, $R^{12}$, $R^{13}$, $R^{14}$, $R^{15}$ $R^{21}$, $R^{21A}$, $R^{22}$, and $R^{22A}$ are independently substituted or unsubstituted 2 to 3 membered heteroalkyl. In embodiments, $R^{12}$, $R^{13}$, $R^{14}$, $R^{15}$ $R^{21}$, $R^{21A}$, $R^{22}$, and $R^{22A}$ are independently $R^{45a}$-substituted or unsubstituted heteroalkyl (e.g., 2 to 8 membered, 2 to 5 membered, 2 to 3 membered). In embodiments, $R^{12}$, $R^{13}$, $R^{14}$, $R^{15}$ $R^{21}$, $R^{21A}$, $R^{22}$, and $R^{22A}$ are independently $R^{45a}$-substituted or unsubstituted 2 to 8 membered heteroalkyl. In embodiments, $R^{12}$, $R^{13}$, $R^{14}$, $R^{15}$ $R^{21}$, $R^{21A}$, $R^{22}$, are $R^{22A}$ independently $R^{45a}$-substituted or unsubstituted 2 to 5 membered heteroalkyl. In embodiments, $R^{12}$, $R^{13}$, $R^{14}$, $R^{15}$ $R^{21}$, $R^{21A}$, $R^{22}$, and $R^{22A}$ are independently $R^{45a}$-substituted or unsubstituted 2 to 3 membered heteroalkyl. In embodiments, $R^{12}$, $R^{13}$, $R^{14}$, $R^{15}$ $R^{21}$, $R^{21A}$, $R^{22}$, and $R^{22A}$ are independently unsubstituted heteroalkyl (e.g., 2 to 8 membered, 2 to 5 membered, 2 to 3 membered). In embodiments, $R^{12}$, $R^{13}$, $R^{14}$, $R^{15}$ $R^{21}$, $R^{21A}$, $R^{22}$, and $R^{22A}$ are independently unsubstituted 2 to 8 membered heteroalkyl. In embodiments, $R^{12}$, $R^{13}$, $R^{14}$, $R^{15}$ $R^{21}$, $R^{21A}$, $R^{22}$, and $R^{22A}$ are independently unsubstituted 2 to 5 membered heteroalkyl. In embodiments, $R^{12}$, $R^{13}$, $R^{14}$, $R^{15}$ $R^{21}$, $R^{21A}$, $R^{22}$, and $R^{22A}$ are independently unsubstituted 2 to 3 membered heteroalkyl. In embodiments, $R^{45a}$ is as described herein, including embodiments thereof.

In embodiments, $R^{12}$, $R^{13}$, $R^{14}$, $R^{15}$ $R^{21}$, $R^{21A}$, $R^{22}$, and $R^{22A}$ are independently substituted or unsubstituted cycloalkyl (e.g., $C_3$-$C_8$, $C_3$-$C_5$, or $C_3$). In embodiments, $R^{12}$, $R^{13}$, $R^{14}$, $R^{15}$ $R^{21}$, $R^{21A}$, $R^{22}$, and $R^{22A}$ are independently substituted or unsubstituted 3 to 8 membered cycloalkyl. In embodiments, $R^{12}$, $R^{13}$, $R^{14}$, $R^{15}$ $R^{21}$, $R^{21A}$, $R^{22}$, and $R^{22A}$ are independently substituted or unsubstituted 3 to 5 membered cycloalkyl. In embodiments, $R^{12}$, $R^{13}$, $R^{14}$, $R^{15}$ $R^{21}$, $R^{21A}$, $R^{22}$, and $R^{22A}$ are independently substituted or unsubstituted 3 membered cycloalkyl. In embodiments, $R^{12}$, $R^{13}$, $R^{14}$, $R^{15}$ $R^{21}$, $R^{21A}$, $R^{22}$, and $R^{22A}$ are independently substituted or unsubstituted 4 membered cycloalkyl. In embodiments, $R^{12}$, $R^{13}$, $R^{14}$, $R^{15}$ $R^{21}$, $R^{21A}$, $R^{22}$, and $R^{22A}$ are independently substituted or unsubstituted 5 membered cycloalkyl. In embodiments, $R^{12}$, $R^{13}$, $R^{14}$, $R^{15}$ $R^{21}$, $R^{21A}$, $R^{22}$, and $R^{22A}$ are independently $R^{45a}$-substituted or unsubstituted cycloalkyl (e.g., $C_3$-$C_8$, $C_3$-$C_5$, or $C_3$). In embodiments, $R^{12}$, $R^{13}$, $R^{14}$, $R^{15}$ $R^{21}$, $R^{21A}$, $R^{22}$, and $R^{22A}$ are independently $R^{45a}$-substituted or unsubstituted 3 to 8 membered cycloalkyl. In embodiments, $R^{12}$, $R^{13}$, $R^{14}$, $R^{15}$ $R^{21}$, $R^{21A}$, $R^{22}$, and $R^{22A}$ are independently $R^{45a}$-substituted or unsubstituted 3 to 5 membered cycloalkyl. In embodiments, $R^{12}$, $R^{13}$, $R^{14}$, $R^{15}$ $R^{21}$, $R^{21A}$, $R^{22}$, and $R^{22A}$ are independently $R^{45a}$-substituted or unsubstituted 3 membered cycloalkyl. In embodiments, $R^{12}$, $R^{13}$, $R^{14}$, $R^{15}$ $R^{21}$, $R^{21A}$, $R^{22}$, and $R^{22A}$ are independently $R^{45a}$-substituted or unsubstituted 4 membered cycloalkyl. In embodiments, $R^{12}$, $R^{13}$, $R^{14}$, $R^{15}$ $R^{21}$, $R^{21A}$, $R^{22}$, and $R^{22A}$ are independently $R^{45a}$-substituted or unsubstituted 5 membered cycloalkyl. In embodiments, $R^{12}$, $R^{13}$, $R^{14}$, $R^{15}$ $R^{21}$, $R^{21A}$, $R^{22}$, and $R^{22A}$ are independently unsubstituted cycloalkyl (e.g., $C_3$-$C_8$, $C_3$-$C_5$, or $C_3$). In embodiments, $R^{12}$, $R^{13}$, $R^{14}$, $R^{15}$ $R^{21}$, $R^{21A}$, $R^{22}$, and $R^{22A}$ are independently unsubstituted 3 to 8 membered cycloalkyl. In embodiments, $R^{12}$, $R^{13}$, $R^{14}$, $R^{15}$ $R^{21}$, $R^{21A}$, $R^{22}$, and $R^{22A}$ are independently unsubstituted 3 to 5 membered cycloalkyl. In embodiments, $R^{12}$, $R^{13}$, $R^{14}$, $R^{15}$ $R^{21}$, $R^{21A}$, $R^{22}$, and $R^{22A}$ are independently unsubstituted 3 membered cycloalkyl. In embodiments, $R^{12}$, $R^{13}$, $R^{14}$, $R^{15}$ $R^{21}$, $R^{21A}$, $R^{22}$, and $R^{22A}$ are independently unsubstituted 4 membered cycloalkyl. In embodiments, $R^{12}$, $R^{13}$, $R^{14}$, $R^{15}$ $R^{21}$, $R^{21A}$, $R^{22}$, and $R^{22A}$ are independently unsubstituted 5 membered cycloalkyl. In embodiments, $R^{45a}$ is as described herein, including embodiments thereof.

In embodiments, $R^{12}$, $R^{13}$, $R^{14}$, $R^{15}$ $R^{21}$, $R^{21A}$, $R^{22}$, and $R^{22A}$ are independently substituted or unsubstituted heterocycloalkyl (e.g., 3 to 8 membered, 3 to 6 membered, or 4 membered). In embodiments, $R^{12}$, $R^{13}$, $R^{14}$, $R^{15}$ $R^{21}$, $R^{21A}$, $R^{22}$, and $R^{22A}$ are independently substituted or unsubstituted 3 to 6 membered heterocycloalkyl. In embodiments, $R^{12}$, $R^{13}$, $R^{14}$, $R^{15}$ $R^{21}$, $R^{21A}$, $R^{22}$, and $R^{22A}$ are independently substituted or unsubstituted 4 membered heterocycloalkyl. In embodiments, $R^{12}$, $R^{13}$, $R^{14}$, $R^{15}$ $R^{21}$, $R^{21A}$, $R^{22}$, and $R^{22A}$ are independently substituted or unsubstituted 5 membered heterocycloalkyl. In embodiments, $R^{12}$, $R^{13}$, $R^{14}$, $R^{15}$ $R^{21}$, $R^{21A}$, $R^{22}$, and $R^{22A}$ are independently substituted or unsubstituted 6 membered heterocycloalkyl. In embodiments, $R^{12}$, $R^{13}$, $R^{14}$, $R^{15}$ $R^{21}$, $R^{21A}$, $R^{22}$, and $R^{22A}$ are independently $R^{45a}$-substituted or unsubstituted heterocycloalkyl (e.g., 3 to 8 membered, 3 to 6 membered, or 4 membered). In embodiments, $R^{12}$, $R^{13}$, $R^{14}$, $R^{15}$ $R^{21}$, $R^{21A}$, $R^{22}$, and $R^{22A}$ are independently $R^{45a}$-substituted or unsubstituted 3 to 6 membered heterocycloalkyl. In embodiments, $R^{12}$, $R^{13}$, $R^{14}$, $R^{15}$ $R^{21}$, $R^{21A}$, $R^{22}$, and $R^{22A}$ are independently $R^{45a}$-substituted or unsubstituted 4 membered heterocycloalkyl. In embodiments, $R^{12}$, $R^{13}$, $R^{14}$, $R^{15}$ $R^{21}$, $R^{21A}$, $R^{22}$, and $R^{22A}$ are independently $R^{45a}$-substituted or unsubstituted 5 membered heterocycloalkyl. In embodiments, $R^{12}$, $R^{13}$, $R^{14}$, $R^{15}$ $R^{21}$, $R^{21A}$, $R^{22}$, and $R^{22A}$ are independently $R^{45a}$-substituted or unsubstituted 6 membered heterocycloalkyl. In embodiments, $R^{12}$, $R^{13}$, $R^{14}$, $R^{15}$ $R^{21}$, $R^{21A}$, $R^{22}$, and $R^{22A}$ are independently unsubstituted heterocycloalkyl (e.g., 3 to 8 membered, 3 to 6 membered, or 4 membered). In embodiments, $R^{12}$, $R^{13}$, $R^{14}$, $R^{15}$ $R^{21}$, $R^{21A}$, $R^{22}$, and $R^{22A}$ are independently 3 to 6 membered heterocycloalkyl. In embodiments, $R^{12}$, $R^{13}$, $R^{14}$, $R^{15}$ $R^{21}$, $R^{21A}$, $R^{22}$, and $R^{22A}$ are independently unsubstituted 4 membered heterocycloalkyl. In embodiments, $R^{12}$, $R^{13}$, $R^{14}$, $R^{15}$ $R^{21}$, $R^{21A}$, $R^{22}$, and $R^{22A}$ are independently unsubstituted 5 membered heterocycloalkyl. In embodiments, $R^{12}$, $R^{13}$, $R^{14}$, $R^{15}$ $R^{21}$, $R^{21A}$, $R^{22}$, and $R^{22A}$ are independently unsubstituted 6 membered heterocycloalkyl. In embodiments, $R^{45a}$ is as described herein, including embodiments thereof.

In embodiments, $R^{12}$, $R^{13}$, $R^{14}$, $R^{15}$ $R^{21}$, $R^{21A}$, $R^{22}$, and $R^{22A}$ are independently substituted or unsubstituted aryl (e.g., $C_5$-$C_8$, $C_5$-$C_6$, or phenyl). In embodiments, $R^{12}$, $R^{13}$, $R^{14}$, $R^{15}$ $R^{21}$, $R^{21A}$, $R^{22}$, and $R^{22A}$ are independently substituted or unsubstituted 5 to 6 membered aryl. In embodiments, $R^{12}$, $R^{13}$, $R^{14}$, $R^{15}$ $R^{21}$, $R^{21A}$, $R^{22}$, and $R^{22A}$ are independently substituted or unsubstituted 5 membered aryl. In embodiments, $R^{12}$, $R^{13}$, $R^{14}$, $R^{15}$ $R^{21}$, $R^{21A}$, $R^{22}$, and $R^{22A}$ are independently substituted or unsubstituted 6 membered aryl. In embodiments, $R^{12}$, $R^{13}$, $R^{14}$, $R^{15}$ $R^{21}$, $R^{21A}$, $R^{22}$, and $R^{22A}$ are independently $R^{45a}$-substituted or unsubstituted aryl (e.g., $C_5$-$C_8$, $C_5$-$C_6$, or phenyl). In embodiments, $R^{12}$, $R^{13}$, $R^{14}$, $R^{15}$ $R^{21}$, $R^{21A}$, $R^{22}$, and $R^{22A}$ are independently $R^{45a}$-substituted or unsubstituted 5 to 6 membered aryl. In embodiments, $R^{12}$, $R^{13}$, $R^{14}$, $R^{15}$ $R^{21}$, $R^{21A}$, $R^{22}$, and $R^{22A}$ are independently b $R^{45a}$-substituted or unsubstituted 5 membered aryl. In embodiments, $R^{12}$, $R^{13}$, $R^{14}$, $R^{15}$ $R^{21}$, $R^{21A}$, $R^{22}$, and $R^{22A}$ are independently $R^{45a}$-substituted or unsubstituted 6 membered aryl. In embodiments, $R^{12}$, $R^{13}$, $R^{14}$, $R^{15}$ $R^{21}$, $R^{21A}$, $R^{22}$, and $R^{22A}$ are independently unsubstituted aryl (e.g., $C_5$-$C_8$, $C_5$-$C_6$, or phenyl). In embodiments, $R^{12}$, $R^{13}$, $R^{14}$, $R^{15}$ $R^{21}$, $R^{21A}$, $R^{22}$, and $R^{22A}$ are independently unsubstituted 5 to 6 membered aryl. In embodiments, $R^{12}$, $R^{13}$, $R^{14}$, $R^{15}$ $R^{21}$, $R^{21A}$, $R^{22}$, and $R^{22A}$ are independently unsubstituted 5 membered aryl. In embodiments, $R^{12}$, $R^{13}$, $R^{14}$, $R^{15}$ $R^{21}$, $R^{21A}$, $R^{22}$, and $R^{22A}$ are independently unsubstituted 6 membered aryl. In embodiments, $R^{45a}$ is as described herein, including embodiments thereof.

In embodiments, $R^{12}$, $R^{13}$, $R^{14}$, $R^{15}$ $R^{21}$, $R^{21A}$, $R^{22}$, and $R^{22A}$ are independently substituted or unsubstituted heteroaryl (e.g., 5 to 8 membered, 5 to 6 membered, or 6 membered). In embodiments, $R^{12}$, $R^{13}$, $R^{14}$, $R^{15}$ $R^{21A}$, $R^{22}$, and $R^{22A}$ are independently substituted or unsubstituted 5 to 6 membered heteroaryl. In embodiments, $R^{12}$, $R^{13}$, $R^{14}$, $R^{15}$ $R^{21}$, $R^{21A}$, $R^{22}$, and $R^{22A}$ are independently substituted or unsubstituted 5 membered heteroaryl. In embodiments, $R^{12}$, $R^{13}$, $R^{14}$, $R^{15}$ $R^{21}$, $R^{21A}$, $R^{22}$, and $R^{22A}$ are independently substituted or unsubstituted 6 membered heteroaryl. In embodiments, $R^{12}$, $R^{13}$, $R^{14}$, $R^{15}$ $R^{21}$, $R^{21A}$, $R^{22}$, and $R^{22A}$ are independently $R^{45a}$-substituted or unsubstituted heteroaryl (e.g., 5 to 8 membered, 5 to 6 membered, or 6 membered). In embodiments, $R^{12}$, $R^{13}$, $R^{14}$, $R^{15}$ $R^{21}$, $R^{21A}$, $R^{22}$, and $R^{22A}$ are independently $R^{45a}$-substituted or unsubstituted 5 to 6 membered heteroaryl. In embodiments, $R^{12}$, $R^{13}$, $R^{14}$, $R^{15}$ $R^{21}$, $R^{21A}$, $R^{22}$, and $R^{22A}$ are independently $R^{45a}$-substituted or unsubstituted 5 membered heteroaryl. In embodiments, $R^{12}$, $R^{13}$, $R^{14}$, $R^{15}$ $R^{21}$, $R^{21A}$, $R^{22}$, and $R^{22A}$ are independently $R^{45a}$-substituted or unsubstituted 6 membered heteroaryl. In embodiments, $R^{12}$, $R^{13}$, $R^{14}$, $R^{15}$ $R^{21}$, $R^{21A}$, $R^{22}$, and $R^{22A}$ are independently unsubstituted heteroaryl (e.g., 5 to 8 membered, 5 to 6 membered, or 6 membered). In embodiments, $R^{12}$, $R^{13}$, $R^{14}$, $R^{15}$ $R^{21}$, $R^{21A}$, $R^{22}$, and $R^{22A}$ are independently unsubstituted 5 to 6 membered heteroaryl. In embodiments, $R^{12}$, $R^{13}$, $R^{14}$, $R^{15}$ $R^{21}$, $R^{21A}$, $R^{22}$, and $R^{22A}$ are independently unsubstituted 5 membered heteroaryl. In embodiments, $R^{12}$, $R^{13}$, $R^{14}$, $R^{15}$ $R^{21}$, $R^{21A}$, $R^{22}$, and $R^{22A}$ are independently unsubstituted 6 membered heteroaryl. In embodiments, $R^{45}$ is as described herein, including embodiments thereof.

In embodiments, $R^{12}$, $R^{13}$, $R^{14}$, $R^{15}$, $R^{21}$, $R^{21A}$, $R^{22}$, and $R^{22A}$ are independently hydrogen, halogen (e.g. —F, —Cl, —Br, or —I), —$N_3$, —$CF_3$, —$CCl_3$, —$CBr_3$, —$CI_3$, —CN, —CHO, —$OR^{33M}$, —$NR^{34M}R^{35M}$, —$COOR^{33M}$, —$CONR^{34M}R^{35M}$, —$NO_2$, —$SR^{36M}$, —$SO_{n13}R^{34M}$, —$SO_{n13}OR^{34M}$, —$SO_{n13}NR^{34M}R^{35M}$, —$NHNR^{34M}R^{35M}$, —$ONR^{34M}R^{35M}$, —$NHC(O)NHNR^{34M}R^{35M}$ (e.g., —OH, —$OCH_3$, —$NH2$, —$NHCH_3$, $NCH_3NCH_3$, —COOH, —$COOCH_3$, —$CONH_2$, —$CONHCH_3$, —$NO_2$, —SH, —$SCH_3$, —SOH, —$SOCH_3$, —$SO_2H$, —$SO_2CH_3$, —S(O)OH, —$S(O)OCH_3$, —$S(O)_2H$, $S(O)_2OCH_3$, —$S(O)NH_2$, —$S(O)NHCH_3$, —$S(O)_2NH_2$, $S(O)_2NHCH_3$, —$NHNH_2$, —$NHNHCH_3$, —$NHNCH_3CH_3$, —$ONH_2$, —$ONHCH_3$, —$NHC(O)NHNH_2$, or —$NHC(O)NHNHCH_3$), substituted or unsubstituted alkyl (e.g., $C_1$-$C_8$, $C_1$-$C_5$, or $C_1$-$C_3$), substituted or unsubstituted heteroalkyl (e.g., 2 to 8 membered, 2 to 5 membered, 2 to 3 membered), substituted or unsubstituted cycloalkyl (e.g., $C_3$-$C_8$, $C_3$-$C_5$, or $C_3$), substituted or unsubstituted heterocycloalkyl (e.g., 3 to 8 membered, 3 to 6 membered, or 4 membered), substituted or unsubstituted aryl (e.g., $C_5$-$C_8$, $C_5$-$C_6$, or phenyl), or substituted or unsubstituted heteroaryl (e.g., 5 to 8 membered, 5 to 6 membered, or 6 membered).

In embodiments, $R^{12}$, $R^{13}$, $R^{14}$, $R^5$, $R^{21}$, $R^{21A}$, $R^{22}$, and $R^{22A}$ are independently hydrogen, halogen (e.g. —F, —Cl, —Br, or —I), —$N_3$, —$CF_3$, —$CCl_3$, —$CBr_3$, —$CI_3$, —CN, —CHO, —$OR^{33M}$, —$NR^{34M}R^{35M}$, —$COOR^{33M}$, —$CONR^{34M}R^{35M}$, —$NO_2$, —$SR^{36M}$, —$SO_{n13}R^{34M}$, —$SO_{n13}OR^{34M}$, —$SO_{n13}NR^{34M}R^{35M}$, —$NHNR^{34M}R^{35M}$, —$ONR^{34M}R^{35M}$, —$NHC(O)NHNR^{34M}R^{35M}$ (e.g., —OH, —$OCH_3$, —NH2, —$NHCH_3$, $NCH_3NCH_3$, —COOH, —$COOCH_3$, —$CONH_2$, —$CONHCH_3$, —$NO_2$, —SH, —$SCH_3$, —SOH, —$SOCH_3$, —$SO_2H$, —$SO_2CH_3$, —S(O)OH, —S(O)$OCH_3$, —S(O)$_2$H, S(O)$_2$$OCH_3$, —S(O)$NH_2$, —S(O)$NHCH_3$, —S(O)$_2$$NH_2$, S(O)$_2$$NHCH_3$, —$NHNH_2$, —$NHNHCH_3$, —$NHNCH_3CH_3$, —$ONH_2$, —$ONHCH_3$, —$NHC(O)NHNH_2$, or —$NHC(O)NHNHCH_3$), $R^{45a}$-substituted or unsubstituted alkyl (e.g., $C_1$-$C_8$, $C_1$-$C_5$, or $C_1$-$C_3$), $R^{45a}$-substituted or unsubstituted heteroalkyl (e.g., 2 to 8 membered, 2 to 5 membered, 2 to 3 membered), $R^{45a}$-substituted or unsubstituted cycloalkyl (e.g., $C_3$-$C_8$, $C_3$-$C_3$, or $C_3$), $R^{45a}$-substituted or unsubstituted heterocycloalkyl (e.g., 3 to 8 membered, 3 to 6 membered, or 4 membered), $R^{45a}$-substituted or unsubstituted aryl (e.g., $C_5$-$C_6$, $C_5$-$C_6$, or phenyl), or $R^{45a}$-substituted or unsubstituted heteroaryl (e.g., 5 to 8 membered, 5 to 6 membered, or 6 membered).

In embodiments, $R^{12}$, $R^{13}$, $R^{14}$, $R^{15}$, $R^{21}$, $R^{21A}$, $R^{22}$, and $R^{22A}$ are independently hydrogen, halogen (e.g. —F, —Cl, —Br, or —I), —$N_3$, —$CF_3$, —$CCl_3$, —$CBr_3$, —$CI_3$, —CN, —CHO, —$OR^{33M}$, —$NR^{34M}R^{35M}$, —$COOR^{33M}$, —$CONR^{34M}R^{35M}$, —$NO_2$, —$SR^{36M}$, —$SO_{n13}R^{34M}$, —$SO_{n13}OR^{34M}$, —$SO_{n13}NR^{34M}R^{35M}$, —$NHNR^{34M}R^{35M}$, —$ONR^{34M}R^{35M}$, —$NHC(O)NHNR^{34M}R^{35M}$ (e.g., —OH, —$OCH_3$, —NH2, —$NHCH_3$, $NCH_3NCH_3$, —COOH, —$COOCH_3$, —$CONH_2$, —$CONHCH_3$, —$NO_2$, —SH, —$SCH_3$, —SOH, —$SOCH_3$, —$SO_2H$, —$SO_2CH_3$, —S(O)OH, —S(O)$OCH_3$, —S(O)$_2$H, S(O)$_2$$OCH_3$, —S(O)$NH_2$, —S(O)$NHCH_3$, —S(O)$_2$$NH_2$, S(O)$_2$$NHCH_3$, —$NHNH_2$, —$NHNHCH_3$, —$NHNCH_3CH_3$, —$ONH_2$, —$ONHCH_3$, —$NHC(O)NHNH_2$, or —$NHC(O)NHNHCH_3$), unsubstituted alkyl (e.g., $C_1$-$C_8$, $C_1$-$C_5$, or $C_1$-$C_3$), unsubstituted heteroalkyl (e.g., 2 to 8 membered, 2 to 5 membered, 2 to 3 membered), unsubstituted cycloalkyl (e.g., $C_3$-$C_8$, $C_3$-$C_3$, or $C_3$), unsubstituted heterocycloalkyl (e.g., 3 to 8 membered, 3 to 6 membered, or 4 membered), unsubstituted aryl (e.g., $C_5$-$C_8$, $C_5$-$C_6$, or phenyl), or unsubstituted heteroaryl (e.g., 5 to 8 membered, 5 to 6 membered, or 6 membered).

In embodiments, $R^{12}$, $R^{13}$, $R^{14}$, $R^{15}$, $R^{21}$, $R^{21A}$, $R^{22}$, and $R^{22A}$ are independently hydrogen, halogen (e.g. —F, —Cl, —Br, or —I), —OH, —$OCH_3$, —NH2, —$NHCH_3$, $NCH_3NCH_3$, —COOH, —$COOCH_3$, —$CONH_2$, —$CONHCH_3$, —$NO_2$, —SH, —$SCH_3$, —SOH, —$SOCH_3$, —$SO_2H$, —$SO_2CH_3$, —S(O)OH, —S(O)$OCH_3$, —S(O)$_2$H, S(O)$_2$$OCH_3$, —S(O)$NH_2$, —S(O)$NHCH_3$, —S(O)$_2$$NH_2$, S(O)$_2$$NHCH_3$, —$NHNH_2$, —$NHNHCH_3$, —$NHNCH_3CH_3$, —$ONH_2$, —$ONHCH_3$, —$NHC(O)NHNH_2$, or —$NHC(O)NHNHCH_3$), $R^{45a}$-substituted or unsubstituted $C_1$-$C_3$ alkyl, $R^{45a}$-substituted or unsubstituted 2 to 3 membered heteroalkyl, $R^{45a}$-substituted or unsubstituted $C_3$-$C_5$ cycloalkyl, $R^{45a}$-substituted or unsubstituted 5 to 6 membered heterocycloalkyl, $R^{45a}$-substituted or unsubstituted phenyl, or $R^{45a}$-substituted or unsubstituted 5 to 6 membered heteroaryl. In embodiments, $R^{12}$, $R^{13}$, $R^{14}$, $R^{15}$, $R^{21}$, $R^{21A}$, $R^{22}$, and $R^{22A}$ are independently hydrogen, —F, —Cl, —Br, —I, —OH, —OH, —$OCH_3$, —NH2, —$NHCH_3$, $NCH_3NCH_3$, —COOH, —$COOCH_3$, —$CONH_2$, —$CONHCH_3$, —$NO_2$, —SH, —$SCH_3$, —SOH, —$SOCH_3$, —$SO_2H$, —$SO_2CH_3$, —S(O)OH, —S(O)$OCH_3$, —S(O)$_2$H, S(O)$_2$$OCH_3$, —S(O)$NH_2$, —S(O)$NHCH_3$, —S(O)$_2$$NH_2$, S(O)$_2$$NHCH_3$, —$NHNH_2$, —$NHNHCH_3$, —$NHNCH_3CH_3$, —$ONH_2$, —$ONHCH_3$, —$NHC(O)NHNH_2$, or —$NHC(O)NHNHCH_3$), unsubstituted $C_1$-$C_3$ alkyl, unsubstituted 2 to 3 membered heteroalkyl, unsubstituted $C_3$-$C_5$ cycloalkyl, unsubstituted 5 to 6 membered heterocycloalkyl, unsubstituted phenyl, or unsubstituted 5 to 6 membered heteroaryl.

In embodiments, $R^{33M}$, $R^{34M}$, $R^{35M}$, and $R^{36M}$ are independently hydrogen, substituted or unsubstituted alkyl (e.g., $C_1$-$C_8$, $C_1$-$C_5$, or $C_1$-$C_3$), substituted or unsubstituted heteroalkyl (e.g., 2 to 8 membered, 2 to 5 membered, 2 to 3 membered), substituted or unsubstituted cycloalkyl (e.g., $C_3$-$C_8$, $C_3$-$C_5$, or $C_3$), substituted or unsubstituted heterocycloalkyl (e.g., 3 to 8 membered, 3 to 6 membered, or 4 membered), substituted or unsubstituted aryl (e.g., $C_5$-$C_8$, $C_5$-$C_6$, or phenyl), or substituted or unsubstituted heteroaryl (e.g., 5 to 8 membered, 5 to 6 membered, or 6 membered).

In embodiments, $R^{33M}$, $R^{34M}$, $R^{35M}$, and $R^{36M}$ are independently hydrogen, $R^{44a}$-substituted or unsubstituted alkyl (e.g., $C_1$-$C_8$, $C_1$-$C_5$, or $C_1$-$C_3$), $R^{44a}$-substituted or unsubstituted heteroalkyl (e.g., 2 to 8 membered, 2 to 5 membered, 2 to 3 membered), $R^{44a}$-substituted or unsubstituted cycloalkyl (e.g., $C_3$-$C_8$, $C_3$-$C_5$, or $C_3$), $R^{44a}$-substituted or unsubstituted heterocycloalkyl (e.g., 3 to 8 membered, 3 to 6 membered, or 4 membered), $R^{44a}$-substituted or unsubstituted aryl (e.g., $C_5$-$C_8$, $C_5$-$C_6$, or phenyl), or $R^{44a}$-substituted or unsubstituted heteroaryl (e.g., 5 to 8 membered, 5 to 6 membered, or 6 membered). In embodiments, $R^{33M}$, $R^{34M}$, $R^{35M}$, and $R^{36M}$ are independently hydrogen, unsubstituted alkyl (e.g., $C_1$-$C_8$, $C_1$-$C_5$, or $C_1$-$C_3$), unsubstituted heteroalkyl (e.g., 2 to 8 membered, 2 to 5 membered, 2 to 3 membered), unsubstituted cycloalkyl (e.g., $C_3$-$C_8$, $C_3$-$C_5$, or $C_3$), unsubstituted heterocycloalkyl (e.g., 3 to 8 membered, 3 to 6 membered, or 4 membered), unsubstituted aryl (e.g., $C_5$-$C_8$, $C_5$-$C_6$, or phenyl), or unsubstituted heteroaryl (e.g., 5 to 8 membered, 5 to 6 membered, or 6 membered). In embodiments, $R^{44a}$ is as described herein, including embodiments thereof.

In embodiments, the compound of formula (IV) has the following formula:

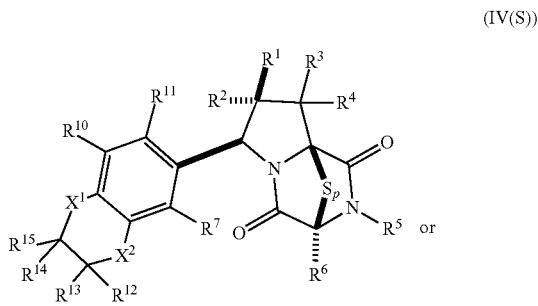

(IV(S))

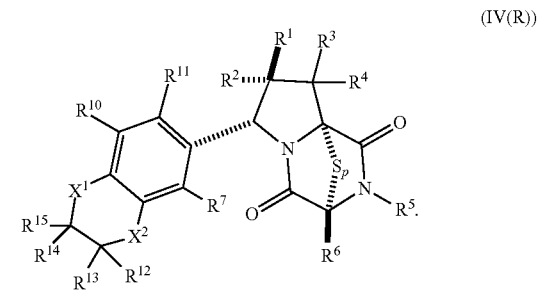

(IV(R))

In embodiments, the compound of formula (IV) has the following formula:

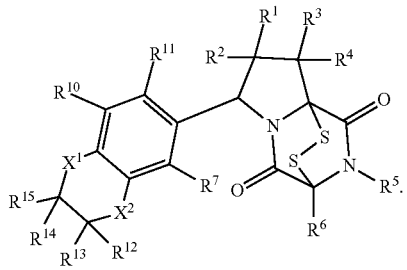
(IV1)

In embodiments, the compound of formula (IV1) has the following formula:

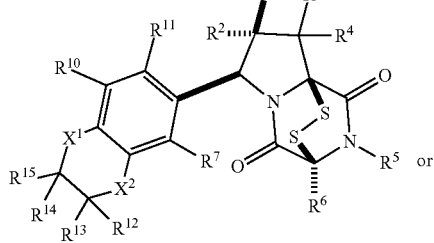
(IV1(S))

or

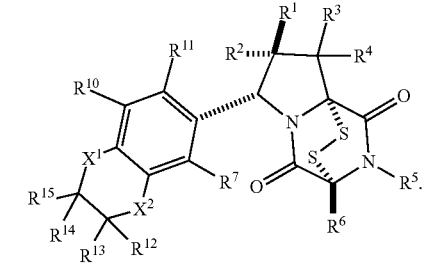
(IV1(R))

In embodiments, the compound of formula (IV1) has the following formula:

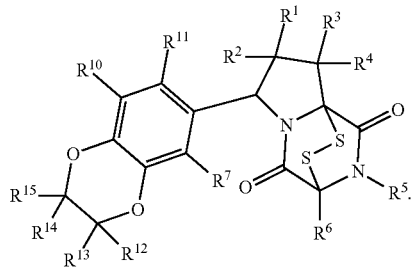
(IV2)

In embodiments, the compound of formula (IV2) has the following formula:

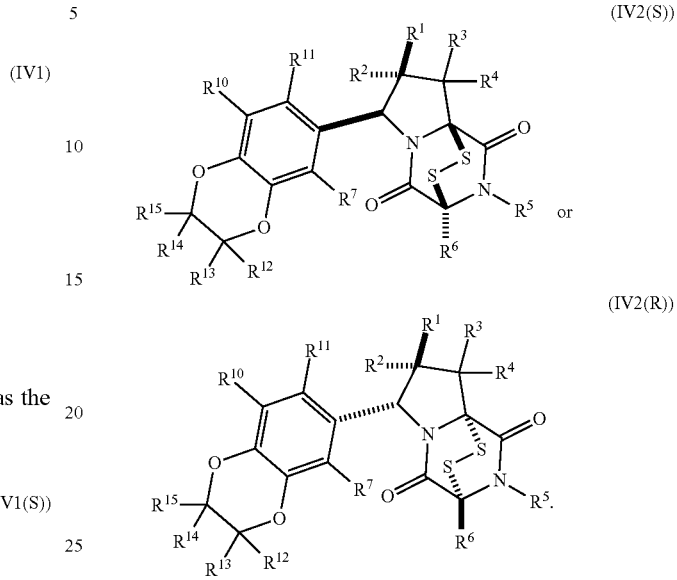
(IV2(S))

or (IV2(R))

In embodiments, the compound of formula (IV2) has the following formula:

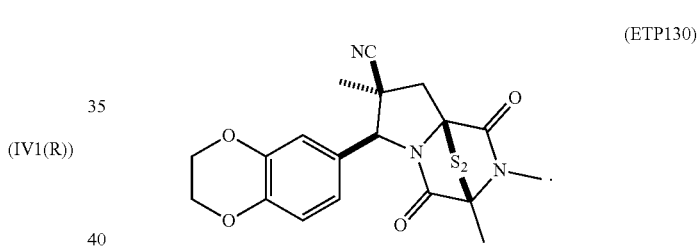
(ETP130)

In embodiments, the compound of formula (I) has the following formula:

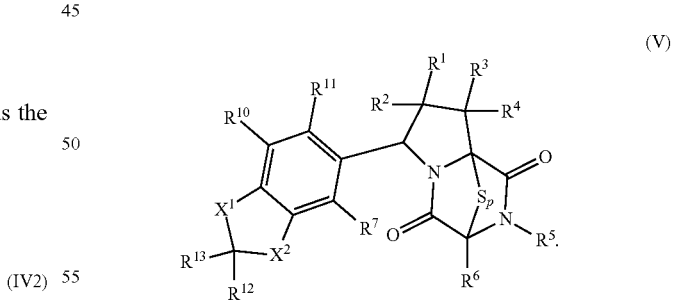
(V)

$X^1$, $X^2$, p, $R^1$, $R^2$, $R^3$, $R^4$, $R^5$, $R^6$, $R^7$, $R^{10}$, $R^{11}$ $R^{12}$, and $R^{13}$ are as described herein, including embodiments thereof.

In embodiments, $R^5$ and $R^6$ are independently unsubstituted $C_1$-$C_3$ alkyl or unsubstituted 3 to 5 membered cycloalkyl. In embodiments, $R^7$, $R^{10}$, and $R^{11}$ are independently hydrogen, halogen (e.g. —F, —Cl, —Br, or —I), unsubstituted methyl, —OCH$_3$ or —O(CH$_2$)$_2$=CH$_2$. In embodiments, $R^1$ is —CN or unsubstituted 2 to 5 membered heteroalkyl. In embodiments, $R^1$ is —CN. $R^1$ may be —COOCH$_3$. In embodiments, $R^1$ is unsubstituted methyl. In embodiments, $R^2$ is $C_1$-$C_3$ unsubstituted alkyl. In embodiments, when $R^1$ is —CN, $R^2$ is unsubstituted methyl. In embodiments, $R^3$ and $R^4$ are hydrogen. In embodiments, $R^{10}$ and $R^{11}$ are hydrogen. In embodiments, $R^{12}$ and $R^{13}$ are hydrogen.

In embodiments, the compound of formula (V) has the following formula:

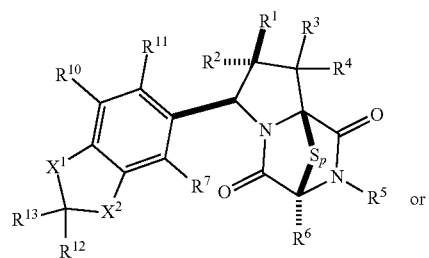
(V(S))

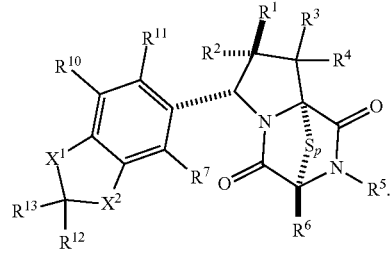
(V(R))

In embodiments, the compound of formula (V) has the following formula:

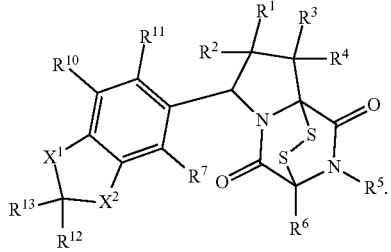
(VI)

In embodiments, the compound of formula (V1) has the following formula:

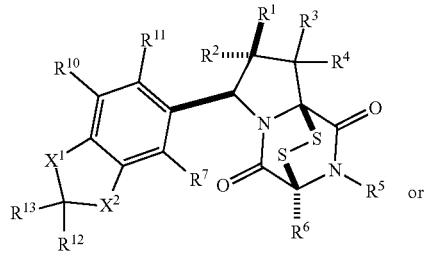
(V1(S))

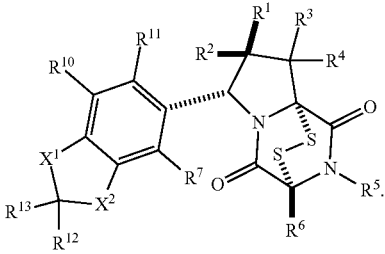
(V1(R))

In embodiments, the compound of formula (V1) has the following formula:

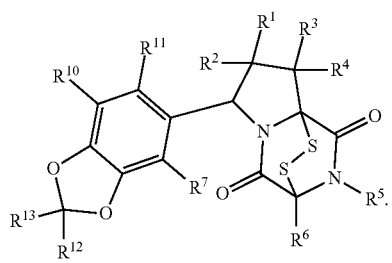
(V2)

In embodiments, the compound of formula (V2) has the following formula:

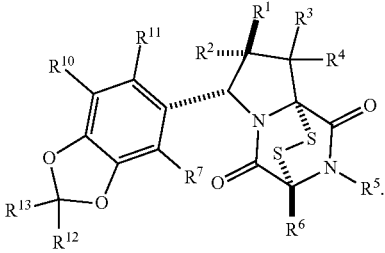
(V2(S))

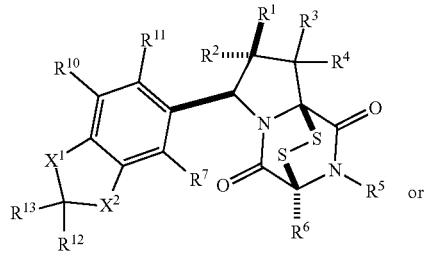
(V2(R))

In embodiments, the compound of formula (V) has the following formula:

(V3)
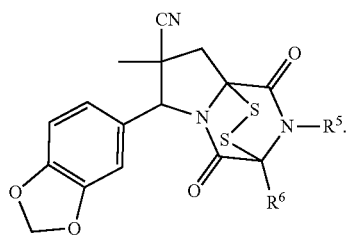
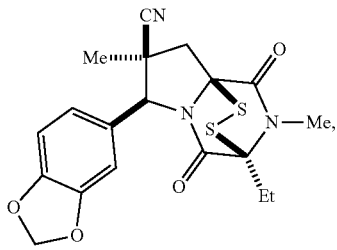
(ETP406)
In embodiments, the compound of formula (V3) has the following formula:
(ETP69)
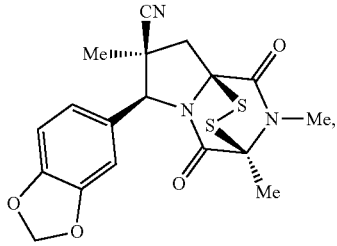
(ETP417)
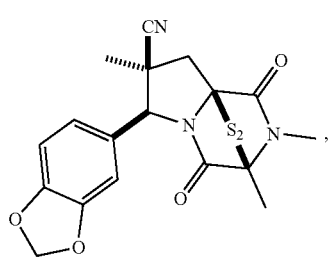
(ETP128)
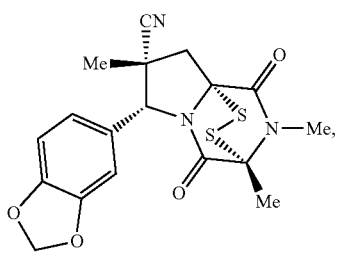
(ETP422)
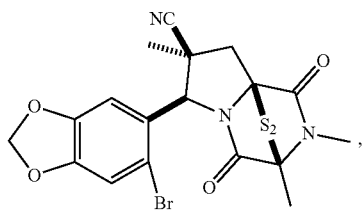
(ETP344)
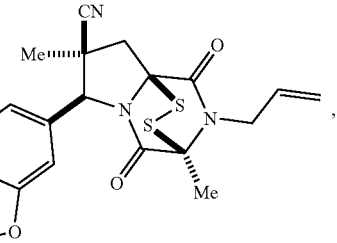
(ETP425) or
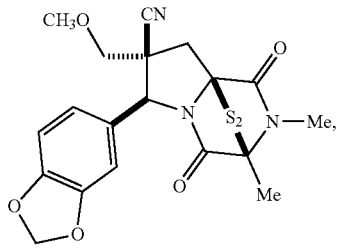
(ETP382)
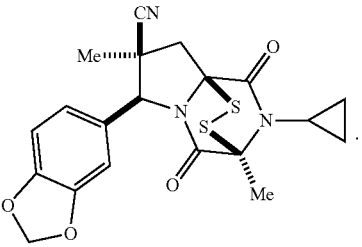
(ETP452)
In embodiments, the compound of formula (V) has the following formula:
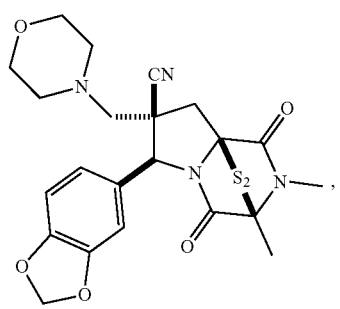
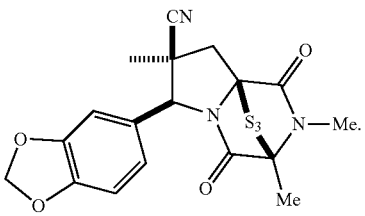
(ETP341)

In embodiments, the compound of formula (V1) has the following formula:

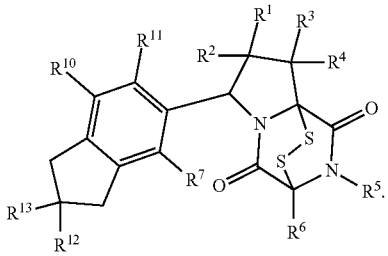
(V4)

In embodiments, the compound of formula (V4) has the following formula:

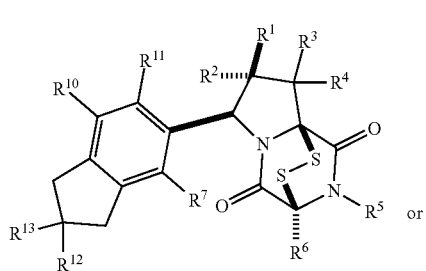
(V4(S))

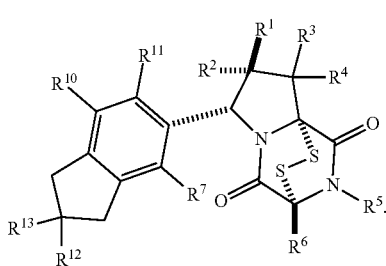
(V4(R))

In embodiments, the compound of formula (V4) has the following formula:

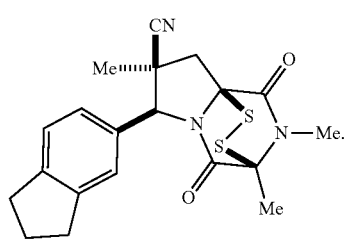
(ETP493)

In embodiments, the compound of formula (I) has the following formula:

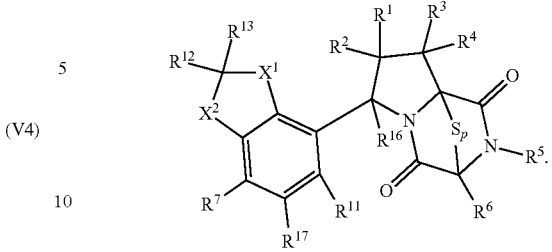
(VI)

$X^1$, $X^2$, p, $R^1$, $R^2$, $R^3$, $R^4$, $R^5$, $R^6$, $R^7$, $R^{11}$, $R^{12}$, $R^{13}$, and $R^{16}$ are as described herein, including embodiments thereof. In embodiments, $R^5$ and $R^6$ are independently unsubstituted $C_1$-$C_3$ alkyl or unsubstituted 3 to 5 membered cycloalkyl. In embodiments, $R^7$ and $R^{11}$ are independently hydrogen, halogen (e.g. —F, —Cl, —Br, or —I), unsubstituted methyl, —OCH$_3$ or —O(CH$_2$)$_2$=CH$_2$. In embodiments, $R^1$ is —CN or unsubstituted 2 to 5 membered heteroalkyl. In embodiments, $R^1$ is —CN. In embodiments, $R^1$ is —COOCH$_3$. In embodiments, $R^1$ is unsubstituted methyl. In embodiments, $R^2$ is $C_1$-$C_3$ unsubstituted alkyl. In embodiments, when $R^1$ is —CN, $R^2$ is unsubstituted methyl. In embodiments, $R^3$ and $R^4$ are hydrogen. In embodiments, $R^7$ and $R^{11}$ are hydrogen. In embodiments, $R^{12}$ and $R^{13}$ are hydrogen. In embodiments, $R^7$ and $R^{17}$ are hydrogen.

In embodiments, $R^{17}$ is hydrogen, halogen (e.g. —F, —Cl, —Br, or —I), —N$_3$, —CF$_3$, —CCl$_3$, —CBr$_3$, —CI$_3$, —CN, —CHO, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC(O)NHNH$_2$. In embodiments, $R^{17}$ is substituted or unsubstituted alkyl (e.g., $C_1$-$C_8$, $C_1$-$C_5$, or $C_1$-$C_3$). In embodiments, $R^{17}$ is substituted or unsubstituted $C_1$-$C_5$ alkyl. In embodiments, $R^{17}$ is substituted or unsubstituted $C_1$-$C_5$ alkyl. In embodiments, $R^{17}$ is substituted or unsubstituted $C_1$-$C_3$ alkyl. In embodiments, $R^1$ is $R^{17a}$-substituted or unsubstituted alkyl (e.g., $C_1$-$C_8$, $C_1$-$C_5$, or $C_1$-$C_3$). In embodiments, $R^{17}$ is $R^{17a}$-substituted or unsubstituted $C_1$-$C_8$ alkyl. In embodiments, $R^1$ is $R^{17a}$-substituted or unsubstituted $C_1$-$C_5$ alkyl. In embodiments, $R^{17}$ is $R^{17a}$-substituted or unsubstituted $C_1$-$C_3$ alkyl. In embodiments, $R^{17a}$ is as described herein, including embodiments thereof. In embodiments, $R^{17}$ is unsubstituted alkyl (e.g., $C_1$-$C_8$, $C_1$-$C_5$, or $C_1$-$C_3$). In embodiments, $R^{17}$ is unsubstituted $C_1$-$C_8$ alkyl. In embodiments, $R^{17}$ is unsubstituted $C_1$-$C_5$ alkyl. In embodiments, $R^{17}$ is unsubstituted $C_1$-$C_3$ alkyl.

In embodiments, $R^{17}$ is substituted or unsubstituted heteroalkyl (e.g., 2 to 8 membered, 2 to 5 membered, 2 to 3 membered). In embodiments, $R^{17}$ is substituted or unsubstituted 2 to 8 membered heteroalkyl. In embodiments, $R^{17}$ is substituted or unsubstituted 2 to 5 membered heteroalkyl. In embodiments, $R^{17}$ is substituted or unsubstituted 2 to 3 membered heteroalkyl. In embodiments, $R^{17}$ is $R^{17a}$-substituted or unsubstituted heteroalkyl (e.g., 2 to 8 membered, 2 to 5 membered, 2 to 3 membered). In embodiments, $R^{17}$ is $R^{17a}$-substituted or unsubstituted 2 to 8 membered heteroalkyl. In embodiments, $R^{17}$ is $R^{17a}$-substituted or unsubstituted 2 to 5 membered heteroalkyl. In embodiments, $R^{17}$ is $R^{17a}$-substituted or unsubstituted 2 to 3 membered heteroalkyl. In embodiments, $R^{17}$ is unsubstituted heteroalkyl (e.g., 2 to 8 membered, 2 to 5 membered, 2 to 3 membered). In embodiments, $R^{17}$ is unsubstituted 2 to 8 membered heteroalkyl. In embodiments, $R^{17}$ is unsubstituted 2 to 5 membered heteroalkyl. In embodiments, $R^{17}$ is unsubstituted 2 to 3 membered heteroalkyl. In embodiments, $R^{17a}$ is as described herein, including embodiments thereof.

In embodiments, $R^{17}$ is substituted or unsubstituted cycloalkyl (e.g., $C_3$-$C_8$, $C_3$-$C_5$, or $C_3$). In embodiments, $R^{17}$ is substituted or unsubstituted 3 to 8 membered cycloalkyl. In embodiments, $R^{17}$ is substituted or unsubstituted 3 to 5 membered cycloalkyl. In embodiments, $R^{17}$ is substituted or unsubstituted 3 membered cycloalkyl. In embodiments, $R^{17}$ is substituted or unsubstituted 4 membered cycloalkyl. In embodiments, $R^{17}$ is substituted or unsubstituted 5 membered cycloalkyl. In embodiments, $R^{17}$ is $R^{17a}$-substituted or unsubstituted cycloalkyl (e.g., $C_3$-$C_8$, $C_3$-$C_5$, or $C_3$). In embodiments, $R^{17}$ is $R^{17a}$-substituted or unsubstituted 3 to 8 membered cycloalkyl. In embodiments, $R^{17}$ is $R^{17a}$-substituted or unsubstituted 3 to 5 membered cycloalkyl. In embodiments, $R^{17}$ is $R^{17a}$-substituted or unsubstituted 3 membered cycloalkyl. In embodiments, $R^{17}$ is $R^{17a}$-substituted or unsubstituted 4 membered cycloalkyl. In embodiments, $R^{17}$ is $R^{17a}$-substituted or unsubstituted 5 membered cycloalkyl. In embodiments, $R^{17}$ is unsubstituted cycloalkyl (e.g., $C_3$-$C_8$, $C_3$-$C_5$, or $C_3$). In embodiments, $R^{17}$ is unsubstituted 3 to 8 membered cycloalkyl. In embodiments, $R^{17}$ is unsubstituted 3 to 5 membered cycloalkyl. In embodiments, $R^{17}$ is unsubstituted 3 membered cycloalkyl. In embodiments, $R^{17}$ is unsubstituted 4 membered cycloalkyl. In embodiments, $R^{17}$ is unsubstituted 5 membered cycloalkyl.

In embodiments, $R^{17}$ is substituted or unsubstituted heterocycloalkyl (e.g., 3 to 8 membered, 3 to 6 membered, or 4 membered). In embodiments, $R^{17}$ is substituted or unsubstituted 3 to 6 membered heterocycloalkyl. In embodiments, $R^{17}$ is substituted or unsubstituted 4 membered heterocycloalkyl. In embodiments, $R^{17}$ is substituted or unsubstituted 5 membered heterocycloalkyl. In embodiments, $R^{17}$ is substituted or unsubstituted 6 membered heterocycloalkyl. In embodiments, $R^{17}$ is $R^{17a}$-substituted or unsubstituted heterocycloalkyl (e.g., 3 to 8 membered, 3 to 6 membered, or 4 membered). In embodiments, $R^{17}$ is $R^{17a}$-substituted or unsubstituted 3 to 6 membered heterocycloalkyl. In embodiments, $R^{17}$ is $R^{17a}$-substituted or unsubstituted 4 membered heterocycloalkyl. In embodiments, $R^{17}$ is $R^{17a}$-substituted or unsubstituted 5 membered heterocycloalkyl. In embodiments, $R^{17}$ is $R^{17a}$-substituted or unsubstituted 6 membered heterocycloalkyl. In embodiments, $R^{17}$ is unsubstituted heterocycloalkyl (e.g., 3 to 8 membered, 3 to 6 membered, or 4 membered). In embodiments, $R^{17}$ is unsubstituted 3 to 6 membered heterocycloalkyl. In embodiments, $R^{17}$ is unsubstituted 4 membered heterocycloalkyl. In embodiments, $R^{17}$ is unsubstituted 5 membered heterocycloalkyl. In embodiments, $R^{17}$ is unsubstituted 6 membered heterocycloalkyl.

In embodiments, $R^{17}$ is substituted or unsubstituted aryl (e.g., $C_5$-$C_8$, $C_5$-$C_6$, or phenyl). In embodiments, $R^{17}$ is substituted or unsubstituted 5 to 6 membered aryl. In embodiments, $R^{17}$ is substituted or unsubstituted 5 membered aryl. In embodiments, $R^{17}$ is substituted or unsubstituted 6 membered aryl or phenyl. In embodiments, $R^{17}$ is $R^{17a}$-substituted or unsubstituted aryl (e.g., $C_5$-$C_8$, $C_5$-$C_6$, or phenyl). In embodiments, $R^{17}$ is $R^{17a}$-substituted or unsubstituted 5 to 6 membered aryl. In embodiments, $R^{17}$ is $R^{17a}$-substituted or unsubstituted 5 membered aryl. In embodiments, $R^{17}$ is $R^{17a}$-substituted or unsubstituted 6 membered aryl or phenyl. In embodiments, $R^{17}$ is unsubstituted aryl (e.g., $C_5$-$C_8$, $C_5$-$C_6$, or phenyl). In embodiments, $R^{17}$ is unsubstituted 5 to 6 membered aryl. In embodiments, $R^{17}$ is unsubstituted 5 membered aryl. In embodiments, $R^{17}$ is unsubstituted 6 membered aryl or phenyl.

In embodiments, $R^{17}$ is substituted or unsubstituted heteroaryl (e.g., 5 to 8 membered, 5 to 6 membered, or 6 membered). In embodiments, $R^{17}$ is substituted or unsubstituted 5 to 6 membered heteroaryl. In embodiments, $R^{17}$ is substituted or unsubstituted 5 membered heteroaryl. In embodiments, $R^{17}$ is substituted or unsubstituted 6 membered heteroaryl. In embodiments, $R^{17}$ is $R^{17a}$-substituted or unsubstituted heteroaryl (e.g., 5 to 8 membered, 5 to 6 membered, or 6 membered). In embodiments, $R^{17}$ is $R^{17a}$-substituted or unsubstituted 5 to 6 membered heteroaryl. In embodiments, $R^{17}$ is $R^{17a}$-substituted or unsubstituted 5 membered heteroaryl. In embodiments, $R^{17}$ is $R^{17a}$-substituted or unsubstituted 6 membered heteroaryl. In embodiments, $R^{17}$ is unsubstituted heteroaryl (e.g., 5 to 8 membered, 5 to 6 membered, or 6 membered). In embodiments, $R^{17}$ is unsubstituted 5 to 6 membered heteroaryl. In embodiments, $R^{17}$ is unsubstituted 5 membered heteroaryl. In embodiments, $R^{17}$ is unsubstituted 6 membered heteroaryl.

In embodiments, $R^{17}$ is hydrogen, halogen (e.g. —F, —Cl, —Br, or —I), —$N_3$, —$CF_3$, —$CCl_3$, —$CBr_3$, —$CI_3$, —CN, —CHO, —$OR^{33P}$, —$NR^{34P}R^{35P}$, —$COOR^{33P}$, —$CONR^{34P}R^{35P}$, —$NO_2$, —$SR^{36P}$, —$SO_{n14}R^{34P}$, —$SO_{n14}OR^{34P}$, —$SO_{n14}NR^{34P}R^{35P}$, —$NHNR^{34P}R^{35P}$, —$ONR^{34P}R^{35P}$, —$NHC(O)NHNR^{34P}R^{35P}$ (e.g., —OH, —$OCH_3$, —NH2, —$NHCH_3$, $NCH_3NCH_3$, —COOH, —$COOCH_3$, —$CONH_2$, —$CONHCH_3$, —$NO_2$, —SH, —$SCH_3$, —SOH, —$SOCH_3$, —$SO_2H$, —$SO_2CH_3$, —S(O)OH, —S(O)$OCH_3$, —S(O)$_2$H, S(O)$_2OCH_3$, —S(O)$NH_2$, —S(O)$NHCH_3$, —S(O)$_2NH_2$, S(O)$_2NHCH_3$, —$NHNH_2$, —$NHNHCH_3$, —$NHNCH_3CH_3$, —$ONH_2$, —$ONHCH_3$, —$NHC(O)NHNH_2$, or —$NHC(O)NHNHCH_3$), substituted or unsubstituted alkyl (e.g., $C_1$-$C_8$, $C_1$-$C_5$, or $C_1$-$C_3$), substituted or unsubstituted heteroalkyl (e.g., 2 to 8 membered, 2 to 5 membered, 2 to 3 membered), substituted or unsubstituted cycloalkyl (e.g., $C_3$-$C_8$, $C_3$-$C_5$, or $C_3$), substituted or unsubstituted heterocycloalkyl (e.g., 3 to 8 membered, 3 to 6 membered, or 4 membered), substituted or unsubstituted aryl (e.g., $C_5$-$C_8$, $C_5$-$C_6$, or phenyl), or substituted or unsubstituted heteroaryl (e.g., 5 to 8 membered, 5 to 6 membered, or 6 membered).

In embodiments, $R^{17}$ is hydrogen, halogen (e.g. —F, —Cl, —Br, or —I), —$N_3$, —$CF_3$, —$CCl_3$, —$CBr_3$, —$CI_3$, —CN, —CHO, —$OR^{33P}$, —$NR^{34P}R^{35P}$, —$COOR^{33P}$, —$CONR^{34P}R^{35P}$, —$NO_2$, —$SR^{36P}$, —$SO_{n14}R^{34P}$, —$SO_{n14}OR^{34P}$, —$SO_{n14}NR^{34P}R^{35P}$, —$NHNR^{34P}R^{35P}$, —$ONR^{34P}R^{35P}$, —$NHC(O)NHNR^{34P}R^{35P}$ (e.g., —OH, —$OCH_3$, —NH2, —$NHCH_3$, $NCH_3NCH_3$, —COOH, —$COOCH_3$, —$CONH_2$, —$CONHCH_3$, —$NO_2$, —SH, —$SCH_3$, —SOH, —$SOCH_3$, —$SO_2H$, —$SO_2CH_3$, —S(O)OH, —S(O)$OCH_3$, —S(O)$_2$H, S(O)$_2OCH_3$, —S(O)$NH_2$, —S(O)$NHCH_3$, —S(O)$_2NH_2$, S(O)$_2NHCH_3$, —$NHNH_2$, —$NHNHCH_3$, —$NHNCH_3CH_3$, —$ONH_2$, —$ONHCH_3$, —$NHC(O)NHNH_2$, or —$NHC(O)NHNHCH_3$), $R^{17a}$-substituted or unsubstituted alkyl (e.g., $C_1$-$C_8$, $C_1$-$C_5$, or $C_1$-$C_3$), $R^{17a}$-substituted or unsubstituted heteroalkyl (e.g., 2 to 8 membered, 2 to 5 membered, 2 to 3 membered), $R^{17a}$-substituted or unsubstituted cycloalkyl (e.g., $C_3$-$C_8$, $C_3$-$C_3$, or $C_3$), $R^{17a}$-substituted or unsubstituted heterocycloalkyl (e.g., 3 to 8 membered, 3 to 6 membered, or 4 membered), $R^{17a}$-substituted or unsubstituted aryl (e.g., $C_5$-$C_8$, $C_5$-$C_6$, or phenyl), or $R^{17a}$-substituted or unsubstituted heteroaryl (e.g., 5 to 8 membered, 5 to 6 membered, or 6 membered).

In embodiments, $R^{17}$ is hydrogen, halogen (e.g. —F, —Cl, —Br, or —I), —$N_3$, —$CF_3$, —$CCl_3$, —$CBr_3$, —$CI_3$, —CN, —CHO, —$OR^{33P}$, —$NR^{34P}R^{35P}$, —$COOR^{33P}$, —$CONR^{34P}R^{35P}$, —$NO_2$, —$SR^{36P}$, —$SO_{n14}R^{34P}$, —$SO_{n14}OR^{34P}$, —$SO_{n14}NR^{34P}R^{35P}$, —$NHNR^{34P}R^{35P}$, —$ONR^{34P}R^{35P}$, —$NHC(O)NHNR^{34P}R^{35P}$ (e.g., —OH, —$OCH_3$, —NH2, —$NHCH_3$, $NCH_3NCH_3$, —COOH, —COOCH$_3$, —CONH$_2$, —CONHCH$_3$, —NO$_2$, —SH, —SCH$_3$, —SOH, —SOCH$_3$, —SO$_2$H, —SO$_2$CH$_3$, —S(O)OH, —S(O)OCH$_3$, —S(O)$_2$H, S(O)$_2$OCH$_3$, —S(O)NH$_2$, —S(O)NHCH$_3$, —S(O)$_2$NH$_2$, S(O)$_2$NHCH$_3$, —NHNH$_2$, —NHNHCH$_3$, —NHNCH$_3$CH$_3$, —ONH$_2$, —ONHCH$_3$, —NHC(O)NHNH$_2$, or —NHC(O)NHNHCH$_3$), unsubstituted alkyl (e.g., C$_1$-C$_8$, C$_1$-C$_5$, or C$_1$-C$_3$), unsubstituted heteroalkyl (e.g., 2 to 8 membered, 2 to 5 membered, 2 to 3 membered), unsubstituted cycloalkyl (e.g., C$_3$-C$_8$, C$_3$-C$_5$, or C$_3$), unsubstituted heterocycloalkyl (e.g., 3 to 8 membered, 3 to 6 membered, or 4 membered), unsubstituted aryl (e.g., C$_5$-C$_8$, C$_5$-C$_6$, or phenyl), or unsubstituted heteroaryl (e.g., 5 to 8 membered, 5 to 6 membered, or 6 membered).

In embodiments, R$^{17}$ is hydrogen, halogen (e.g. —F, —Cl, —Br, or —I), —OH, —OCH$_3$, —NH2, —NHCH$_3$, NCH$_3$NCH$_3$, —COOH, —COOCH$_3$, —CONH$_2$, —CONHCH$_3$, —NO$_2$, —SH, —SCH$_3$, —SOH, —SOCH$_3$, —SO$_2$H, —SO$_2$CH$_3$, —S(O)OH, —S(O)OCH$_3$, —S(O)$_2$H, S(O)$_2$OCH$_3$, —S(O)NH$_2$, —S(O)NHCH$_3$, —S(O)$_2$NH$_2$, S(O)$_2$NHCH$_3$, —NHNH$_2$, —NHNHCH$_3$, —NHNCH$_3$CH$_3$, —ONH$_2$, —ONHCH$_3$, —NHC(O)NHNH$_2$, or —NHC(O)NHNHCH$_3$), R$^{17a}$-substituted or unsubstituted C$_1$-C$_3$ alkyl, R$^{17a}$-substituted or unsubstituted 2 to 3 membered heteroalkyl, R$^{17a}$-substituted or unsubstituted C$_3$-C$_5$ cycloalkyl, R$^{17a}$-substituted or unsubstituted 5 to 6 membered heterocycloalkyl, R$^{17a}$-substituted or unsubstituted phenyl, or R$^{17a}$-substituted or unsubstituted 5 to 6 membered heteroaryl. In embodiments, R$^{17}$ is hydrogen, —F, —Cl, —Br, —I, —OH, —OH, —OCH$_3$, —NH2, —NHCH$_3$, NCH$_3$NCH$_3$, —COOH, —COOCH$_3$, —CONH$_2$, —CONHCH$_3$, —NO$_2$, —SH, —SCH$_3$, —SOH, —SOCH$_3$, —SO$_2$H, —SO$_2$CH$_3$, —S(O)OH, —S(O)OCH$_3$, —S(O)$_2$H, S(O)$_2$OCH$_3$, —S(O)NH$_2$, —S(O)NHCH$_3$, —S(O)$_2$NH$_2$, S(O)$_2$NHCH$_3$, —NHNH$_2$, —NHNHCH$_3$, —NHNCH$_3$CH$_3$, —ONH$_2$, —ONHCH$_3$, —NHC(O)NHNH$_2$, or —NHC(O)NHNHCH$_3$), unsubstituted C$_1$-C$_3$ alkyl, unsubstituted 2 to 3 membered heteroalkyl, unsubstituted C$_3$-C$_5$ cycloalkyl, unsubstituted 5 to 6 membered heterocycloalkyl, unsubstituted phenyl, or unsubstituted 5 to 6 membered heteroaryl.

R$^{17a}$ is halogen (e.g. —F, —Cl, —Br, or —I), —N$_3$, —CF$_3$, —CCl$_3$, —CBr$_3$, —CI$_3$, —CN, —CHO, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC(O)NHNH$_2$, substituted or unsubstituted alkyl (e.g., C$_1$-C$_8$, C$_1$-C$_6$, C$_1$-C$_4$, or C$_1$-C$_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., C$_3$-C$_8$, C$_3$-C$_6$, C$_4$-C$_6$, or C$_5$-C$_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., C$_6$-C$_{12}$, C$_6$-C$_{10}$, or phenyl), or substituted or unsubstituted heteroaryl (e.g., 5 to 12 membered, 5 to 10 membered, 5 to 9 membered, or 5 to 6 membered). In embodiments, R$^{17a}$ is halogen (e.g. —F, —Cl, —Br, or —I), —N$_3$, —CF$_3$, —CCl$_3$, —CBr$_3$, —CI$_3$, —CN, —CHO, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC(O)NHNH$_2$, R$^{17n}$-substituted or unsubstituted alkyl (e.g., C$_1$-C$_8$, C$_1$-C$_6$, C$_1$-C$_4$, or C$_1$-C$_2$), R$^{17b}$-substituted or unsubstituted heteroalkyl (e.g., 2 to 8 membered, 2 to 6 membered, 4 to 6 membered, 2 to 3 membered, or 4 to 5 membered), R$^{17b}$-substituted or unsubstituted cycloalkyl (e.g., C$_3$-C$_8$, C$_3$-C$_6$, C$_4$-C$_6$, or C$_5$-C$_6$), R$^{17b}$-substituted or unsubstituted heterocycloalkyl (e.g., 3 to 8 membered, 3 to 6 membered, 4 to 6 membered, 4 to 5 membered, or 5 to 6 membered), R$^{17b}$-substituted or unsubstituted aryl (e.g., C$_6$-C$_{12}$, C$_6$-C$_{10}$, or phenyl), or R$^{17b}$-substituted or unsubstituted heteroaryl (e.g., 5 to 12 membered, 5 to 10 membered, 5 to 9 membered, or 5 to 6 membered). In embodiments, R$^{17a}$ is halogen (e.g. —F, —Cl, —Br, or —I), —N$_3$, —CF$_3$, —CCl$_3$, —CBr$_3$, —CI$_3$, —CN, —CHO, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC(O)NHNH$_2$, unsubstituted alkyl (e.g., C$_1$-C$_8$, C$_1$-C$_6$, C$_1$-C$_4$, or C$_1$-C$_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., C$_3$-C$_8$, C$_3$-C$_6$, C$_4$-C$_6$, or C$_5$-C$_6$), unsubstituted heterocycloalkyl (e.g., 3 to 8 membered, 3 to 6 membered, 4 to 6 membered, 4 to 5 membered, or 5 to 6 membered), unsubstituted aryl (e.g., C$_6$-C$_{12}$, C$_6$-C$_{10}$, or phenyl), or unsubstituted heteroaryl (e.g., 5 to 12 membered, 5 to 10 membered, 5 to 9 membered, or 5 to 6 membered).

In embodiments, R$^{17b}$ is halogen (e.g. —F, —Cl, —Br, or —I), —N$_3$, —CF$_3$, —CCl$_3$, —CBr$_3$, —CI$_3$, —CN, —CHO, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC(O)NHNH$_2$, unsubstituted alkyl (e.g., C$_1$-C$_8$, C$_1$-C$_6$, C$_1$-C$_4$, or C$_1$-C$_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., C$_3$-C$_8$, C$_3$-C$_6$, C$_4$-C$_6$, or C$_5$-C$_6$), unsubstituted heterocycloalkyl (e.g., 3 to 8 membered, 3 to 6 membered, 4 to 6 membered, 4 to 5 membered, or 5 to 6 membered), unsubstituted aryl (e.g., C$_6$-C$_{12}$, C$_6$-C$_{10}$, or phenyl), or unsubstituted heteroaryl (e.g., 5 to 12 membered, 5 to 10 membered, 5 to 9 membered, or 5 to 6 membered).

In embodiments, R$^{33P}$, R$^{34P}$, R$^{35P}$, and R$^{36P}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, R$^{33P}$, R$^{34P}$, R$^{35P}$, and R$^{36P}$ are independently hydrogen, R$^{44a}$-substituted or unsubstituted alkyl, R$^{44a}$-substituted or unsubstituted heteroalkyl, R$^{44a}$-substituted or unsubstituted cycloalkyl, R$^{44a}$-substituted or unsubstituted heterocycloalkyl, R$^{44a}$-substituted or unsubstituted aryl, or R$^{44a}$-substituted or unsubstituted heteroaryl. In embodiments, R$^{33I}$, R$^{34I}$, R$^{35I}$, R$^{36I}$, R$^{33L}$, R$^{34L}$, R$^{35L}$, R$^{36L}$, R$^{33M}$, R$^{34M}$, R$^{35M}$, R$^{36M}$, R$^{33P}$, R$^{34P}$, R$^{35P}$, and R$^{36P}$, are independently hydrogen, unsubstituted alkyl, unsubstituted heteroalkyl, unsubstituted cycloalkyl, unsubstituted heterocycloalkyl, unsubstituted aryl, or unsubstituted heteroaryl. In embodiments, R$^{44a}$ is as described herein, including embodiments thereof. In embodiments, the symbol n14 is independently 1 or 2. In embodiments, n14 is 1. In embodiments, n14 is 2.

In embodiments, the compound of formula (VI) has the following formula:

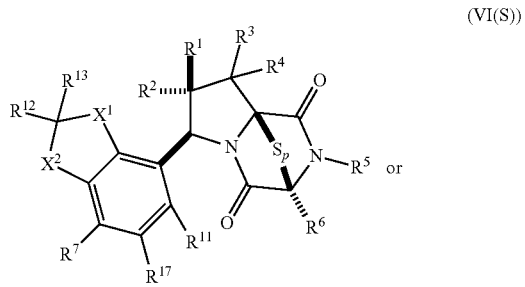

(VI(S))

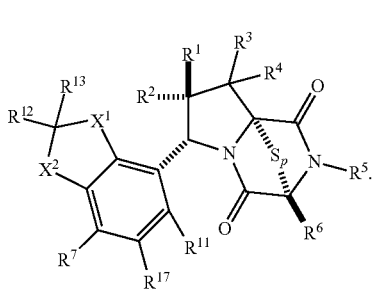
(VI(R))

In embodiments, the compound formula (VI) has the following formula:

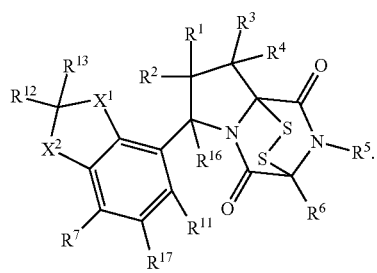
(VI1)

In embodiments, the compound of formula (VI1) has the following formula:

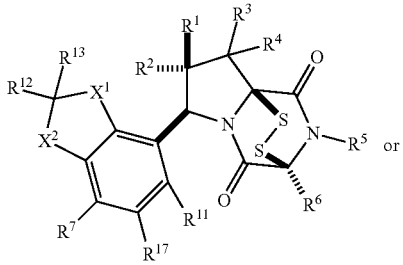
(VI1(S))

or

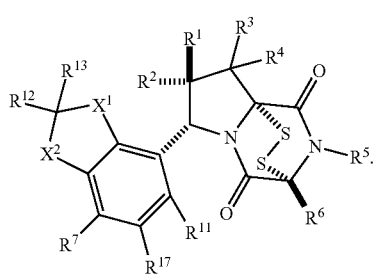
(VI1(R))

In embodiments, the compound of formula (VI) has the following formula:

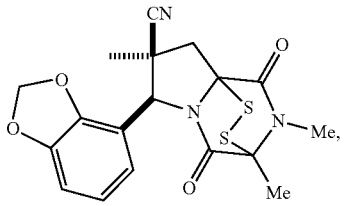
(ETP365)

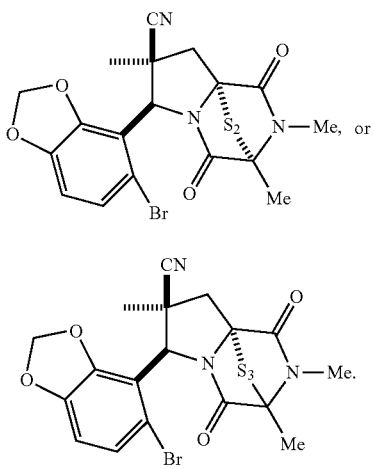
(ETP328)

(ETP331)

In certain embodiments the compound is a compound as set forth in Table 1 following.

TABLE 1

Exemplary embodiments of compounds provided herein.

| Structure | Reference |
| --- | --- |
| (pyrrolidine-diketopiperazine structure) | ETP6 |
| (4-fluorophenyl CO₂Me diketopiperazine structure) | ETP8 |
| (2-bromo-5-methoxyphenyl CO₂Me diketopiperazine structure) | ETP12 |

TABLE 1-continued

Exemplary embodiments of compounds provided herein.

| Structure | Reference |
|---|---|
| | ETP14 |
| | ETP27 |
| | ETP49 |
| | ETP56 |
| | ETP69 |
| | ETP95 |
| 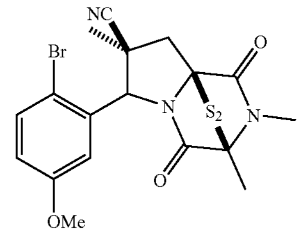 | ETP100 |
| 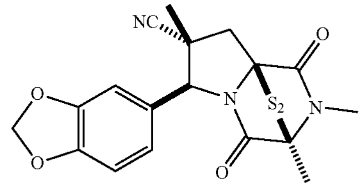 | ETP120 |
| 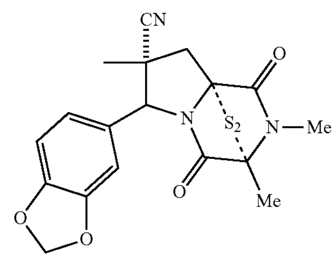 | ETP125 |
| 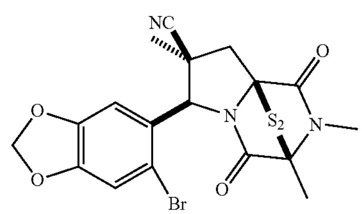 | ETP128 |
| 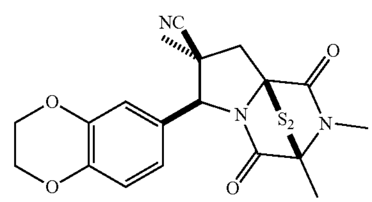 | ETP130 |
| 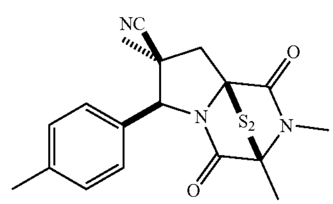 | ETP154 |
| 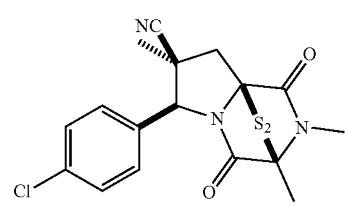 | ETP167 |

TABLE 1-continued

Exemplary embodiments of compounds provided herein.

| Structure | Reference |
|---|---|
| (structure) | ETP178 |
| (structure) | ETP195 |
| (structure) | ETP204 |
| (structure) | ETP206 |
| (structure) | ETP214 |
| (structure) | ETP218 |
| (structure) | ETP223 |
| (structure) | ETP229 |
| (structure) | ETP303 |
| (structure) 3:1 mix epimers | ETP309 |
| (structure) 3:1 mix epimers | ETP313 |
| (structure) | ETP328 |
| (structure) | ETP331 |

TABLE 1-continued

Exemplary embodiments of compounds provided herein.

| Structure | Reference |
|---|---|
| 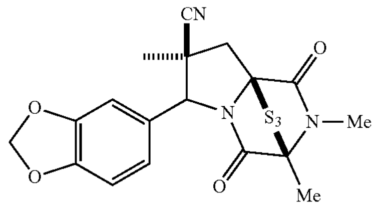 | ETP341 |
| 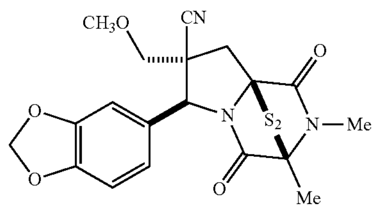 | ETP344 |
| 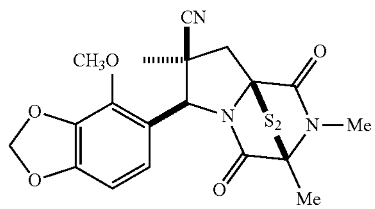 | ETP356 |
| 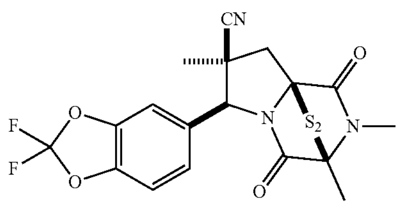 | ETP359 |
| 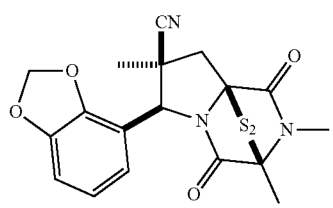 | ETP365 |
| 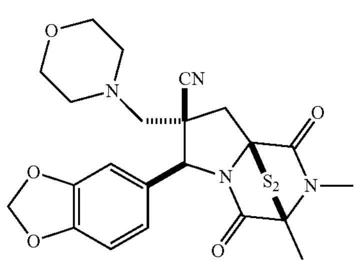 | ETP382 |
| 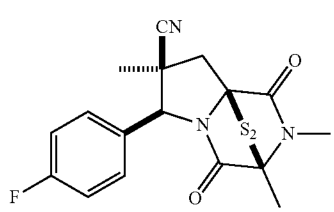 | ETP384 |
| 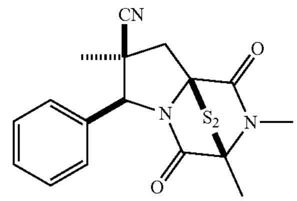 | ETP390 |
| 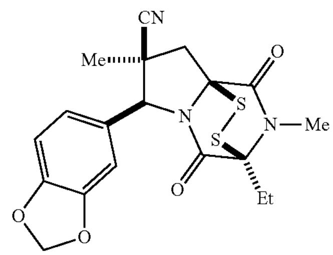 | ETP406 |
| 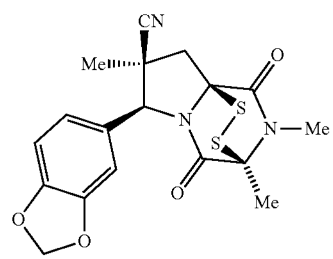 [SMILES: CN1C(=O)[C@@]23C[C@](C)(C#N)[C@H](c4ccc5c(c4)OCO5)N2C(=O)[C@]1(C)SS3] | ETP417 |
| 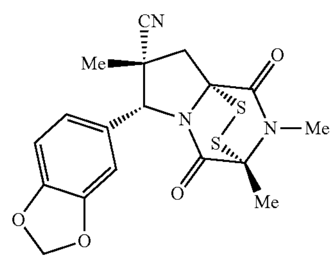 [SMILES: CN1C(=O)[C@]23C[C@@](C)(C#N)[C@@H](c4ccc5c(c4)OCO5)N2C(=O)[C@@]1(C)SS3] | ETP422 |
| 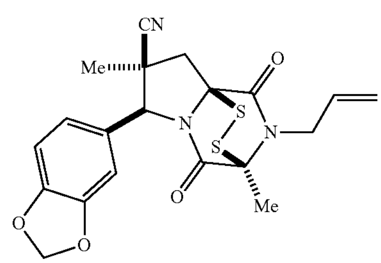 | ETP425 |
| 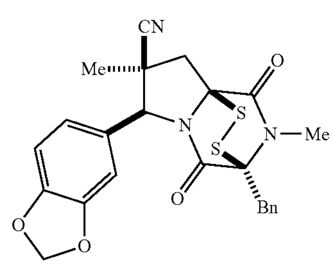 | ETP442 |

TABLE 1-continued

Exemplary embodiments of compounds provided herein.

| Structure | Reference |
|---|---|
| 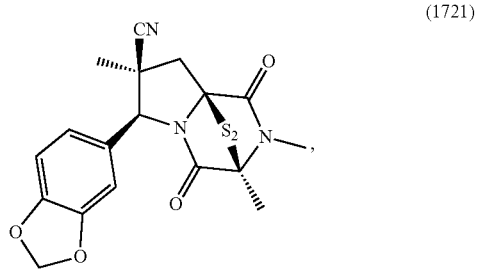 | ETP450 |
| (structure) | ETP452 |
| (structure) | ETP469 |
| (structure) | ETP484 |
| (structure) | ETP493 |

EXAMPLES

Example 1—Conversion of Trisulfides to Disulfides with Base in ETP Analog Synthesis Compound 1721 of the formula:

(1721)

possesses potent anticancer activity in vitro and in vivo.

A trisulfide byproduct is the major byproduct in the last step of a synthesis of compound 1721. Direct separation of the trisulfide and the desired disulfide (1721) is difficult.

1,8-diazabicyclo[5.4.0]undec-7-ene (DBU) was effective in converting the trisulfide byproduct to the desired disulfide product (1721). Treatment of a 3:2 disulfide:trisulfide mixture with DBU converted the mixture into a disulfide: trisulfide ratio of 70:1. See Scheme 1 following.

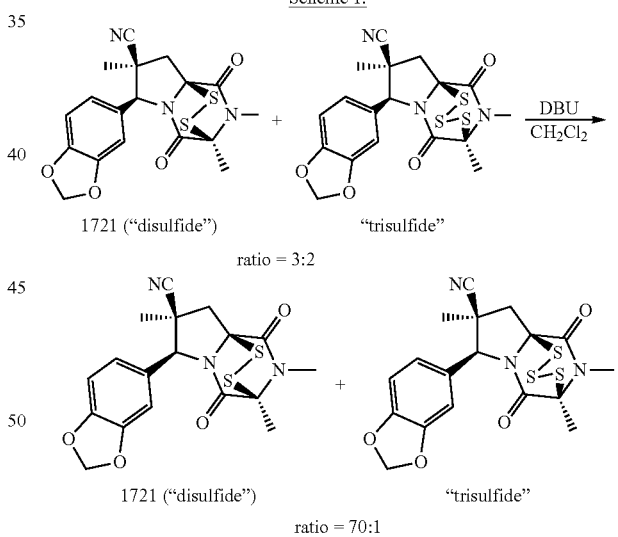

Scheme 1.

EMBODIMENTS

Embodiment 1

A method for converting a ring bridging trisulfide compound to a ring bridging disulfide compound, comprising combining the ring bridging trisulfide compound with a non-nucleophilic base, thereby affording the corresponding ring bridging disulfide compound

Embodiment 2

The method of embodiment 1, wherein, prior to the combining, the ring bridging trisulfide compound is present as a mixture with a ring bridging disulfide compound.

Embodiment 3

The method of embodiment 1 or 2, wherein the ring bridging trisulfide compound is:

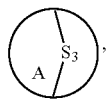

and the ring bridging disulfide compound is:

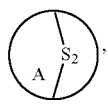

wherein A is substituted or unsubstituted cycloalkyl, substituted or unsubstituted heterocycloalkyl, substituted or unsubstituted aryl or substituted or unsubstituted heteroaryl.

Embodiment 4

The method of any one of embodiments 1-3, wherein the non-nucleophilic base is an organic non-nucleophilic base.

Embodiment 5

The method of embodiment 4, wherein the organic non-nucleophilic base comprises an amino group.

Embodiment 6

The method of embodiment 4, wherein the organic non-nucleophilic base is a sterically hindered organic non-nucleophilic base.

Embodiment 7

The method of embodiment 1, wherein the non-nucleophilic base is 1,5,7-triazabicyclo(4.4.0)dec-5-ene (TBD), 7-methyl-1,5,7-triazabicyclo(4.4.0)dec-5-ene (MTBD), 1,8-diazabicyclo[5.4.0]undec-7-ene (DBU), 1,5-diazabicyclo[4.3.0]non-5-ene (DBN), 1,1,3,3-tetramethylguanidine (TMG), quinuclidine, 2,2,6,6-tetramethylpiperidine (TMP), pempidine (PMP), tributylamine, triethylamine, N,N-triisopropylamine, 1,4-diazabicyclo[2.2.2]octan (TED), collidine, 2,6-dimethylpyridine, sodium tert-butoxide, potassium tert-butoxide, lithium diisopropylamide (LDA), potassium bis(trimethylsilyl)amide (KHMDS) or sodium trimethylsilyl)amide (NaHMDS).

Embodiment 8

The method of any one of embodiments 1-7 wherein the ring bridging trisulfide compound is:

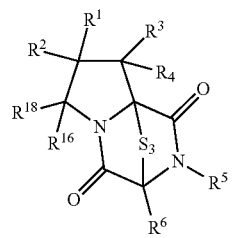

(Ia)

and the ring bridging disulfide compound is:

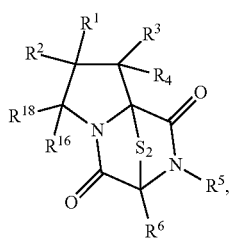

(Ib)

wherein:

$R^1$ is hydrogen, halogen, $-N_3$, $-CF_3$, $-CCl_3$, $-CBr_3$, $-CI_3$, $-CN$, $-CHO$, $-OR^{33A}$, $-NR^{34A}R^{35A}$, $-COOR^{33A}$, $-CONR^{34A}R^{35A}$, $-NO_2$, $-SR^{36A}$, $-SO_{n1}R^{34A}$, $-SO_{n1}OR^{34A}$, $-SO_{n1}NR^{34A}R^{35A}$, $-NHNR^{34A}R^{35A}$, $-ONR^{34A}R^{35A}$, $-NHC(O)NHNR^{34A}R^{35A}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^2$ is hydrogen, halogen, $-N_3$, $-CF_3$, $-CCl_3$, $-CBr_3$, $-CI_3$, $-CN$, $-CHO$, $-OR^{33B}$, $-NR^{34B}R^{35B}$, $-COOR^{33B}$, $-CONR^{34B}R^{35B}$, $-NO_2$, $-SR^{36B}$, $-SO_{n2}R^{34b}$, $-SO_{n2}OR^{34B}$, $-SO_{n2}NR^{34B}R^{35B}$, $-NHNR^{34B}R^{35B}$, $-ONR^{34B}R^{35B}$, $-NHC(O)NHNR^{34B}R^{35B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^3$ is hydrogen, halogen, $-N_3$, $-CF_3$, $-CCl_3$, $-CBr_3$, $-CI_3$, $-CN$, $-CHO$, $-OR^{33C}$, $-NR^{34C}R^{35C}$, $-COOR^{33C}$, $-CONR^{34C}R^{35C}$, $-NO_2$, $-SR^{36C}$, $-SO_{n3}R^{34C}$, $-SO_{n3}OR^{34C}$, $-SO_{n3}NR^{34C}R^{35C}$, $-NHNR^{34C}R^{35C}$, $-ONR^{34C}R^{35C}$, $-NHC(O)NHNR^{34C}R^{35C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^4$ is hydrogen, halogen, $-N_3$, $-CF_3$, $-CCl_3$, $-CBr_3$, $-CI_3$, $-CN$, $-CHO$, $-OR^{33D}$, $-NR^{34D}R^{35D}$, $-COOR^{33D}$, $-CONR^{34D}R^{35D}$, $-NO_2$, $-SR^{36D}$, $-SO_{n4}R^{34D}$, $-SO_{n4}OR^{34D}$, $-SO_{n4}NR^{34D}R^{35D}$, $-NHNR^{34D}R^{35D}$, $-ONR^{34D}R^{35D}$, $-NHC(O)$ NHNR$^{34D}$R$^{35D}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^5$ is hydrogen, halogen, —N$_3$, —CF$_3$, —CCl$_3$, —CBr$_3$, —CI$_3$, —CN, —CHO, —OR$^{33E}$, —NR$^{34E}$R$^{35E}$, —COOR$^{33E}$, —CONR$^{34E}$R$^{35E}$, —NO$_2$, —SR$^{36E}$, —SO$_{n5}$R$^{34E}$, —SO$_{n5}$OR$^{34E}$, —SO$_{n5}$NR$^{34E}$R$^{35E}$, —NHNR$^{34E}$R$^{35E}$, —ONR$^{34E}$R$^{35E}$, —NHC(O)NHNR$^{34E}$R$^{35E}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^6$ is hydrogen, halogen, —N$_3$, —CF$_3$, —CCl$_3$, —CBr$_3$, —CI$_3$, —CN, —CHO, —OR$^{33F}$, —NR$^{34F}$R$^{35F}$, —COOR$^{33F}$, —CONR$^{34F}$R$^{35F}$, —NO$_2$, —SR$^{36F}$, —SO$_{n6}$R$^{34F}$, —SO$_{n6}$OR$^{34F}$, —SO$_{n6}$NR$^{34F}$R$^{35F}$, —NHNR$^{34F}$R$^{35F}$, —ONR$^{34F}$R$^{35F}$, —NHC(O)NHNR$^{34F}$R$^{35F}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^{16}$ is hydrogen, halogen, —N$_3$, —CF$_3$, —CCl$_3$, —CBr$_3$, —CI$_3$, —CN, —CHO, —OR$^{33G}$, —NR$^{34G}$R$^{35G}$, —COOR$^{33G}$, —CONR$^{34G}$R$^{35G}$, —NO$_2$, —SR$^{36G}$, —SO$_{n7}$R$^{34G}$, —SO$_{n7}$OR$^{34G}$, —SO$_{n7}$NR$^{34G}$R$^{35G}$, —NHNR$^{34G}$R$^{35G}$, —ONR$^{34G}$R$^{35G}$, —NHC(O)NHNR$^{34G}$R$^{35G}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^{18}$ is hydrogen, halogen, —N$_3$, —CF$_3$, —CCl$_3$, —CBr$_3$, —CI$_3$, —CN, —CHO, —OR$^{33H}$, —NR$^{34H}$R$^{35H}$, —COOR$^{33H}$, —CONR$^{34H}$R$^{35H}$, —NO$_2$, —SR$^{36H}$, —SO$_{n8}$R$^{34H}$, —SO$_{n8}$OR$^{34H}$, —SO$_{n8}$NR$^{34H}$R$^{35H}$, —NHNR$^{34H}$R$^{35H}$, —ONR$^{34H}$R$^{35H}$, —NHC(O)NHNR$^{34H}$R$^{35H}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^{33A}$, R$^{34A}$, R$^{35A}$, R$^{36A}$, R$^{33B}$, R$^{34B}$, R$^{35B}$, R$^{36B}$, R$^{33C}$, R$^{34C}$, R$^{35C}$, R$^{36C}$, R$^{33D}$, R$^{34D}$, R$^{35D}$, R$^{36D}$, R$^{33E}$, R$^{34E}$, R$^{35E}$, R$^{36E}$, R$^{33F}$, R$^{34F}$, R$^{35F}$, R$^{36F}$, R$^{33G}$, R$^{34G}$, R$^{35G}$, R$^{36G}$, R$^{33H}$, R$^{34H}$, R$^{35H}$, and R$^{36H}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and n1, n2, n3, n4, n5, n6, n7, and n8 are independently 1 or 2.

Embodiment 9

The method of embodiment 8, wherein R$^{18}$ is substituted or unsubstituted heterocycloalkyl, substituted or unsubstituted aryl, or substituted or unsubstituted heteroaryl.

Embodiment 10

The method of embodiment 9, wherein:

R$^{18}$ is R$^{18a}$-substituted or unsubstituted 5 membered heterocycloalkyl, R$^{18a}$-substituted or unsubstituted 6 membered aryl, R$^{18a}$-substituted or unsubstituted 6 membered heteroaryl, R$^{18a}$-substituted or unsubstituted 6,6 fused ring aryl-heterocycloalkyl, R$^{18a}$-substituted or unsubstituted 6,5 fused ring aryl-heterocycloalkyl, R$^{18a}$-substituted or unsubstituted 5,6 fused ring aryl-heterocycloalkyl;

R$^{85a}$ is halogen, —N$_3$, —CF$_3$, —CCl$_3$, —CBr$_3$, —CI$_3$, —CN, —CHO, —OH, —NH$_2$, —COOH, —CONH$_2$, —NO$_2$, —SH, —SO$_2$Cl, —SO$_3$H, —SO$_4$H, —SO$_2$Ph, —SO$_2$NH$_2$, —NHNH$_2$, —ONH$_2$, —NHC(O)NHNH$_2$, R$^{18b}$-substituted or unsubstituted C$_1$-C$_8$ alkyl, R$^{18b}$-substituted or unsubstituted 2 to 8 membered heteroalkyl, R$^{18b}$-substituted or unsubstituted 3 to 8 membered cycloalkyl, R$^{18b}$-substituted or unsubstituted 3 to 6 membered heterocycloalkyl, R$^{18b}$-substituted or unsubstituted 5 to 6 membered aryl, or R$^{18b}$-substituted or unsubstituted 5 to 6 membered heteroaryl; and R$^{18b}$ is halogen, —N$_3$, —CF$_3$, —CCl$_3$, —CBr$_3$, —CI$_3$, —CN, —CHO, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC(O)NHNH$_2$, unsubstituted C$_1$-C$_8$ alkyl, unsubstituted 2 to 8 membered heteroalkyl, unsubstituted 3 to 8 membered cycloalkyl, unsubstituted 3 to 6 membered heterocycloalkyl, unsubstituted 5 to 6 membered aryl, or unsubstituted 5 to 6 membered heteroaryl.

Embodiment 11

The method of embodiment 10, wherein:

R$^{18a}$ is halogen, —SO$_2$Ph, R$^{18b}$-substituted or unsubstituted C$_1$-C$_5$ alkyl, or R$^{18b}$-substituted or unsubstituted 2 to 5 membered heteroalkyl, unsubstituted 5 to 6 membered heterocycloalkyl, or unsubstituted phenyl; and R$^{18b}$ is halogen, unsubstituted C$_1$-C$_8$ alkyl, or unsubstituted 2 to 8 membered heteroalkyl.

Embodiment 12

The method of embodiment 11, wherein the R$^{18a}$-substituted 5 membered heterocycloalkyl is an R$^{18a}$-substituted thiophenyl, R$^{18a}$-substituted thiazolyl, R$^{18a}$-substituted oxazolyl, or R$^{18a}$-substituted imidazolyl, and wherein R$^5$18 is halogen, unsubstituted C$_1$-C$_5$ alkyl, or unsubstituted 2 to 5 membered heteroalkyl.

Embodiment 13

The method of embodiment 10, wherein R$^{18}$ is unsubstituted heterocycloalkyl, unsubstituted aryl, or unsubstituted heteroaryl.

Embodiment 14

The method of any one of embodiments 8-13, wherein R$^{16}$ is hydrogen.

Embodiment 15

The method of any one of embodiments 8-13, wherein R$^3$ and R$^4$ are hydrogen.

Embodiment 16

The method of any one of embodiments 8-13, wherein R$^1$ is —CN or unsubstituted 2 to 5 membered heteroalkyl.

Embodiment 17

The method of embodiment 8, wherein $R^1$ is —CN.

Embodiment 18

The method of embodiment 8, wherein $R^1$ is —COOR$^{33A}$, and wherein
$R^{33A}$ is $C_1$-$C_3$ unsubstituted alkyl.

Embodiment 19

The method of any one of embodiments 8-13 or 17-18, wherein:
$R^2$ is —N$_3$, —CF$_3$, —CCl$_3$, —CBr$_3$, —CI$_3$, —CN, —CHO, —OH, —NH$_2$, —COOH, —CONH$_2$, —NO$_2$, —SH, —SO$_2$Cl, —SO$_3$H, —SO$_4$H, —SO$_2$Ph, —SO$_2$NH$_2$, —NHNH$_2$, —ONH$_2$, $R^{2a}$-substituted or unsubstituted $C_1$-$C_3$ alkyl, or 2 to 3 membered $R^{2a}$-substituted or unsubstituted heteroalkyl;
$R^{2a}$ is —N$_3$, —CF$_3$, —CCl$_3$, —CBr$_3$, —CI$_3$, —CN, —CHO, —OH, —NH$_2$, —COOH, —CONH$_2$, —NO$_2$, —SH, —SO$_2$Cl, —SO$_3$H, —SO$_4$H, —SO$_2$Ph, —SO$_2$NH$_2$, —NHNH$_2$, —ONH$_2$, $R^{2b}$-substituted or unsubstituted $C_1$-$C_5$ alkyl, $R^{2b}$-substituted or unsubstituted 2 to 5 membered heteroalkyl, $R^{2b}$-substituted or unsubstituted 3 to 6 membered heterocycloalkyl, $R^{2b}$-substituted or unsubstituted 5 or 6 membered aryl, or $R^{2b}$-substituted or unsubstituted 5 or 6 membered heteroaryl; and
$R^{2b}$ is halogen, —N$_3$, —CF$_3$, —CCl$_3$, —CBr$_3$, —CI$_3$, —CN, —CHO, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC(O)NHNH$_2$, unsubstituted $C_1$-$C_8$ alkyl, unsubstituted 2 to 8 membered heteroalkyl, unsubstituted 3 to 8 membered cycloalkyl, unsubstituted 3 to 6 membered heterocycloalkyl, unsubstituted 5 to 6 membered aryl, or unsubstituted 5 to 6 membered heteroaryl.

Embodiment 20

The method of any one of embodiments 8-13 or 17-18, wherein $R^2$ is methyl or methoxy.

Embodiment 21

The method of any one of embodiments 8-13 or 17-18, wherein:
$R^2$ is $R^{2a}$-substituted or unsubstituted $C_1$-$C_5$ alkyl, or $R^{2a}$-substituted or unsubstituted 2 to 5 membered heteroalkyl; and
$R^{2a}$ is unsubstituted 3 to 6 membered heterocycloalkyl, unsubstituted 5 or 6 membered aryl, or unsubstituted 5 or 6 membered heteroaryl.

Embodiment 22

The method of any one of embodiments 8-13 or 17-18, wherein $R^{2a}$ is unsubstituted pyridinyl.

Embodiment 23

The method of any one of embodiments 8-13 or 17-18, wherein $R^2$ is substituted or unsubstituted $C_1$-$C_5$ heteroalkyl.

Embodiment 24

The method of any one of embodiments 8-13 or 17-18, wherein $R^2$ is a polar substituent.

Embodiment 25

The method of embodiment 8, wherein $R^5$ and $R^6$ are independently hydrogen, halogen, —N$_3$, —CF$_3$, —CCl$_3$, —CBr$_3$, —CI$_3$, —CN, —CHO, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, unsubstituted alkyl, or unsubstituted cycloalkyl.

Embodiment 26

The method of embodiment 8 or 25, wherein $R^5$ and $R^6$ are independently hydrogen, unsubstituted $C_1$-$C_3$ alkyl or unsubstituted 3 to 5 membered cycloalkyl.

Embodiment 27

The method of embodiment 8 or 25, wherein $R^5$ and $R^6$ are independently hydrogen, methyl, ethyl, allyl or cyclopropyl.

Embodiment 28

The method of embodiment 8, wherein the ring bridging trisulfide compound is:

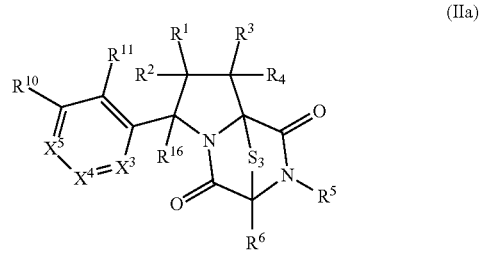

(IIa)

and the ring bridging disulfide compound is:

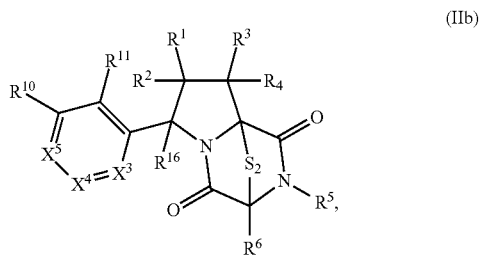

(IIb)

wherein:
$X^3$ is N or CR$^7$;
$X^4$ is N or CR$^8$;
$X^5$ is N or CR$^9$;
$R^7$ is hydrogen, halogen, —N$_3$, —CF$_3$, —CCl$_3$, —CBr$_3$, —CI$_3$, —CN, —CHO, —OR$^{33I}$, —NR$^{34I}$R$^{35I}$, —COOR$^{33I}$, —CONR$^{34I}$R$^{35I}$, —NO$_2$, —SR$^{36I}$, —SO$_{n9}$R$^{34I}$, —SO$_{n9}$OR$^{34I}$, —SO$_{n9}$NR$^{34I}$R$^{35I}$, —NHNR$^{34I}$R$^{35I}$, —ONR$^{34I}$R$^{35I}$, —NHC(O)NHNR$^{34I}$R$^{35I}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^8$ is hydrogen, halogen, $-N_3$, $-CF_3$, $-CCl_3$, $-CBr_3$, $-CI_3$, $-CN$, $-CHO$, $-OR^{33J}$, $-NR^{34J}R^{35J}$, $-COOR^{33J}$, $-CONR^{34J}R^{35J}$, $-NO_2$, $-SR^{36J}$, $-SO_{n10}R^{34J}$, $-SO_{n10}OR^{34J}$, $-SO_{n10}NR^{34J}R^{35J}$, $-NHNR^{34J}R^{35J}$, $-ONR^{34J}R^{35J}$, $-NHC(O)NHNR^{34J}R^{35J}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^9$ is hydrogen, halogen, $-N_3$, $-CF_3$, $-CCl_3$, $-CBr_3$, $-CI_3$, $-CN$, $-CHO$, $-OR^{33K}$, $-NR^{34K}R^{35K}$, $-COOR^{33K}$, $-CONR^{34K}R^{35K}$, $-NO_2$, $-SR^{36K}$, $-SO_{n11}R^{34K}$, $-SO_{n11}OR^{34K}$, $-SO_{n11}NR^{34K}R^{35K}$, $-NHNR^{34K}R^{35K}$, $-ONR^{34K}R^{35K}$, $-NHC(O)NHNR^{34K}R^{35K}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{10}$ and $R^{11}$ are independently hydrogen, halogen, $-N_3$, $-CF_3$, $-CCl_3$, $-CBr_3$, $-CI_3$, $-CN$, $-CHO$, $-OR^{33L}$, $-NR^{34L}R^{35L}$, $-COOR^{33L}$, $-CONR^{34L}R^{35L}$, $-NO_2$, $-SR^{36L}$, $-SO_{n12}R^{34L}$, $-SO_{n12}OR^{34L}$, $-SO_{n12}NR^{34L}R^{35L}$, $-NHNR^{34L}R^{35L}$, $-ONR^{34L}R^{35L}$, $-NHC(O)NHNR^{34L}R^{35L}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, or are optionally joined together to form a substituted or unsubstituted cycloalkyl, a substituted or unsubstituted heterocycloalkyl, a substituted or unsubstituted aryl, or a substituted or unsubstituted heteroaryl;

$R^{33I}$, $R^{34I}$, $R^{35I}$, $R^{36I}$, $R^{33J}$, $R^{34J}$, $R^{35J}$, $R^{36J}$, $R^{33K}$, $R^{34K}$, $R^{35K}$, $R^{36K}$, $R^{33L}$, $R^{34L}$, $R^{35L}$, and $R^{36L}$, are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and n9, n10, n11, and n12 are independently 1 or 2.

Embodiment 29

The method of embodiment 28, wherein the ring bridging disulfide compound is:

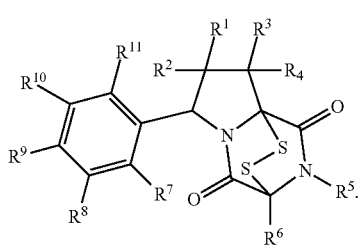

(III)

Embodiment 30

The method of embodiment 28, wherein the ring bridging trisulfide compound is:

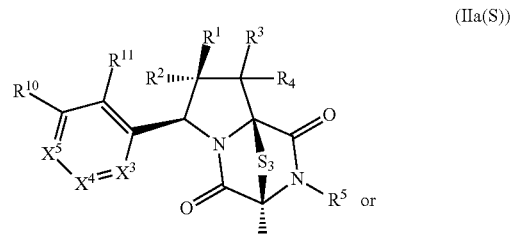

(IIa(S))

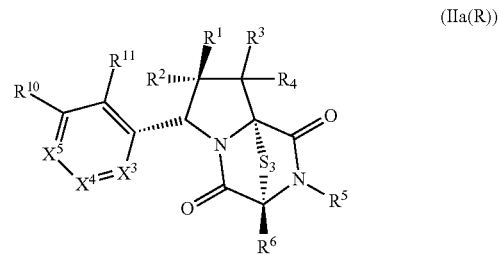

(IIa(R))

and the ring bridging disulfide compound is:

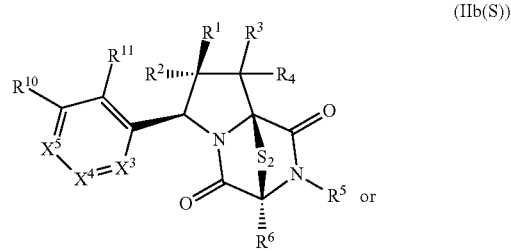

(IIb(S))

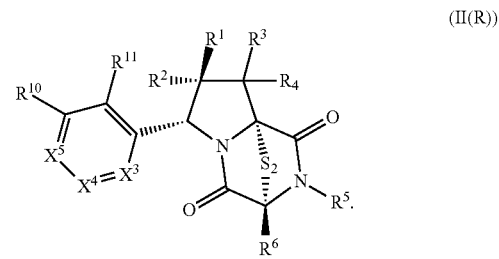

(II(R)).

Embodiment 31

The method of embodiment 28, wherein $R^1$ is $-CN$ or unsubstituted 2 to 5 membered heteroalkyl.

Embodiment 32

The method of any one of embodiments 28-31, wherein $R^3$ and $R^4$ are hydrogen.

Embodiment 33

The method of embodiment 28, wherein the ring bridging disulfide compound is:

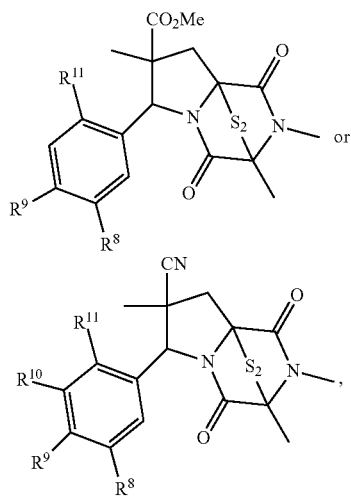

or wherein:
$R^8$ is hydrogen or $—OR^{33J}$;
$R^9$, $R^{10}$, and $R^{11}$ are independently hydrogen or halogen; and
$R^{33J}$ is hydrogen, or unsubstituted alkyl.

Embodiment 34

The method of embodiment 8, wherein the ring bridging trisulfide compound is:

(IVa)

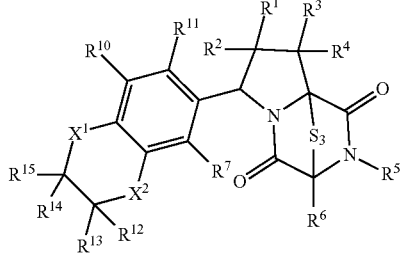

and the ring bridging disulfide compound is:

(IVb)

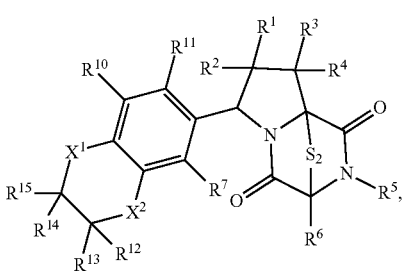

wherein:
$X^1$ is $CR^{21}R^{21A}$, O, $NR^{21A}$, or S;
$X^2$ is $CR^{22}R^{22A}$, O, $NR^{22A}$, or S; and
$R^{12}$, $R^{13}$, $R^{14}$, $R^{15}$ $R^{21}$, $R^{21A}$, $R^{22}$, and $R^{22A}$ are independently hydrogen, halogen, $—N_3$, $—CF_3$, $—CCl_3$, $—CBr_3$, $—CI_3$, $—CN$, $—CHO$, $—OR^{33M}$, $—NR^{34M}R^{35M}$, $—COOR^{33M}$, $—CONR^{34M}R^{35M}$, $—NO_2$, $—SR^{36M}$, $—SO_{n13}R^{34M}$, $—SO_{n13}OR^{34M}$, $—SO_{n13}NR^{34M}R^{35M}$, $—NHNR^{34M}R^{35M}$, $—ONR^{34M}R^{35M}$, $—NHC(O)NHNR^{34M}R^{35M}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{33M}$, $R^{34M}$, $R^{35M}$, and $R^{36M}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and n13 is 1 or 2.

Embodiment 35

The method of embodiment 34, wherein the ring bridging trisulfide compound is:

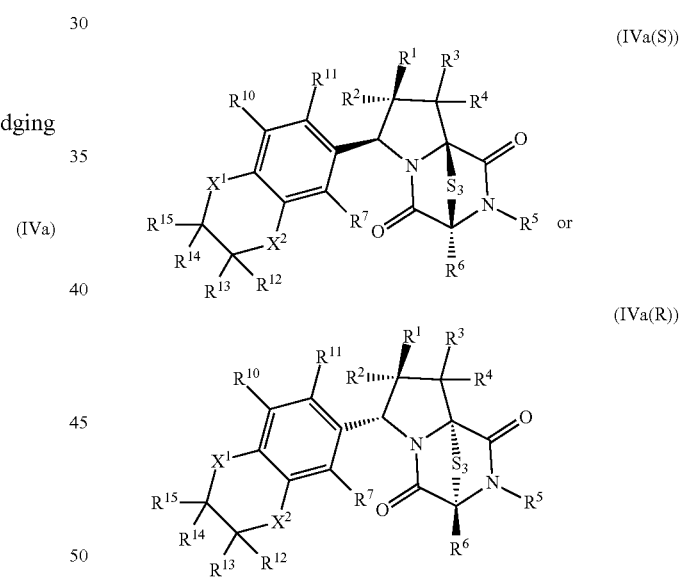

and the ring bridging disulfide compound is:

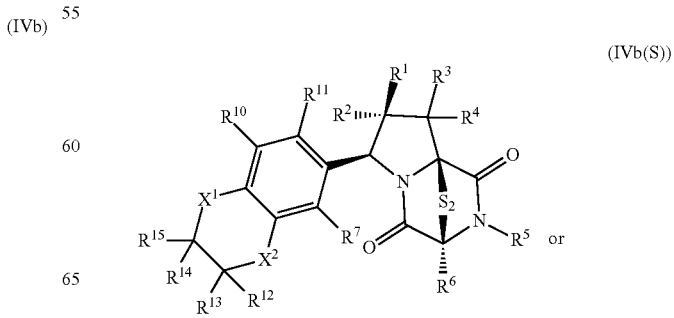

-continued (IVb(R))

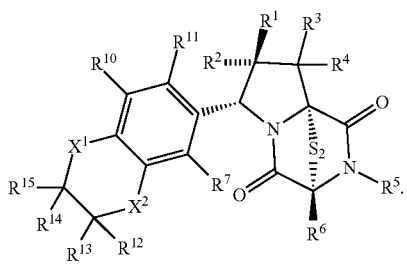

Embodiment 36

The method of embodiment 34, wherein $R^1$ is —CN or unsubstituted 2- to 5-membered heterocycloalkyl.

Embodiment 37

The method of any one of embodiments 34-36, wherein $R^3$ and $R^4$ are hydrogen.

Embodiment 38

The method of any one of embodiments 35-36, wherein $R^{10}$ and $R^{11}$ are hydrogen.

Embodiment 39

The method of any one of embodiments 34-36, wherein $R^{12}$, $R^{13}$, $R^{14}$, and $R^{15}$ are hydrogen.

Embodiment 40

The method of embodiment 34, wherein ring bridging disulfide compound is:

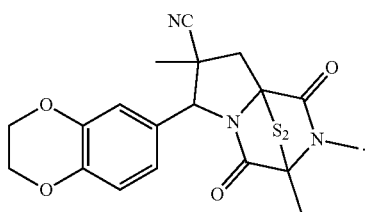

Embodiment 41

The method of embodiment 8, wherein the ring bridging trisulfide compound is:

(IIIa)

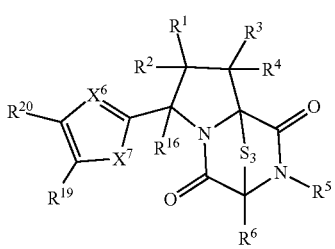

and ring bridging disulfide compound is:

(IIIb)

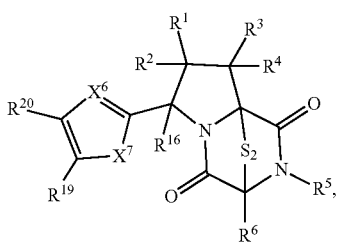

wherein:

$X^6$ is $CR^{24}$ or N;

$X^7$ is $CR^{24}R^{24A}$, S, O, or $NR^{24A}$;

$R^{19}$, $R^{20}$, $R^{23}$, $R^{24}$ and $R^{24A}$, are independently hydrogen, halogen, —$N_3$, —$CF_3$, —$CCl_3$, —$CBr_3$, —$CI_3$, —CN, —CHO, —$OR^{33M}$, —$NR^{34M}R^{35M}$, —$COOR^{33M}$, —$CONR^{34M}R^{35M}$, —$NO_2$, —$SR^{36M}$, —$SO_{n13}R^{34M}$, —$SO_{n13}OR^{34M}$, —$SO_{n13}NR^{34M}R^{35M}$, —$NHNR^{34M}R^{35M}$, —$ONR^{34M}R^{35M}$, —NHC(O)NHNR^{34M}R^{35M}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{33M}$, $R^{34M}$, $R^{35M}$, and $R^{36M}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and n13 is 1 or 2.

Embodiment 42

The method of embodiment 8 or 41, wherein the ring bridging trisulfide compound is:

(IIIa(S))

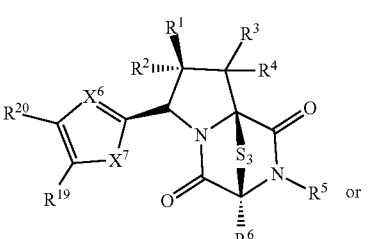

or (IIIa(R))

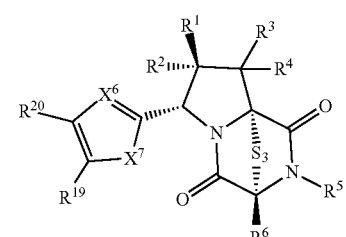

and the ring bridging disulfide compound is:

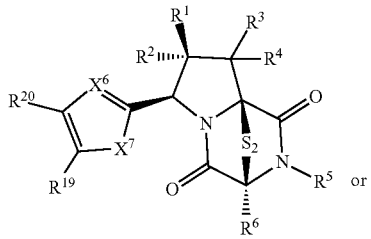
(IIIb(S))

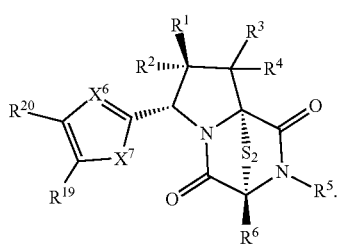
(IIIb(R))

Embodiment 43

The method of embodiment 41, wherein $R^1$ is —CN or unsubstituted 2 to 5 membered heteroalkyl.

Embodiment 44

The method of any one of embodiments 41-43, wherein $R^3$ and $R^4$ are hydrogen.

Embodiment 45

The method of any one of embodiments 41-43, wherein $R^{19}$ and $R^{20}$ are hydrogen.

Embodiment 46

The method of embodiment 8, wherein the ring bridging trisulfide compound is:

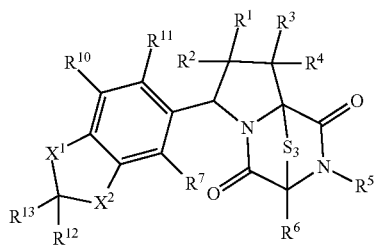
(Va)

and the ring bridging disulfide compound is:

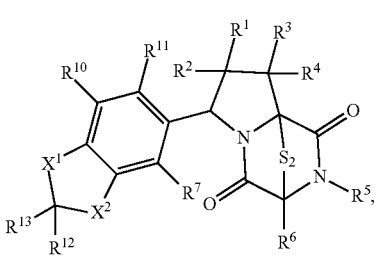
(Vb)

wherein:

$X^1$ is $CR^{21}R^{21A}$, O, $NR^{21A}$, or S;

$X^2$ is $CR^{22}R^{22A}$, O, $NR^{22A}$, or S;

$R^7$ is hydrogen, halogen, —$N_3$, —$CF_3$, —$CCl_3$, —$CBr_3$, —$CI_3$, —CN, —CHO, —$OR^{33I}$, —$NR^{34I}R^{35I}$, —$COOR^{33I}$, —$CONR^{34I}R^{35I}$, —$NO_2$, —$SR^{36I}$, —$SO_{n9}R^{34I}$, —$SO_{n9}OR^{34I}$, —$SO_{n9}NR^{34I}R^{35}$, —$NHNR^{34I}R^{35I}$, —$ONR^{34I}R^{35I}$, —NHC(O)NHNR^{34I}R^{35I}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{10}$ and $R^{11}$ are independently hydrogen, halogen, —$N_3$, —$CF_3$, —$CCl_3$, —$CBr_3$, —$CI_3$, —CN, —CHO, —$OR^{33L}$, —$NR^{34L}R^{35L}$, —$COOR^{33L}$, —$CONR^{34L}R^{35L}$, —$NO_2$, —$SR^{36L}$, —$SO_{n12}R^{34L}$, —$SO_{n12}OR^{34L}$, —$SO_{n12}NR^{34L}R^{35L}$, —$NHNR^{34L}R^{35L}$, —$ONR^{34L}R^{35L}$, —NHC(O)NHNR^{34L}R^{35L}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, or are optionally joined together to form a substituted or unsubstituted cycloalkyl, a substituted or unsubstituted heterocycloalkyl, a substituted or unsubstituted aryl, or a substituted or unsubstituted heteroaryl;

$R^{12}$, $R^{13}$, $R^{21}$, $R^{21A}$, $R^{22}$ and $R^{22A}$ are independently hydrogen, halogen, —$N_3$, —$CF_3$, —$CCl_3$, —$CBr_3$, —$CI_3$, —CN, —CHO, —$OR^{33M}$, —$NR^{34M}R^{35M}$, —$COOR^{33M}$, —$CONR^{34M}R^{35M}$, —$NO_2$, —$SR^{36M}$, —$SO_{n13}R^{34M}$, —$SO_{n13}OR^{34M}$, —$SO_{n13}NR^{34M}R^{35M}$, —$NHNR^{34M}R^{35M}$, —$ONR^{34M}R^{35M}$, —NHC(O)NHNR^{34M}R^{35M}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{33M}$, $R^{34M}$, $R^{35M}$, and $R^{36M}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and n9, n11, and n13 are independently 1 or 2.

Embodiment 47

The method of embodiment 46, wherein the ring bridging trisulfide compound is:

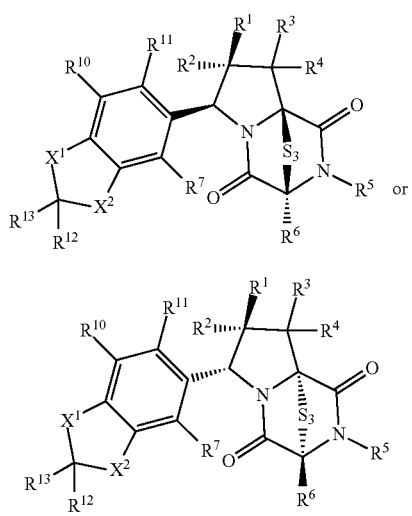

(Va(S))

(Va(R))

and the ring bridging disulfide compound is:

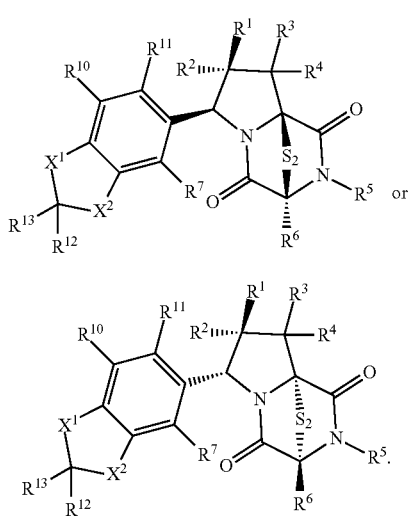

(Vb(S))

(Vb(R))

Embodiment 48

The method of embodiment 46, wherein the ring bridging disulfide compound is:

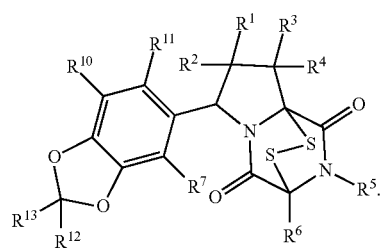

(V2)

Embodiment 49

The method of embodiment 48, wherein the ring bridging disulfide compound is:

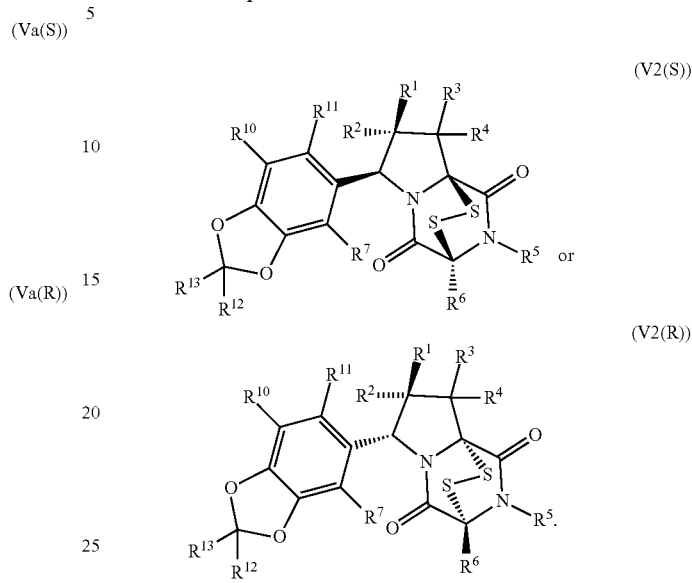

(V2(S))

(V2(R))

Embodiment 50

The method of embodiment 46, wherein $R^1$ is —CN or unsubstituted 2 to 5 membered heteroalkyl.

Embodiment 51

The method of any one of embodiments 46-50, wherein $R^3$ and $R^4$ are hydrogen.

Embodiment 52

The method of any one of embodiments 46-50, wherein $R^{12}$ and $R^{13}$ are hydrogen.

Embodiment 53

The method of any one of embodiments 46-50, wherein $R^{10}$ and $R^{11}$ are hydrogen.

Embodiment 54

The method of any one of embodiments 8 or 47-50, wherein the ring bridging disulfide compound is:

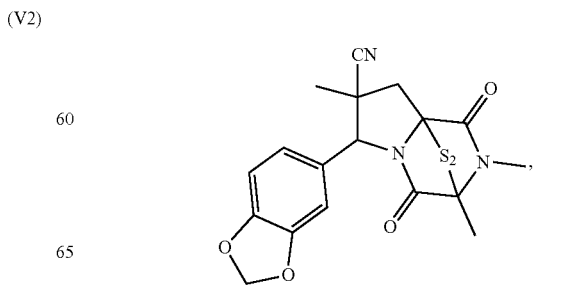

-continued

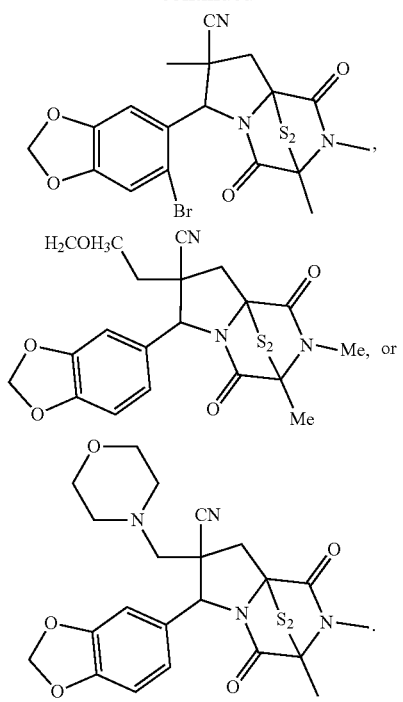

Embodiment 55

The method of any one of embodiments 8, 46, or 47, wherein the ring bridging trisulfide compound is:

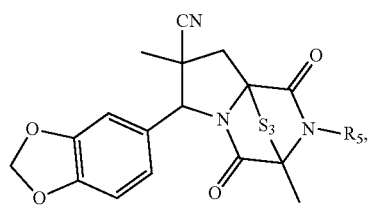
(V3a)

and the ring bridging disulfide compound is:

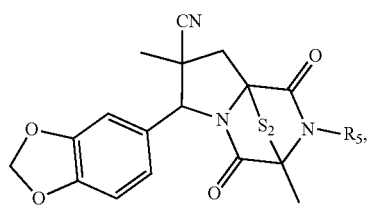
(V3b)

wherein:

$R^5$ is unsubstituted 3- to 5-membered cycloalkyl or $R^{5a}$-substituted or unsubstituted $C_1$-$C_5$ alkyl; and $R^{5a}$ is unsubstituted 2- to 5-membered heteroalkyl or 5 to 6 membered heterocycloalkyl.

Embodiment 56

The method of any one of embodiments 8, 46-50, or 55, wherein the ring bridging disulfide compound is:

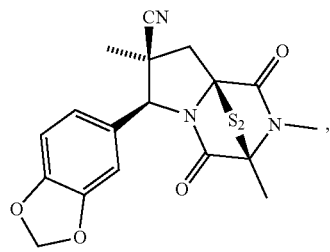
(ETP69)

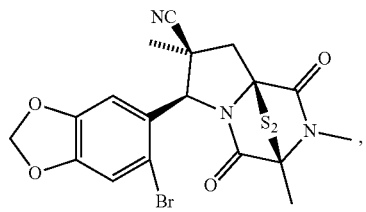
(ETP128)

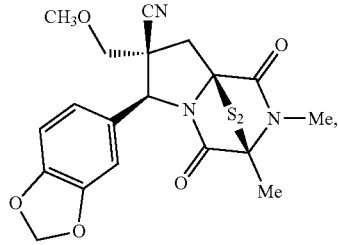
(ETP344)

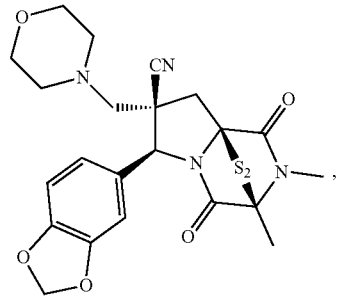
(ETP382)

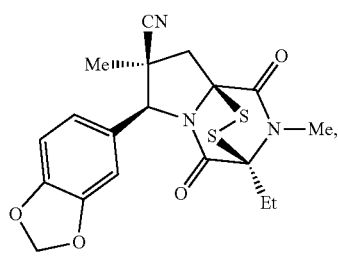
(ETP406)

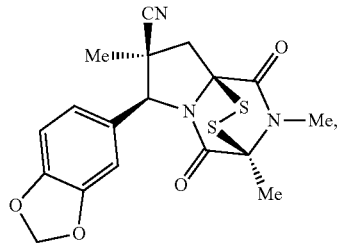
(ETP417)

-continued
(ETP422)
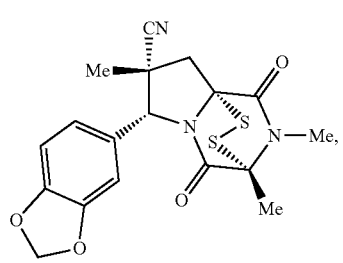
(ETP425)
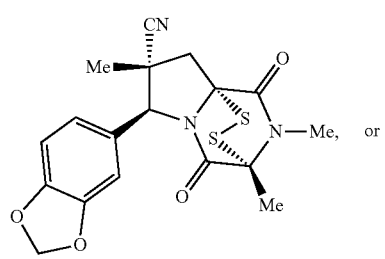
or
(ETP452)
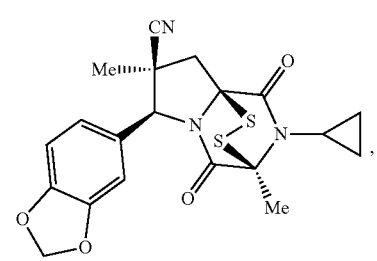
and the ring bridging trisulfide compound is:
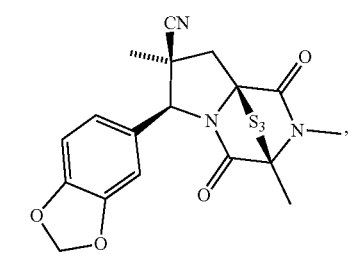
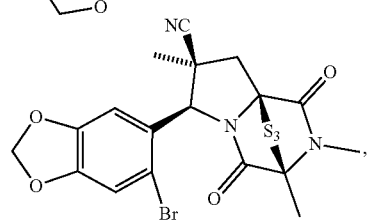
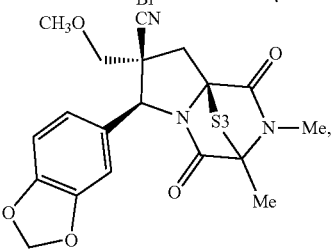
-continued
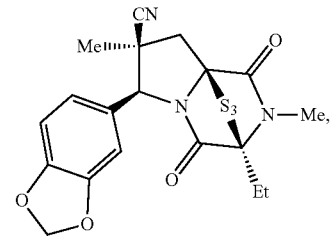
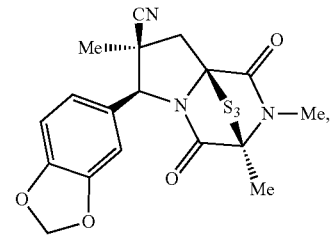
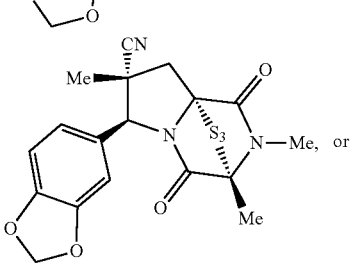
or
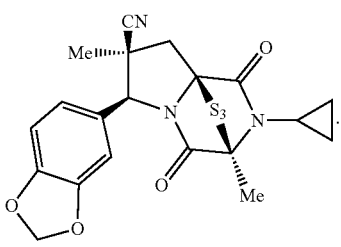

Embodiment 57

The method of embodiment 8, wherein the ring bridging trisulfide compound is:

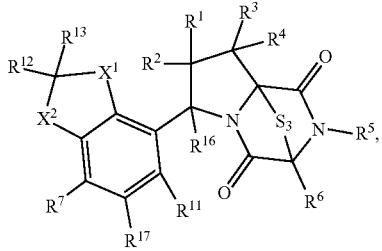
(VIa)

and the ring bridging disulfide compound is:

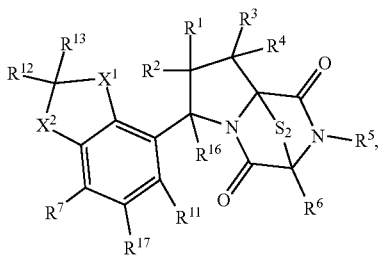
(VIb)

wherein:
$X^1$ is $CR^{21}R^{21A}$, O, $NR^{21A}$, or S;
$X^2$ is $CR^{22}R^{22A}$, O, $NR^{22A}$, or S;
$R^7$ is hydrogen, halogen, $-N_3$, $-CF_3$, $-CCl_3$, $-CBr_3$, $-CI_3$, $-CN$, $-CHO$, $-OR^{33I}$, $-NR^{34I}R^{35I}$, $-COOR^{33I}$, $-CONR^{34I}R^{35I}$, $-NO_2$, $-SR^{36I}$, $-SO_{n9}R^{34I}$, $-SO_{n9}OR^{34I}$, $-SO_{n9}NR^{34I}R^{35}$, $-NHNR^{34I}R^{35I}$, $-ONR^{34I}R^{35I}$, $-NHC(O)NHNR^{34I}R^{35I}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$R^{11}$ is hydrogen, halogen, $-N_3$, $-CF_3$, $-CCl_3$, $-CBr_3$, $-CI_3$, $-CN$, $-CHO$, $-OR^{33L}$, $-NR^{34L}R^{35L}$, $-COOR^{33L}$, $-CONR^{34L}R^{35L}$, $-NO_2$, $-SR^{36L}$, $-SO_{n12}R^{34L}$, $-SO_{n12}OR^{34L}$, $-SO_{n12}NR^{34L}R^{35L}$, $-NHNR^{34L}R^{35L}$, $-ONR^{34L}R^{35L}$, $-NHC(O)NHNR^{34L}R^{35L}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, or are optionally joined together to form a substituted or unsubstituted cycloalkyl, a substituted or unsubstituted heterocycloalkyl, a substituted or unsubstituted aryl, or a substituted or unsubstituted heteroaryl;
$R^{12}$, $R^{13}$, $R^{21}$, $R^{21A}$, $R^{22}$, and $R^{22A}$ are independently hydrogen, halogen, $-N_3$, $-CF_3$, $-CCl_3$, $-CBr_3$, $-CI_3$, $-CN$, $-CHO$, $-OR^{33M}$, $-NR^{34M}R^{35M}$, $-COOR^{33M}$, $-CONR^{34M}R^{35M}$, $-NO_2$, $-SR^{36M}$, $-SO_{n13}R^{34M}$, $-SO_{n13}OR^{34M}$, $-SO_{n13}NR^{34M}R^{35M}$, $-NHNR^{34M}R^{35M}$, $-ONR^{34M}R^{35M}$, $-NHC(O)NHNR^{34M}R^{35M}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$R^{17}$ is hydrogen, halogen, $-N_3$, $-CF_3$, $-CCl_3$, $-CBr_3$, $-CI_3$, $-CN$, $-CHO$, $-OR^{33P}$, $-NR^{34P}R^{35P}$, $-COOR^{33P}$, $-CONR^{34P}R^{35P}$, $-NO_2$, $-SR^{36P}$, $-SO_{n14}R^{34P}$, $-SO_{n14}OR^{34P}$, $-SO_{n14}NR^{34P}R^{35P}$, $-NHNR^{34P}R^{35P}$, $-ONR^{34P}R^{35P}$, $-NHC(O)NHNR^{34P}R^{35P}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, or are optionally bonded together to form a substituted or unsubstituted cycloalkyl, a substituted or unsubstituted heterocycloalkyl, a substituted or unsubstituted aryl, or a substituted or unsubstituted heteroaryl;
$R^{33I}$, $R^{34I}$, $R^{35I}$, $R^{36I}$, $R^{33L}$, $R^{34L}$, $R^{35L}$, $R^{36L}$, $R^{33M}$, $R^{34M}$, $R^{35M}$, $R^{36M}$, $R^{33P}$, $R^{34P}$, $R^{35P}$, and $R^{36P}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and n9, n12, n13 and n15 are independently 1 or 2.

Embodiment 58

The method of embodiment 57, wherein the ring bridging trisulfide compound is:

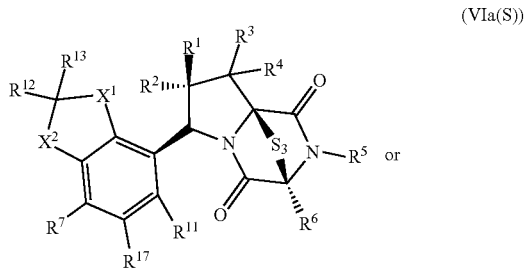
(VIa(S))

or

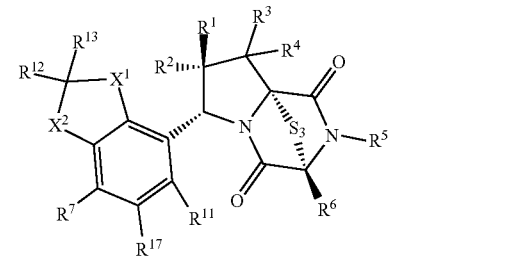
(VIa(R))

and the ring bridging disulfide compound is:

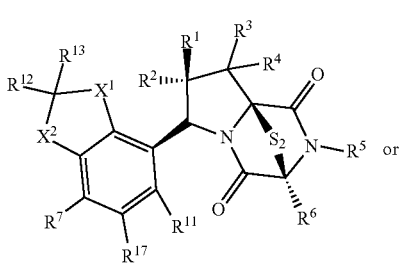

(VIb(S))

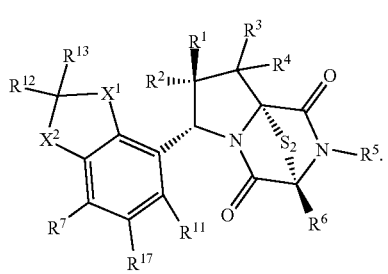

(VIb(R))

Embodiment 59

The method of embodiment 57, wherein $R^1$ is —CN or unsubstituted 2 to 5 membered heteroalkyl.

Embodiment 60

The method of any one of embodiments 57-59, wherein $R^3$ and $R^4$ are hydrogen.

Embodiment 61

The method of any one of embodiments 57-59, wherein $R^{12}$ and $R^{13}$ are hydrogen.

Embodiment 62

The method of any one of embodiments 57-59, wherein $R^7$, $R^{10}$, and $R^{17}$ are hydrogen.

Embodiment 63

The method of embodiment 57, wherein the ring bridging disulfide compound is:

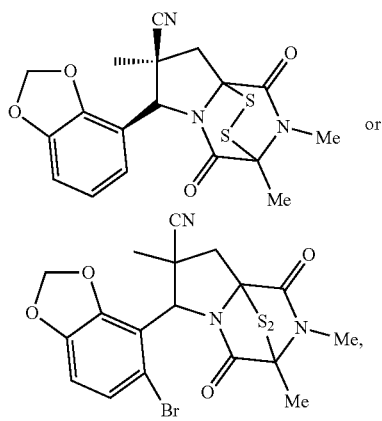

and the ring bridging trisulfide compound is

Embodiment 64

The method of any one of embodiments 28-31, 34-36, 41-43, 46-50, or 57-59, wherein $R^2$ is a polar substituent.

Embodiment 65

The method of any one of embodiments 28-31, 34-36, 41-43, 46-50, or 57-59, wherein:

$R^2$ is —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2Cl$, —$SO_3H$, —$SO_4H$, —$SO_2Ph$, —$SO_2NH_2$, —$NHNH_2$, —$ONH_2$, $R^{2a}$-substituted or unsubstituted $C_1$-$C_3$ alkyl, or $R^{2a}$-substituted or unsubstituted 2 to 3 membered heteroalkyl;

$R^{2a}$ is —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2Cl$, —$SO_3H$, —$SO_4H$, —$SO_2Ph$, —$SO_2NH_2$, —$NHNH_2$, —$ONH_2$, $R^{2b}$-substituted or unsubstituted $C_1$-$C_5$ alkyl, $R^{2b}$-substituted or unsubstituted 2 to 5 membered heteroalkyl, $R^{2b}$-substituted or unsubstituted 3 to 6 membered heterocycloalkyl, $R^{2b}$-substituted or unsubstituted 5 or membered aryl, or $R^{2b}$-substituted or unsubstituted 5 or 6 membered heteroaryl; and $R^{2b}$ is halogen, —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —$NHC(O)NHNH_2$, unsubstituted $C_1$-$C_8$ alkyl, unsubstituted 2 to 8 membered heteroalkyl, unsubstituted 3 to 8 membered cycloalkyl, unsubstituted 3 to 6 membered heterocycloalkyl, unsubstituted 5 to 6 membered aryl, or unsubstituted 5 to 6 membered heteroaryl.

Embodiment 66

The method of any one of embodiments 28-31, 34-36, 41-43, 46-50, or 57-59, wherein:

$R^2$ is $R^{2a}$-substituted or unsubstituted $C_1$-$C_3$ alkyl, or $R^{2a}$-substituted or unsubstituted 2 to 3 membered heteroalkyl; and $R^{2a}$ is unsubstituted 3 to 6 membered heterocycloalkyl, unsubstituted 5 or 6 membered aryl, or unsubstituted 5 or 6 membered heteroaryl.

Embodiment 67

The method of any one of embodiments 28-31, 34-36, 41-43, 46-50, or 57-59, wherein $R^2$ is methyl or methoxy.

Embodiment 68

The method of any one of embodiments 28-31, 34-36, 41-43, 46-50, or 57-59, wherein $R^{2a}$ is pyridinyl.

Embodiment 69

The method of any one of embodiments 28-31, 34-36, 41-43, 46-50, or 57-59, wherein $R^5$ and $R^6$ are independently hydrogen, halogen, —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, unsubstituted alkyl, or unsubstituted cycloalkyl.

Embodiment 70

The method of any one of embodiments 28-31, 34-36, 41-43, 46-50, or 57-59, wherein $R^5$ and $R^6$ are independently hydrogen, $C_1$-$C_3$ unsubstituted alkyl or 3 to 5 membered cycloalkyl.

Embodiment 71

The method of any one of embodiments 28-31, 34-36, 41-43, 46-50, or 57-59, wherein $R^5$ and $R^6$ are independently hydrogen, methyl, ethyl, allyl, or cyclopropyl.

Embodiment 72

The method of embodiment 1 or 2, wherein the ring bridging disulfide compound is:

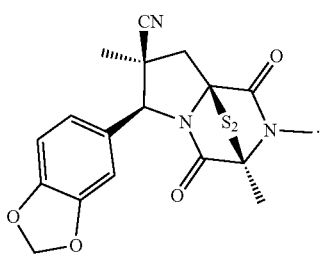

Embodiment 73

The method of embodiment 2, wherein the ratio of the ring bridging trisulfide to the ring bridging disulfide in the mixture is between about 100:0.01 and 0.01:100.

Embodiment 74

The method of embodiment 2, wherein the ratio of the ring bridging trisulfide to the ring bridging disulfide in the mixture is between about 10:0.1 and 0.1:10.

Embodiment 75

The method of embodiment 2, wherein the ratio of the ring bridging trisulfide to the ring bridging disulfide in the mixture is between about 5:1 and 1:5.

Embodiment 76

The method of embodiment 2, wherein the ratio of the ring bridging trisulfide to the ring bridging disulfide in the mixture is about 2:3.

Embodiment 77

The method of embodiment 2, wherein the ratio of the ring bridging trisulfide to the ring bridging disulfide in the mixture is about 1:70.

Embodiment 78

The method of embodiment 2, wherein the ring bridging trisulfide decreases in amount in the mixture by about 10% (w/w).

Embodiment 79

The method of embodiment 2, wherein the ring bridging trisulfide decreases in amount in the mixture by about 30% (w/w).

Embodiment 80

The method of embodiment 2, wherein the ring bridging trisulfide decreases in amount in the mixture by about 50% (w/w).

Embodiment 81

The method of any one of embodiments 1-80, wherein the non-nucleophilic base is DBU.

Embodiment 82

A composition, comprising:
(i) a ring bridging trisulfide compound;
(ii) a ring bridging disulfide compound; and
(iii) a non-nucleophilic base, wherein the molar ratio of the ring bridging trisulfide compound to the ring bridging disulfide compound is greater than 0.1, and further wherein the non-nucleophilic base is present in a quantity effective to convert at least an amount of the ring bridging trisulfide compound to the ring bridging disulfide compound.

Embodiment 83

The composition of embodiment 82, wherein the ring bridging trisulfide compound is:

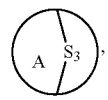

and the ring bridging disulfide compound is:

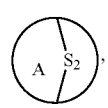

wherein A is substituted or unsubstituted cycloalkyl, substituted or unsubstituted heterocycloalkyl, substituted or unsubstituted aryl or substituted or unsubstituted heteroaryl.

Embodiment 84

The composition of embodiment 82, wherein the non-nucleophilic base is an organic non-nucleophilic base.

Embodiment 85

The composition of embodiment 84, wherein the organic non-nucleophilic base comprises an amino group.

Embodiment 86

The composition of embodiment 85, wherein the organic non-nucleophilic base is a sterically hindered organic non-nucleophilic base.

Embodiment 87

The composition of embodiment 86, wherein the non-nucleophilic base is 1,5,7-triazabicyclo(4.4.0)dec-5-ene (TBD), 7-methyl-1,5,7-triazabicyclo(4.4.0)dec-5-ene (MTBD), 1,8-diazabicyclo[5.4.0]undec-7-ene (DBU), 1,5-diazabicyclo[4.3.0]non-5-ene (DBN), 1,1,3,3-tetramethylguanidine (TMG), quinuclidine, 2,2,6,6-tetramethylpiperidine (TMP), pempidine (PMP), tributylamine, triethylamine, N,N-triisopropylamine, 1,4-diazabicyclo[2.2.2]octan (TED), collidine, 2,6-dimethylpyridine, sodium tert-butoxide, potassium tert-butoxide, lithium diisopropylamide (LDA), potassium bis(trimethylsilyl)amide (KHMDS) or sodium trimethylsilyl)amide (NaHMDS).

Embodiment 88

The composition of embodiment 82, wherein the ring bridging trisulfide compound is:

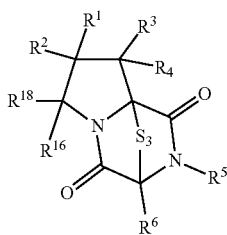
(Ia)

and the ring bridging disulfide compound is:

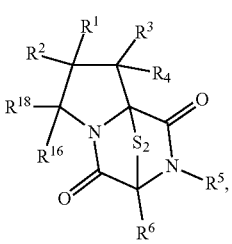
(Ib)

wherein:

$R^1$ is hydrogen, halogen, $-N_3$, $-CF_3$, $-CCl_3$, $-CBr_3$, $-CI_3$, $-CN$, $-CHO$, $-OR^{33A}$, $-NR^{34A}R^{35A}$, $-COOR^{33A}$, $-CONR^{34A}R^{35A}$, $-NO_2$, $-SR^{36A}$, $-SO_{n1}R^{34A}$, $-SO_{n1}OR^{34A}$, $-SO_{n1}NR^{34A}R^{35A}$, $-NHNR^{34A}R^{35A}$, $-ONR^{34A}R^{35A}$, $-NHC(O)NHNR^{34A}R^{35A}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^2$ is hydrogen, halogen, $-N_3$, $-CF_3$, $-CCl_3$, $-CBr_3$, $-CI_3$, $-CN$, $-CHO$, $-OR^{33B}$, $-NR^{34B}R^{35B}$, $-COOR^{33B}$, $-CONR^{34B}R^{35B}$, $-NO_2$, $-SR^{36B}$, $-SO_{n2}R^{34b}$, $-SO_{n2}OR^{34B}$, $-SO_{n2}NR^{34B}R^{35B}$, $-NHNR^{34B}R^{35B}$, $-ONR^{34B}R^{35B}$, $-NHC(O)NHNR^{34B}R^{35B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^3$ is hydrogen, halogen, $-N_3$, $-CF_3$, $-CCl_3$, $-CBr_3$, $-CI_3$, $-CN$, $-CHO$, $-OR^{33C}$, $-NR^{34C}R^{35C}$, $-COOR^{33C}$, $-CONR^{34C}R^{35C}$, $-NO_2$, $-SR^{36C}$, $-SO_{n3}R^{34C}$, $-SO_{n3}OR^{34C}$, $-SO_{n3}NR^{34C}R^{35C}$, $-NHNR^{34C}R^{35C}$, $-ONR^{34C}R^{35C}$, $-NHC(O)NHNR^{34C}R^{35C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^4$ is hydrogen, halogen, $-N_3$, $-CF_3$, $-CCl_3$, $-CBr_3$, $-CI_3$, $-CN$, $-CHO$, $-OR^{33D}$, $-NR^{34}R^{35D}$, $-COOR^{33D}$, $-CONR^{34D}R^{35D}$, $-NO_2$, $-SR^{36D}$, $-SO_{n4}R^{34D}$, $-SO_{n4}OR^{34D}$, $-SO_{n4}NR^{34D}R^{35D}$, $-NHNR^{34D}R^{35D}$, $-ONR^{34D}R^{35D}$, $-NHC(O)NHNR^{34D}R^{35D}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^5$ is hydrogen, halogen, $-N_3$, $-CF_3$, $-CCl_3$, $-CBr_3$, $-CI_3$, $-CN$, $-CHO$, $-OR^{33E}$, $-NR^{34E}R^{35E}$, $-COOR^{33E}$, $-CONR^{34E}R^{35E}$, $-NO_2$, $-SR^{36E}$, $-SO_{n5}R^{34E}$, $-SO_{n5}OR^{34E}$, $-SO_{n5}NR^{34E}R^{35E}$, $-NHNR^{34E}R^{35E}$, $-ONR^{34E}R^{35E}$, $-NHC(O)NHNR^{34E}R^{35E}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^6$ is hydrogen, halogen, $-N_3$, $-CF_3$, $-CCl_3$, $-CBr_3$, $-CI_3$, $-CN$, $-CHO$, $-OR^{33F}$, $-NR^{34F}R^{35F}$, $-COOR^{33F}$, $-CONR^{34F}R^{35F}$, $-NO_2$, $-SR^{36F}$, $-SO_{n6}R^{34F}$, $-SO_{n6}OR^{34F}$, $-SO_{n6}NR^{34F}R^{35F}$, $-NHNR^{34F}R^{35F}$, $-ONR^{34F}R^{35F}$, $-NHC(O)NHNR^{34F}R^{35F}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{16}$ is hydrogen, halogen, $-N_3$, $-CF_3$, $-CCl_3$, $-CBr_3$, $-CI_3$, $-CN$, $-CHO$, $-OR^{33G}$, $-NR^{34G}R^{35G}$, $-COOR^{33G}$, $-CONR^{34G}R^{35G}$, $-NO_2$, $-SR^{36G}$, $-SO_{n7}R^{34G}$, $-SO_{n7}OR^{34G}$, $-SO_{n7}NR^{34G}R^{35G}$, $-NHNR^{34G}R^{35G}$, $-ONR^{34G}R^{35G}$, $-NHC(O)NHNR^{34G}R^{35G}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{18}$ is hydrogen, halogen, $-N_3$, $-CF_3$, $-CCl_3$, $-CBr_3$, $-CI_3$, $-CN$, $-CHO$, $-OR^{33H}$, $-NR^{34H}R^{35H}$, $-COOR^{33H}$, $-CONR^{34H}R^{35H}$, $-NO_2$, $-SR^{36H}$, $-SO_{n8}R^{34H}$, $-SO_{n8}OR^{34H}$, $-SO_{n8}NR^{34H}R^{35H}$, $-NHNR^{34H}R^{35H}$, $-ONR^{34H}R^{35H}$, $-NHC(O)NHNR^{34H}R^{35H}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{33A}$, $R^{34A}$, $R^{35A}$, $R^{36A}$, $R^{33B}$, $R^{34B}$, $R^{35B}$, $R^{36B}$, $R^{33C}$, $R^{34C}$, $R^{35C}$, $R^{36C}$, $R^{33D}$, $R^{34D}$, $R^{35D}$, $R^{36D}$, $R^{33E}$, $R^{34E}$, $R^{35E}$, $R^{36E}$, $R^{33F}$, $R^{34F}$, $R^{35F}$, $R^{36F}$, $R^{33G}$, $R^{34G}$, $R^{35G}$, $R^{36G}$, $R^{33H}$, $R^{34H}$, $R^{35H}$, and $R^{36H}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and n1, n2, n3, n4, n5, n6, n7, and n8 are independently 1 or 2.

Embodiment 89

The composition of embodiment 82, wherein the mixture comprises at least 0.05 mol of the ring bridging disulfide compound.

Embodiment 90

A reaction vessel, comprising the composition of any one of embodiments 82-89.

Embodiment 91

The reaction vessel of embodiment 90, wherein the reaction vessel is configured to produce at least 10 g of the ring bridging disulfide compound].

What is claimed is:

1. A method for converting a ring bridging trisulfide compound to a ring bridging disulfide compound, comprising combining the ring bridging trisulfide compound with a non-nucleophilic base, thereby affording the corresponding ring bridging disulfide compound, wherein the ring bridging trisulfide compound is of formula (Ia):

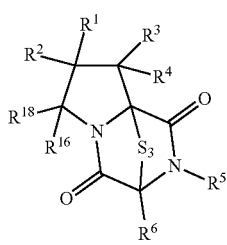

(Ia)

and the ring bridging disulfide compound is of formula (Ib):

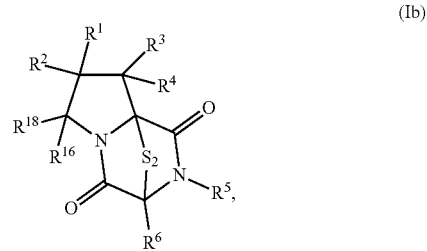

(Ib)

wherein:

$R^1$ is hydrogen, halogen, $-N_3$, $-CF_3$, $-CCl_3$, $-CBr_3$, $-CI_3$, $-CN$, $-CHO$, $-OR^{33A}$, $-NR^{34A}R^{35A}$, $-COOR^{33A}$, $-CONR^{34A}R^{35A}$, $-NO_2$, $-SR^{36A}$, $-SO_{n1}R^{34A}$, $-SO_{n1}OR^{34A}$, $-SO_{n1}NR^{34A}R^{35A}$, $-NHNR^{34A}R^{35A}$, $-ONR^{34A}R^{35A}$, $-NHC(O)NHNR^{34A}R^{35A}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, $R^2$ is hydrogen, halogen, $-N_3$, $-CF_3$, $-CCl_3$, $-CBr_3$, $-CI_3$, $-CN$, $-CHO$, $-OR^{33B}$, $-NR^{34B}R^{35B}$, $-COOR^{33B}$, $-CONR^{34B}R^{35B}$, $-NO_2$, $-SR^{36B}$, $-SO_{n2}R^{34B}$, $-SO_{n2}OR^{34B}$, $-SO_{n2}NR^{34B}R^{35B}$, $-NHNR^{34B}R^{35B}$, $-ONR^{34B}R^{35B}$, $-NHC(O)NHNR^{34B}R^{35B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^3$ is hydrogen, halogen, $-N_3$, $-CF_3$, $-CCl_3$, $-CBr_3$, $-CI_3$, $-CN$, $-CHO$, $-OR^{33C}$, $-NR^{34C}R^{35C}$, $-NR^{34C}R^{35C}$, $-COOR^{33C}$, $-CONR^{34C}R^{35C}$, $-NO_2$, $-SR^{36C}$, $-SO_{n3}R^{34C}$, $-SO_{n3}OR^{34C}$, $-SO_{n3}NR^{34C}R^{35C}$, $-NHNR^{34C}R^{35C}$, $-ONR^{34C}R^{35C}$, $-NHC(O)NHNR^{34C}R^{35C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^4$ is hydrogen, halogen, $-N_3$, $-CF_3$, $-CCl_3$, $-CBr_3$, $-CI_3$, $-CN$, $-CHO$, $-OR^{33D}$, $-NR^{34D}R^{35D}$, $-COOR^{33D}$, $-CONR^{34D}R^{35D}$, $-NO_2$, $-SR^{36D}$, $-SO_{n4}R^{34D}$, $-SO_{n4}OR^{34D}$, $-SO_{n4}NR^{34D}R^{35D}$, $-NHNR^{34D}R^{35D}$, $-ONR^{34D}R^{35D}$, $-NHC(O)NHNR^{34D}R^{35D}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^5$ is hydrogen, halogen, $-N_3$, $-CF_3$, $-CCl_3$, $-CBr_3$, $-CI_3$, $-CN$, $-CHO$, $-OR^{33E}$, $-NR^{34E}R^{35E}$, $-COOR^{33E}$, $-CONR^{34E}R^{35E}$, $-NO_2$, $-SR^{36E}$, $-SO_{n5}R^{34E}$, $-SO_{n5}OR^{34E}$, $-SO_{n5}NR^{34E}R^{35E}$, $NHNR^{34E}R^{35E}$, $-ONR^{34E}R^{35E}$, $-NHC(O)NHNR^{34E}R^{35E}$ substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^6$ is hydrogen, halogen, —$N_3$, —$CF_3$, —$CCl_3$, —$CBr_3$, —$CI_3$, —CN, —CHO, —$OR^{33F}$, —$NR^{34F}R^{35F}$, —$COOR^{33F}$, —$CONR^{34F}R^{35F}$, —$NO_2$, —$SR^{36F}$, —$SO_{n6}R^{34F}$, —$SO_{n6}OR^{34F}$, —$SO_{n6}NR^{34F}R^{35F}$, —$NHNR^{34F}R^{35F}$, —$ONR^{34F}R^{35F}$, —NHC(O)$NHNR^{34F}R^{35F}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{16}$ is hydrogen, halogen, —$N_3$, —$CF_3$, —$CCl_3$, —$CBr_3$, —$CI_3$, —CN, —CHO, —$OR^{33G}$, —$NR^{34G}R^{35G}$, —$COOR^{33G}$, —$CONR^{34G}R^{35G}$, —$NO_2$, —$SR^{36G}$, —$SO_{n7}R^{34G}$, —$SO_{n7}OR^{34G}$, —$SO_{n7}NR_{34G}R^{35G}$, —$NHNR^{34G}R^{35G}$, —$ONR^{34G}R^{35G}$, —NHC(O)$NHNR^{34G}R^{35G}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{18}$ is hydrogen, halogen, —$N_3$, —$CF_3$, —$CCl_3$, —$CBr_3$, —$CI_3$, —CN, —CHO, —$OR^{33H}$, —$NR^{34H}R^{35H}$, —$COOR^{33H}$, —$CONR^{34H}R^{35H}$, —$NO_2$, —$SR^{36H}$, —$SO_{n8}R^{34H}$, —$SO_{n8}OR^{34H}$, —$SO_{n8}NR^{34H}R^{35H}$, —$NHNR^{34H}R^{35H}$, —$ONR^{34H}R^{35H}$, —NHC(O)$NHNR^{34H}R^{35H}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{33A}$, $R^{34A}$, $R^{35A}$, $R^{36A}$, $R^{33B}$, $R^{34B}$, $R^{35B}$, $R^{36B}$, $R^{33C}$, $R^{34C}$, $R^{35C}$, $R^{36C}$, $R^{33D}$, $R^{34D}$, $R^{35D}$, $R^{36D}$, $R^{33E}$, $R^{34E}$, $R^{35E}$, $R^{36E}$, $R^{33F}$, $R^{34F}$, $R^{35F}$, $R^{36F}$, $R^{33G}$, $R^{34G}$, $R^{35G}$, $R^{36G}$, $R^{33H}$, $R^{34H}$, $R^{35H}$, and $R^{36H}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and n1, n2, n3, n4, n5, n6, n7, and n8 are independently 1 or 2.

2. The method of claim 1, wherein the ring bridging trisulfide compound is:

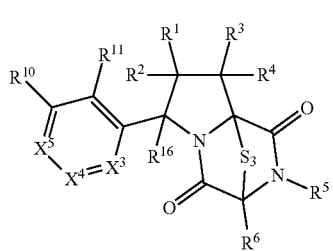

(IIa)

and the ring bridging disulfide compound is:

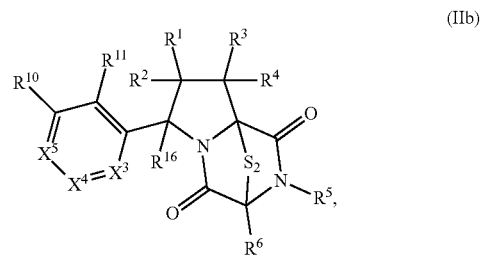

(IIb)

wherein:
$X^3$ is N or $CR^7$;
$X^4$ is N or $CR^8$;
$X^5$ is N or $CR^9$;
$R^7$ is hydrogen, halogen, —$N_3$, —$CF_3$, —$CCl_3$, —$CBr_3$, —$CI_3$, —CN, —CHO, —$OR^{33I}$, —$NR^{34I}R^{35I}$, —$COOR^{33I}$, —$CONR^{34I}R^{35I}$, —$NO_2$, —$SR^{36I}$, —$SO_{n9}R^{34I}$, —$SO_{n9}OR^{34I}$, —$SO_{n9}NR^{34I}R^{35I}$, —$NHNR^{34I}R^{35I}$, —$ONR^{34I}R^{35I}$, —NHC(O)$NHNR^{35I}R^{34I}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^8$ is hydrogen, halogen, —$N_3$, —$CF_3$, —$CCl_3$, —$CBr_3$, —$CI_3$, —CN, —CHO, —$OR^{33J}$, —$NR^{34J}R^{35J}$, —$COOR^{33J}$, —$CONR^{34J}R^{35J}$, —$NO_2$, —$SR^{36J}$, —$SO_{n10}R^{34J}$, —$SO_{n10}OR^{34J}$, —$SO_{n10}NR^{34J}R^{35J}$, —$NHNR^{34J}R^{35J}$, —$ONR^{34J}R^{35J}$, —NHC(O)$NHNR^{34J}R^{35J}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^9$ is hydrogen, halogen, —$N_3$, —$CF_3$, —$CCl_3$, —$CBr_3$, —$CI_3$, —CN, —CHO, —$OR^{33K}$, —$NR^{34K}R^{35K}$, —$COOR^{33K}$, —$CONR^{34K}R^{35K}$, —$NO_2$, —$SR^{36K}$, —$SO_{n11}R^{34K}$, —$SO_{n11}OR^{34K}$, —$SO_{n11}NR^{34K}R^{35K}$, —$NHNR^{34K}R^{35K}$, —$ONR^{34K}R^{35K}$, —NHC(O)$NHNR^{34K}R^{35K}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{10}$ and $R^{11}$ are independently hydrogen, halogen, —$N_3$, —$CF_3$, —$CCl_3$, —$CBr_3$, —$CI_3$, —CN, —CHO, —$OR^{33L}$, —$NR^{34L}R^{35L}$, —$COOR^{33L}$, —$CONR^{34L}R^{35L}$, —$NO_2$, —$SR^{36L}$, —$SO_{n12}R^{34L}$, —$SO_{n12}OR^{34L}$, —$SO_{n12}NR^{34L}R^{35L}$, —$NHNR^{34L}R^{35L}$, —$ONR^{34L}R^{35L}$, —NHC(O)$NHNR^{34L}R^{35L}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, or are optionally joined together to form a substituted or unsubstituted cycloalkyl, a substituted or unsubstituted heterocycloalkyl, a substituted or unsubstituted aryl, or a substituted or unsubstituted heteroaryl;

$R^{33I}$, $R^{34I}$, $R^{35I}$, $R^{36I}$, $R^{33J}$, $R^{34J}$, $R^{35J}$, $R^{36J}$, $R^{33K}$, $R^{34K}$, $R^{35K}$, $R^{36K}$, $R^{33L}$, $R^{34L}$, $R^{35L}$, and $R^{36L}$, are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and n9, n10, n11, and n12 are independently 1 or 2.

3. The method of claim 1, wherein the ring bridging trisulfide compound is:

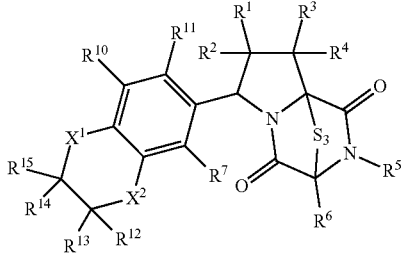
(IVa)

and the ring bridging disulfide compound is:

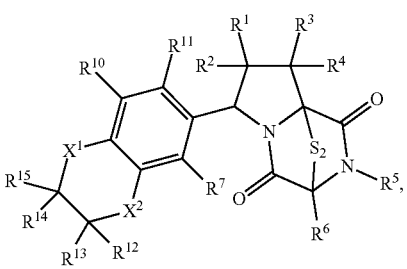
(IVb)

wherein:

$X^1$ is $CR^{21}R^{21A}$, O, $NR^{21A}$, or S;

$X^2$ is $CR^{22}R^{22A}$, O, $NR^{22A}$, or S; and $R^{12}$, $R^{13}$, $R^{14}$, $R^{15}$ $R^{21}$, $R^{21A}$, $R^{22}$, and $R^{22A}$ are independently hydrogen, halogen, $-N_3$, $-CF_3$, $-CCl_3$, $-CBr_3$, $-CI_3$, $-CN$, $-CHO$, $-OR^{33M}$, $-NR^{34M}R^{35M}$, $-COOR^{33M}$, $-CONR^{34M}R^{35M}$, $-NO_2$, $-SR^{36M}$, $-SO_{n13}R^{34M}$, $-SO_{n13}OR^{34M}$, $-SO_{n13}NR^{34M}R^{35M}$, $-NHNR^{34M}R^{35M}$, $-ONR^{34M}R^{35M}$, $-NHC(O)NHNR^{34M}R^{35M}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{33M}$, $R^{34M}$, $R^{35M}$, and $R^{36M}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and n13 is 1 or 2.

4. The method of claim 3, wherein the ring bridging trisulfide compound is:

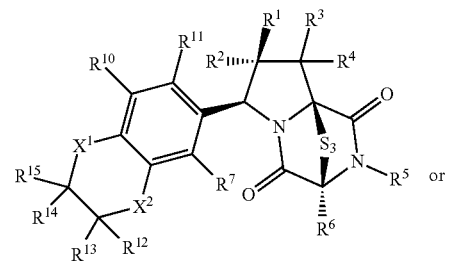
(IVa(S))

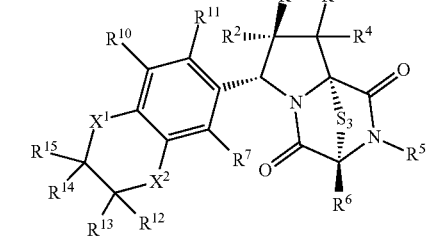
(IVa(R))

and the ring bridging disulfide compound is:

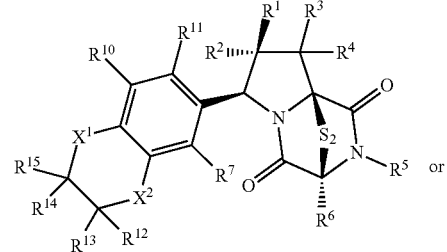
(IVb(S))

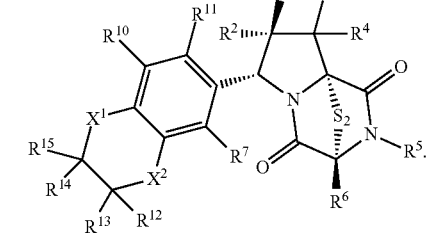
(IVb(R))

5. The method of claim 3, wherein ring bridging disulfide compound is:

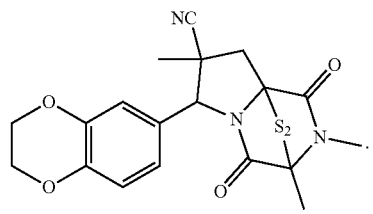

6. The method of claim 1, wherein the ring bridging trisulfide compound is:

(IIIa)

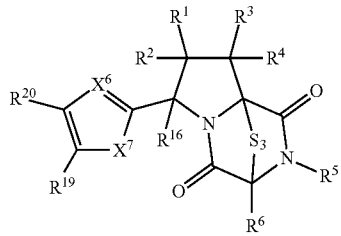

and ring bridging disulfide compound is:

(IIIb)

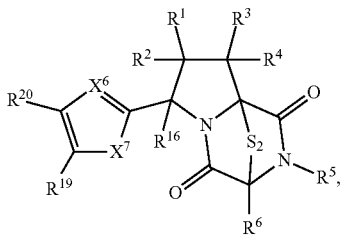

wherein:

$X^6$ is $CR^{24}$ or N;

$X^7$ is $CR^{24}R^{24A}$, S, O, or $NR^{24A}$;

$R^{19}$, $R^{20}$, $R^{24}$ and $R^{24A}$, are independently hydrogen, halogen, —$N_3$, —$CF_3$, —$CCl_3$, —$CBr_3$, —$CI_3$, —CN, —CHO, —$OR^{33M}$, —$NR^{34M}R^{35M}$, —$COOR^{33M}$, —$CONR^{34M}R^{35M}$, —$NO_2$, —$SR^{36M}$, —$SO_{n13}R^{34M}$, —$SO_{n13}OR^{34M}$, —$SO_{n13}NR^{34M}R^{35M}$, —$NHR^{34M}R^{35M}$, —$ONR^{34M}R^{35M}$, —NHC(O)$NHNR^{34M}R^{35M}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{33M}$, $R^{34M}$, $R^{35M}$, and $R^{36M}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and n13 is 1 or 2.

7. The method of claim 1, wherein the ring bridging trisulfide compound is:

(IIIa(S))

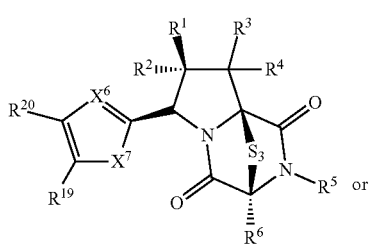

(IIIa(R))

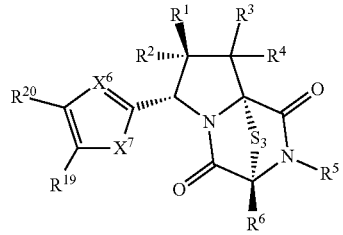

and the ring bridging disulfide compound is:

(IIIb(S))

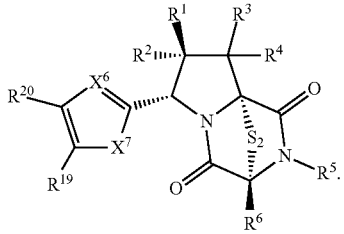

(IIIb(R))

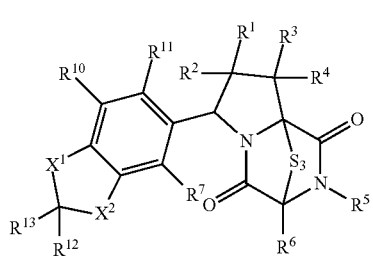

8. The method of claim 1, wherein the ring bridging trisulfide compound is:

(Va)

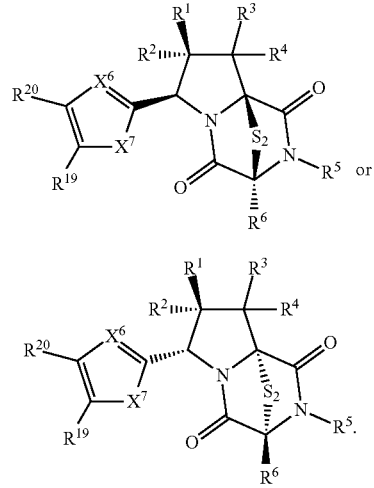

and the ring bridging disulfide compound is:

(Vb)

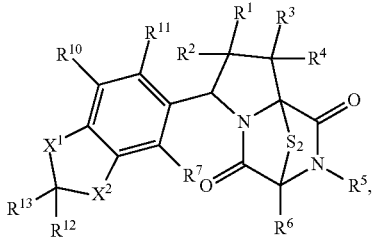

wherein:

$X^1$ is $CR^{21}R^{21A}$, O, $NR^{21A}$, or S;

$X^2$ is $CR^{22}R^{22A}$, O, $NR^{22A}$, or S;

$R^7$ is hydrogen, halogen, —$N_3$, —$CF_3$, —$CCl_3$, —$CBr_3$, —$CI_3$, —CN, —CHO, —$OR^{33I}$, —$NR^{34I}R^{35I}$, —$COOR^{33I}$, —$CONR^{34I}R^{35I}$, —$NO_2$, —$SR^{36I}$, —$SO_{n9}R^{34I}$, —$SO_{n9}OR^{34I}$, —$SO_{n9}NR^{34I}R^{35I}$, —$NHNR^{34I}R^{35I}$, —$ONR^{34I}R^{35I}$, —NHC(O)NHNR^{34I}R^{35I}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{10}$ and $R^{11}$ are independently hydrogen, halogen, —$N_3$, —$CF_3$, —$CCl_3$, —$CBr_3$, —$CI_3$, —CN, —CHO, —$OR^{33L}$, —$NR^{34L}R^{35L}$, —$COOR^{33L}$, —$CONR^{34L}R^{35L}$, —$NO_2$, —$SR^{36L}$, —$SO_{n12}R^{34L}$, —$SO_{n12}OR^{34L}$, —$SO_{n12}NR^{34L}R^{35L}$, —$NHNR^{34L}R^{35L}$, —$ONR^{34L}R^{35L}$, —NHC(O)NHNR^{34L}R^{35L}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, or are optionally joined together to form a substituted or unsubstituted cycloalkyl, a substituted or unsubstituted heterocycloalkyl, a substituted or unsubstituted aryl, or a substituted or unsubstituted heteroaryl;

$R^{12}$, $R^{13}$, $R^{21}$, $R^{21A}$, $R^{22}$ and $R^{22A}$ are independently hydrogen, halogen, —$N_3$, —$CF_3$, —$CCl_3$, —$CBr_3$, —$CI_3$, —CN, —CHO, —$OR^{33M}$, —$NR^{34M}R^{35M}$, —$COOR^{33M}$, —$CONR^{34M}R^{35M}$, —$NO_2$, —$SR^{36M}$, —$SO_{n13}R^{34M}$, —$SO_{n13}OR^{34M}$, —$SO_{n13}NR^{34M}R^{35M}$, —$NHNR^{34M}R^{35M}$, —$ONR^{34M}R^{35M}$, —NHC(O)NHNR^{34M}R^{35M}$, substituted or unsubstituted alkyl, substituted or substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{33M}$, $R^{34M}$, $R^{35M}$, and $R^{36M}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and n9, n12, and n13 are independently 1 or 2.

9. The method of claim 8, wherein the ring bridging trisulfide compound is:

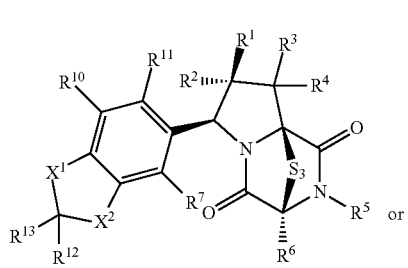

(Va(S))

and the ring bridging disulfide compound is:

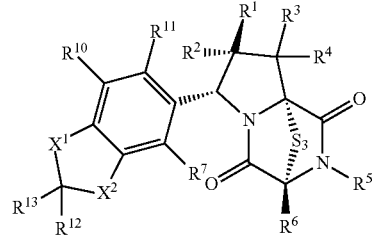

(Va(R))

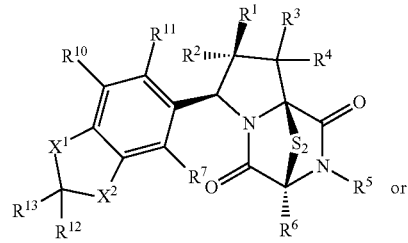

(Vb(S))

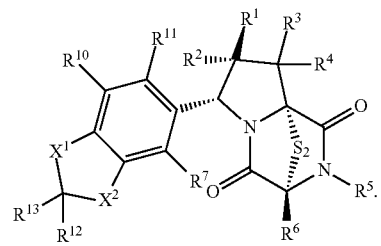

(Vb(R))

10. The method of claim 8, wherein the ring bridging disulfide compound is:

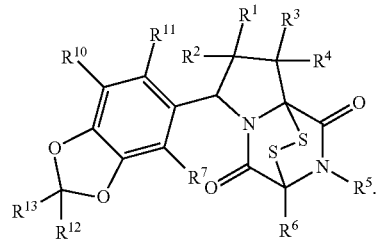

(V2)

11. The method of claim 10, wherein the ring bridging disulfide compound is:

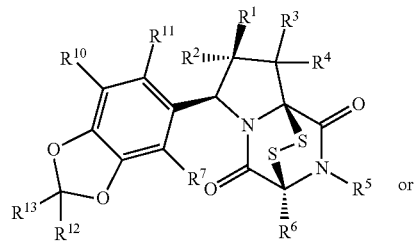

(V2(S))

(V2(R))

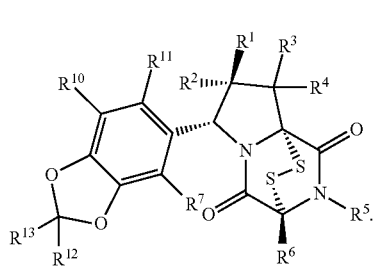

12. The method of claim 1, wherein the ring bridging disulfide compound is:

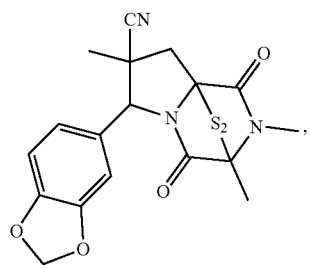

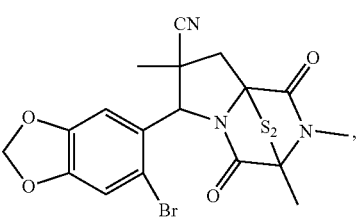

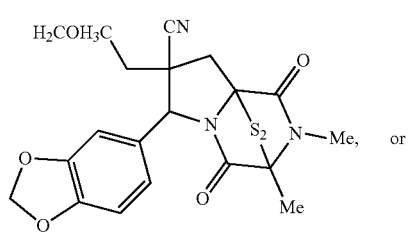

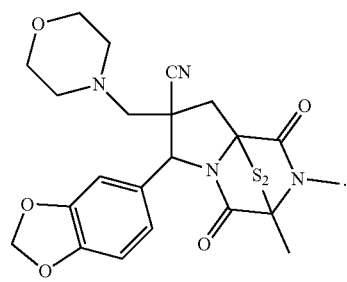

13. The method of claim 1, wherein the ring bridging trisulfide compound is:

(V3a)

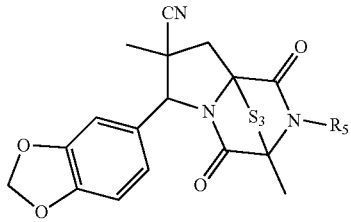

and the ring bridging disulfide compound is:

(V3b)

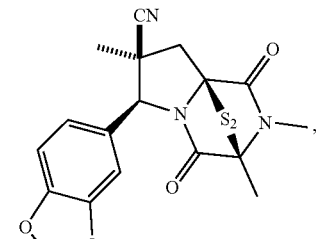

wherein:
R⁵ is unsubstituted 3- to 5-membered cycloalkyl or R⁵ᵃ-substituted or unsubstituted $C_1$-$C_5$ alkyl; and
R⁵ᵃ is unsubstituted 2 to 5 membered heteroalkyl or 5 to 6 membered heterocycloalkyl.

14. The method of claim 1, wherein the ring bridging disulfide compound is:

(ETP69)

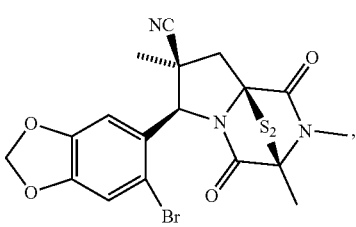

(ETP128)

(ETP344)

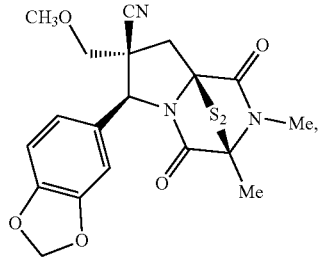

(ETP382)
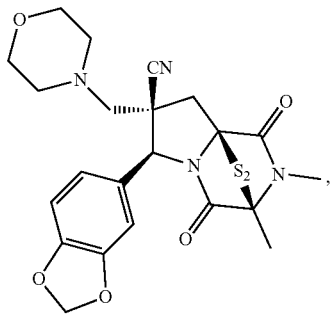
(ETP406)
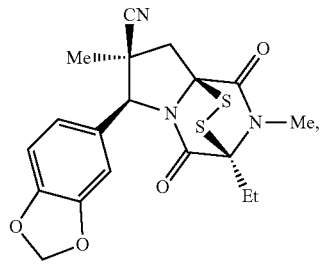
(ETP417)
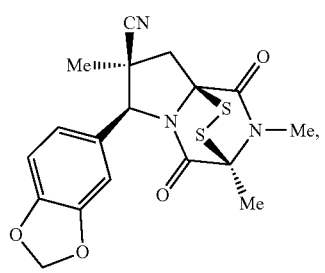
(ETP422)
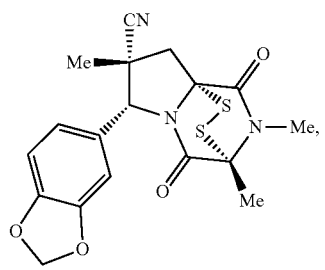
(ETP425)
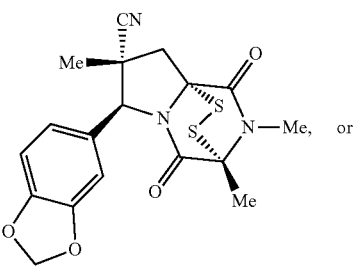, or
(ETP452)
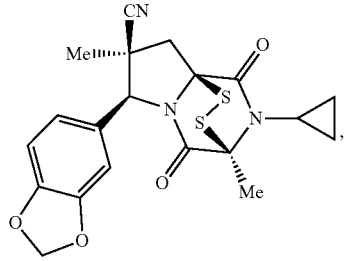
and the ring bridging trisulfide compound is:
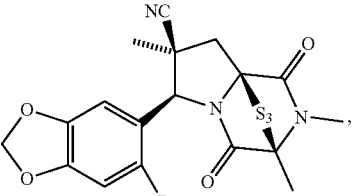
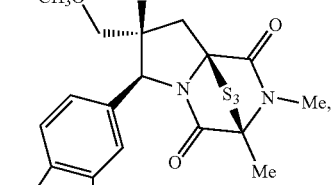
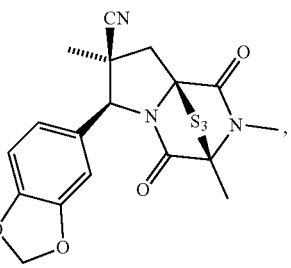
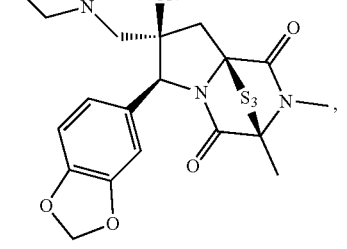
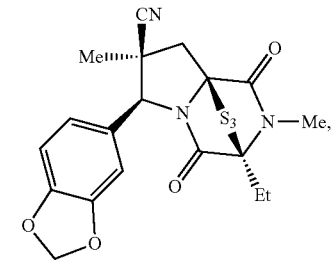

-continued

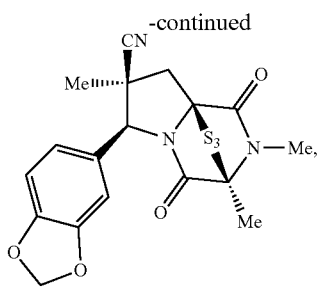

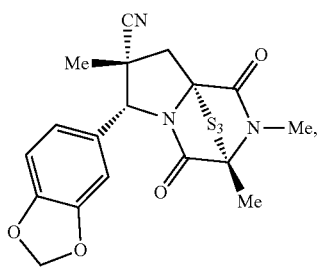

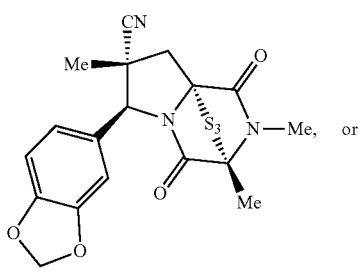

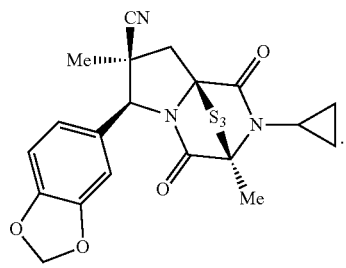

15. The method of claim 1, wherein the ring bridging trisulfide compound is:

(VIa)

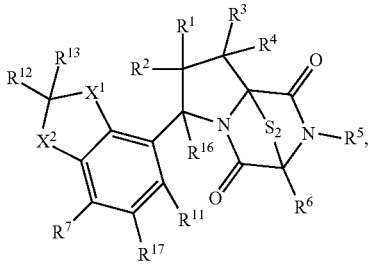

and the ring bridging disulfide compound is:

(VIb)

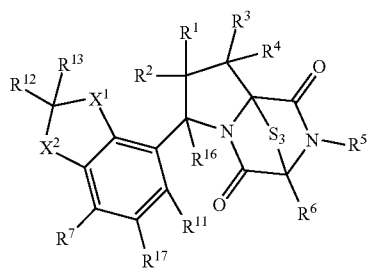

wherein:
$X^1$ is $CR^{21}R^{21A}$, O, $NR^{21A}$, or S;
$X^2$ is $CR^{22}R^{22A}$, O, $NR^{22A}$, or S;
$R^7$ is hydrogen, halogen, —$N_3$, —$CF_3$, —$CCl_3$, —$CBr_3$, —$CI_3$, —CN, —CHO, —$OR^{33I}$, —$NR^{34I}R^{35I}$, —$COOR^{33I}$, —$CONR^{34I}R^{35I}$, —$NO_2$, —$SR^{36I}$, —$SO_{n9}R^{34I}$, —$SO_{n9}OR^{34I}$, —$SO_{n9}NR^{34I}R^{35}$, —$NHNR^{34I}R^{35I}$, —$ONR^{34I}R^{35I}$, —NHC(O) $NHNR^{34I}R^{35I}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$R^{11}$ is hydrogen, halogen, —$N_3$, —$CF_3$, —$CCl_3$, —$CBr_3$, —$CI_3$, —CN, —CHO, —$OR^{33L}$, —$NR^{34L}R^{35L}$, —$COOR^{33L}$, —$CONR^{34L}R^{35L}$, —$NO_2$, —$SR^{36L}$, —$SO_{n12}R^{34L}$, —$SO_{n12}OR^{34L}$, —$SO_{n12}NR^{34L}R^{35L}$, —$NHNR^{34L}R^{35L}$, —$ONR^{34L}R^{35L}$, —NHC(O) $NHNR^{34L}R^{35L}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, or are optionally joined together to form a substituted or unsubstituted cycloalkyl, a substituted or unsubstituted heterocycloalkyl, a substituted or unsubstituted aryl, or a substituted or unsubstituted heteroaryl;
$R^{12}$, $R^{13}$, $R^{21}$, $R^{21A}$, $R^{22}$ and $R^{22A}$ are independently hydrogen, halogen, —$N_3$, —$CF_3$, —$CCl_3$, —$CBr_3$, —$CI_3$, —CN, —CHO, —$OR^{33M}$, —$NR^{34M}R^{35M}$, —$COOR^{33M}$, —$CONR^{34M}R^{35M}$, —$NO_2$, —$SR^{36M}$, —$SO_{n13}R^{34M}$, —$SO_{n13}OR^{34M}$, —$SO_{n13}NR^{34M}R^{35M}$, —$NHNR^{34M}R^{35M}$, —$ONR^{34M}R^{35M}$, —NHC(O) $NHNR^{34M}R^{35M}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$R^{17}$ is hydrogen, halogen, —$N_3$, —$CF_3$, —$CCl_3$, —$CBr_3$, —$CI_3$, —CN, —CHO, —$OR^{33P}$, —$NR^{34P}R^{35P}$, —$COOR^{33P}$, —$CONR^{34P}R^{35P}$, —$NO_2$, —$SR^{36P}$, —$SO_{n14}R^{34P}$, —$SO_{n14}OR^{34P}$, —$SO_{n14}NR^{34P}R^{35P}$, —$NHNR^{34P}R^{35P}$, —$ONR^{34P}R^{35P}$, —NHC(O) $NHNR^{34P}R^{35P}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, or are optionally bonded together to form a substituted or unsubstituted cycloalkyl, a substituted or unsubstituted heterocycloalkyl, a substituted or unsubstituted aryl, or a substituted or unsubstituted heteroaryl;

$R^{33I}$, $R^{34I}$, $R^{35I}$, $R^{36I}$, $R^{33L}$, $R^{34L}$, $R^{35L}$, $R^{36L}$, $R^{33M}$, $R^{34M}$, $R^{35M}$, $R^{36M}$, $R^{33P}$, $R^{34P}$, $R^{35P}$, and $R^{36P}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and n9, n12, n13 and n14 are independently 1 or 2.

16. The method of claim 15, wherein the ring bridging trisulfide compound is:

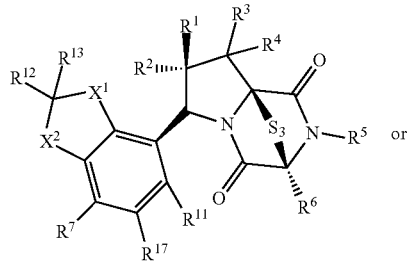
(VIa(S))

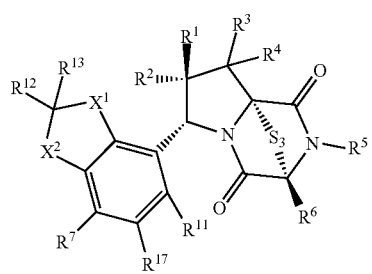
(VIa(R))

and the ring bridging disulfide compound is:

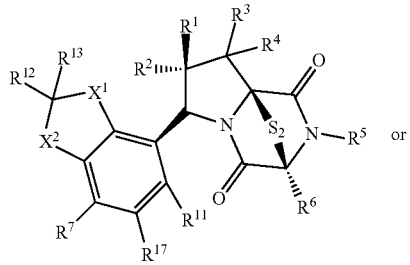
(VIb(S))

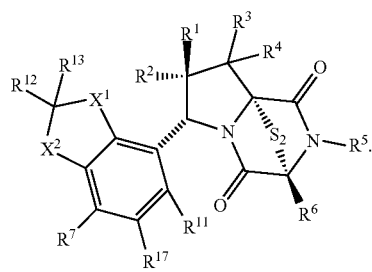
(VIb(R))

17. The method of claim 1, wherein the non-nucleophilic base is an organic non-nucleophilic base.

18. The method of claim 17, wherein the organic non-nucleophilic base comprises an amino group.

19. The method of claim 17, wherein the organic non-nucleophilic base is a sterically hindered organic non-nucleophilic base.

20. The method of claim 1, wherein the non-nucleophilic base is 1,5,7-triazabicyclo(4.4.0)dec-5-ene (TBD), 7-methyl-1,5,7-triazabicyclo(4.4.0)dec-5-ene (MTBD), 1,8-diazabicyclo[5.4.0]undec-7-ene (DBU), 1,5-diazabicyclo[4.3.0]non-5-ene (DBN), 1,1,3,3-tetramethylguanidine (TMG), quinuclidine, 2,2,6,6-tetramethylpiperidine (TMP), pempidine (PMP), tributylamine, triethylamine, N,N-triisopropylamine, 1,4-diazabicyclo[2.2.2]octan (TED), collidine, 2,6-dimethylpyridine, sodium tert-butoxide, potassium tert-butoxide, lithium diisopropylamide (LDA), potassium bis(trimethylsilyl)amide (KHMDS) or sodium trimethylsilyl)amide (NaHMDS).

21. The method of claim 20, wherein the non-nucleophilic base is DBU.

22. The method of claim 1, wherein the ring bridging trisulfide compound and the ring bridging disulfide compound are in a mixture having a ratio of the ring bridging trisulfide compound to the ring bridging disulfide compound in the mixture between about 100:0.01 and 0.01:100.

23. The method of claim 22, wherein the ratio of the ring bridging trisulfide to the ring bridging disulfide in the mixture is about 1:70.

* * * * *